US012630552B2

(12) United States Patent
Ji et al.

(10) Patent No.: US 12,630,552 B2
(45) Date of Patent: May 19, 2026

(54) INHIBITORS OF KRAS G12C

(71) Applicant: BEIGENE, LTD., Grand Cayman (KY)

(72) Inventors: Qi Ji, Beijing (CN); Chao Yu, Beijing (CN); Ce Wang, Beijing (CN); Hanzi Sun, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 937 days.

(21) Appl. No.: 17/763,720

(22) PCT Filed: Sep. 29, 2020

(86) PCT No.: PCT/CN2020/118665

§ 371 (c)(1),
(2) Date: Mar. 25, 2022

(87) PCT Pub. No.: WO2021/058018

PCT Pub. Date: Apr. 1, 2021

(65) Prior Publication Data

US 2022/0389021 A1 Dec. 8, 2022

(30) Foreign Application Priority Data

Sep. 29, 2019 (WO) ................ PCT/CN2019/109137

(51) Int. Cl.
*C07D 487/04* (2006.01)
*A61K 31/519* (2006.01)
*A61P 35/00* (2006.01)

(52) U.S. Cl.
CPC .................................. *C07D 487/04* (2013.01)

(58) Field of Classification Search
CPC ...... C07D 487/04; A61K 31/519; A61P 35/00
See application file for complete search history.

(56) References Cited

U.S. PATENT DOCUMENTS

| | | | | |
|---|---|---|---|---|
| 2009/0099195 A1* | 4/2009 | Bayrakdarian | ...... | C07D 519/00 514/258.1 |
| 2019/0233440 A1* | 8/2019 | Planken | ............... | C07D 403/14 |
| 2021/0147418 A1 | 5/2021 | Cai et al. | | |

FOREIGN PATENT DOCUMENTS

| | | | |
|---|---|---|---|
| CN | 101687875 | A | 3/2010 |
| WO | WO-2008099210 | A2 | 8/2008 |
| WO | WO-2009047255 | A1 | 4/2009 |
| WO | 2014152588 | A1 | 9/2014 |
| WO | WO-2014160521 | A1 | 10/2014 |
| WO | 2016049524 | A1 | 3/2016 |
| WO | 2016164675 | A1 | 10/2016 |
| WO | 2016168540 | A1 | 10/2016 |
| WO | 2017015562 | A1 | 1/2017 |
| WO | 2017058728 | A1 | 4/2017 |
| WO | 2017058792 | A1 | 4/2017 |
| WO | 2017058805 | A1 | 4/2017 |
| WO | WO-2017058915 | A1 | 4/2017 |
| WO | WO-2017087528 | A1 | 5/2017 |
| WO | WO-2017158388 | A1 | 9/2017 |
| WO | 2018068017 | A1 | 4/2018 |
| WO | WO-2018064510 | A1 | 4/2018 |
| WO | 2018119183 | A1 | 6/2018 |
| WO | WO-2018206539 | A1 | 11/2018 |
| WO | WO-2018218069 | A1 | 11/2018 |
| WO | 2019055540 | A1 | 3/2019 |
| WO | WO-2019051291 | A1 | 3/2019 |
| WO | 2019110751 | A1 | 6/2019 |
| WO | 2019137985 | A1 | 7/2019 |
| WO | WO-2019141250 | A1 | 7/2019 |
| WO | 2019150305 | A1 | 8/2019 |
| WO | WO-2019155399 | A1 | 8/2019 |

OTHER PUBLICATIONS

Jiang et al., Research progress on small molecule inhibitors targeting KRAS G12C with acrylamide structure and the strategies for solving KRAS inhibitor resistance, Bioorg. Med. Chem., 100, art. No. 117627 (Year: 2024).*
Song et al., Identification of novel Pyrrolo[2,3-d]Pyrimidine-based KRAS G12C inhibitors with anticancer effects, Eur. J. Med. Chem. , 245, art. No. 114907, pp. 1-19 (Year: 2023).*
International Search Report & Written Opinion in PCT/CN2020/118665, mailed Apr. 1, 2021, 13 pages.
Cox, Adrienne D., et al. "Drugging the undruggable RAS: Mission possible?," Nature reviews Drug discovery 13 (11):828-851, 2014.
Fell, Jay B., et al. "Discovery of tetrahydropyridopyrimidines as irreversible covalent inhibitors of KRAS-G12C with in vivo activity," ACS medicinal chemistry letters 9(12): 1230-1234, 2018.
Greene, Theodora W., and Peter GM Wuts. "Protective groups in organic synthesis," 1-52, 1999.
Jiang, Z. et al., "Research progress on small molecule inhibitors targeting KRAS G12C with acrylamide structure and the strategies for solving KRAS inhibitor resistance," Bioorg. Med. Chem., 100(117627): 1-12, 2024.
Kessler, Dirk, et al. "Drugging an undruggable pocket on KRAS," Proceedings of the National Academy of Sciences, 116(32): 15823-15829, 2019.
Lochmuller, C. H. et al., "Chromatographic Resolution of Enantiomers," Journal of Chromatography, 113:283-302, 1975.
Papke, Bjoern, and Channing J. Der. "Drugging RAS: Know the enemy," Science 355(6330): 1158-1163, 2017.
Patricelli, Matthew P., et al. "Selective inhibition of oncogenic KRAS output with small molecules targeting the inactive state." Cancer discovery 6(3):316-329, 2016.
Song, Z. et al., "Identification of novel Pyrrolo[2,3-d]Pyrimidine-based Kras G12C inhibitors with anticancer effects," Eur. J. Med. Chem., 245(114907): 1-19, 2023.
U.S. Non-Final Office Action for U.S. Appl. No. 17/763,720, dated Mar. 27, 2025, (17 pages).
U.S. Office Action (Non-Final Rejection) dated Mar. 27, 2025 for U.S. Appl. No. 17/763,720 (pp. 1-13).

* cited by examiner

*Primary Examiner* — Jeffrey S Lundgren
*Assistant Examiner* — Alexander K. Showalter
(74) *Attorney, Agent, or Firm* — Foley & Lardner LLP

(57) ABSTRACT

Disclosed herein are compounds that inhibit KRas G12C, pharmaceutical compositions, methods of preparation and uses thereof.

25 Claims, No Drawings

INHIBITORS OF KRAS G12C

CROSS-REFERENCE TO RELATED APPLICATIONS

This application is a U.S. National Stage Application under 35 U.S.C. § 371 of International Application No. PCT/CN2020/118665, filed Sep. 29, 2020, which claims priority to Patent Application No. PCT/CN2019/109137 (CN), filed Sep. 29, 2019.

FIELD OF THE INVENTION

Disclosed herein are compounds (including stereoisomers, pharmaceutical acceptable salts) that are useful for inhibiting Kras G12C mutant protein, pharmaceutical compositions thereof, methods of preparation thereof and method of treating diseases or disorders mediated by Kras G12C.

BACKGROUND OF THE INVENTION

RAS is one of the most well-known oncogene. In human, three RAS genes (HRAS, KRAS and NRAS) encode four highly homologous RAS proteins (HRAS, KRAS-4A, KRAS-4B and NRAS). RAS proteins are small GTPases, they function as binary molecular switches that involved in transduction of extracellular growth and differentiation signaling.

RAS generally cycles between a GDP-bound "off" state and a GTP-bound "on" state. This cycle is regulated by several factors. Guanine nucleotide exchange factors (GEFs), including SOS1 and SOS2 facilitate the exchange and formation of GTP-bound RAS. While, GTPase-activating proteins (GAPs), for example NF-1 promote the hydrolysis of GTP and therefore turn RAS back to GDP-bound inactivate state (Kessler et al, PNAS, 2019, 116 (32): 15823-15829). Once bound to GTP, RAS initiate conformational changes in two specific regions Switch 1 and Switch 2, which allows engagement and activation of downstream effector proteins to initiate a cascade of intracellular signaling pathways. These effectors include RAF-MEK-ERK and PI3K-AKT-mTOR pathways, both of which have crucial roles in regulating cell proliferation, differentiation and survival (Cox et al., Nature Reviews Drug Discovery, 2014, 13:828-851).

RAS mutations have been identified in around 30% of human tumors. These mutations occur frequently as single-base missense mutations in codons 12, 13 or 61, resulting in stabilization of the activated GTP-bound RAS form and constitutive activation of RAS downstream signaling pathways. KRAS is the most frequently mutated RAS in cancer, account for 85% of all RAS-driven cancers, followed by NRAS (12%) and HRAS (3%). KRAS mutation has been detected in around 95% of pancreatic ductal adenocarcinoma, 50% of colorectal adenocarcinoma and 30% of lung adenocarcinoma. The majority of KRAS mutations occur at residue 12, and the mutation type varied in different cancers. In colon cancer and pancreatic cancer, the predominant KRAS mutation is G12D (glycine to lysine), while in non-small cell lung cancer (NSCLC), nearly half of KRAS mutations are G12C (glycine to cysteine) (Cox et al., Nature Reviews Drug Discovery, 2014, 13:828-851).

Based on the critical role of RAS in cell proliferation and its high mutation rate in human cancers, RAS has long been considered as a therapeutic target for many cancers. However, despite several decades of research effort, no anti-RAS small molecular has been clinically approved. The main reason is that druggable pockets on the surface of RAS is lacking (Papke et al., Science, 2017, 355: 1158-1163). Recently, more and more studies suggested that RAS might be able to be drugged with small molecules. Several inhibitors that directly target KRAS G12C are under the investigation (Patricelli et al, Cancer Discovery, 2016, 6(3); 316-29) (Fell et al, ACS Med. Chem. Lett. 2018, 9, 12, 1230-1234).

Small molecule selectively inhibitors of KRAS are being developed to prevent or treat diseases, For example, WO2015/054572A1 provides compounds having activity as inhibitors of G12C mutant RAS protein. WO2016/164675A1 and WO2017/015562A1 disclose substituted quinazoline compounds as KRAS G12C inhibitors. Compounds with KRAS G12C inhibitory activity are further reported by WO2014/152588 A1, WO2016/049524 A1, WO2016/168540 A1, WO2017/058728 A1, WO2017/058792 A1, WO2017/058805A1, WO2017/058915 A1, WO2017/087528 A1, WO2018/064510 A1, WO2018/068017 A1, WO2018/119183 A2, WO2018/206539 A1, WO2018/218069 A1, WO2019/051291 A1, WO2019/055540 A1, WO2019/137985 A1, WO2019/141250 A1, WO2019/150305 A1 and WO2019/155399 A1. In particular, WO2019/110751A1 discloses tetracyclic compounds as inhibitors of G12C mutant Ras protein as anti-cancer agents.

Thus, new inhibitors that selectively target mutant KRAS with high efficacy and safety are still highly desirable. Continued efforts on developing KRAS G12C inhibitors will arise new therapeutic way for KRAS G12C driven cancers.

SUMMARY OF THE INVENTION

One objective of the present invention is to provide compounds exhibiting potent KRAS G12C inhibitory activity. Disclosed herein are compounds, or pharmaceutically acceptable salts, stereoisomers thereof.

Aspect 1: A compound of Formula (I):

(I)

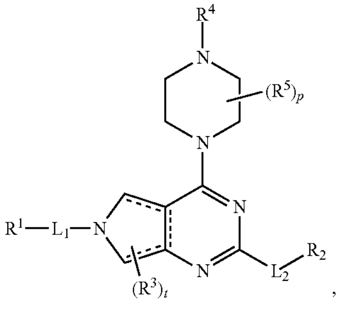

, or a pharmaceutically acceptable salt thereof, or a stereoisomer thereof, wherein

- ⎓ is a single bond or a double bond;
- $L_1$ and $L_2$ are each selected from a single bond, —CO—NH—, —NH—CO—, —O—, —$NR^a$—, —$NR^a(CH_2)_m$—, —S—, —$(CH_2)_m$—, —O—$(CH_2)_m$—, —O—$CH(R^a)$—, —$CH(R^a)$—, —$CH(R^a)(CH_2)_m$—, —$(CH_2)_m$—O—, —CO—, —$SO_2$—, cycloalkylene, oxetandiyl, tetrahydrofurandiyl, tetrahydropyrandiyl, azetidindiyl, pyrrilidindiyl, piperidindiyl, or piperizindiyl;
- $R^1$ is selected from —$C_{1-8}$alkyl, —$C_{2-8}$alkenyl, —$C_{2-8}$ alkynyl, —$NR^bR^c$, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with at least one $R^6$ (in case there are more than one $R^6$, each $R^6$ are identical or different to each other);

$R^2$ is selected from —$NR^bR^c$, cycloalkyl, heterocyclyl, aryl, or heteroaryl, each of said cycloalkyl, heterocyclyl, aryl, or heteroaryl is optionally substituted with at least one $R^6$ (such as —$(R^6)_q$, wherein each $R^6$ are the same or different in case q is more than 1);

each $R^6$ is selected from —$C_{1-8}$alkyl, halogen, hydroxy, oxo, —$C_{1-8}$alkoxy, —$NR^bR^c$, cycloalkyl, heterocyclyl, aryl, or heteroaryl; said —$C_{1-8}$alkyl, —$C_{1-8}$alkoxy, cycloalkyl, heterocyclyl, aryl, or heteroaryl is optionally substituted with at least one hydroxy, amino, CN or cycloalkyl, heterocyclyl, aryl or heteroaryl;

$R^3$ is selected from hydrogen, oxo, —$C_{1-8}$alkyl, —$C_{2-8}$ alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^5$ is selected from —$C_{1-8}$alkyl, —$C_{2-8}$alkenyl, —$C_{2-8}$ alkynyl, oxo, —$NR^bR^c$, —CO—$NR^dR^e$, cycloalkyl, heterocyclyl, aryl, or heteroaryl, —$(CH_2)_m$—CN, or hydrogen;

$R^4$ is selected from

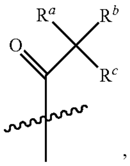 , 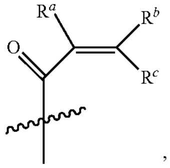 , 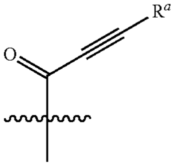 ,

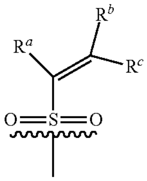 , or 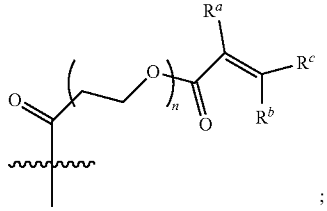 ;

each $R^a$, $R^b$ and $R^c$ are independently hydrogen, deuterium (D), cyano (CN), halogen, hydroxy, —$C_{1-8}$ alkoxy, —$C_{1-8}$alkyl, —$C_{2-8}$alkenyl, —$C_{2-8}$alkynyl, cycloalkyl, heterocyclyl, aryl, heteroaryl, —CO—$NR^dR^e$, each of said —$C_{1-8}$alkyl, —$C_{2-8}$alkenyl, —$C_{2-8}$alkynyl, cycloalkyl, heterocyclyl, aryl, or heteroaryl is optionally substituted with $R^f$; or ($R^a$ and $R^b$), or ($R^a$ and $R^c$) together with the atom(s) to which they are attached, form a 4- to 6 membered ring, said ring is optionally substituted with at least one $R^9$;

each $R^f$ is selected from halogen, hydroxy, oxo, —$C_{1-8}$alkoxy, —$NR^dR^e$, —CO—$NR^dR^e$, —$NR^d$—CO—$R^e$, cycloalkyl, heterocyclyl, aryl, or heteroaryl, wherein each said —$C_{1-8}$alkoxy, cycloalkyl, heterocyclyl, aryl, or heteroaryl is optionally substituted with halogen, hydroxy or —$C_{1-4}$alkyl;

$R^d$, $R^e$ and $R^g$ are each independently hydrogen, deuterium (D), halogen, oxo, —$C_{1-8}$alkyl; each said —$C_{1-8}$alkyl is optionally substituted with at least one halogen, oxo, $CF_3$ or —$COCH_3$;

p, q and t are independently selected from 0, 1, 2, 3 or 4; each m and n are independently 0, 1, 2, 3, 4, 5 or 6.

Aspect 2: The compound according to Aspect 1, wherein $R^1$ is selected from —$C_{2-4}$alkenyl, 5- to 6-membered carbocyclic aromatic ring (such as phenyl), 7- to 12-membered bi-carbocyclic ring (such as naphthalene, indene, or indane), 10- to 15-membered tri-carbocyclic ring (such as fluorene, anthracene, phenalene, phenanthrene), 7- to 12-membered bicyclic heteroaryl comprising at least one heteroatom selected from N, O and S with the remaining ring atoms being carbon; each of said —$C_{2-4}$alkenyl, 5- to 6-membered carbocyclic aromatic ring, 7- to 12-membered bi-carbocyclic ring, 10-15 membered tri-carbocyclic ring, and 7- to 12-membered bicyclic heteroaryl is optionally substituted with at least one $R^6$ (such as —$(R^6)_q$, wherein each $R^6$ are the same or different in case q is more than 1); $R^6$ is selected from halogen, hydroxy, oxo, —$NR^bR^c$, —$C_{1-8}$ alkyl, —$C_{1-8}$ alkoxy, -halo$C_{1-8}$ alkyl, cycloalkyl, heterocyclyl, aryl, or heteroaryl; $R^b$ and $R^c$ are independently hydrogen, deuterium(D), or —$C_{1-8}$alkyl.

Aspect 3: The compound according to any one of Aspects 1 or 2, wherein $R^1$ is selected from phenyl, naphthalene, indane, fluorene, indazole, or dihydroacenaphthylene, quinoline, isoquinoline, or indole, wherein said phenyl, naphthalene, indane, fluorene, indazole, dihydroacenaphthylene, quinoline, isoquinoline, or indole is optionally substituted with at least one $R^6$, $R^6$ is selected from —$C_{1-8}$alkyl, —$C_{1-8}$alkoxy, -halo$C_{1-8}$ alkyl, oxo, halogen, hydroxy, —$NH_2$, or $C_{3-6}$ cycloalkyl.

Aspect 4: The compound according to any one of Aspects 1-3, wherein $R^1$ is selected from

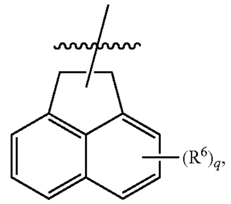 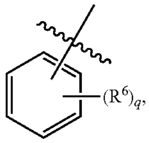

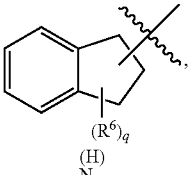 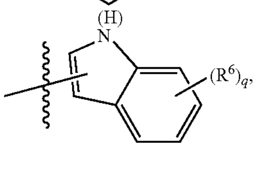

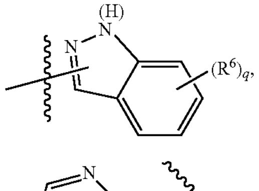 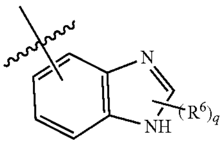 ,

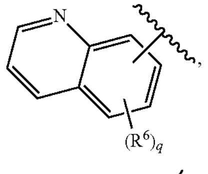 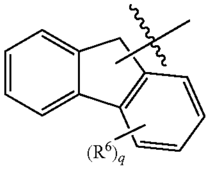 ,

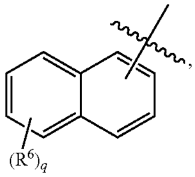 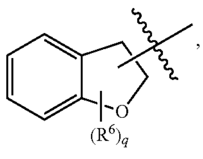 ,

-continued
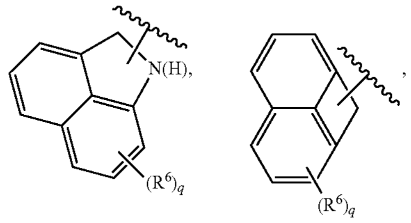
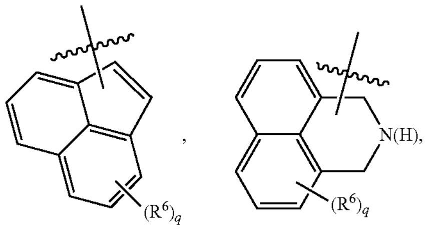
or
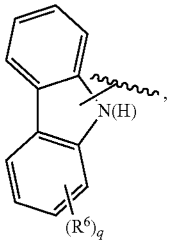
wherein $R^6$ is selected from F, Br, Cl, OH, —$OCH_3$, oxo, CN, —$NH_2$, —$CF_3$, —$CF_2H$,
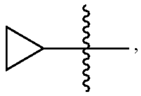
$CH_2CH_3$, or $CH_3$; and wherein q=0, 1 or 2.
Aspect 5: The compound according to any one of Aspects 1-4, wherein $R^1$ is selected from
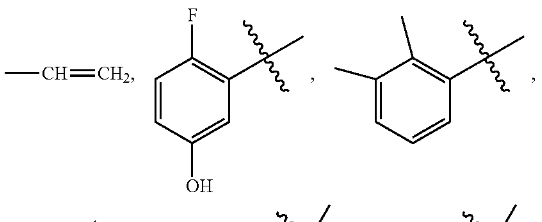
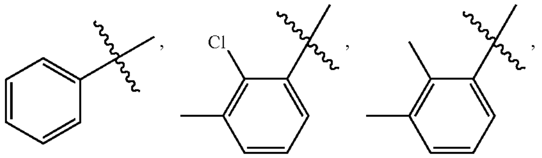
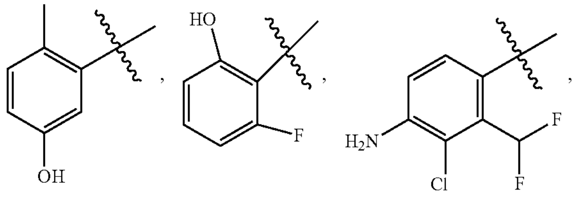
-continued
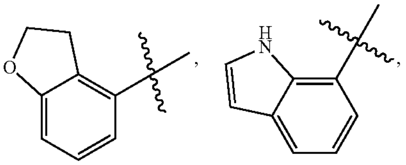
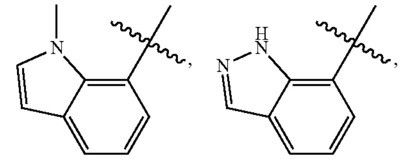
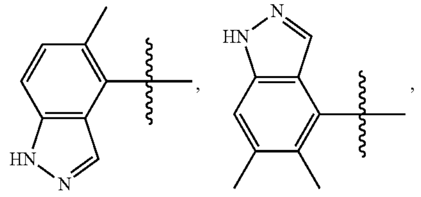
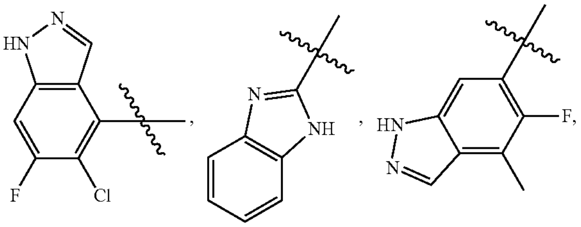
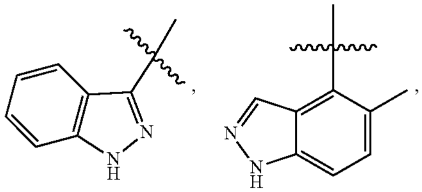
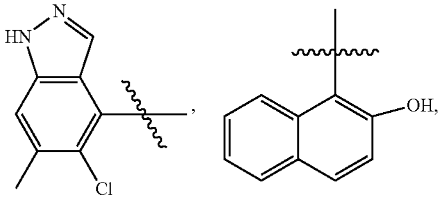
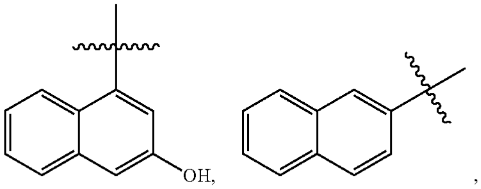
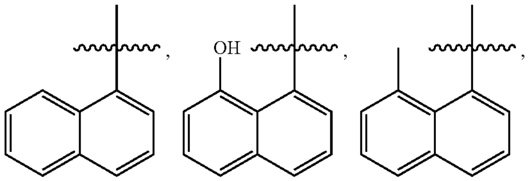
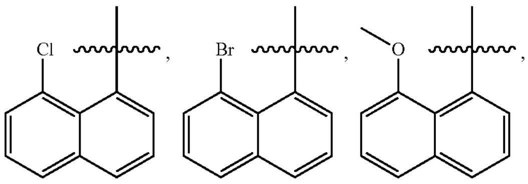

-continued
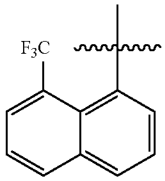,
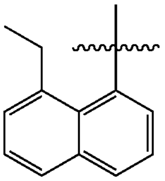,
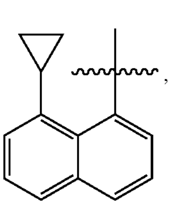,
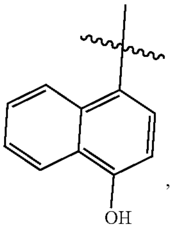,
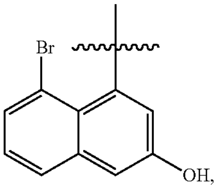,
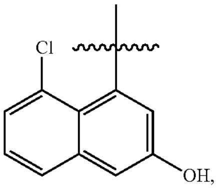,
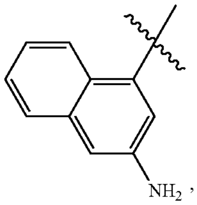,
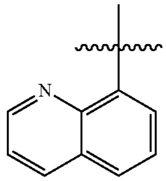,
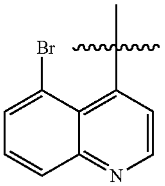,
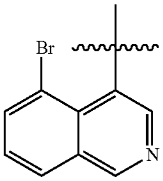,
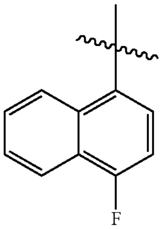,
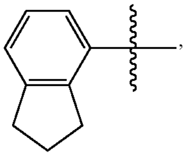,
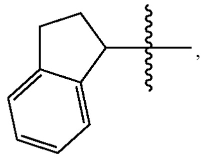,
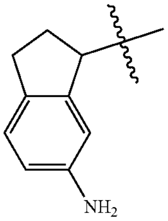,
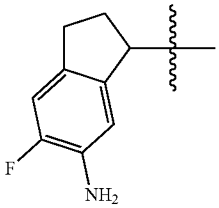,
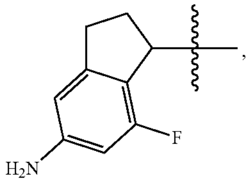,
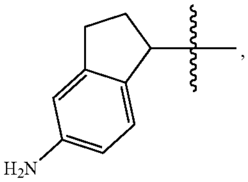,
-continued
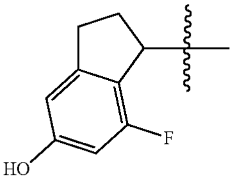,
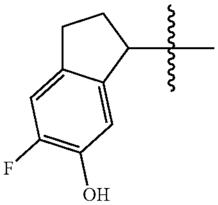,
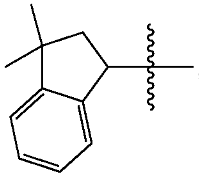,
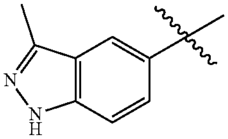,
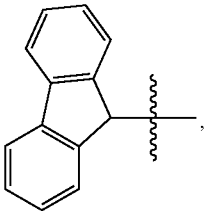,
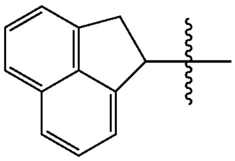,
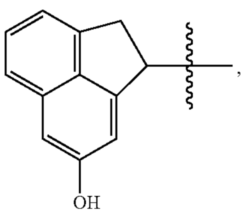,
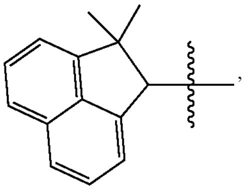,
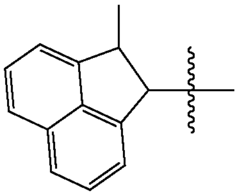,
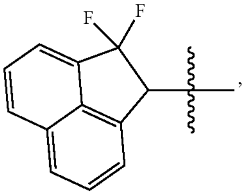,
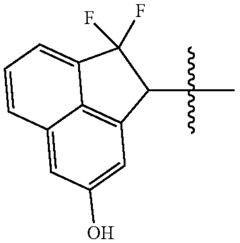,
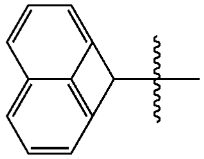,
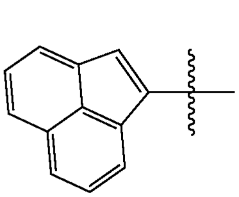,
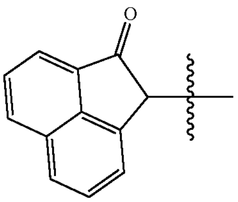,
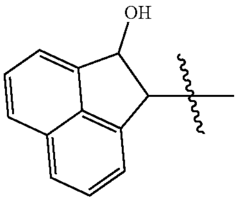,
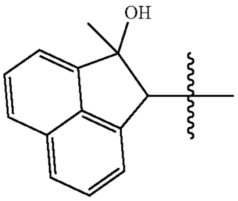, -continued

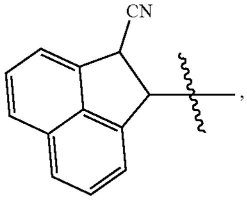, 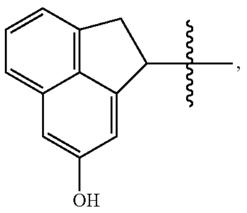,

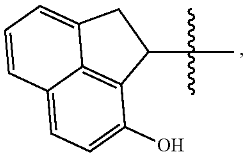, 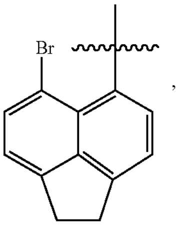,

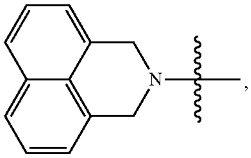, 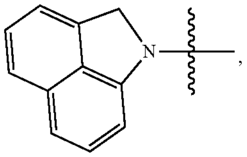,

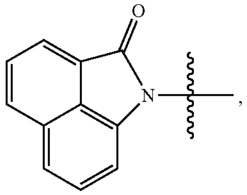, 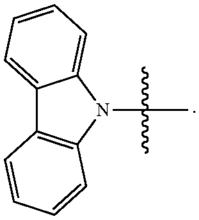.

Aspect 6: The compound according to any one of Aspects 1-4, wherein $R^1$ is selected from

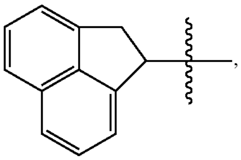, 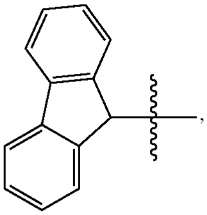,

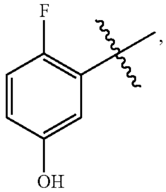, 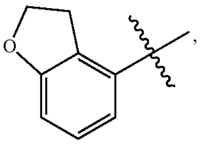,

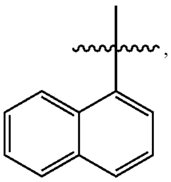, 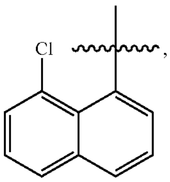, 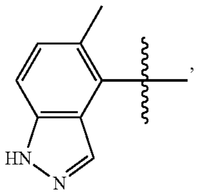,

-continued

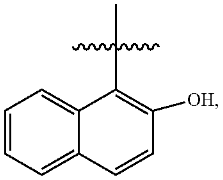, 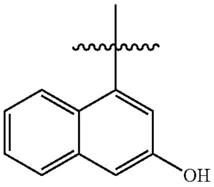,

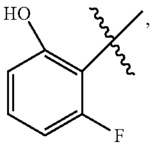, 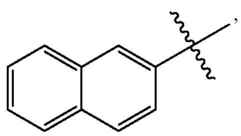,

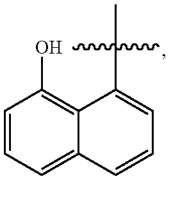, 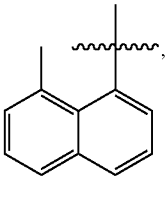, 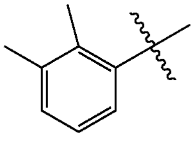, $-CH{=}CH_2$, 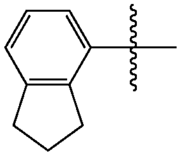, or

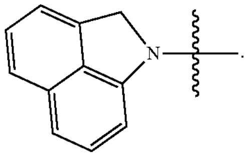.

Aspect 7: The compound according to any one of Aspects 1-6, wherein $L_1$ is selected from single bond, —CO—NH—, $-CH_2-$, —CO—, or $-CH(CH_3)-$.

Aspect 8: The compound according to any one of Aspects 1-7, wherein $L_2$ is selected from —O—, $-O-(CH_2)_m-$, $-O-CH(R^a)-$, $-O-CH(R^a)-(CH_2)_m-$, cyclopropylene, azetidindiyl, and $-NR^a(CH_2)_m-$, m=1 or 2; $R^a$ is selected from hydrogen, methyl, or deuterium(D).

Aspect 9: The compound according to any one of Aspects 1-8, wherein $L_2$ is selected from a single bond, $-O-CH_2-$, $-O-CH_2CH_2-$, $-O-CH_2CH_2CH_2-$, —O—, $-O-CH(CH_3)-$, $-NH-CH_2-$, $-NH-CH_2CH_2-$, $-O-CH(CH_3)CH_2-$,

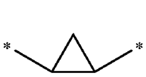, 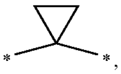, 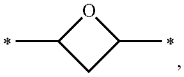,

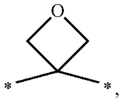, 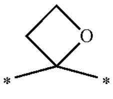, 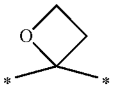 or

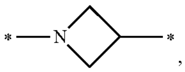, wherein the asterisks refers to linking positions.

Aspect 10: The compound according to any one of Aspects 1-9, wherein $R^2$ is selected from

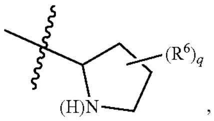, 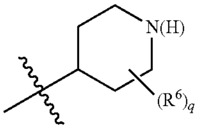,

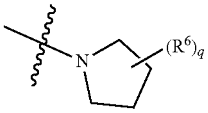, —$NR^bR^c$, 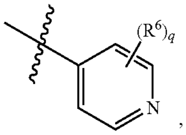,

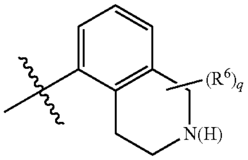, or 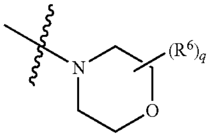, each $R^6$ is selected from halogen, hydroxy, —$C_{1-8}$alkyl, —$C_{1-8}$alkoxy; —$C_{1-8}$alkyl is optionally substituted with hydroxy, or halogen; each q is 0, 1, 2 or 3; $R^b$ and $R^c$ are independently hydrogen, deuterium(D), halogen, or —$C_{1-8}$ alkyl.

Aspect 11: The compound according to Aspect 10, wherein $R^6$ is selected from $CH_3$, OH, $CH_2OH$, F, —$CHF_2$, —$OCH_3$, Cl, or Br, or

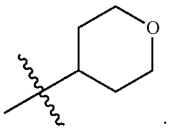 [SMILES: *C1CCOCC1].

Aspect 12: The compound according to any one of Aspects 1-11, wherein $R^2$ is selected from

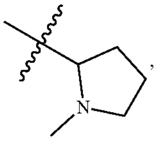, 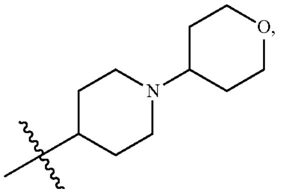

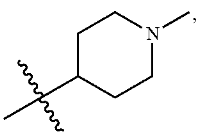, 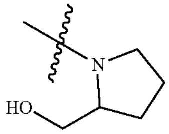, 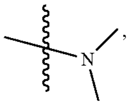,

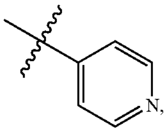 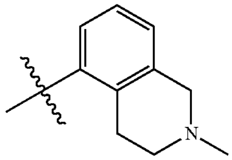,

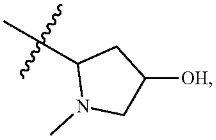 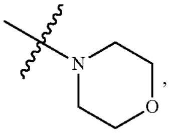,

-continued

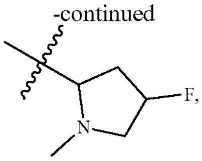

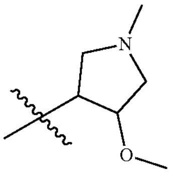 (such as 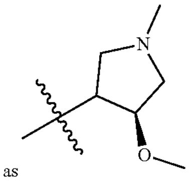),

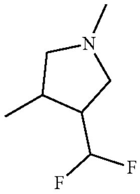 (such as 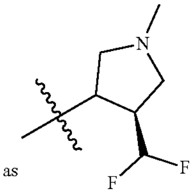),

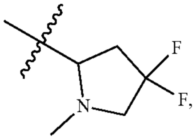, or 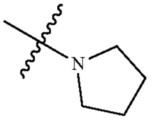.

Aspect 13: The compound according to any one of Aspects 1-12, wherein $R^2$ is selected from

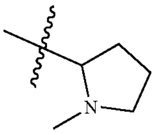, 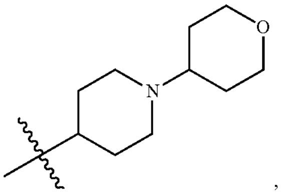,

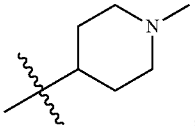, 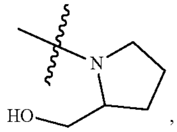,

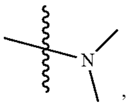, or 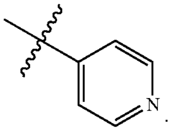.

Aspect 14: The compound according to any one of Aspects 1-13, wherein $R^3$ is selected from hydrogen, oxo, or —$C_{1-8}$alkyl.

Aspect 15: The compound according to any one of Aspects 1-14, wherein

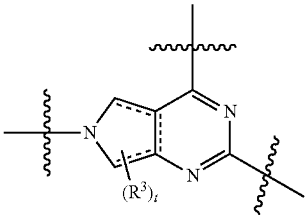

is selected from

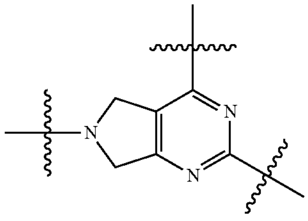
,
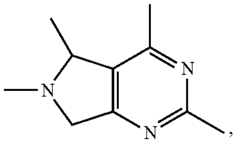
,
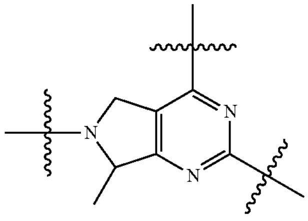
,
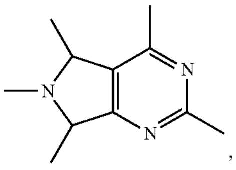
,
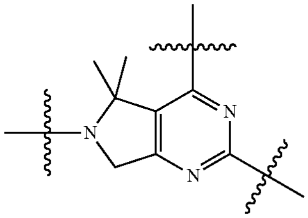
,
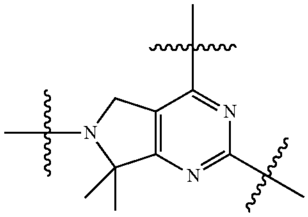
,
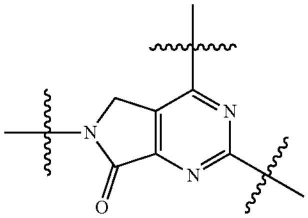
,
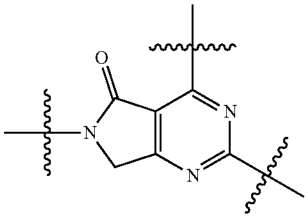
, or
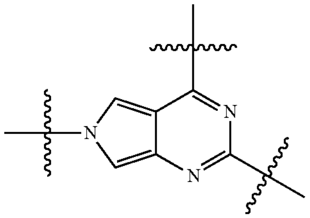
.

Aspect 16: The compound according to any one of Aspects 1-15, wherein $R^4$ is selected from

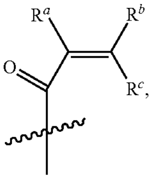

$R^a$ is selected from hydrogen, deuterium(D), halogen (F, Cl, Br or I), —$C_{1-8}$alkyl or —$C_{1-8}$alkoxy, said —$C_{1-8}$ alkyl or —$C_{1-8}$alkoxy is optionally substituted with at least one halogen (such as F, Cl), hydroxy, —$C_{1-8}$ alkoxy, or —$NR^dCOR^e$;

$R^b$ is selected from hydrogen and —$C_{1-8}$alkyl;

$R^c$ is selected from hydrogen, halogen (such as Cl), —$C_{1-8}$alkyl, —CN, —$NR^dR^e$, —CO—$NR^dR^e$, or heteroaryl (such as pyridinyl, pyrazole or imidazole) said —$C_{1-8}$alkyl is optionally substituted with at least one $R^f$;

each $R^f$ is selected from halogen (e.g., F, Br, Cl), hydroxy, —$NR^dR^e$, —$C_{1-8}$alkoxy, —$C_{4-7}$ heterocyclyl (such as azetidine, pyrrolidine, piperidine, morpholine), wherein each said —$C_{1-8}$alkoxy or —$C_{4-7}$ heterocyclyl is optionally substituted with halogen, hydroxy or —$C_{1-4}$alkyl;

$R^d$ and $R^e$ are each independently hydrogen, deuterium(D), halogen or —$C_{1-8}$alkyl, wherein each said —$C_{1-8}$alkyl is optionally substituted with at least one halogen or —$COCH_3$; or $R^a$ and $R^b$ together with the atoms to which they are attached, form a 4- to 6-membered ring selected from

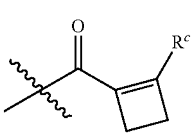
or
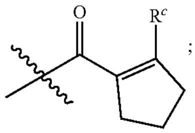
;

$R^c$ is selected from hydrogen, hydroxy, —$C_{1-8}$alkoxy, or —$C_{1-8}$alkyl; said ring is optionally substituted with oxo.

Aspect 17: The compound according to any one of Aspects 1-16, wherein $R^4$ is selected

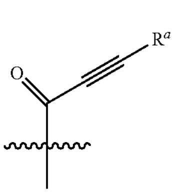
or
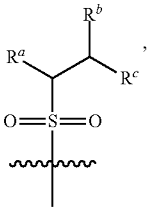
, wherein $R^a$ is selected from hydrogen, hydroxy, or —$C_{1-8}$ alkyl (such as —$CH_3$); each $R^b$ and $R^c$ are independently selected from hydrogen or —$C_{1-8}$alkyl(such as —$CH_3$).

Aspect 18: The compound according to any one of Aspects 1-17 wherein $R^4$ is selected from

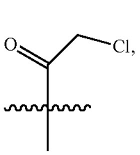 , 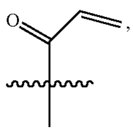 , 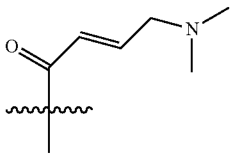 ,
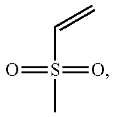 , 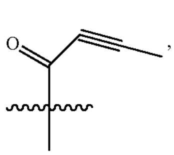 , 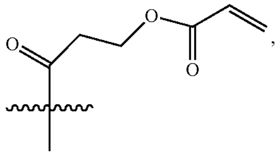 ,
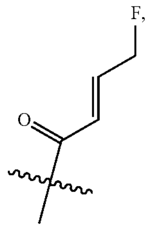 , 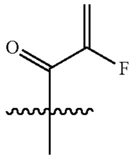 , 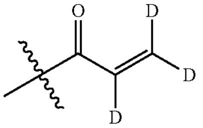 ,
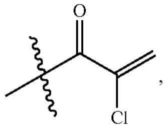 , 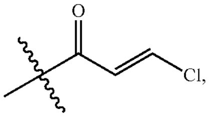 ,
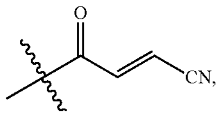 , 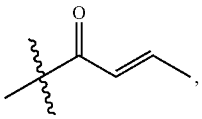 ,
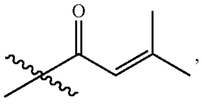 , 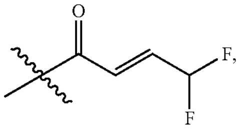 ,
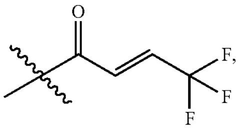 , 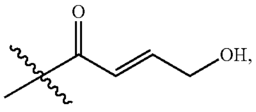 ,
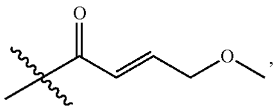 , 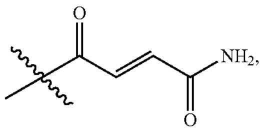 ,
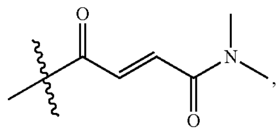 , 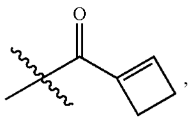 ,
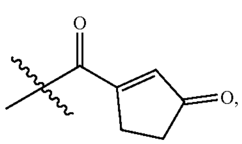 , 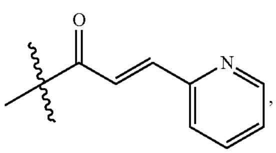 ,
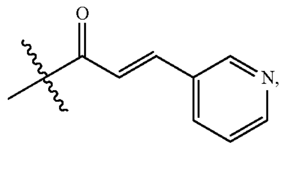 , 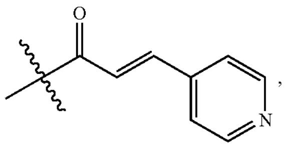 ,
-continued
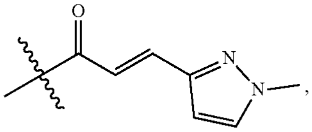 ,
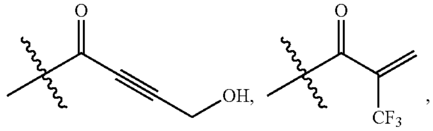 ,
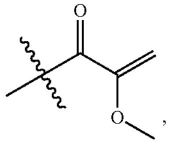 , 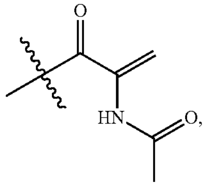 , 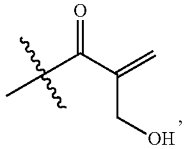 ,
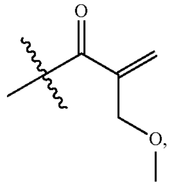 , 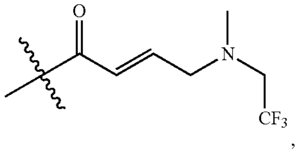 ,
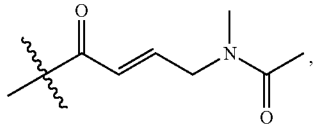 ,
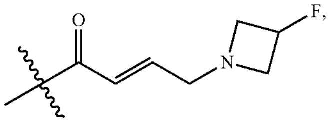 ,
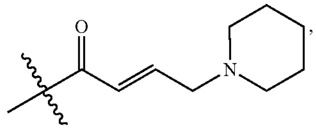 ,
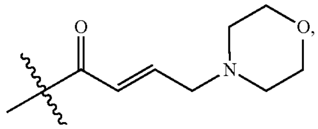 ,
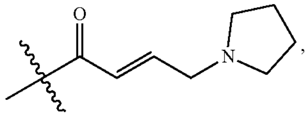 ,
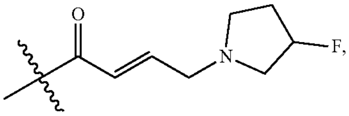 ,
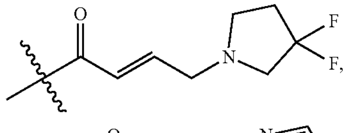 or
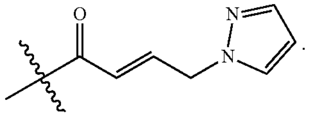 .
Aspect 19 The compound according to any one of Aspects 1-18 wherein $R^4$ is selected from

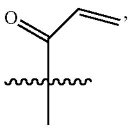,
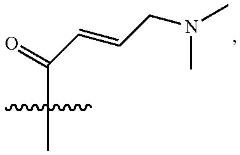,
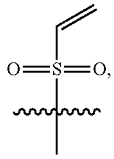,
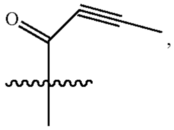,
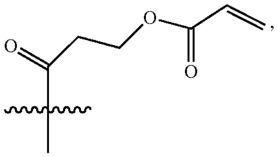,
Aspect 20 The compound according to any one of Aspects 1-20 wherein $R^5$ is selected from $-(CH_2)_m-CN$, or hydrogen, wherein m=0 or 1; and p=1.
Aspect 21 The compound according to Aspect 1, selected from
1
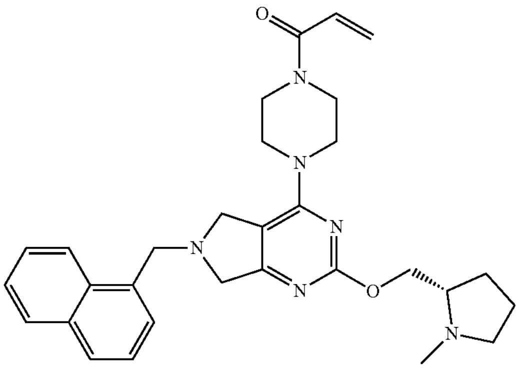
2
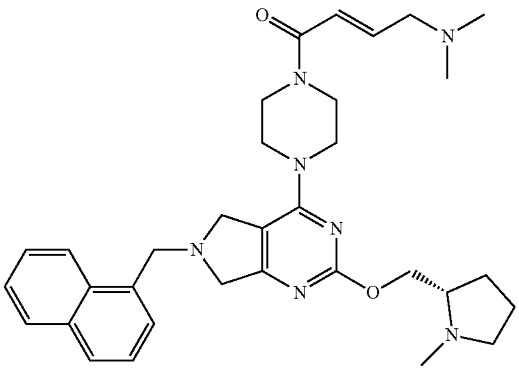
-continued
3
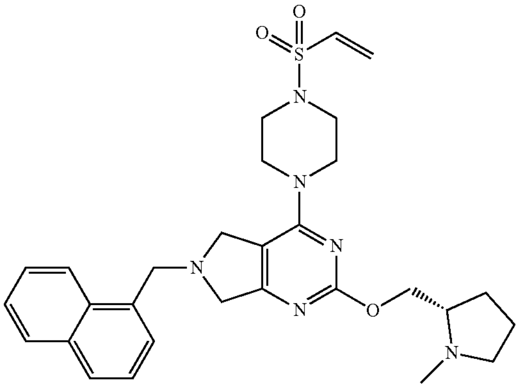
4
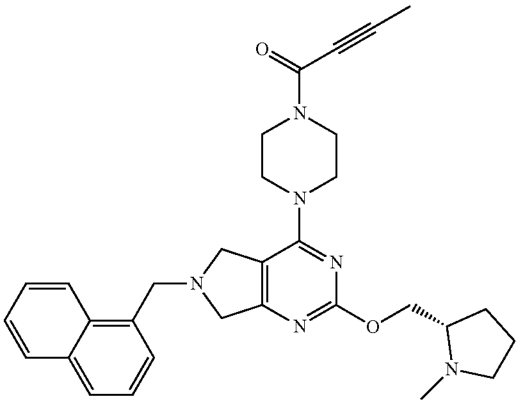
5
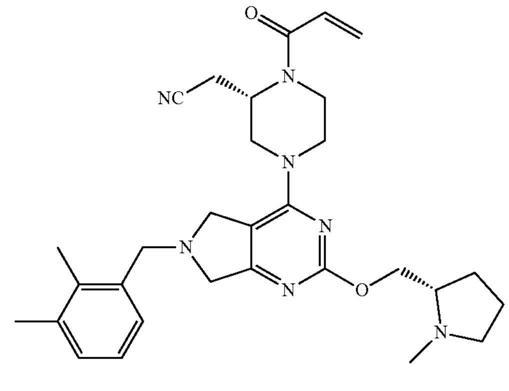
6
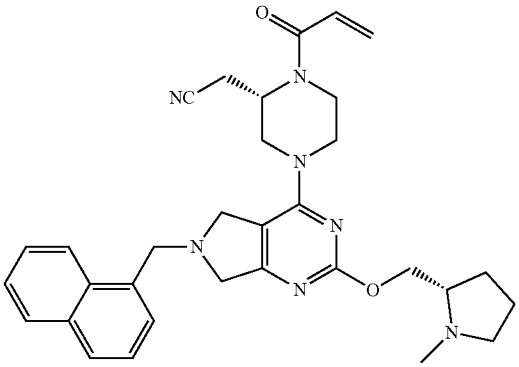

-continued
7
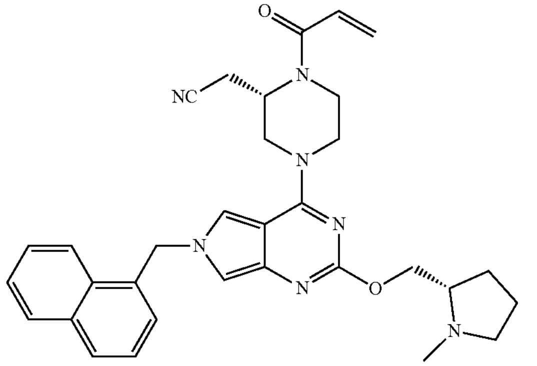
8
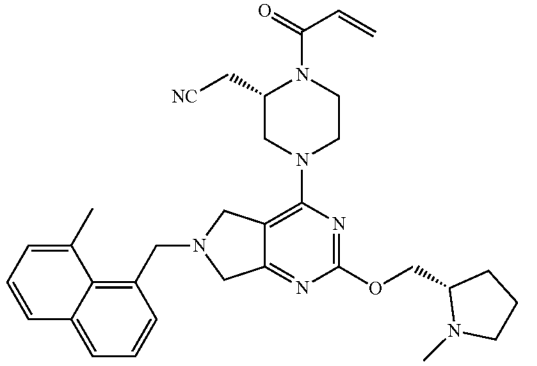
9
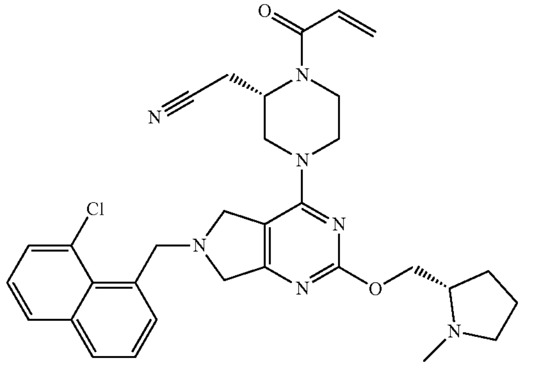
10
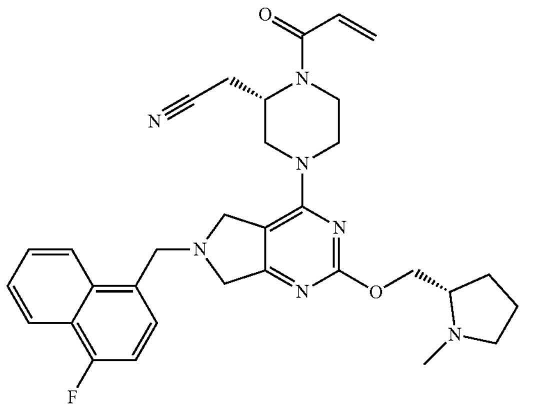
-continued
11
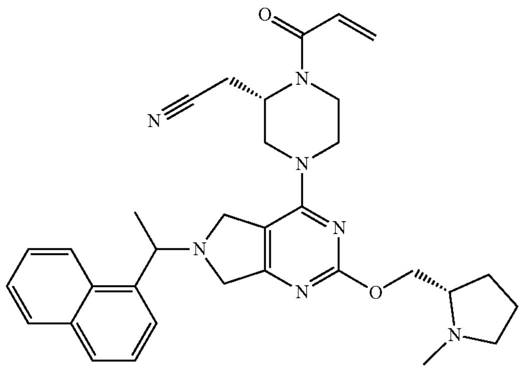
12
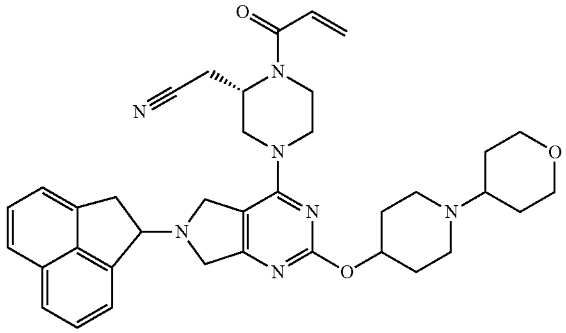
13
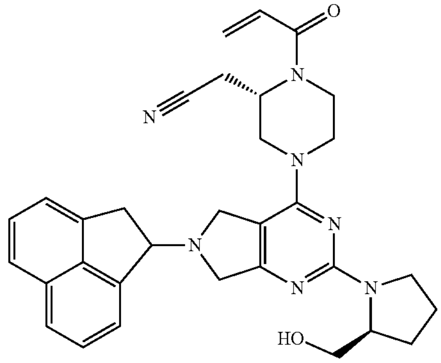
14
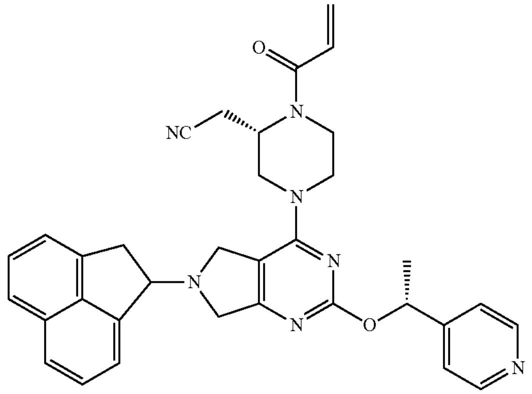

-continued
15
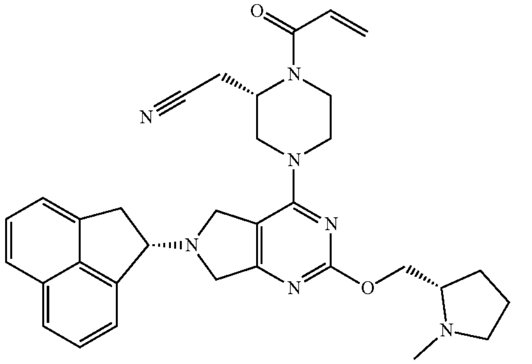
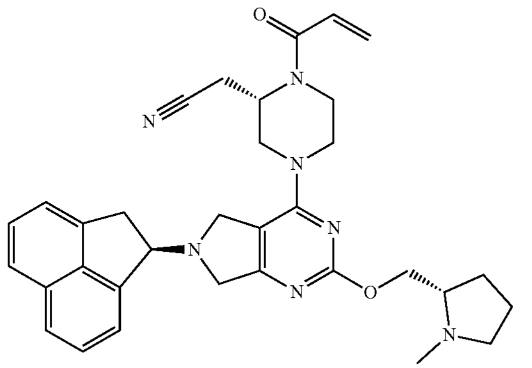
16
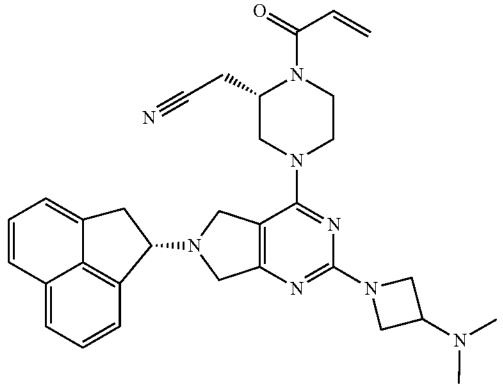
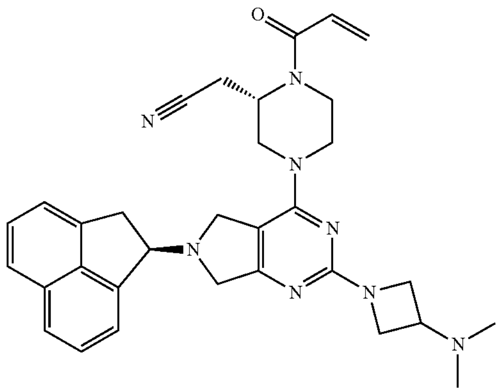
-continued
17
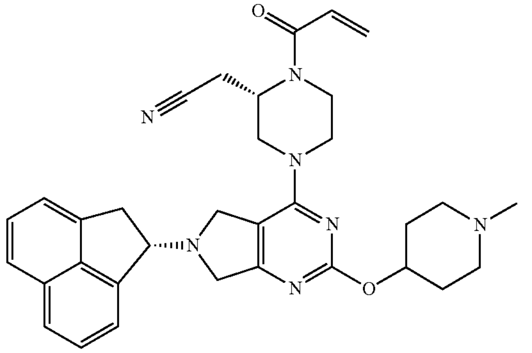
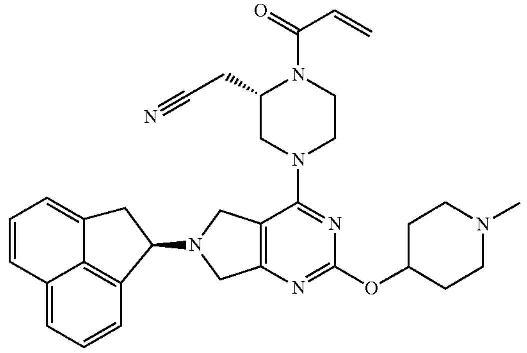
18
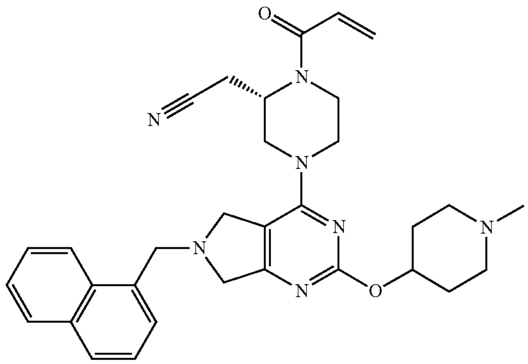
19
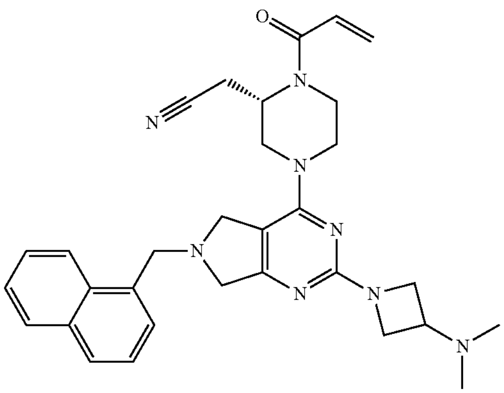

-continued
20
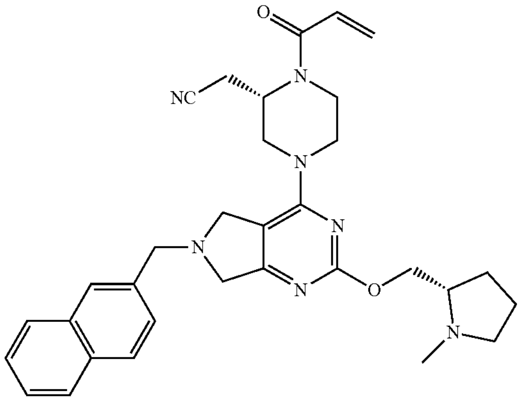
21
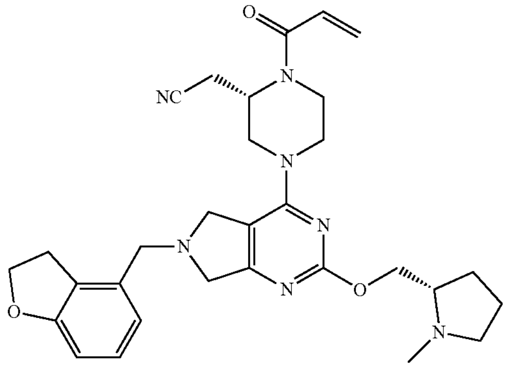
22
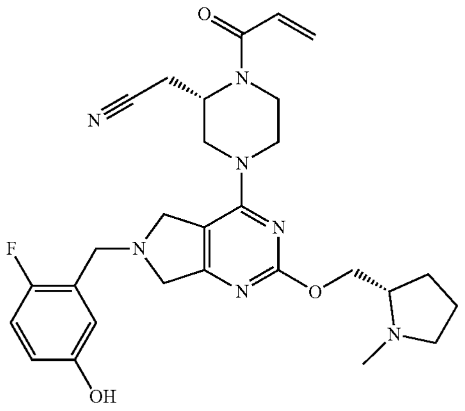
23
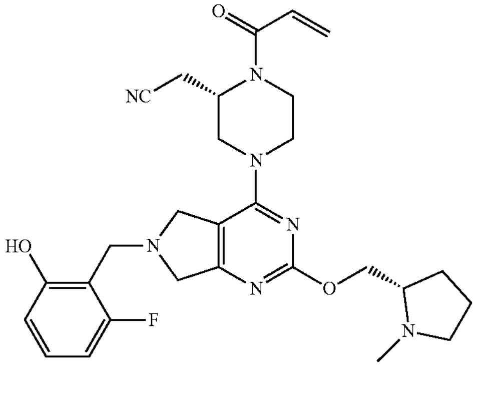
-continued
24
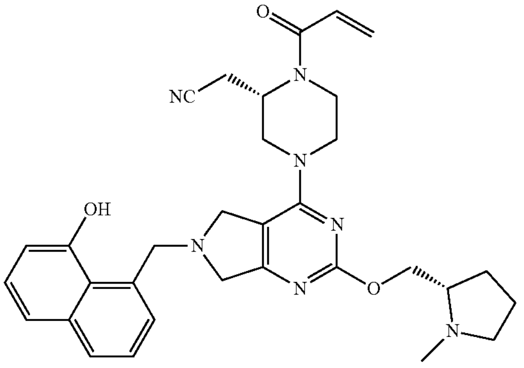
25
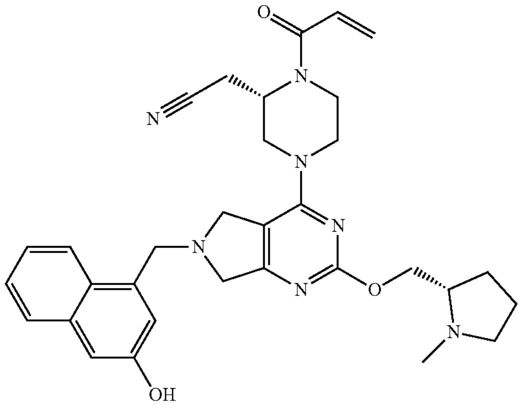
26
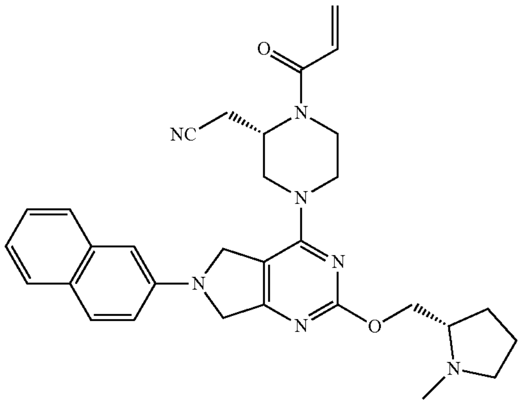
27
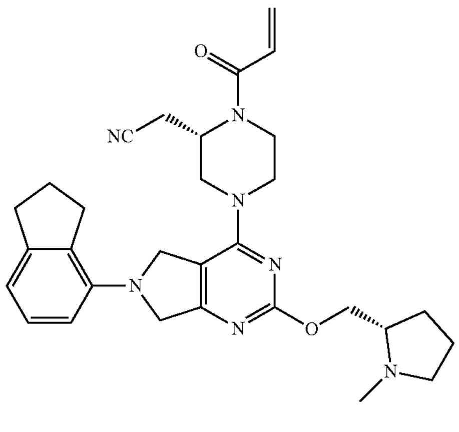

-continued
28
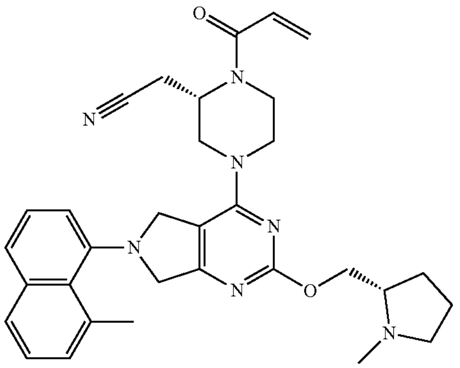
29
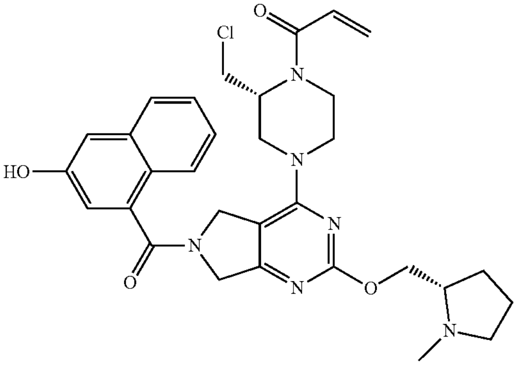
30
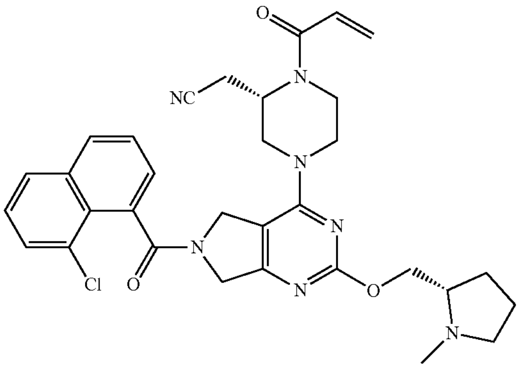
31
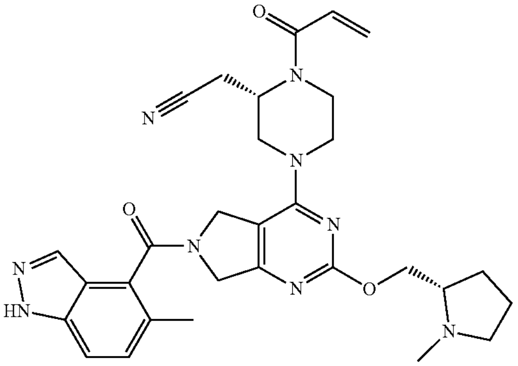
-continued
32
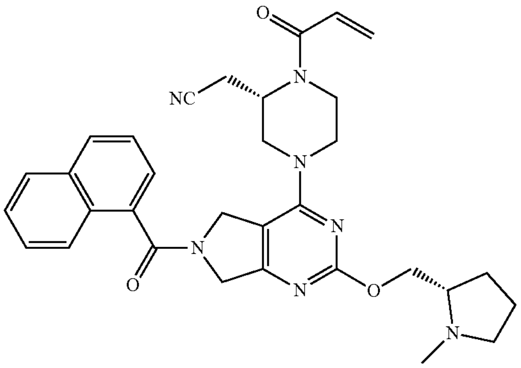
33
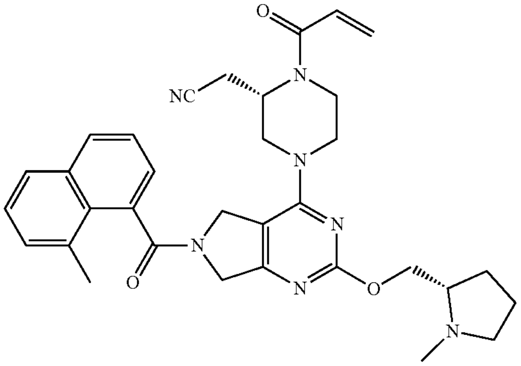
34
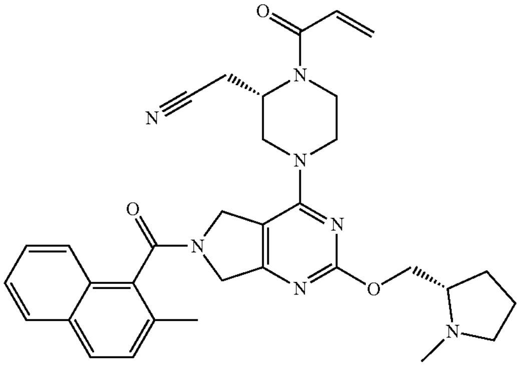
35
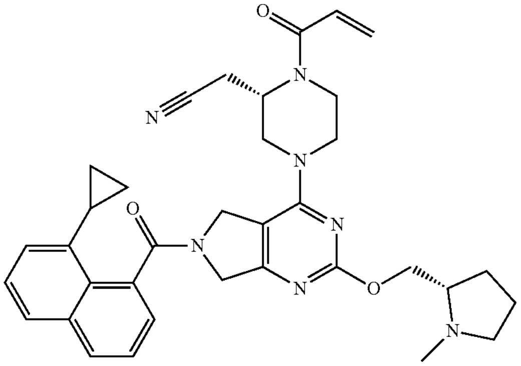

-continued
36
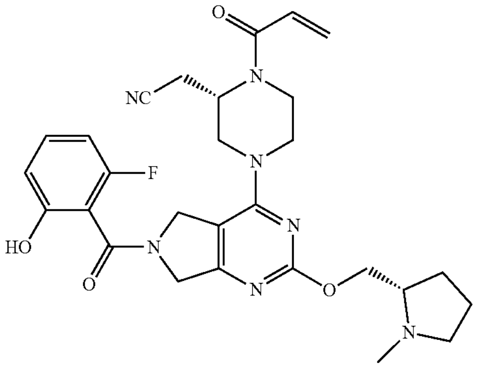
37
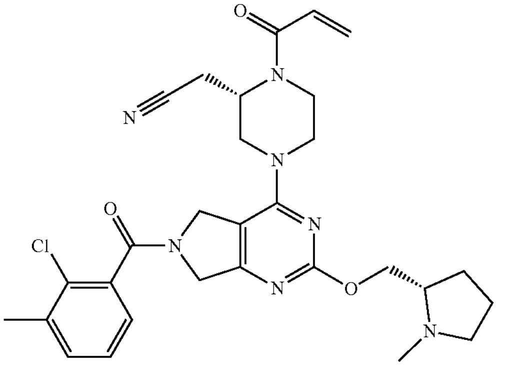
38
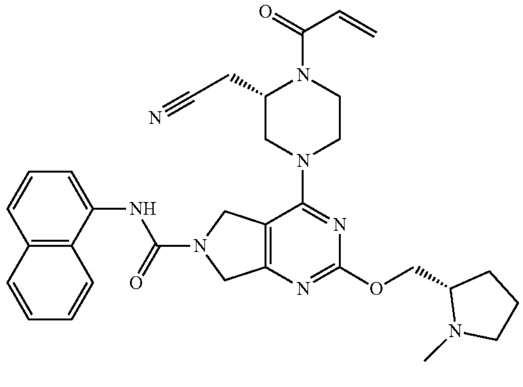
39
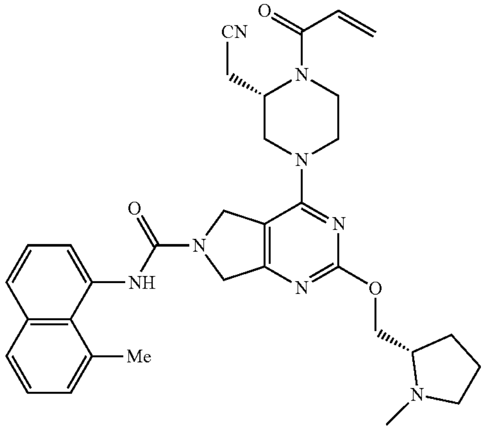
-continued
40
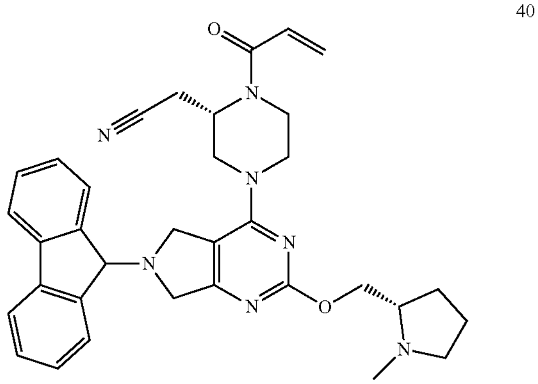
41
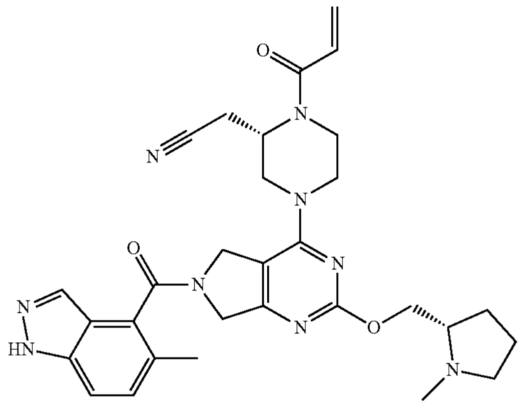
42
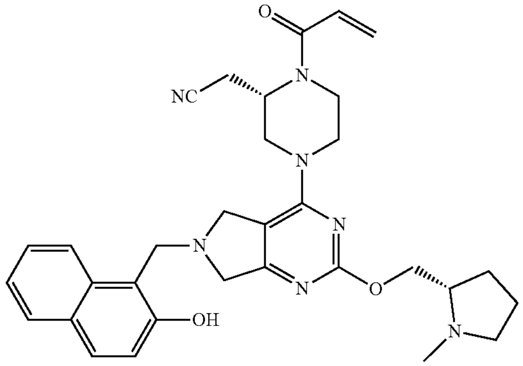
43
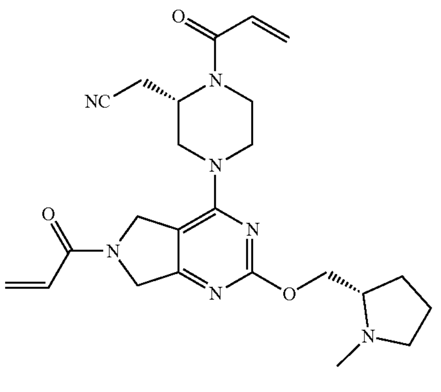

-continued
44
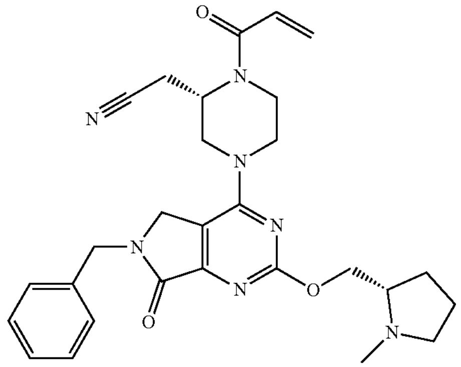
45
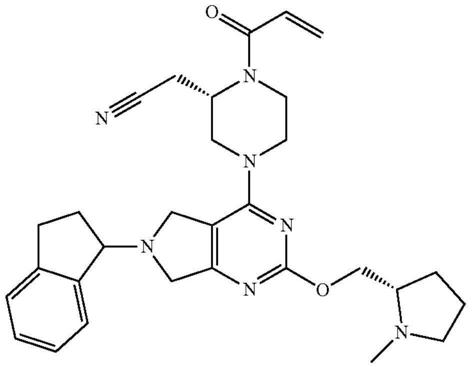
46
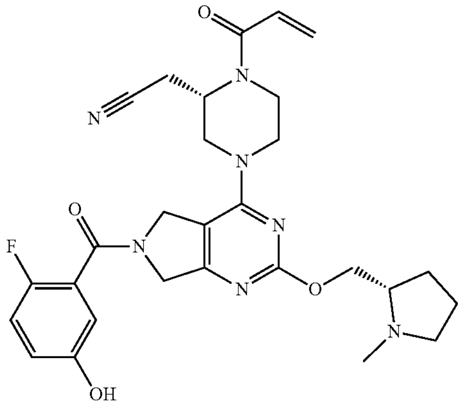
47
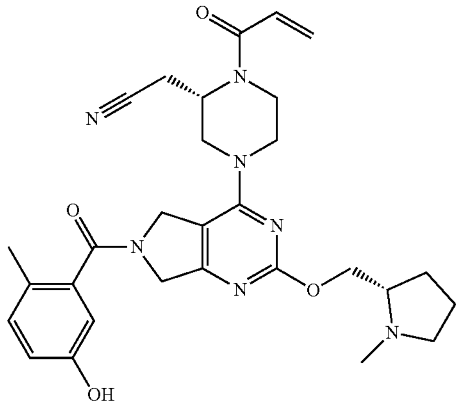
-continued
48
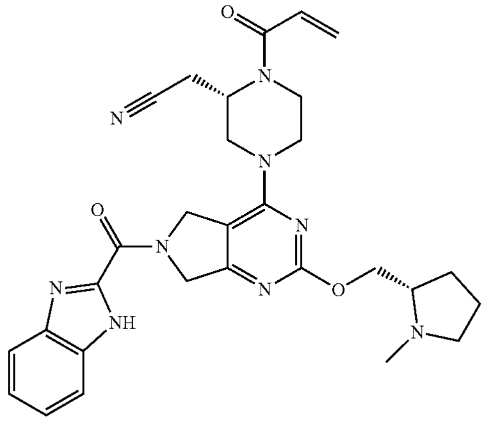
49
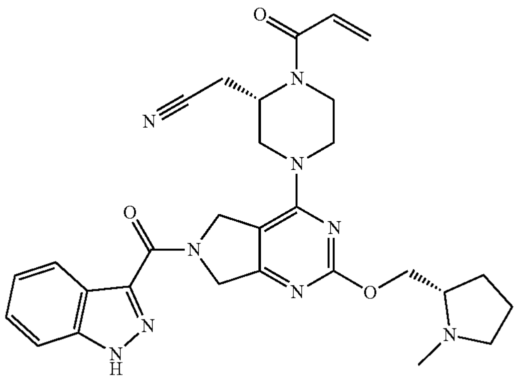
50
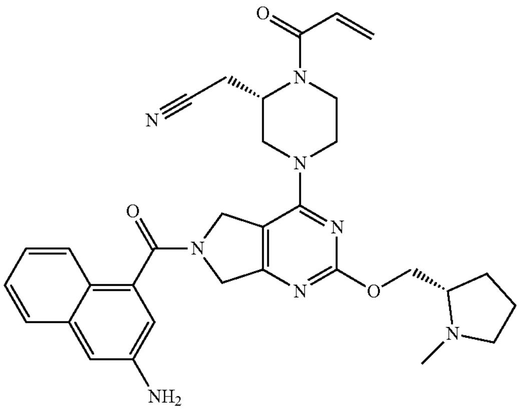
51
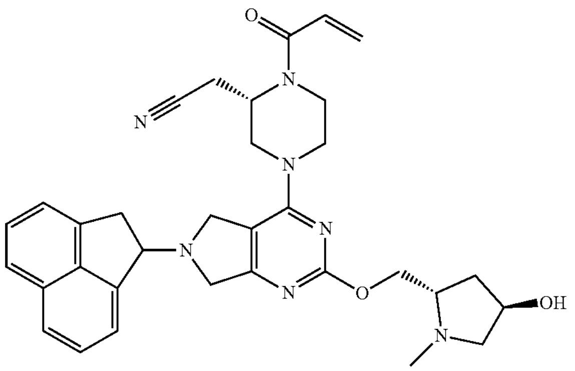

-continued
52
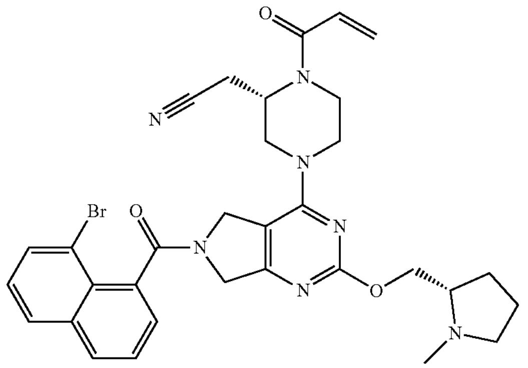
53
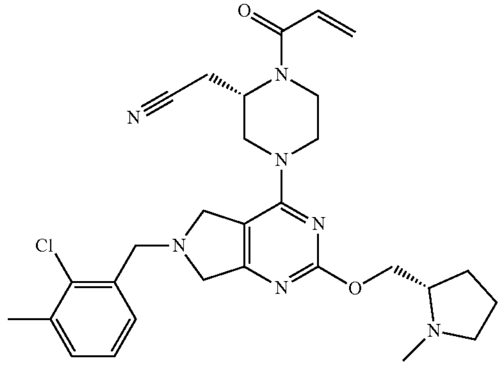
54
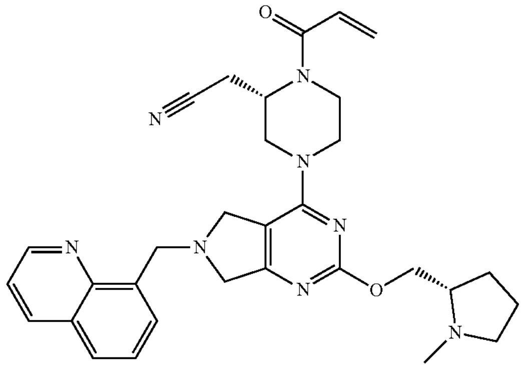
55
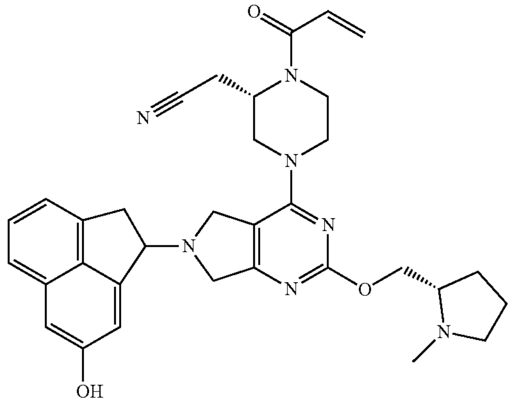
-continued
56
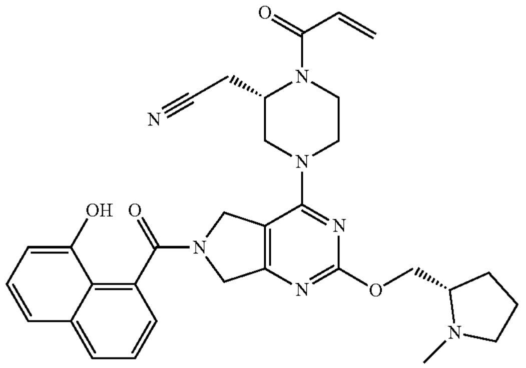
57
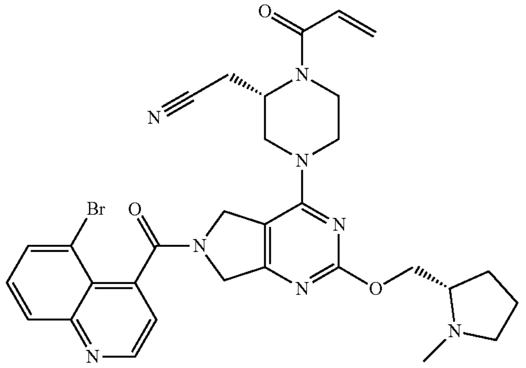
58
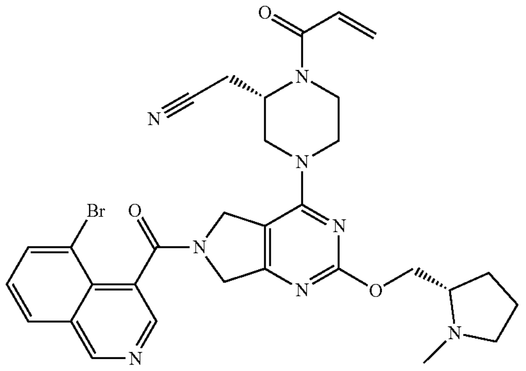
59
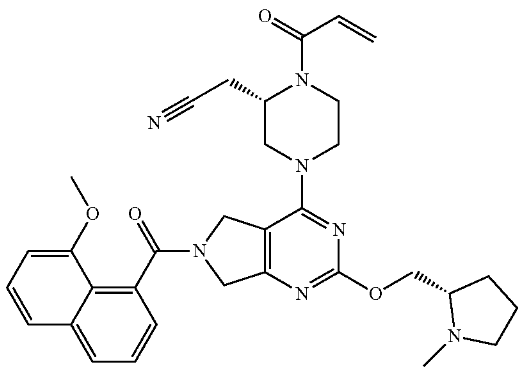

-continued
60
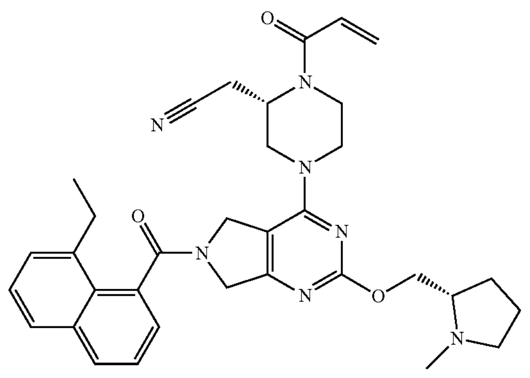
61
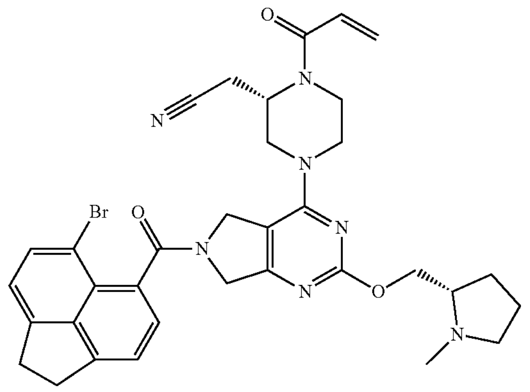
62
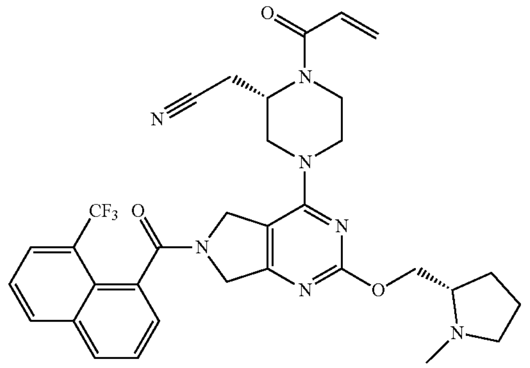
63
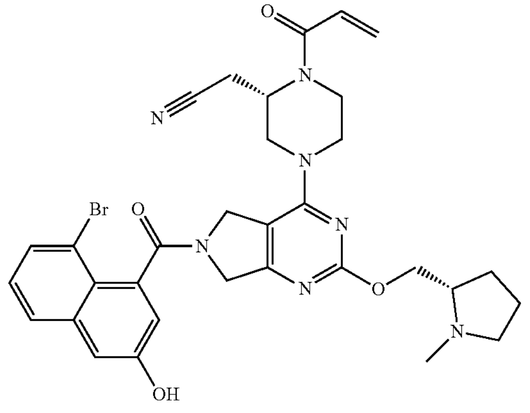
-continued
64
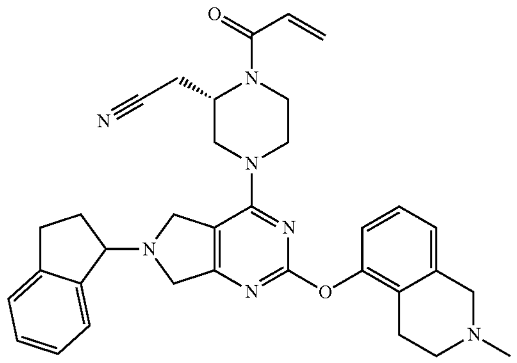
65
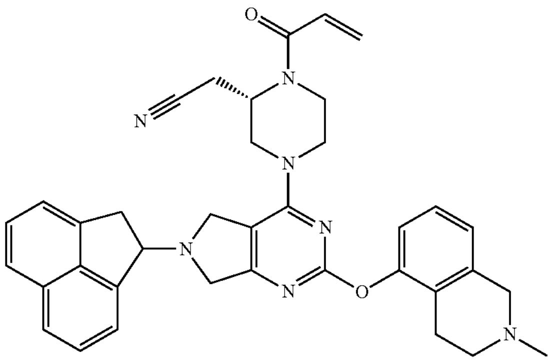
66
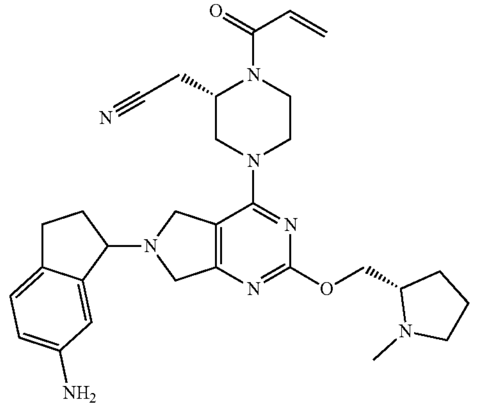
67
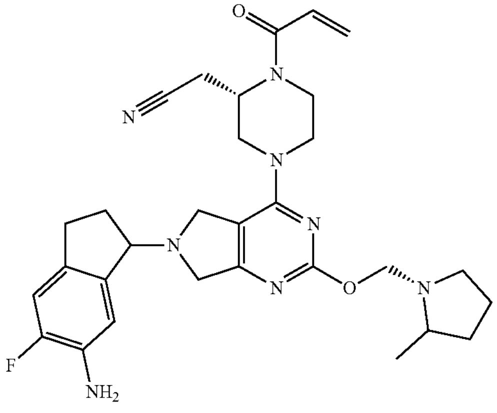

-continued
68
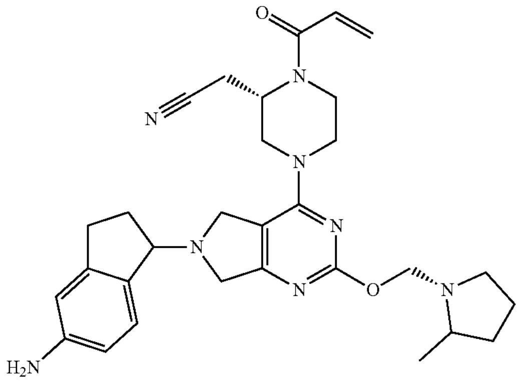
69
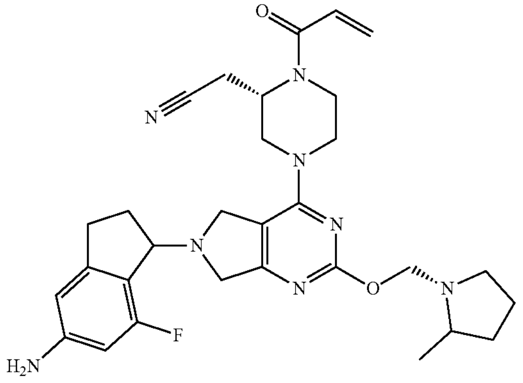
70
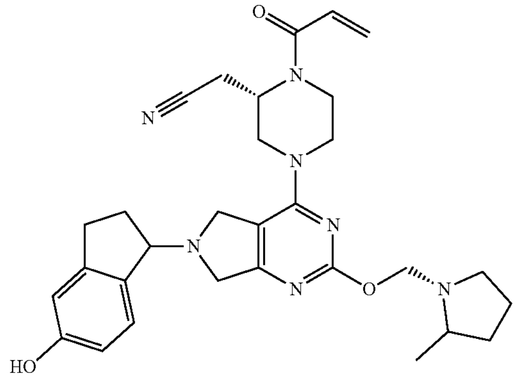
71
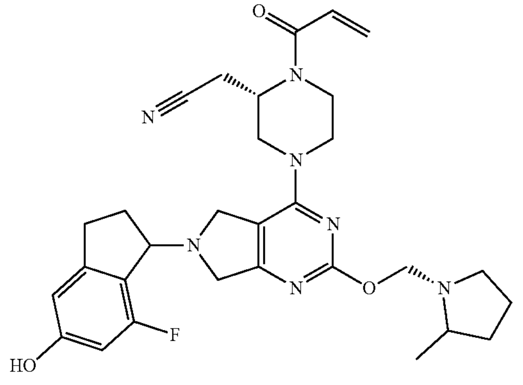
-continued
72
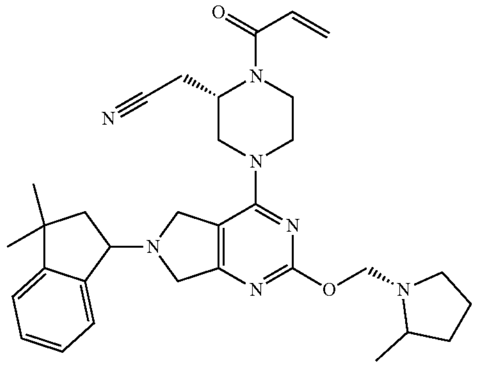
73
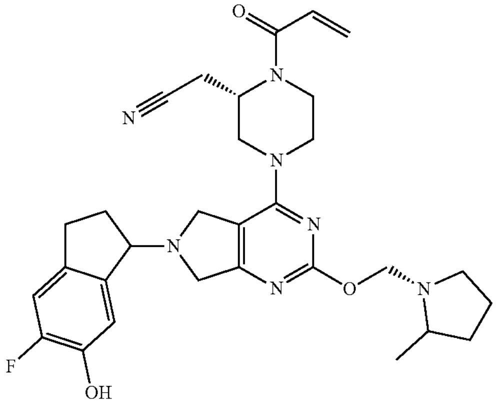
74
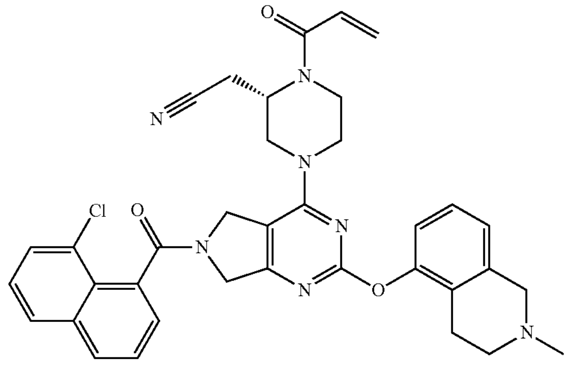
75
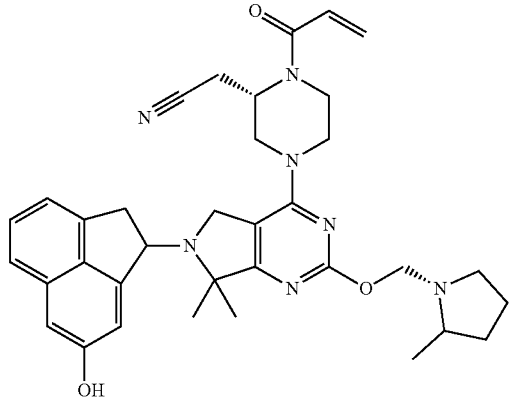

-continued
76
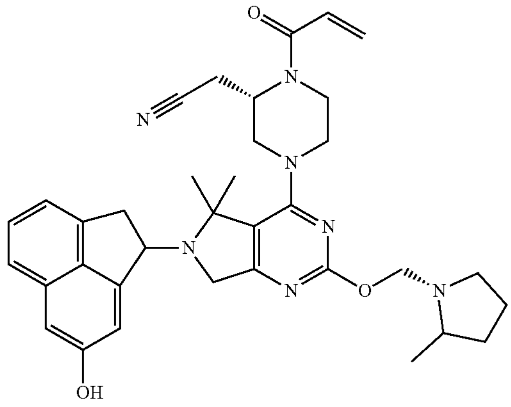
77
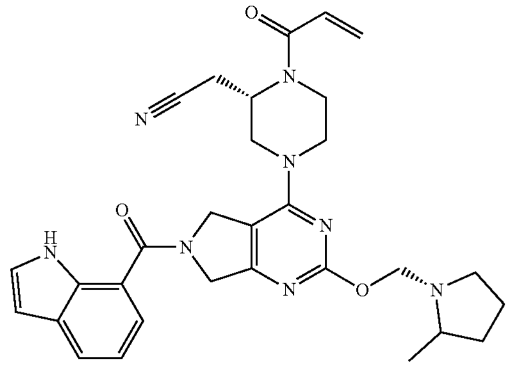
78
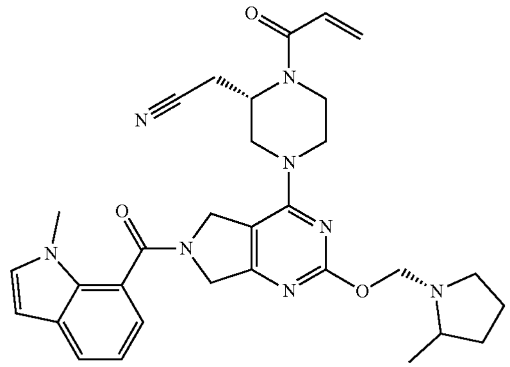
79
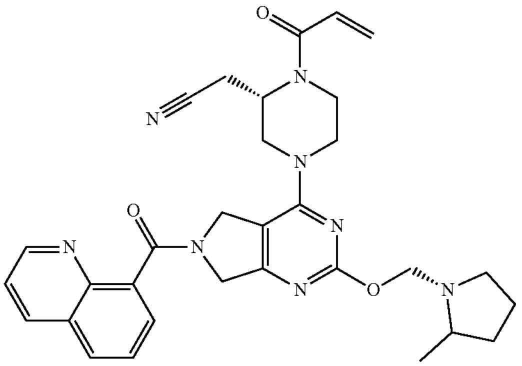
-continued
80
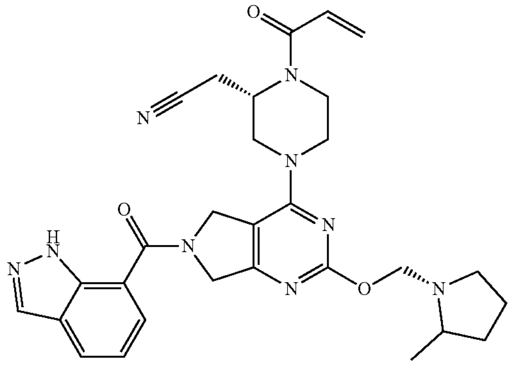
81
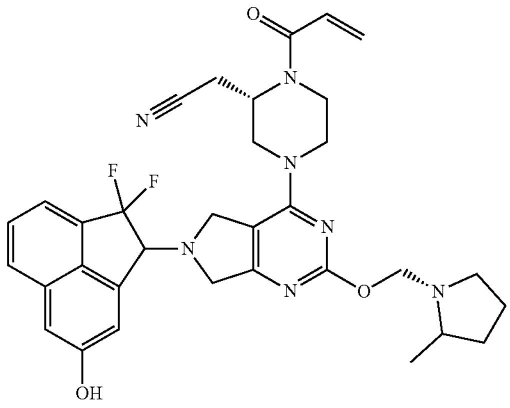
82
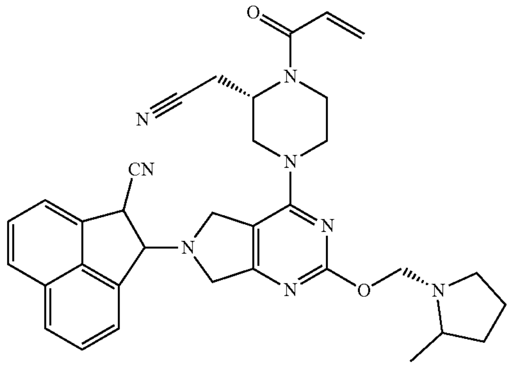
83
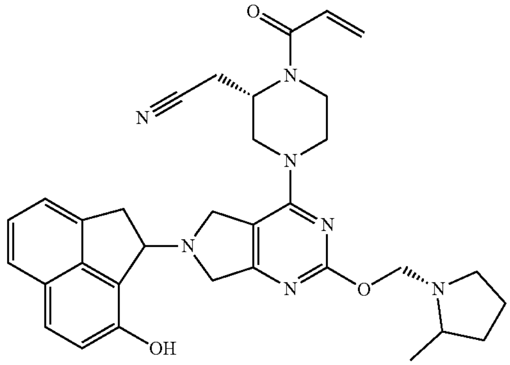

-continued
84
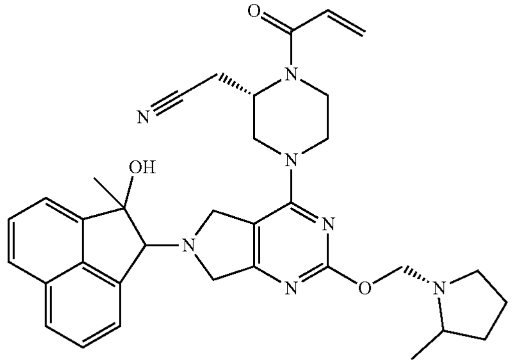
85
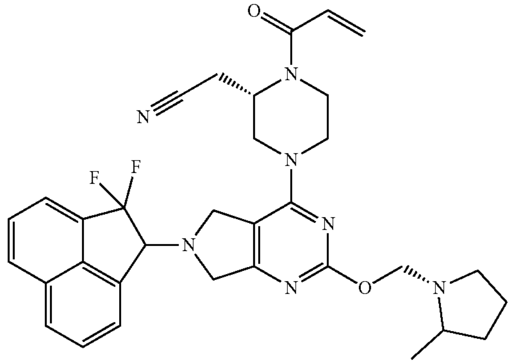
86
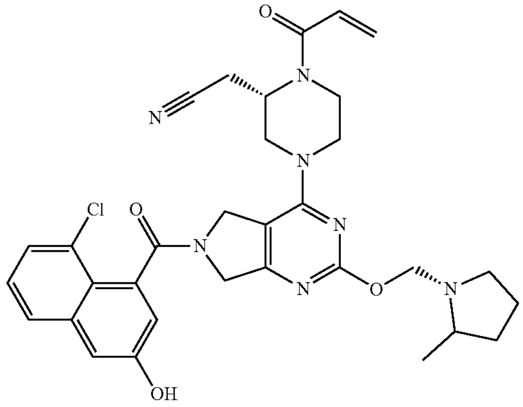
87
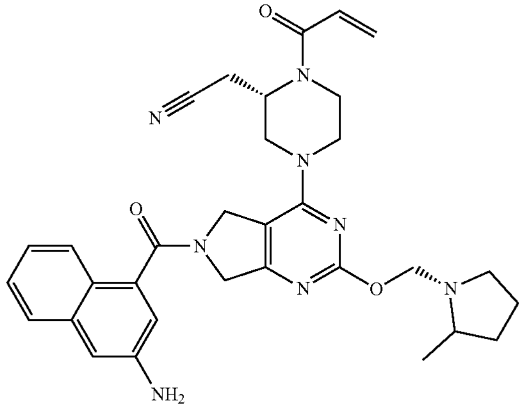
-continued
88
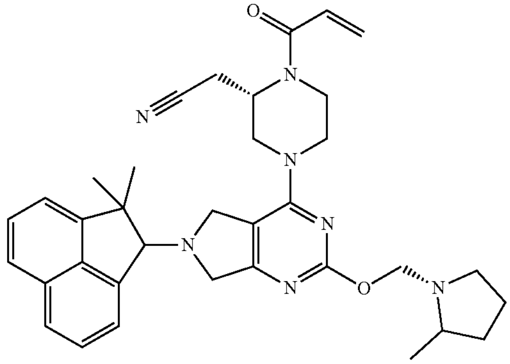
89
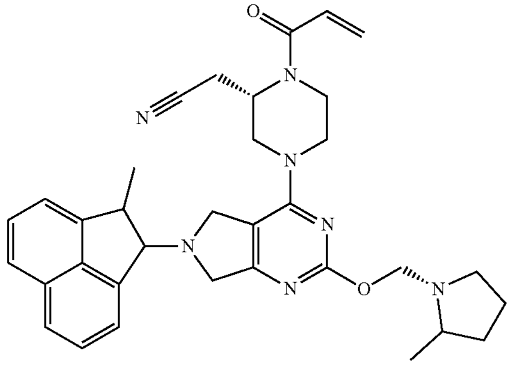
90
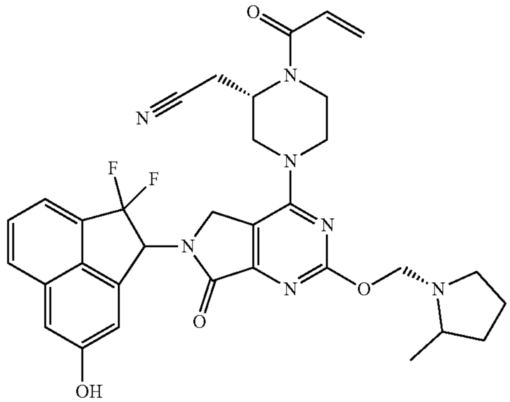
91
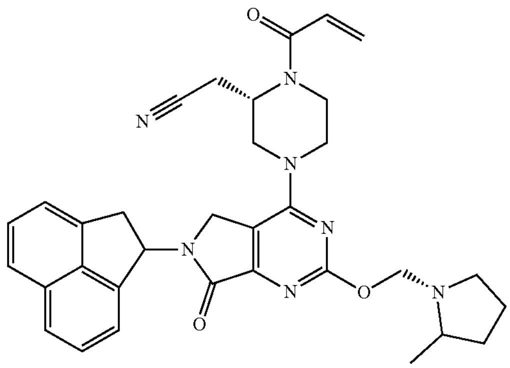

-continued
92
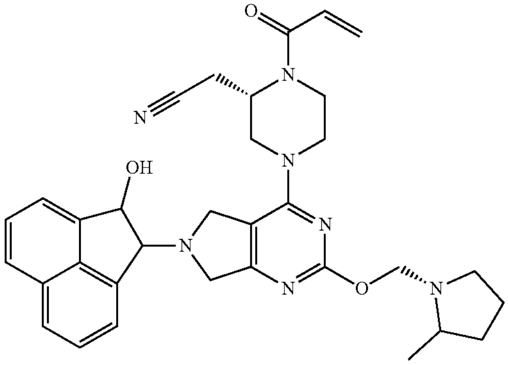
93
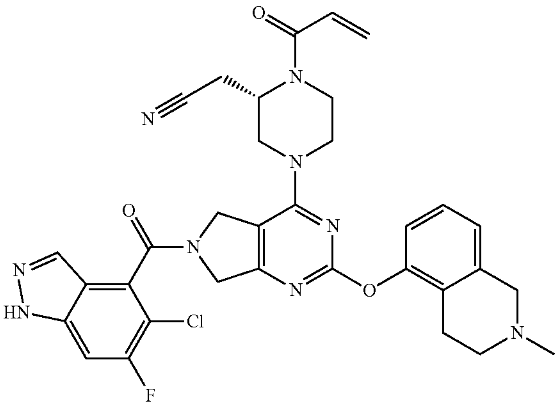
94
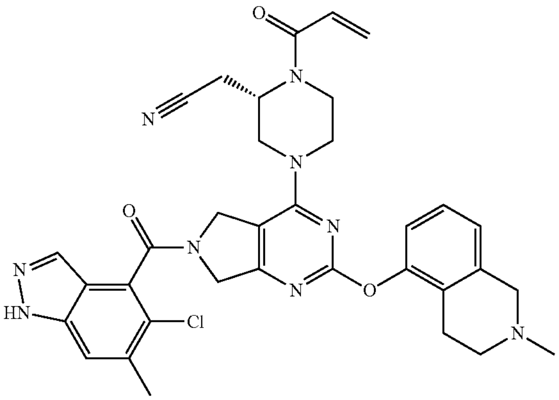
95
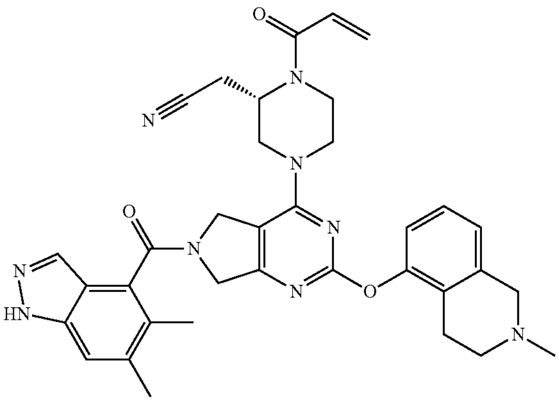
-continued
96
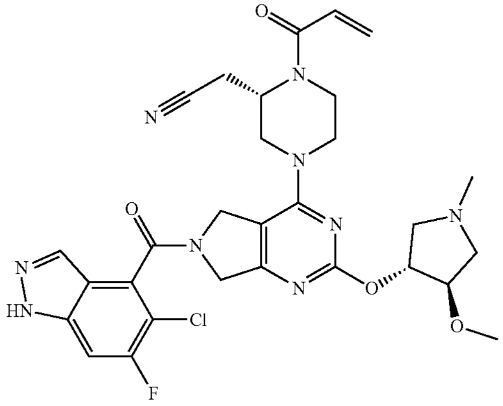
97
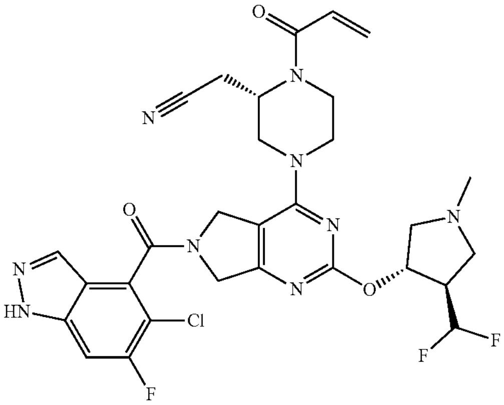
98
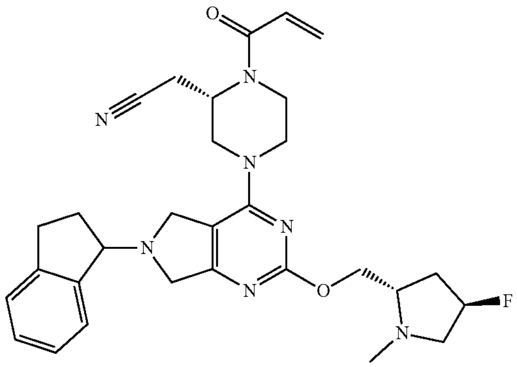
99
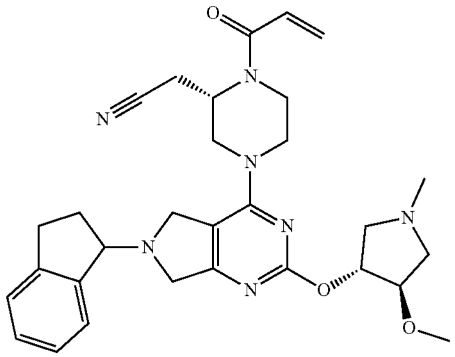
or a pharmaceutically acceptable salt thereof, or a stereoisomer thereof.

Aspect 22: A compound of Formula (II):

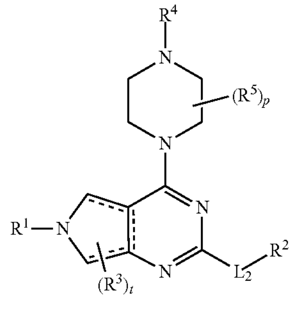

or a pharmaceutically acceptable salt thereof, or a stereoisomer thereof, wherein $\overset{---}{=}$ is a single bond or a double bond;

$L_2$ is selected from single bond, —CO—NH—, —NH—CO—, —O—, —$NR^a$—, —$NR^a(CH_2)_m$—, —S—, —$(CH_2)_m$—, —O—$(CH_2)_m$—, —O—$CH(R^a)$—, —$CH(R^a)$—, —$CH(R^a)(CH_2)_m$—, —$(CH_2)_m$—O—, —CO—, —$SO_2$—, cycloalkylene, oxetandiyl, tetrahydrofurandiyl, tetrahydropyrandiyl, azetidindiyl, pyrrilidindiyl, piperidindiyl, or piperizindiyl;

$R^1$ is selected from hydrogen, —$C_{1-8}$alkyl, Fmoc, Ac, Bn, PMB, Tr, Ts, Boc or Cbz;

$R^2$ is selected from —$NR^bR^c$, cycloalkyl, heterocyclyl, aryl, or heteroaryl, each of said cycloalkyl, heterocyclyl, aryl, or heteroaryl is optionally substituted with at least one $R^6$ (such as —$(R^6)_q$, wherein each $R^6$ are the same or different in case q is more than 1);

each $R^6$ is selected from —$C_{1-8}$alkyl, halogen, hydroxy, oxo, —$C_{1-8}$alkoxy, —$NR^bR^c$, cycloalkyl, heterocyclyl, aryl, or heteroaryl; said —$C_{1-8}$alkyl, —$C_{1-8}$alkoxy, cycloalkyl, heterocyclyl, aryl, or heteroaryl is optionally substituted with at least one hydroxy, amino, CN or cycloalkyl, heterocyclyl, aryl or heteroaryl;

$R^3$ is selected from hydrogen, oxo, —$C_{1-8}$alkyl, —$C_{2-8}$ alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^5$ is selected from —$C_{1-8}$alkyl, —$C_{2-8}$alkenyl, —$C_{2-8}$ alkynyl, oxo, —$NR^bR^c$, —CO—$NR^dR^e$, cycloalkyl, heterocyclyl, aryl, or heteroaryl, —$(CH_2)_m$—CN, or hydrogen;

$R^4$ is selected from hydrogen, Fmoc, Ac, Bn, PMB, Tr, Ts, Boc, or Cbz;

each $R^a$, $R^b$ and $R^c$ are independently hydrogen, deuterium (D), cyano (CN), halogen, hydroxy, —$C_{1-8}$ alkoxy, —$C_{1-8}$alkyl, —$C_{2-8}$alkenyl, —$C_{2-8}$alkynyl, cycloalkyl, heterocyclyl, aryl, heteroaryl, —CO—$NR^dR^e$, each of said —$C_{1-8}$alkyl, —$C_{2-8}$alkenyl, —$C_{2-8}$alkynyl, cycloalkyl, heterocyclyl, aryl, or heteroaryl is optionally substituted with $R^f$; or ($R^a$ and $R^b$), or ($R^a$ and $R^c$) together with the atom(s) to which they are attached, form a 4- to 6 membered ring, said ring is optionally substituted with at least one $R^g$;

each $R^f$ is selected from halogen, hydroxy, oxo, —$C_{1-8}$alkoxy, —$NR^dR^e$, —CO—$NR^dR^e$, —$NR^d$—CO—$R^e$, cycloalkyl, heterocyclyl, aryl, or heteroaryl, wherein each said —$C_{1-8}$alkoxy, cycloalkyl, heterocyclyl, aryl, or heteroaryl is optionally substituted with halogen, hydroxy or —$C_{1-4}$alkyl;

$R^d$, $R^e$ and $R^g$ are each independently hydrogen, deuterium (D), halogen, oxo, —$C_{1-8}$alkyl; each said —$C_{1-8}$alkyl is optionally substituted with at least one halogen, oxo, $CF_3$ or —$COCH_3$;

p, q and t are independently selected from 0, 1, 2, 3 or 4; each m and n is independently 0, 1, 2, 3, 4, 5 or 6.

Aspect 23: The compound according to Aspect 22, wherein, $R^1$ is selected from H, Cbz or Boc.

Aspect 24: The compound according to any one of Aspects 22-23, wherein $L_2$ is selected from —O—, —O—$(CH_2)_m$—, —O—$CH(R^a)$—, cyclopropylene, azetidindiyl, and —$NR^a(CH_2)_m$—, wherein m=1 or 2; and $R^a$ is selected from hydrogen, methyl, or deuterium(D).

Aspect 25: The compound according to any one of Aspects 22-24, wherein $L_2$ is selected from single bond, —O—$CH_2$—, —O—$CH_2CH_2$—, —O—$CH_2CH_2CH_2$—, —O—, —O—$CH(CH_3)$—, —NH—$CH_2$—, —NH—$CH_2CH_2$—, or —O—$CH(CH_3)CH_2$—,

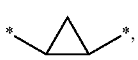, 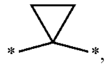,

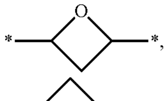, 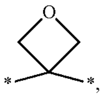,

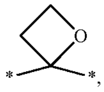, 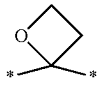 or

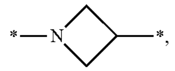, wherein the asterisks * refers to linking positions.

Aspect 26: The compound according to any one of Aspects 22-25, wherein $R^2$ is selected from

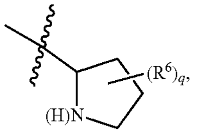 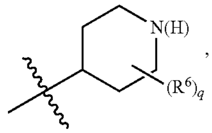,

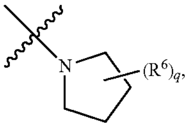 —$NR^bR^c$,

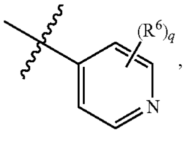, 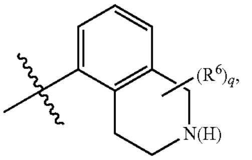 or

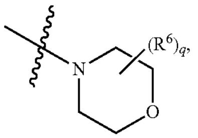

each $R^6$ is selected from halogen, hydroxy, —$C_{1-8}$alkyl; —$C_{1-8}$alkyl is optionally substituted with hydroxy; each q is 0, 1, 2 or 3; $R^b$ and $R^c$ are independently hydrogen, deuterium(D), halogen, or —$C_{1-8}$alkyl.

Aspect 27: The compound according to Aspect 26, wherein $R^6$ is selected from $CH_3$, OH, $CH_2OH$, F, Cl, —$CHF_2$, —$OCH_3$, Br, or

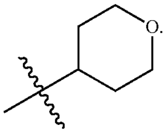 [SMILES: *C1CCOCC1]

Aspect 28: The compound according to any one of Aspects 22-27, wherein $R^2$ is selected from

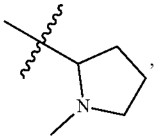
,
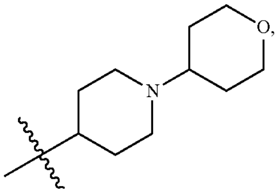

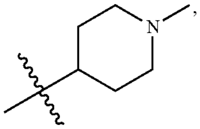
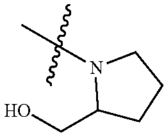
,
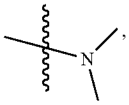

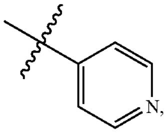
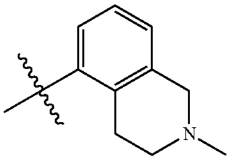
,

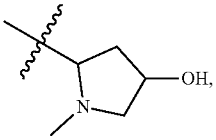
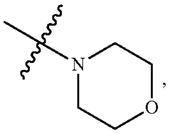

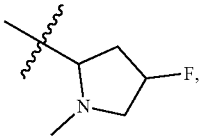

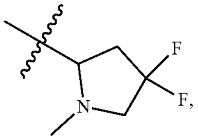
or
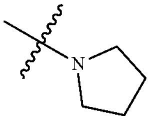
.

Aspect 29: The compound according to any one of Aspects 22-28, wherein $R^2$ is selected from

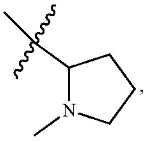

-continued

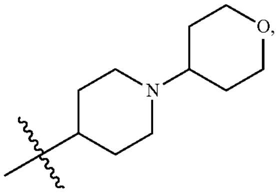

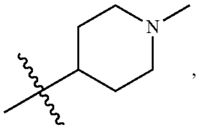
,
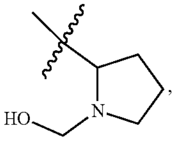

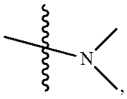
or
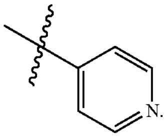

Aspect 30: The compound according to any one of Aspects 22-29, wherein $R^3$ is selected from hydrogen, oxo, or —$C_{1-8}$alkyl.

Aspect 31: The compound according to any one of Aspects 22-30, wherein

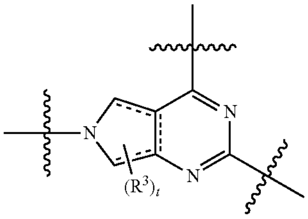

is selected from

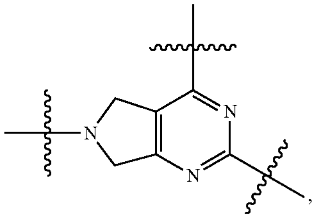

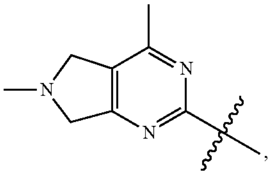

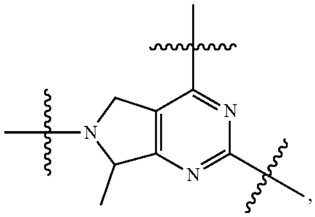

-continued
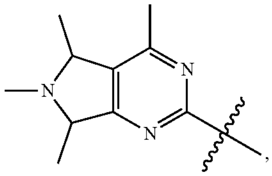
,
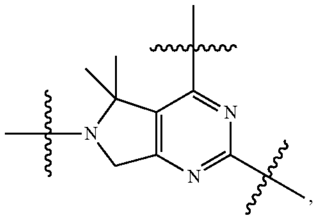
,
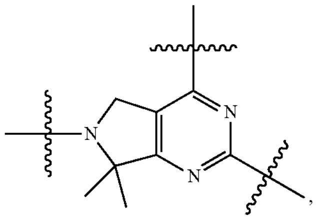
,
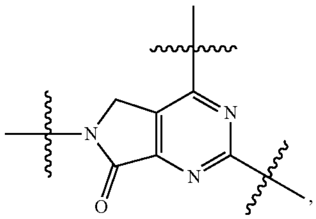
,
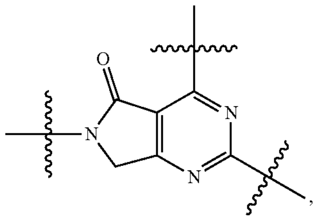
, or
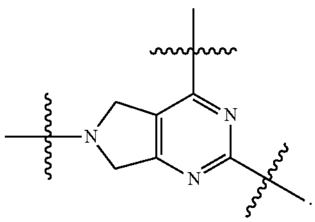 [SMILES: *c1nc(*)c2c(n1)CN(*)C2]
.
Aspect 32: The compound according to any one of Aspects 22-31, wherein $R^4$ is selected from hydrogen, Boc, or Cbz.
Aspect 33: The compound according to any one of Aspects 22-32, selected from
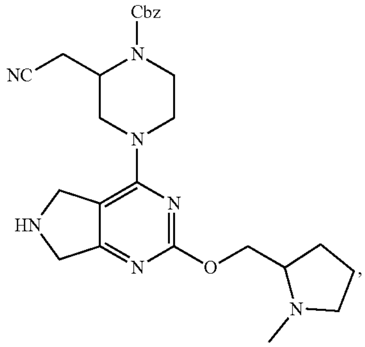
,
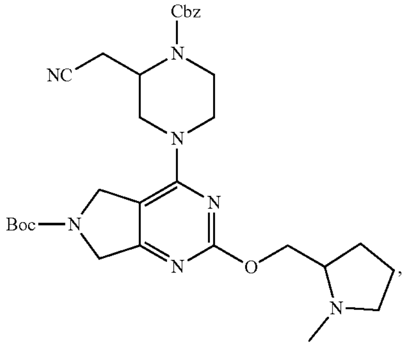
,
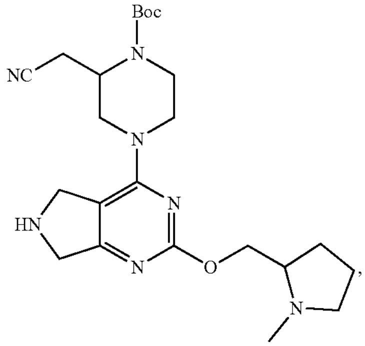
,
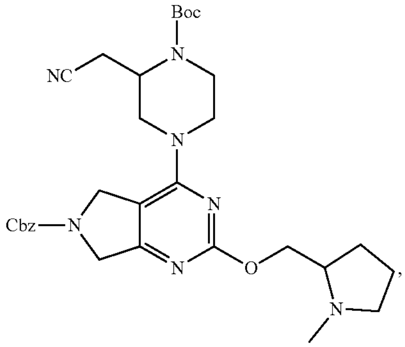
,
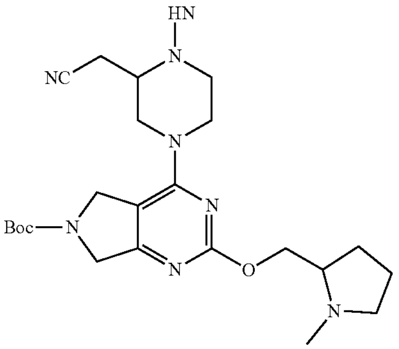
or -continued

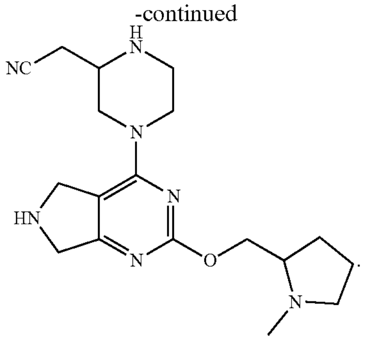

In the second aspect, disclosed herein is a pharmaceutical composition comprising the compound disclosed herein, or a pharmaceutically acceptable salt thereof, and at least one pharmaceutically acceptable carrier or excipient.

In the third aspect, disclosed herein is a method of inhibiting KRAS G12C activity, which comprises administering to an individual the compound disclosed herein, or a pharmaceutically acceptable salt thereof, including the compound of formula (I) or the specific compounds exemplified herein.

In the fourth aspect, disclosed herein is a method of treating a disease or disorder in a patient comprising administering to the patient a therapeutically effective amount of the compound disclosed herein, or a pharmaceutically acceptable salt thereof as a KRAS G12C inhibitor, wherein the compound disclosed herein includes the compound of formula (I) or the specific compounds exemplified herein. In some embodiments, the disease or disorder is associated with inhibition of KRAS G12C interaction. Preferably, the disease or disorder is cancer.

DETAILED DESCRIPTION OF THE INVENTION

As used herein, the following words, phrases and symbols are generally intended to have the meanings as set forth below, except to the extent that the context in which they are used indicates otherwise.

The following abbreviations and terms have the indicated meanings throughout:

The phrase "a" or "an" entity as used herein refers to one or more of that entity. For example, a compound refers to one or more compounds or at least one compound. For another example, " . . . substituted with a substituent . . . " means that one or more substituents are substituted as long as valence and stability permit. As such, the terms "a" (or "an"), "one or more", and "at least one" can be used interchangeably herein.

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl and 3, 3-dimethyl-2-butyl groups.

The term "alkyloxy" herein refers to an alkyl group as defined above bonded to oxygen, represented by —Oalkyl. Examples of an alkyloxy, e.g., $C_{1-6}$ alkyloxy or $C_{1-4}$ alkyloxy includes, but not limited to, methoxy, ethoxyl, isopropoxy, propoxy, n-butoxy, tert-butoxy, pentoxy and hexoxy and the like.

The term "haloalkyl" herein refers to an alkyl group in which one or more hydrogen is/are replaced by one or more halogen atoms such as fluoro, chloro, bromo, and iodo. Examples of the haloalkyl include $C_{1-6}$haloalkyl or $C_{1-4}$haloalkyl, but not limited to $F_3C$—, $ClCH_2$—, $CF_3CH_2$—, $CF_3CCl_2$—, and the like.

The term "alkenyl" herein refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1, 3-dienyl, 2-methylbuta-1, 3-dienyl, hex-1-enyl, hex-2-enyl, hex-3-enyl, hex-4-enyl, and hexa-1, 3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$ cycloalkyl, include, but not limited to cyclopropyl, cyclobutyl, cyclopentyl, cyclohexyl, cycloheptyl, and cyclooctyl groups. Examples of the bicyclic cycloalkyl groups include those having from 7 to 12 ring atoms arranged as a bicyclic ring selected from [4, 4], [4, 5], [5, 5], [5, 6] and [6, 6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5, 6] and [6, 6] ring systems, such as

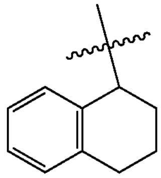

and

-continued

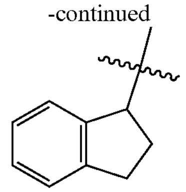

wherein the wavy lines indicate the points of attachment. The ring may be saturated or have at least one double bond (i.e. partially unsaturated), but is not fully conjugated, and is not aromatic, as aromatic is defined herein.

The term "cycloalkylene" refers to a divalent cyclopropyl as defined herein. For example, a cyclopropylene may be represented by

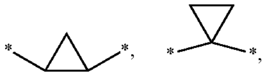

and so on, wherein asterisks refers to linking positions.

The suffix "diyl" refers to a divalent group. For example, oxetandiyl is a divalent group derived from oxetane, which may be represented by

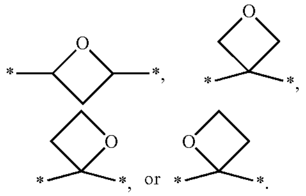

The term "aryl" used alone or in combination with other terms refers to a group selected from: 5- and 6-membered carbocyclic aromatic rings, for example, phenyl; bicyclic ring systems such as 7 to 12 membered bicyclic ring systems wherein at least one ring is carbocyclic and aromatic, selected, for example, from naphthalene, and indane; and tricyclic ring systems such as 10 to 15 membered tricyclic ring systems wherein at least one ring is carbocyclic and aromatic, for example, fluorene.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, for example, but not limited to, phenyl, naphth-1-yl, naphth-2-yl, anthracenyl, phenanthrenyl rings, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "halogen" or "halo" herein refers to F, Cl, Br or I.

The term "heteroaryl" herein refers to a group selected from:

5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The terms "aromatic heterocyclic ring" and "heteroaryl" are used interchangeable throughout the disclosure herein. In some embodiments, a monocyclic or bicyclic aromatic heterocyclic ring has 5- to 10-ring forming members with 1, 2, 3, or 4 heteroatom ring members independently selected from nitrogen, sulfur and oxygen and the remaining ring members being carbon. In some embodiments, the monocyclic or bicyclic aromatic heterocyclic ring is a monocyclic or bicyclic ring comprising 1 or 2 heteroatom ring members independently selected from nitrogen, sulfur and oxygen. In some embodiments, the monocyclic or bicyclic aromatic heterocyclic ring is a 5- to 6-membered heteroaryl ring, which is monocyclic and which has 1 or 2 heteroatom ring members independently selected from nitrogen, sulfur and oxygen. In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2, 4-pyrimidinyl, 3, 5-pyrimidinyl, 2, 4-imidazolyl, imidazopyridinyl, isoxazolyl, oxazolyl, thiazolyl, isothiazolyl, thiadiazolyl (such as 1, 2, 3-thiadiazolyl, 1, 2, 4-thiadiazolyl, or 1, 3, 4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1, 2, 3-oxadiazolyl, 1, 2, 4-oxadiazolyl, or 1, 3, 4-oxadiazolyl), phthalazinyl, pyrazinyl, pyridazinyl, pyrrolyl, triazolyl (such as 1, 2, 3-triazolyl, 1, 2, 4-triazolyl, or 1, 3, 4-triazolyl), quinolinyl, isoquinolinyl, pyrazolyl, pyrrolopyridinyl (such as 1H-pyrrolo[2, 3-b]pyridin-5-yl), pyrazolopyridinyl (such as 1H-pyrazolo[3, 4-b]pyridin-5-yl), benzoxazolyl (such as benzo[d]oxazol-6-yl), pteridinyl, purinyl, 1-oxa-2, 3-diazolyl, 1-oxa-2, 4-diazolyl, 1-oxa-2, 5-diazolyl, 1-oxa-3, 4-diazolyl, 1-thia-2, 3-diazolyl, 1-thia-2, 4-diazolyl, 1-thia-2, 5-diazolyl, 1-thia-3, 4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5, 6, 7, 8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. In some embodiments, a heterocyclyl group is 4- to 7-membered monocyclic ring with one heteroatom selected from N, O and S. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2, 4-imidazolidinyl, 2, 3-pyrazolidinyl, 1-piperidinyl, 2-piperidinyl, 3-piperidinyl, 4-piperidinyl, 2, 5-piperazinyl, pyranyl, 2-morpholinyl, 3-morpholinyl, oxiranyl, aziridinyl, thiiranyl, azetidinyl, oxetanyl, thietanyl, 1, 2-dithietanyl, 1, 3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1, 4-oxathianyl, 1, 4-dioxepanyl, 1, 4-oxathiepanyl, 1, 4-oxaazepanyl, 1, 4-dithiepanyl, 1, 4-thiazepanyl and 1, 4-diazepane 1, 4-dithianyl, 1, 4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1, 4-dioxanyl, 1, 3-dioxolanyl, pyrazolinyl, pyrazolidinyl, dithianyl, dithiolanyl, pyrazolidinyl, imidazolinyl, pyrimidinonyl, 1, 1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1, 1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4, 4], [4, 5], [5, 5], [5, 6] and [6, 6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

Some of the compounds disclosed herein may exist with different points of attachment of hydrogen, referred to as tautomers. For example, compounds including carbonyl $—CH_2C(O)—$ groups (keto forms) may undergo tautomerism to form hydroxyl $—CH{=}C(OH)—$ groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or MosheR$^a$s acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of at least one compound of Formula (I), such as salts of enantiomers, and/or salts of diastereomers.

"Treating", "treat" or "treatment" or "alleviation" refers to administering at least one compound and/or at least one stereoisomer thereof, and/or at least one pharmaceutically acceptable salt thereof disclosed herein to a subject in recognized need thereof that has, for example, cancer.

The term "effective amount" refers to an amount of at least one compound and/or at least one stereoisomer thereof, and/or at least one pharmaceutically acceptable salt thereof disclosed herein effective to "treat" as defined above, a disease or disorder in a subject. The term "at least one substituent" disclosed herein includes, for example, from 1 to 4, such as from 1 to 3, further as 1 or 2, substituents, provided that valence and stability permit. For example, "at least one substituent $R^7$" disclosed herein includes from 1 to 4, such as from 1 to 3, further as 1 or 2, substituents selected from the list of $R^7$ as disclosed herein; and "at least one substituent $R^{10}$" disclosed herein includes from 1 to 4, such as from 1 to 3, further as 1 or 2, substituents selected from the list of $R^{10}$ as disclosed herein.

The compounds disclosed herein, and/or the pharmaceutically acceptable salts thereof, can be synthesized from commercially available starting materials taken together with the disclosure herein.

Compounds of Formula (I) and Formula (II) may be prepared by the exemplary processes described in the working Examples, as well as relevant published literature procedures that are used by one skilled in the art. Exemplary reagents and procedures for these reactions appear hereinafter and in the working Examples. Protection and deprotection in the processes below may be carried out by procedures generally known in the art (see, for example, Greene, T. W. et al., eds., *Protecting Groups in Organic Synthesis*, $3^{rd}$ Edition, Wiley (1999)). *General methods of organic synthesis and functional group transformations* are found in: Trost, B. M. et al., eds., *Comprehensive Organic Synthesis: Selectivity, Strategy & Efficiency in Modern Organic Chemistry*, Pergamon Press, New York, NY (1991); March, J., *Advanced Organic Reactions, Mechanisms, and Structure*. $4^{th}$ Edition, Wiley & Sons, New York, NY (1992); Katritzky, A. R. et al., eds., *Comprehensive Organic Functional Groups Transformations*, $1^{st}$ Edition, Elsevier Science Inc., Tarrytown, NY (1995); Larock, R. C., *Comprehensive Organic Transformations*, VCH Publishers, Inc., New York, NY (1989), and references therein.

Compounds of the invention (I) may be prepared according to the following schemes utilizing chemical transformations familiar to anyone of ordinary proficiency in the art of organic/medicinal chemistry. References to many of these transformations can be found in March's Advanced Organic Chemistry Reactions, Mechanisms, and Structure, Fifth Edition by Michael B. Smith and Jerry March, Wiley-Interscience, New York, 2001, or other standard texts on the topic of synthetic organic chemistry.

General Synthetic Schemes

The target compounds are synthesized according to general schemes A and B.

Scheme A

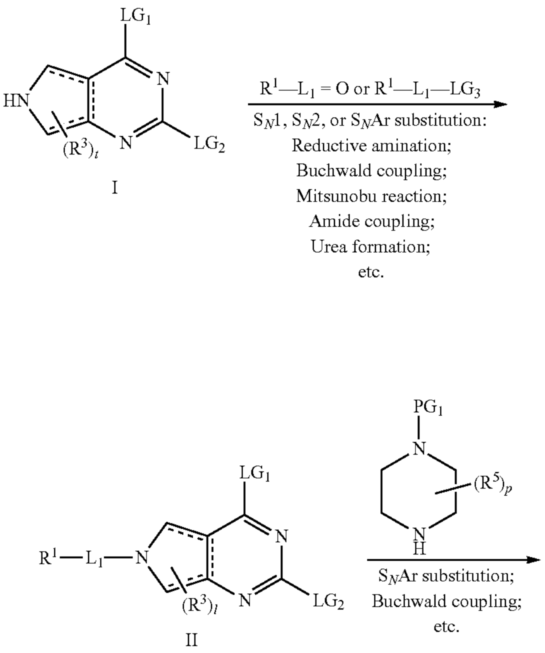

I
II

-continued

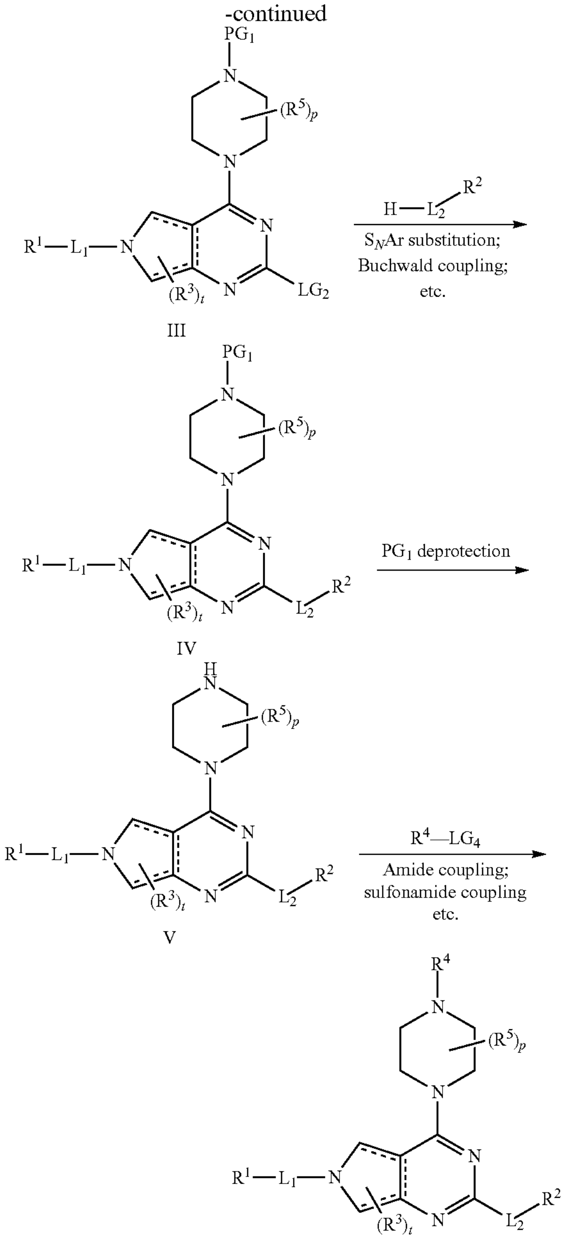

LG1, LG2, LG3 and LG4: Leaving groups, such as halogen, OH, phenol, OMs, OTs etc.; PG1: protective group, such as Boc, Cbz, Bn, PMB etc.

As shown in scheme A, $R^1$-L1 can be linked to the nitrogen of intermediate I, by reduction amination with corresponding aldehyde, Buchwald coupling with corresponding aryl/heteroaryl halogen, $S_N1/S_N2/S_NAr$ substitution with corresponding starting materials, Mitsunobu reaction with corresponding alcohol, amide coupling with corresponding acyl chloride/carboxylic acid or urea formation with corresponding starting materials, to give intermediate II. Then $LG_1$ is substituted by $PG_1$ protected piperazine analogs to give intermediate III. $R^1$-$L_2$ group is installed to the resulting intermediate III, by substitution of $LG_2$ via $S_NAr$ or Buchwald coupling. After removing $PG_1$ protecting group of intermediate IV, $R_4$ is installed onto the top nitrogen of piperazine by Amide/sulfonamide coupling to give target compound VI.

Scheme B

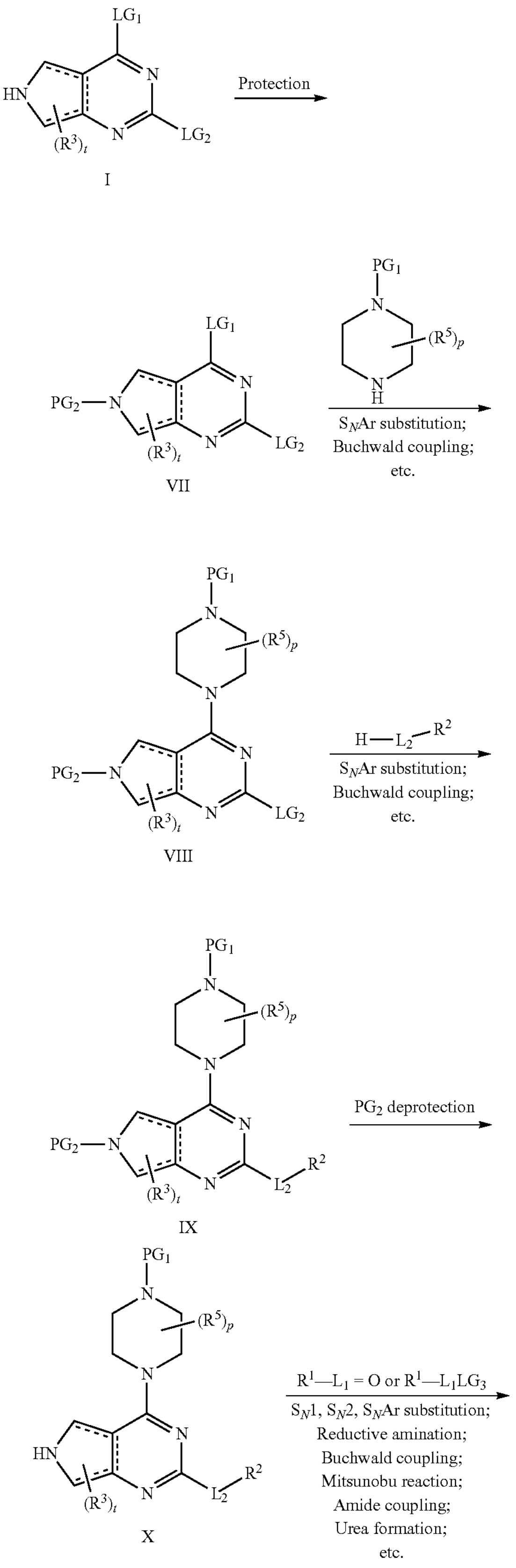

-continued

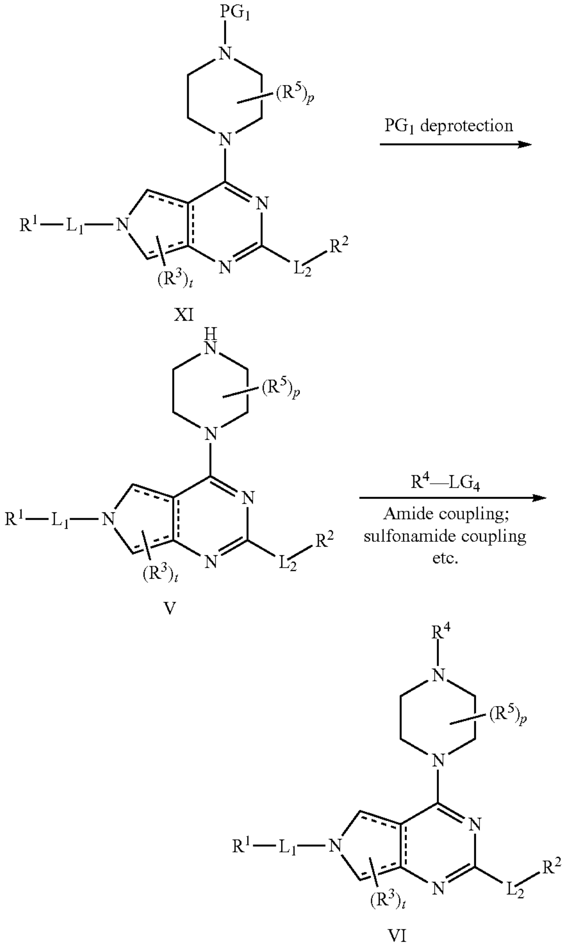

XI

V

VI $LG_1$, $LG_2$, $LG_3$ and $LG_4$: Leaving groups, such as halogen, OH, phenol, OMs, OTs etc.; $PG_1$ and $PG_2$: protective group, such as Boc, Cbz, Bn, PMB etc.

Scheme B is an alternative route for the target compounds, with similar reactions and better efficiency for library production.

EXAMPLES

The Examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and for heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^1$H NMR spectra were recorded on a Varian instrument operating at 400 MHz. $^1$H-NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), hr (broadened), dd (doublet of doublets), dt (doublet of triplets). Coupling constants, when given, are reported in Hertz (Hz). All compound names except the reagents were generated by ChemDraw version 12.0.

In the following Examples, the abbreviations below are used:

Ac Acetyl
AcOH Acetic acid
Aq Aqueous
Brine Saturated aqueous sodium chloride solution
Bn Benzyl
BnBr Benzyl Bromide
Boc Tert-butyloxycarbonyl
Cbz benzyloxycarbonyl
$CH_2Cl_2$ Dichloromethane
DMF N, N-Dimethylformamide
Dppf 1, 1"-bis(diphenylphosphino)ferrocene
DBU 1,8-diazabicyclo[5.4.0]undec-7-ene
DCE 1,2-dichloroethane
DCM Dichloromethane
DIEA or DIPEA N, N-diisopropylethylamine
DIBAL-H Diisobutylaluminium hydride
DMAP 4-N, N-dimethylaminopyridine
DMF N, N-dimethylformamide
DMP Dess-Martin Periodinane
DMSO Dimethyl sulfoxide
EA or EtOAc Ethyl acetate
eq equivalent
ESI electrospray ionization
EtOH Ethanol
$Et_2O$ or ether Diethyl ether
$Et_3N$ Triethylamine
FA Formic acid
Fmoc Fluorenylmethyloxycarbonyl
g Grams
h or hr Hour
HATU O-(7-Azabenzotriazol-1-yl)-N, N, N',N'-tetramethyluronium hexafluorophosphate
HBTU O-(7-Azabenzotriazol-1-yl)-N, N, N',N'-tetramethyluronium hexafluorophosphate
HCl Hydrochloric acid
Hex Hexane
HPLC High-performance liquid chromatography
IPA 2-propanol
i-PrOH Isopropyl alcohol
mg Milligrams
mL Milliliters
Mmol Millimole
MeCN Acetonitrile
MeOH Methanol
Min Minutes
ms or MS Mass spectrum Ms methanesulfonyl
MTBE Methyl tert-butyl ether
$Na_2SO_4$ Sodium sulfate
NMI 1-methyl-1H-imidazole
NMR Nuclear magnetic resonance
Pd/C Palladium on carbon
PE Petroleum ether
$Ph_3PO$ Triphenyl phosphorus oxide
PMB 4-Methoxybenzyl
PPA Polyphosphoric acid
Rt Retention time
Rt., RT. or rt. Room temperature
Ru-Phos/Ru-PHOS 2-dicyclohexylphosphino-2', 6'-di-i-propoxy-1,1'-biphenyl
SEM 2-trimethylsilylethoxymethoxy
SFC supercritical fluid chromatography
STAB Sodium triacetoxyborohydride
T3P propylphosphonic anhydride
TBAF Tetra-butyl ammonium fluoride
TBSCl tert-Butyldimethylsilyl chloride
TCFH N-[Chloro(dimethylamino)methylene]-N-methyl-methanaminium hexafluorophosphate
TEA Triethanolamine
TFA Trifluoroacetic acid
Tf2O Triflic anhydride
THF Tetrahydrofuran
THP tetrahydropyran
TLC thin layer chromatography
TMS trimethylsilyl
Tr Triphenylmethyl
Ts para-toluenesulfonyl
TBS tert-butyldimethylsilyl
L Microliters
UV Ultraviolet

SYNTHESIS

Example 1: (S)-1-(4-(2-((1-methylpyrrolidin-2-yl)methoxy)-6-(naphthalen-1-ylmethyl)-6,7-dihydro-5H-pyrrolo[3,4-d]pyrimidin-4-yl)piperazin-1-yl)prop-2-en-1-one

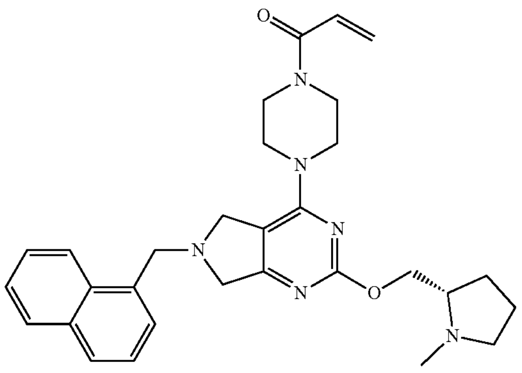 [SMILES: C=CC(=O)N1CCN(c2nc(OC[C@@H]3CCCN3C)nc3c2CN(Cc2cccc4ccccc24)C3)CC1]

Synthetic Route:

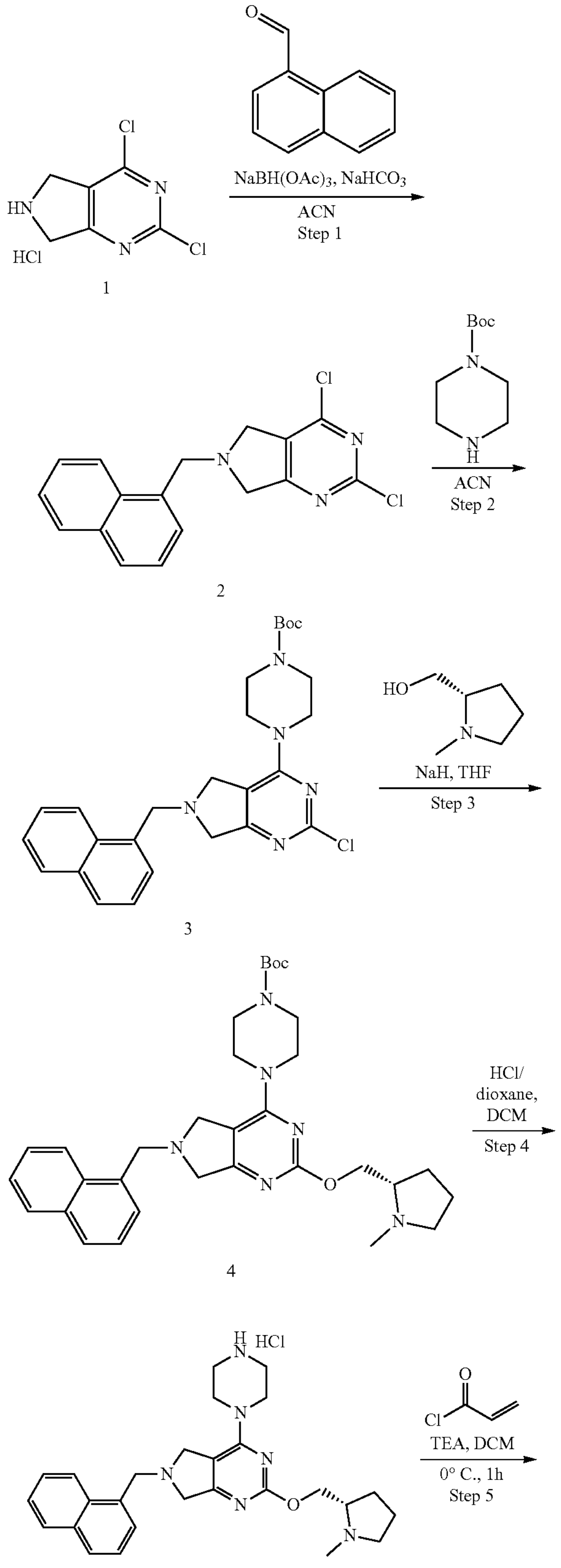

-continued

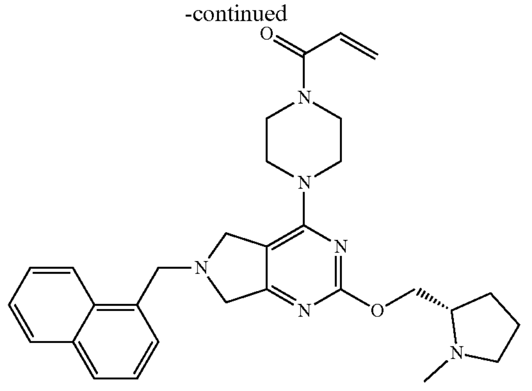

Steps 1 and 2: tert-butyl 4-(2-chloro-6-(naphthalen-1-ylmethyl)-6,7-dihydro-5H-pyrrolo[3,4-d]pyrimidin-4-yl)piperazine-1-carboxylate

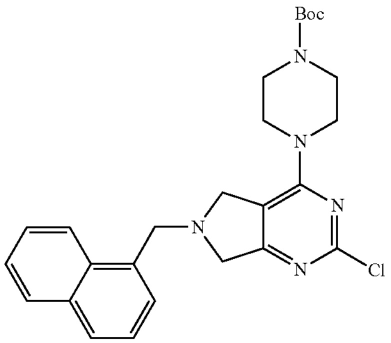 [SMILES: CC(C)(C)OC(=O)N1CCN(c2nc(Cl)nc3c2CN(Cc2cccc4ccccc24)C3)CC1]

To a mixture of 2,4-dichloro-6,7-dihydro-5H-pyrrolo[3,4-d]pyrimidine hydrochloride (1 g, 4.4 mmol) in acetonitrile (40 mL) was added $NaHCO_3$ (1.12 g, 13.3 mmol), 1-naphthaldehyde (0.83 g, 5.3 mmol) and stirred for 3 hours at room temperature. Then sodium triacetoxyborohydride (1.88 g, 8.8 mmol) was added and stirred for 20 hours at room temperature. The resulting mixture was added tert-butyl piperazine-1-carboxylate (1 g, 5.3 mmol) and stirred for 3 hours at 50° C. The cooled resulting mixture was filtered and the filtrate was concentrated and purified by chromatography column on silica (eluting with PE/EtOAc=5/1) to give the title product (340 mg, 23%). $^1H$ NMR (400 MHz, $CDCl_3$) δ 8.25-8.23 (m, 1H), 7.89-7.82 (m, 2H), 7.54-7.42 (m, 4H), 4.33 (s, 2H), 4.03 (s, 2H), 3.94 (s, 2H), 3.66-3.57 (m, 4H), 3.46-3.43 (m, 4H), 1.46 (s, 9H). MS (ESI, m/e) $[M+1]^+$ 479.9.

Step 3: tert-butyl (S)-4-(2-((1-methylpyrrolidin-2-yl)methoxy)-6-(naphthalen-1-ylmethyl)-6,7-dihydro-5H-pyrrolo[3,4-d]pyrimidin-4-yl)piperazine-1-carboxylate

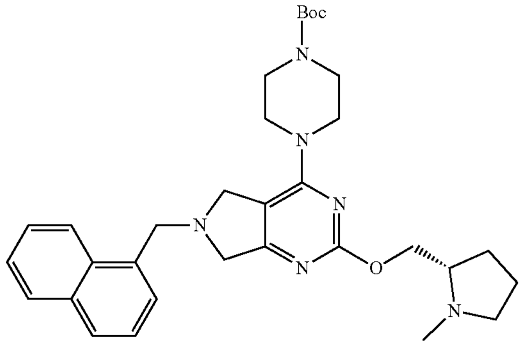 [SMILES: CN1CCC[C@H]1COc1nc2c(c(N3CCN(C(=O)OC(C)(C)C)CC3)n1)CN(Cc1cccc3ccccc13)C2]

To a solution of (S)-(1-methylpyrrolidin-2-yl)methanol (575 mg, 5 mmol) in anhydrous THF (40 mL) was added 60% NaH (240 mg, 16.7 mmol) at room temperature and stirred for 0.5 hour. Then a solution of tert-butyl 4-(2-chloro-6-(naphthalen-1-ylmethyl)-6,7-dihydro-5H-pyrrolo[3,4-d]pyrimidin-4-yl)piperazine-1-carboxylate (300 mg, 0.63 mmol) in anhydrous THF (20 mL) was added and stirred at 60° C. for 3 hours. The resulting cooled solution was added water (1 mL), concentrated and purified by column chromatography (DCM/MeOH=10/1) to give the title product (350 mg, 99%). MS (ESI, m/e) $[M+1]^+$ 559.0.

Step 4: (S)-2-((1-methylpyrrolidin-2-yl)methoxy)-6-(naphthalen-1-ylmethyl)-4-(piperazin-1-yl)-6,7-dihydro-5H-pyrrolo[3,4-d]pyrimidine hydrochloride

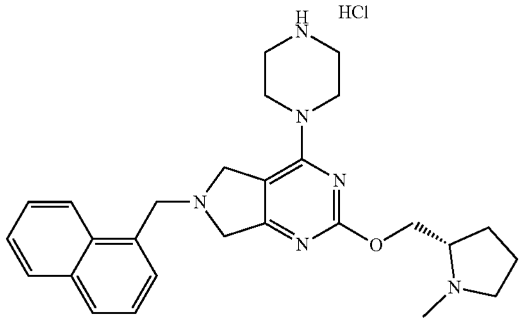 [SMILES: Cl ; CN1CCC[C@H]1COc1nc2c(c(N3CCNCC3)n1)CN(Cc1cccc3ccccc13)C2]

To a solution of tert-butyl (S)-4-(2-((1-methylpyrrolidin-2-yl)methoxy)-6-(naphthalen-1-ylmethyl)-6,7-dihydro-5H-pyrrolo[3,4-d]pyrimidin-4-yl)piperazine-1-carboxylate (350 mg, 0.63 mmol) in DCM (10 mL) was added 4M HCl/1,4-dioxane (4 mL, 16 mmol) and stirred at room temperature for 3 hours. The resulting solution was concentrated in vacuo to give the title product (300 mg, 96.0%). MS (ESI, m/e) $[M+H]^+$ 459.1.

Step 5: (S)-1-(4-(2-((1-methylpyrrolidin-2-yl)methoxy)-6-(naphthalen-1-ylmethyl)-6,7-dihydro-5H-pyrrolo[3,4-d]pyrimidin-4-yl)piperazin-1-yl)prop-2-en-1-one

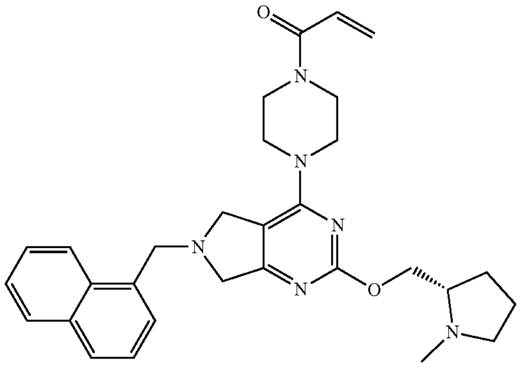 [SMILES: C=CC(=O)N1CCN(c2nc(OC[C@@H]3CCCN3C)nc3c2CN(Cc2cccc4ccccc24)C3)CC1]

To a solution of (S)-2-((1-methylpyrrolidin-2-yl)methoxy)-6-(naphthalen-1-ylmethyl)-4-(piperazin-1-yl)-6,7-dihydro-5H-pyrrolo[3,4-d]pyrimidine hydrochloride (60 mg, 0.12 mmol) in DCM (10 mL) was added TEA (150 mg, 1.49 mmol) and acryloyl chloride (60 mg, 0.67 mmol) at 0° C. in dropwise, stirred for 1 hour at this temperature. The resulting solution was washed with $NaHCO_3/H_2O$ (Sat. 10 mL) and concentrated to give a residue which was further purified by Prep-HPLC to give Example 1 (15 mg, 24%). $^1H$ NMR (400 MHz, $CD_3OD$) δ 8.30-8.27 (m, 1H), 7.88-7.81 (m, 2H), 7.54-7.42 (m, 4H), 6.78-6.71 (m, 1H), 6.25-6.21 (m, 1H), 5.78-5.75 (m, 1H), 4.46-4.36 (m, 2H), 4.32 (s, 2H), 4.11 (s, 2H), 3.74 (s, 2H), 3.70 (s, 8H), 3.65-3.55 (m, 1H), 3.38-3.32 (m, 1H), 3.24-3.22 (m, 1H), 2.72 (s, 3H), 2.22-2.14 (m, 1H), 1.97-1.90 (m, 2H), 1.85-1.79 (m, 1H). MS (ESI, m/e) $[M+H]^+$ 513.0.

Example 2: (S, E)-4-(dimethylamino)-1-(4-(2-((1-methylpyrrolidin-2-yl)methoxy)-6-(naphthalen-1-ylmethyl)-6,7-dihydro-5H-pyrrolo[3,4-d]pyrimidin-4-yl)piperazin-1-yl)but-2-en-1-one

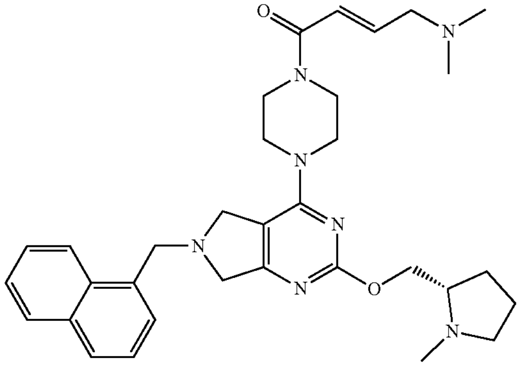 [SMILES: CN(C)C/C=C/C(=O)N1CCN(c2nc(OC[C@@H]3CCCN3C)nc3c2CN(Cc2cccc4ccccc24)C3)CC1]

A solution of (E)-4-(dimethylamino)but-2-enoic acid hydrochloride (100 mg, 0.6 mmol) in DMF (10 mL) was added HATU (229 mg, 0.6 mmol) and DIEA (300 mg, 2.3 mmol), then (S)-2-((1-methylpyrrolidin-2-yl)methoxy)-6-(naphthalen-1-ylmethyl)-4-(piperazin-1-yl)-6,7-dihydro-5H-pyrrolo[3,4-d]pyrimidine hydrochloride (90 mg, 0.18 mmol) was added and stirred for 3 hours at room temperature. The resulting solution was concentrated in vacuo and re-dissolved in DCM (10 mL), washed with $H_2O$ (10 mL), the water phase (contented product desired) was concentrated to give a residue which was further purified by Prep-HPLC to give Example 2 (20 mg, 19%). $^1H$ NMR (400 MHz, $CD_3OD$) δ 8.26 (d, J=8.4 Hz, 1H), 8.07 (d, J=8.3 Hz, 1H), 8.01 (d, J=8.1 Hz, 1H), 7.83 (d, J=6.9 Hz, 1H), 7.72-7.68 (m, 1H), 7.64-7.59 (m, 2H), 6.96-6.93 (m, 1H), 6.75-6.68 (m, 1H), 5.15 (s, 2H), 4.98 (s, 2H), 4.73-4.69 (m, 1H), 4.54-4.80 (m, 3H), 3.96 (d, J=7.1 Hz, 2H), 3.88-3.68 (m, 10H), 3.25-3.18 (m, 1H), 3.04 (s, 3H), 2.91 (s, 6H), 2.40-2.33 (m, 1H), 2.20-2.17 (m, 1H), 2.11-1.97 (m, 2H). MS (ESI, m/e) $[M+H]^+$ 570.0.

Example 3: (S)-2-((1-methylpyrrolidin-2-yl)methoxy)-6-(naphthalen-1-ylmethyl)-4-(4-(vinylsulfonyl)piperazin-1-yl)-6,7-dihydro-5H-pyrrolo[3,4-d]pyrimidine

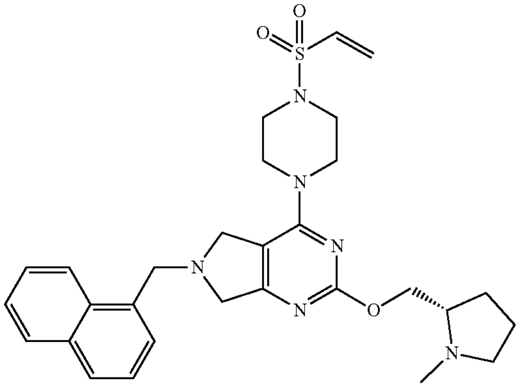 [SMILES: C=CS(=O)(=O)N1CCN(c2nc(OC[C@@H]3CCCN3C)nc3c2CN(Cc2cccc4ccccc24)C3)CC1]

To a solution of (S)-2-((1-methylpyrrolidin-2-yl)methoxy)-6-(naphthalen-1-ylmethyl)-4-(piperazin-1-yl)-6,7-dihydro-5H-pyrrolo[3,4-d]pyrimidine (60 mg, 0.12 mmol) hydrochloride in DCM (10 mL) was added TEA (100 mg, 1 mmol) and 2-chloroethane-1-sulfonyl chloride (80 mg, 0.49 mmol) at 0° C. in dropwise, stirred for 1 hour at this temperature. The resulting solution was added MeOH (5 mL) and concentrated to give a residue which was further purified by Prep-HPLC to give Example 3 (8 mg, 12%). $^1H$ NMR (400 MHz, $CD_3OD$) δ 8.24 (d, J=8.4 Hz, 1H), 8.08 (d, J=8.3 Hz, 1H), 8.02 (d, J=8.0 Hz, 1H), 7.82 (d, J=6.8 Hz, 1H), 7.71-7.68 (m, 1H), 7.65-7.59 (m, 2H), 6.68-6.61 (m, 1H), 6.24-6.15 (m, 2H), 5.14 (s, 2H), 4.94 (s, 2H), 4.70-4.66 (m, 1H), 4.553-4.49 (m, 3H), 3.84-3.68 (m, 6H), 3.23-3.21 (m, 5H), 3.04 (s, 3H), 2.39-2.34 (m, 1H), 2.19-2.16 (m, 1H), 2.11-2.05 (m, 1H), 2.09-1.96 (m, 1H). MS (ESI, m/e) $[M+H]^+$ 549.5.

Example 4: (S)-1-(4-(2-((1-methylpyrrolidin-2-yl)methoxy)-6-(naphthalen-1-ylmethyl)-6,7-dihydro-5H-pyrrolo[3,4-d]pyrimidin-4-yl)piperazin-1l-yl)but-2-yn-1-one

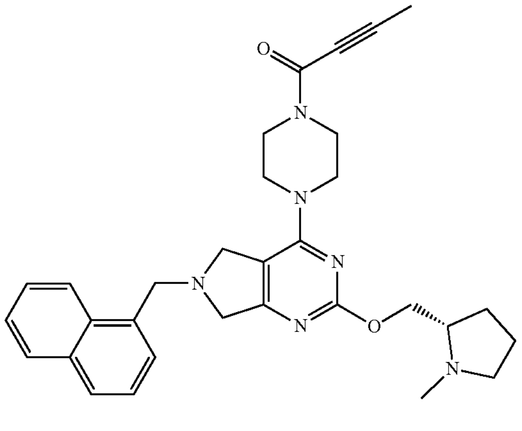 [SMILES: CC#CC(=O)N1CCN(c2nc(OC[C@@H]3CCCN3C)nc3c2CN(Cc2cccc4ccccc24)C3)CC1]

A solution of but-2-ynoic acid (60 mg, 0.71 mmol) in DMF (5 mL) was added HATU (271 mg, 0.71 mmol) and DIEA (460 mg, 3.6 mmol), then (S)-2-((1-methylpyrrolidin-2-yl)methoxy)-6-(naphthalen-1-ylmethyl)-4-(piperazin-1-yl)-6,7-dihydro-5H-pyrrolo[3,4-d]pyrimidine hydrochloride (70 mg, 0.14 mmol) was added and stirred for 1 hour at room temperature. The resulting solution was concentrated in high vacuo and dissolved in DCM (10 mL), washed with $H_2O$ (10 mL), the DCM phase (containing desired product) was concentrated to give a residue which was further purified by Prep-HPLC to give Example 4 (11.4 mg, 16%). $^1H$ NMR (400 MHz, DMSO-$d_6$) δ 8.29 (d, J=8.3 Hz, 1H), 7.93 (d, J=8.0 Hz, 2H), 7.66 (d, J=6.9 Hz, 1H), 7.61-7.50 (m, 3H), 4.70-4.66 (m, 3H), 4.52-4.47 (m, 3H), 4.05 (s, 2H), 3.86-3.85 (m, 3H), 3.76-3.66 (m, 7H), 3.25-3.19 (s, 1H), 3.03 (s, 3H), 2.39-2.32 (m, 1H), 2.21-2.15 (m, 1H), 2.11-2.06 (m, 1H), 2.05 (s, 3H), 2.01-1.97 (m, 1H). MS (ESI, m/e) $[M+H]^+$ 525.5.

Example 5: 2-((S)-1-acryloyl-4-(6-(2,3-dimethylbenzyl)-2-(((S)-1-methylpyrrolidin-2-yl)methoxy)-6,7-dihydro-5H-pyrrolo[3,4-d]pyrimidin-4-yl)piperazin-2-yl)acetonitrile

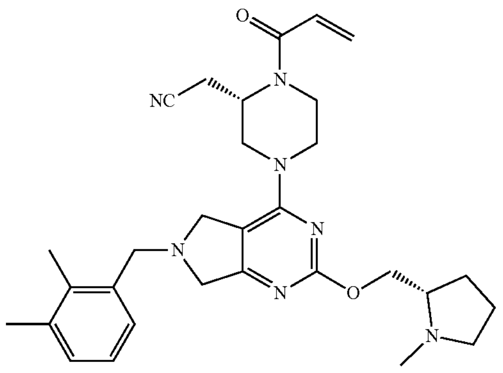 [SMILES: C=CC(=O)N1CCN(c2nc(OC[C@@H]3CCCN3C)nc3c2CN(Cc2cccc(C)c2C)C3)C[C@@H]1CC#N]

Synthetic Route

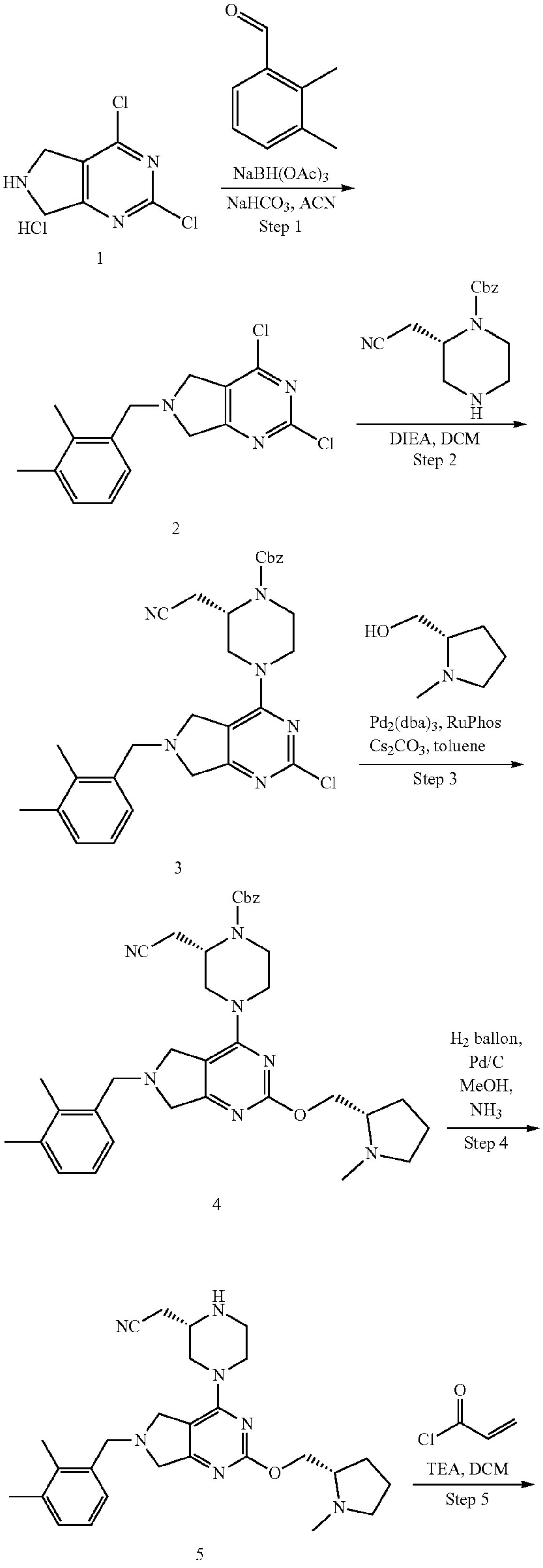

-continued

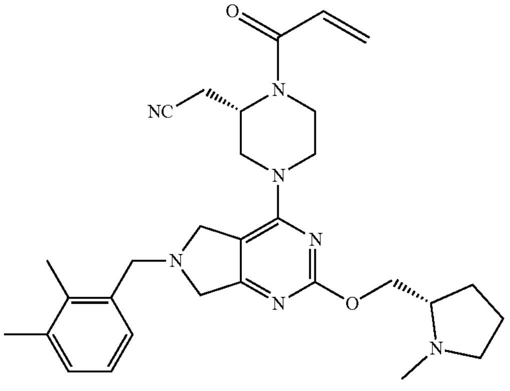 [SMILES: C=CC(=O)N1CCN(c2nc(OC[C@@H]3CCCN3C)nc3c2CN(Cc2cccc(C)c2C)C3)C[C@@H]1CC#N]

Step 1: 2,4-dichloro-6-(2,3-dimethylbenzyl)-6,7-dihydro-5H-pyrrolo[3,4-d]pyrimidine

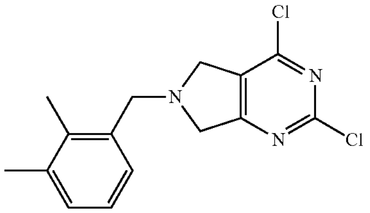 [SMILES: Cc1cccc(CN2Cc3nc(Cl)nc(Cl)c3C2)c1C]

To a mixture of 2,4-dichloro-6,7-dihydro-5H-pyrrolo[3,4-d]pyrimidine hydrochloride (1.12 g, 5 mmol) in acetonitrile (100 mL) was added $NaHCO_3$ (1.32 g, 16 mmol), 2,3-dimethylbenzaldehyde (0.8 g, 6 mmol) and sodium triacetoxyborohydride (2 g, 9.4 mmol) in step-wise. The mixture was stirred for 3 hours at room temperature and then for 2 hours at 70° C. The cooled resulting mixture was concentrated and dissolved in DCM (50 mL) and the solid was filtered off. The filtrate was concentrated to give the crude product (2 g) used directly in next step. $^1$H NMR (400 MHz, DMSO-$d_6$) δ 7.16 (d, J=7.3 Hz, 1H), 7.11-7.03 (m, 2H), 4.02 (s, 2H), 3.92-3.90 (m, 4H), 2.25 (s, 3H), 2.23 (s, 3H). MS (ESI, m/e) $[M+1]^+$ 307.9.

Step 2: benzyl (S)-4-(2-chloro-6-(2,3-dimethylbenzyl)-6,7-dihydro-5H-pyrrolo[3,4-d]pyrimidin-4-yl)-2-(cyanomethyl)piperazine-1-carboxylate

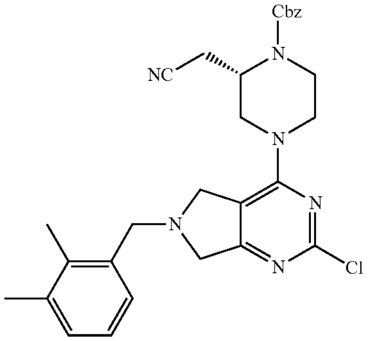 [SMILES: Cc1cccc(CN2Cc3nc(Cl)nc(N4CCN(C(=O)OCc5ccccc5)[C@@H](CC#N)C4)c3C2)c1C]

To a solution of 2,4-dichloro-6-(2,3-dimethylbenzyl)-6,7-dihydro-5H-pyrrolo[3,4-d]pyrimidine (750 mg, 2.44 mmol) in DCM (40 mL) was added benzyl (S)-2-(cyanomethyl)piperazine-1-carboxylate (635 mg, 2.45 mmol) and DIPEA (1 g, 7.75 mmol), stirred at room temperature for 68 hours and at 50° C. for 2 hours. The resulting cooled solution was concentrated and purified by chromatography column on silica (eluting with DCM/EtOAc=4/1) to give the title product (475 mg, 48% for 2 steps). MS (ESI, m/e) $[M+1]^+$ 531.0.

Step 3: benzyl (S)-2-(cyanomethyl)-4-(6-(2,3-dimethylbenzyl)-2-(((S)-1-methylpyrrolidin-2-yl)methoxy)-6,7-dihydro-5H-pyrrolo[3,4-d]pyrimidin-4-yl)piperazine-1-carboxylate

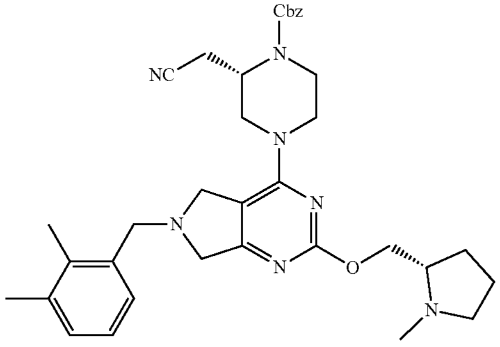 [SMILES: Cc1cccc(CN2Cc3nc(OC[C@@H]4CCCN4C)nc(N4CCN(C(=O)OCc5ccccc5)[C@@H](CC#N)C4)c3C2)c1C]

To a mixture of benzyl (S)-4-(2-chloro-6-(2,3-dimethylbenzyl)-6,7-dihydro-5H-pyrrolo[3,4-d]pyrimidin-4-yl)-2-(cyanomethyl)piperazine-1-carboxylate (335 mg, 0.63 mmol), (S)-(1-methylpyrrolidin-2-yl)methanol (200 mg, 1.74 mmol), $Cs_2CO_3$ (620 mg, 1.9 mmol), $Pd_2(dba)_3$ (100 mg, 0.11 mmol) and RuPhos (100 mg, 0.11 mmol) was added toluene (20 mL), degassed with $N_2$ for 3 times and stirred at 105° C. for 16 hours. The resulting cooled mixture was concentrated and purified by column chromatography (DCM/MeOH=10/1) to give the title product (380 mg, 99%). MS (ESI, m/e) $[M+1]^+$ 609.9.

Step 4: 2-((S)-4-(6-(2,3-dimethylbenzyl)-2-(((S)-1-methylpyrrolidin-2-yl)methoxy)-6,7-dihydro-5H-pyrrolo[3,4-d]pyrimidin-4-yl)piperazin-2-yl)acetonitrile

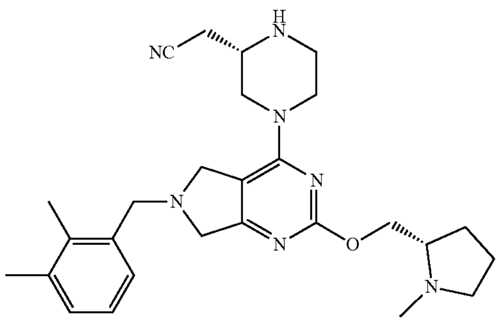 [SMILES: Cc1cccc(CN2Cc3nc(OC[C@@H]4CCCN4C)nc(N4CCN[C@@H](CC#N)C4)c3C2)c1C]

To a solution of benzyl (S)-2-(cyanomethyl)-4-(6-(2,3-dimethylbenzyl)-2-(((S)-1-methylpyrrolidin-2-yl)methoxy)-6,7-dihydro-5H-pyrrolo[3,4-d]pyrimidin-4-yl)piperazine-1- carboxylate (160 mg, 0.26 mmol) in methanol (10 mL) was added 10% Pd/C 160 mg and $NH_3$ in MeOH (7M, 1 mL), stirred at room temperature for 15 hours under hydrogen atmosphere. Then it was filtered and the filtrate was evaporated to give the title product (100 mg, 81.0%). MS (ESI, m/e) $[M+H]^+$ 476.1.

Step 5: 2-((S)-1-acryloyl-4-(6-(2,3-dimethylbenzyl)-2-(((S)-1-methylpyrrolidin-2-yl)methoxy)-6,7-dihydro-5H-pyrrolo[3,4-d]pyrimidin-4-yl)piperazin-2-yl)acetonitrile

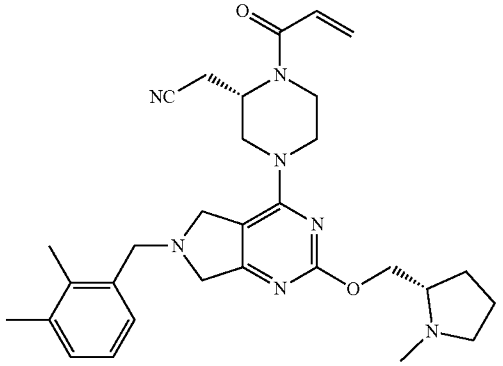 [SMILES: C=CC(=O)N1CCN(c2nc(OC[C@@H]3CCCN3C)nc3c2CN(Cc2cccc(C)c2C)C3)C[C@@H]1CC#N]

To a solution of 2-((S)-4-(6-(2,3-dimethylbenzyl)-2-(((S)-1-methylpyrrolidin-2-yl)methoxy)-6, 7-dihydro-5H-pyrrolo [3, 4-d]pyrimidin-4-yl)piperazin-2-yl)acetonitrile (100 mg, 0.21 mmol) in DCM (20 mL) was added TEA (150 mg, 1.49 mmol) and acryloyl chloride (60 mg, 0.67 mmol) at −70° C. in dropwise, stirred for 0.5 hour at this temperature. The resulting solution was washed with $NaHCO_3/H_2O$ (Sat. 20 mL) and concentrated to give a residue which was further purified by Prep-HPLC to give Example 5 (23 mg, 21%, FA salt). $^1H$ NMR (400 MHz, DMSO-$d_6$) δ 8.19 (s, 1H), 7.17-7.15 (m, 1H), 7.10-7.03 (m, 2H), 6.88-6.77 (m, 1H), 6.19-6.15 (m, 1H), 5.77-5.75 (m, 1H), 4.88-4.72 (m, 1H), 4.31-4.19 (m, 2H), 4.08-3.98 (m, 4H), 3.84 (s, 2H), 3.61 (s, 2H), 3.49-3.43 (m, 1H), 3.27-3.15 (m, 2H), 3.05-3.02 (m, 1H), 2.98-2.88 (m, 3H), 2.58-2.54 (m, 1H), 2.35 (s, 3H), 2.24 (s, 3H), 2.22 (s, 3H), 2.18-2.16 (m, 1H), 1.96-1.87 (m, 1H), 1.70-1.63 (m, 2H), 1.61-1.51 (m, 1H). MS (ESI, m/e) $[M+H]^+$ 530.7.

Procedures of Common Intermediate 5

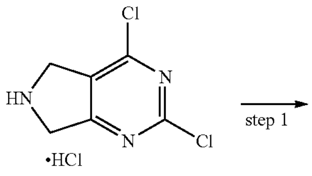

1

-continued

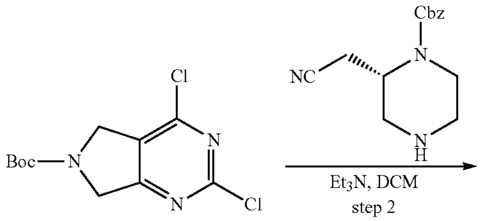

2

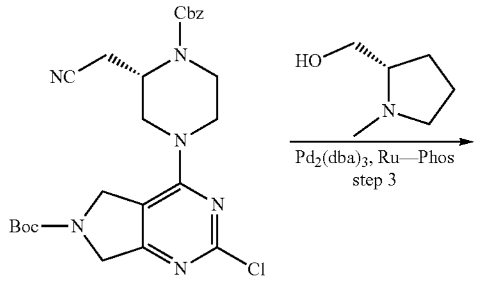

3

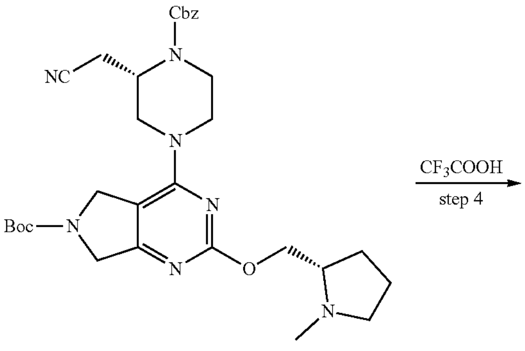

4

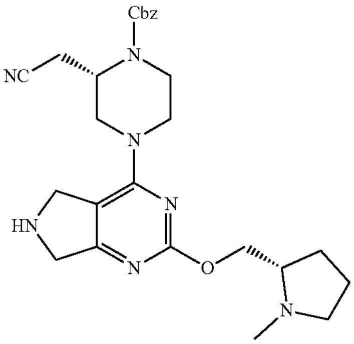

5

Common intermediate: benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate

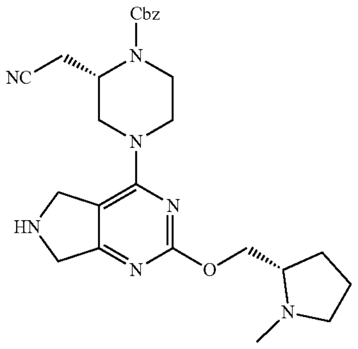 [SMILES: CN1CCC[C@H]1COc1nc2c(c(N3CCN(C(=O)OCc4ccccc4)[C@@H](CC#N)C3)n1)CNC2]

Step 1: tert-butyl 2, 4-dichloro-5, 7-dihydro-6H-pyrrolo[3, 4-d]pyrimidine-6-carboxylate

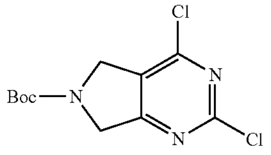 [SMILES: CC(C)(C)OC(=O)N1Cc2nc(Cl)nc(Cl)c2C1]

To a solution of 2, 4-dichloro-6, 7-dihydro-5H-pyrrolo[3, 4-d]pyrimidine (11.20 g, 49.45 mmol) in 200 mL dichloromethane was added triethylamine (10.0 mL), then di-tert-butyl decarbonate (12.0 g, 54.98 mmol) was added dropwise at room temperature. After the addition, the mixture was stirred at room temperature for 4 h. Then it was diluted with dichloromethane and water. The organic layer was combined, dried over sodium sulfate and evaporated. The residue was purified by chromatography column on silica to give the title compound (12.40 g, 86.4%). MS (ESI, m/e) $[M+1]^4$ 289.8.

Step 2: tert-butyl (S)-4-(4-((benzyloxy)carbonyl)-3-(cyanomethyl)piperazin-1-yl)-2-chloro-5, 7-dihydro-6H-pyrrolo[3, 4-d]pyrimidine-6-carboxylate

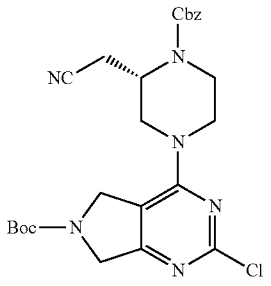 [SMILES: CC(C)(C)OC(=O)N1Cc2nc(Cl)nc(N3CCN(C(=O)OCc4ccccc4)[C@@H](CC#N)C3)c2C1]

To a solution of tert-butyl 2, 4-dichloro-5, 7-dihydro-6H-pyrrolo[3, 4-d]pyrimidine-6-carboxylate (12.40 g, 42.73 mmol) in 120 mL dichloromethane was added triethylamine (10.0 mL) and benzyl (S)-2-(cyanomethyl)piperazine-1-carboxylate (10.30 g, 39.70 mmol) at room temperature and it was stirred at room temperature for 16 h. Then it was diluted with water, the organic layer was combined, dried over sodium sulfate and evaporated. The residue was purified by chromatography column on silica to give the title product (16.20 g, 79.5%). $^1$H NMR (400 MHz, DMSO-$d_6$) δ ppm: 7.48-7.27 (m, 5H), 5.21-5.03 (m, 2H), 4.76-4.68 (m, 2H), 4.62-4.54 (m, 2H), 4.39-4.36 (m, 2H), 4.25-4.13 (m, 1H), 3.95-3.91 (m, 1H), 3.42-3.34 (m, 1H), 3.30-3.17 (m, 2H), 3.03-2.81 (m, 2H), 1.45 (s, 9H). MS (ESI, m/e) $[M+1]^+$ 512.8.

Step 3: tert-butyl 4-((S)-4-((benzyloxy)carbonyl)-3-(cyanomethyl)piperazin-1-yl)-2-(((S)-1-methylpyrrolidin-2-yl)methoxy)-5, 7-dihydro-6H-pyrrolo[3, 4-d]pyrimidine-6-carboxylate

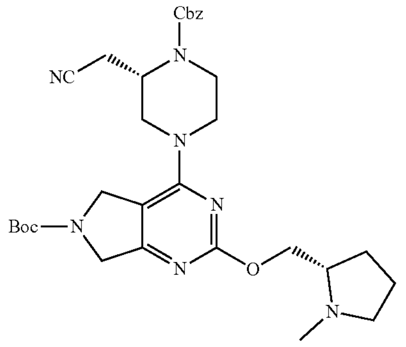 [SMILES: CN1CCC[C@H]1COc1nc2c(c(N3CCN(C(=O)OCc4ccccc4)[C@@H](CC#N)C3)n1)CN(C(=O)OC(C)(C)C)C2]

To a solution of tert-butyl (S)-4-(4-((benzyloxy)carbonyl)-3-(cyanomethyl)piperazin-1-yl)-2-chloro-5, 7-dihydro-6H-pyrrolo[3, 4-d]pyrimidine-6-carboxylate (13.40 g, 26.12 mmol), (S)-(1-methylpyrrolidin-2-yl)methanol (7.30 g, 63.37 mmol), tris(dibenzylideneacetone)dipalladium (1.83 g, 2.00 mmol), 2-dicyclohexylphosphino-2', 6'-di-i-propoxy-1, 1'-biphenyl (1.85 g, 2.00 mmol) and cesium carbonate (21.0 g 64.80 mmol) in 120 mL toluene was stirred at 105° C. for 8 h under nitrogen atmosphere. Then it was cooled down to room temperature. It was filtered and the filtrate was diluted with dichloromethane and water and the organic layer was combined, dried over sodium sulfate and evaporated. The residue was purified by chromatography column on silica to give the title product (10.50 g, 68.0%). $^1$H NMR (400 MHz, DMSO-$d_6$) δ ppm: 7.48-7.30 (m, 5H), 5.19-5.04 (m, 2H), 4.74-4.65 (m, 2H), 4.62-4.54 (m, 1H), 4.39-4.34 (m, 3H), 4.25-4.13 (m, 1H), 4.02-4.00 (m, 2H), 3.97-3.91 (m, 1H), 3.34-3.22 (m, 3H), 3.22-3.13 (m, 1H), 2.98-2.78 (m, 3H), 2.33 (s, 3H), 2.22-2.10 (m, 1H), 1.96-1.85 (m, 1H), 1.71-1.52 (m, 3H), 1.45 (s, 9H). MS (ESI, m/e) $[M+1]^+$ 591.9.

Step 4: benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate

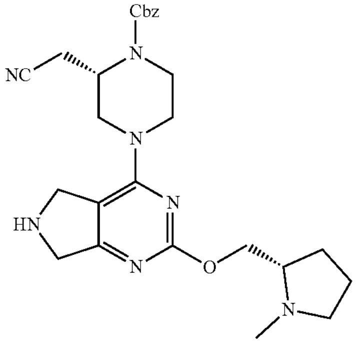 [SMILES: CN1CCC[C@H]1COc1nc2c(c(N3CCN(C(=O)OCc4ccccc4)[C@@H](CC#N)C3)n1)CNC2]

To a solution tert-butyl 4-((S)-4-((benzyloxy)carbonyl)-3-(cyanomethyl)piperazin-1-yl)-2-(((S)-1-methylpyrrolidin-2-yl)methoxy)-5, 7-dihydro-6H-pyrrolo[3, 4-d]pyrimidine-6-carboxylate (6.50 g, 11.00 mmol) in 100 mL dichloromethane was added 25 mL trifluoroacetic acid. And it was stirred at room temperature for 4 h. Then it was evaporated below 35° C. The residue was diluted with dichloromethane:isopropyl alcohol=5:1 and water. The organic layer was combined, dried over sodium sulfate, and evaporated to give the title product (5.08 g, 94.0%) without further purification. MS (ESI, m/e) $[M+1]^+$ 491.9.

Example 6: 2-((S)-1-acryloyl-4-(2-(((S)-1-methylpyrrolidin-2-yl)methoxy)-6-(naphthalen-1-ylmethyl)-6, 7-dihydro-5H-pyrrolo[3, 4-d]pyrimidin-4-yl)piperazin-2-yl)acetonitrile

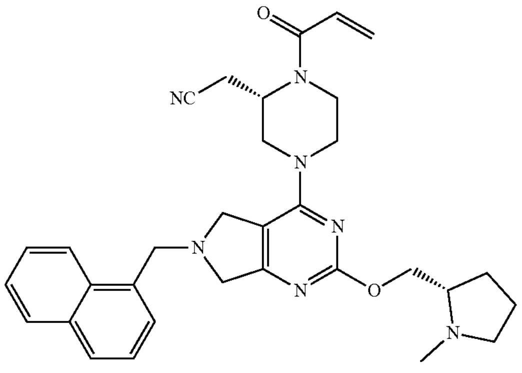 [SMILES: C=CC(=O)N1CCN(c2nc(OC[C@@H]3CCCN3C)nc3c2CN(Cc2cccc4ccccc24)C3)C[C@@H]1CC#N]

Synthetic Route:

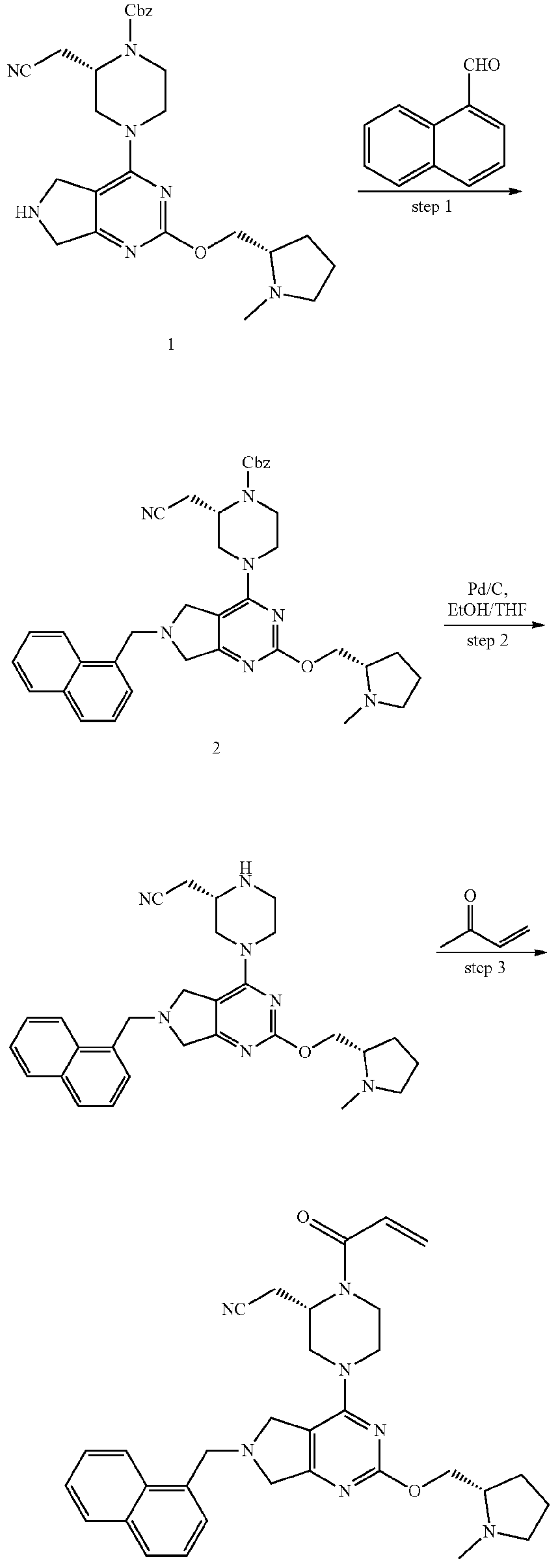

Step 1: benzyl (S)-2-(cyanomethyl)-4-(2-(((S)-1-methylpyrrolidin-2-yl)methoxy)-6-(naphthalen-1-ylmethyl)-6, 7-dihydro-5H-pyrrolo[3, 4-d]pyrimidin-4-yl)piperazine-1-carboxylate

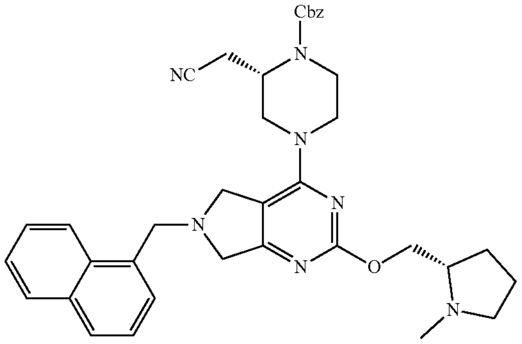 [SMILES: CN1CCC[C@H]1COc1nc2c(c(N3CCN(C(=O)OCc4ccccc4)[C@@H](CC#N)C3)n1)CN(Cc1cccc3ccccc13)C2]

To a solution of benzyl (S)-2-(cyanomethyl)-4-(2-(((S)-1-methylpyrrolidin-2-yl)methoxy)-6, 7-dihydro-5H-pyrrolo [3, 4-d]pyrimidin-4-yl)piperazine-1-carboxylate (120 mg, 0.24 mmol) in 5 mL dichloromethane was added 1-naphthaldehyde (47 mg, 0.30 mmol). After the addition, the mixture was stirred at room temperature for 10 min. Then it was added sodium triacetoxyborohydride (63 mg, 0.30 mmol). Then it was stirred at room temperature for 2 h, it was diluted with dichloromethane and water. The organic layer was combined, dried over sodium sulfate and evaporated. The residue was purified by chromatography column on silica to give the title product (106 mg, 69.9%). MS (ESI, m/e) $[M+1]^+$ 631.9.

Step 2: 2-((S)-4-(2-(((S)-1-methylpyrrolidin-2-yl) methoxy)-6-(naphthalen-1-ylmethyl)-6, 7-dihydro-5H-pyrrolo[3, 4-d]pyrimidin-4-yl)piperazin-2-yl) acetonitrile

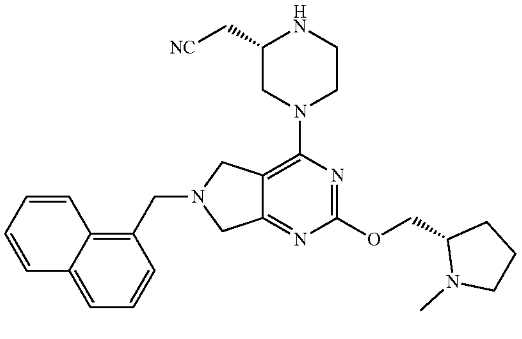 [SMILES: CN1CCC[C@H]1COc1nc2c(c(N3CCN[C@@H](CC#N)C3)n1)CN(Cc1cccc3ccccc13)C2]

To a solution of benzyl (S)-2-(cyanomethyl)-4-(2-(((S)-1-methylpyrrolidin-2-yl)methoxy)-6-(naphthalen-1-ylmethyl)-6, 7-dihydro-5H-pyrrolo[3, 4-d]pyrimidin-4-yl)piperazine-1-carboxylate (106 mg, 0.16 mmol) in ethanol (3 mL) and tetrahydrofuran (3 mL) was added 10% Pd/C (20 mg) and it was stirred at room temperature for 48 h under hydrogen atmosphere. Then it was filtered and the filtrate was evaporated. The residue was used crude for the next step (80 mg, 95.0%). MS (ESI, m/e) $[M+1]^+$ 497.9.

Step 3: 2-((S)-1-acryloyl-4-(2-(((S)-1-methylpyrrolidin-2-yl)methoxy)-6-(naphthalen-1-ylmethyl)-6, 7-dihydro-5H-pyrrolo[3, 4-d]pyrimidin-4-yl)piperazin-2-yl)acetonitrile

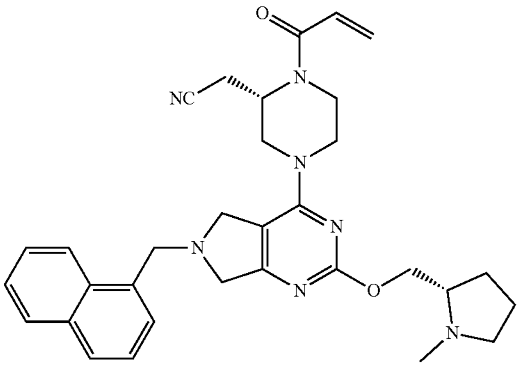 [SMILES: C=CC(=O)N1CCN(c2nc(OC[C@@H]3CCCN3C)nc3c2CN(Cc2cccc4ccccc24)C3)C[C@@H]1CC#N]

To a solution of 2-((S)-4-(2-(((S)-1-methylpyrrolidin-2-yl)methoxy)-6-(naphthalen-1-ylmethyl)-6, 7-dihydro-5H-pyrrolo[3, 4-d]pyrimidin-4-yl)piperazin-2-yl)acetonitrile (80 mg, 0.15 mmol) in 5 mL dichloromethane was added 0.3 mL triethylamine and it was stirred at 0° C., then it was added acryloyl chloride (18 mg, 0.20 mmol) and it was stirred at 0° C. for 1 h. Then it was diluted with dichloromethane and water and the organic layer was combined, dried over sodium sulfate and evaporated. The residue was purified by Prep-TLC to give Example 6 (10 mg, 11.3%). $^1H$ NMR (400 MHz, DMSO-$d_6$) δ ppm: 8.31-8.24 (m, 1H), 7.97-7.92 (m, 1H), 7.90-7.88 (d, 1H, J=8.0 Hz), 7.59-7.46 (m, 4H), 6.89-6.73 (m, 1H), 6.24-6.13 (m, 1H), 5.81-5.71 (m, 1H), 4.91-4.71 (m, 1H), 4.61-4.48 (m, 1H), 4.48-4.39 (m, 1H), 4.38-4.24 (m, 3H), 4.19-4.08 (m, 2H), 4.04-3.89 (m, 1H), 3.82-3.67 (m, 3H), 3.61-3.47 (m, 2H), 3.17-2.97 (m, 4H), 2.95-2.83 (m, 5H), 2.18-2.15 (m, 1H), 2.10-1.98 (m, 1H), 1.96-1.73 (m, 2H). MS (ESI, m/e) $[M+1]^+$ 551.9.

Example 7: 2-((S)-1-acryloyl-4-(2-(((S)-1-methylpyrrolidin-2-yl)methoxy)-6-(naphthalen-1-ylmethyl)-6H-pyrrolo[3, 4-d]pyrimidin-yl)piperazin-2-yl)acetonitrile

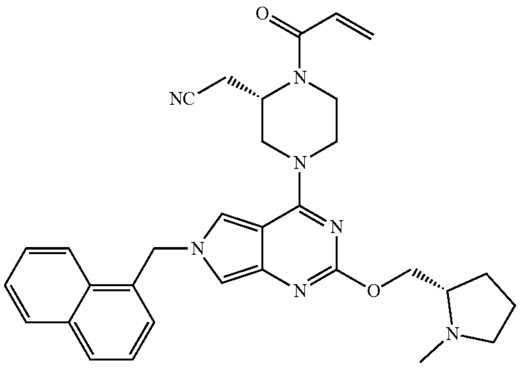 [SMILES: C=CC(=O)N1CCN(c2nc(OC[C@@H]3CCCN3C)nc3cn(Cc4cccc5ccccc45)cc23)C[C@@H]1CC#N]

Synthetic Route:

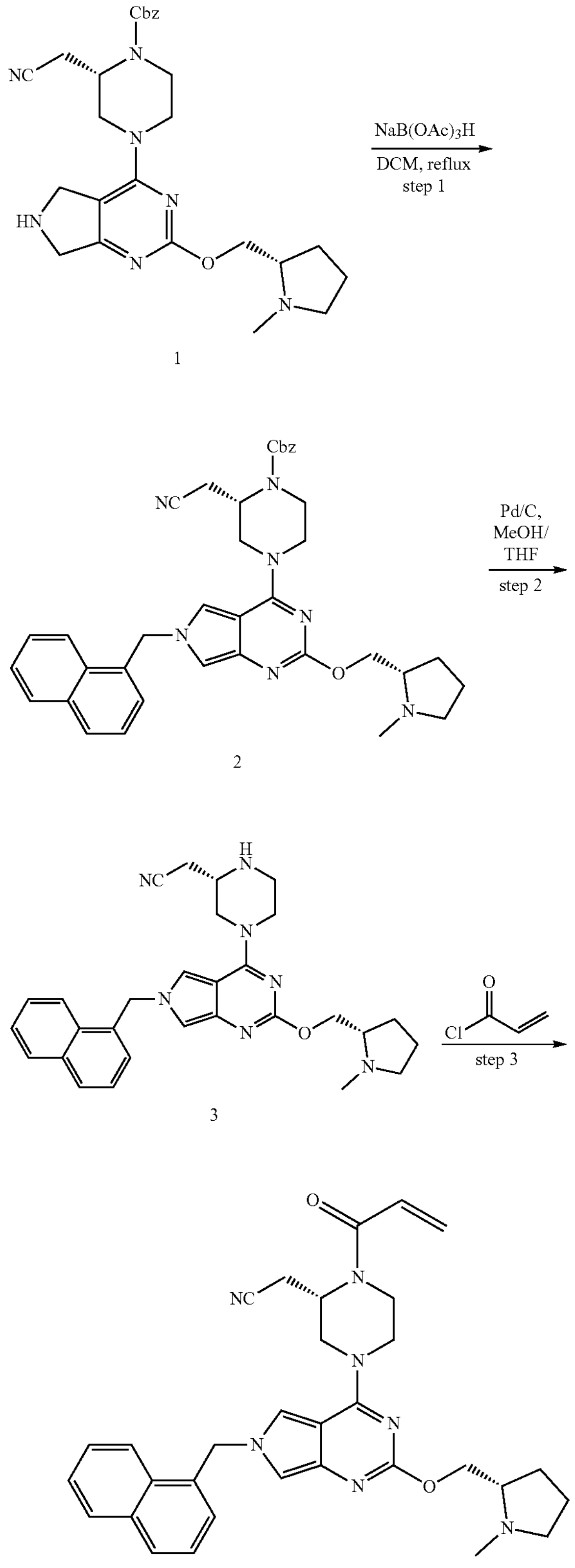

1

2

3

Step 1: benzyl (S)-2-(cyanomethyl)-4-(2-(((S)-1-methylpyrrolidin-2-yl)methoxy)-6-(naphthalen-1-ylmethyl)-6H-pyrrolo[3, 4-d]pyrimidin-4-yl)piperazine-1-carboxylate

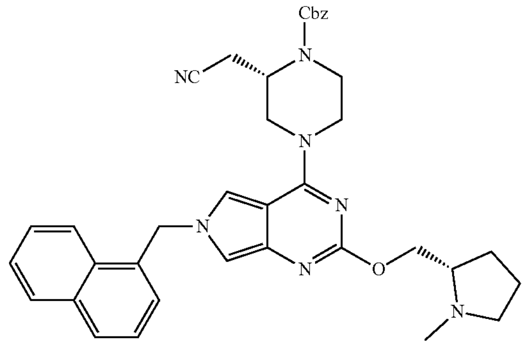 [SMILES: CN1CCC[C@H]1COc1nc(N2CCN(C(=O)OCc3ccccc3)[C@@H](CC#N)C2)c2cn(Cc3cccc4ccccc34)cc2n1]

To a solution of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (200 mg, 0.41 mmol) in 5 mL dichloromethane was added 1-naphthaldehyde (80 mg, 0.52 mmol). After the addition, the mixture was stirred at room temperature for 10 min. Then it was added sodium triacetoxyborohydride (210 mg, 1.00 mmol). Then it was stirred at reflux for 4 h, it was diluted with dichloromethane and water. The organic layer was combined, dried over sodium sulfate and evaporated. The residue was purified by chromatography column on silica to give the title product (150 mg, 58.2%). MS (ESI, m/e) $[M+1]^+$ 629.9.

Step 2: 2-((S)-4-(2-(((S)-1-methylpyrrolidin-2-yl)methoxy)-6-(naphthalen-1-ylmethyl)-6H-pyrrolo[3, 4-d]pyrimidin-4-yl)piperazin-2-yl)acetonitrile

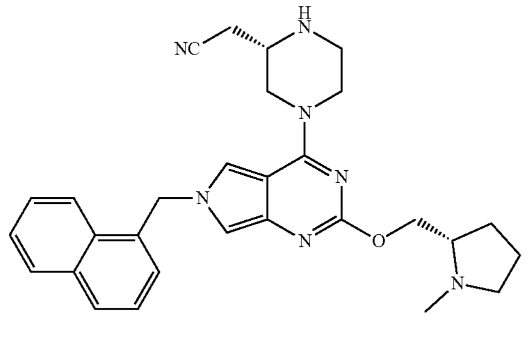 [SMILES: CN1CCC[C@H]1COc1nc(N2CCN[C@@H](CC#N)C2)c2cn(Cc3cccc4ccccc34)cc2n1]

To a solution of benzyl (S)-2-(cyanomethyl)-4-(2-(((S)-1-methylpyrrolidin-2-yl)methoxy)-6-(naphthalen-1-ylmethyl)-6H-pyrrolo[3, 4-d]pyrimidin-4-yl)piperazine-1-carboxylate (150 mg, 0.24 mmol) in methanol (4 mL) and tetrahydrofuran (4 mL) was added 10% Pd/C (100 mg) and ammonia in methanol (0.5 mL, 7M). Then it was stirred at room temperature for 16 h under hydrogen atmosphere. Then it was filtered and the filtrate was evaporated. The residue was used as crude for next step (100 mg, 84.7%). MS (ESI, m/e) $[M+1]^+$ 495.9.

Step 3: 2-((S)-1-acryloyl-4-(2-(((S)-1-methylpyrrolidin-2-yl)methoxy)-6-(naphthalen-1-ylmethyl)-6H-pyrrolo[3, 4-d]pyrimidin 4-yl)piperazin-2-yl)acetonitrile

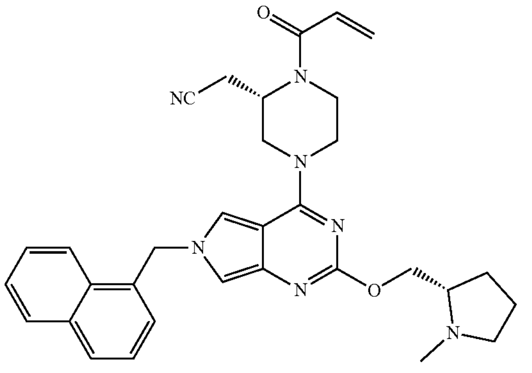 [SMILES: C=CC(=O)N1CCN(c2nc(OC[C@@H]3CCCN3C)nc3cn(Cc4cccc5ccccc45)cc23)C[C@@H]1CC#N]

To a solution of 2-((S)-4-(2-(((S)-1-methylpyrrolidin-2-yl)methoxy)-6-(naphthalen-1-ylmethyl)-6H-pyrrolo[3, 4-d] pyrimidin-4-yl)piperazin-2-yl)acetonitrile (100 mg, 0.20 mmol) in 5 mL dichloromethane was added 0.3 mL triethylamine and it was stirred at −10° C., then it was added acryloyl chloride (27 mg, 0.30 mmol) and it was stirred at −10° C. for 2 h. Then it was diluted with dichloromethane and water and the organic layer was combined, dried over sodium sulfate and evaporated. The residue was purified by Prep-TLC to give Example 7 (10 mg, 11.4%). $^{1}$H NMR (400 MHz, DMSO-$d_6$) δ ppm: 8.22-8.20 (d, 1H, J=7.2 Hz), 8.02-7.89 (m, 2H), 7.64-7.54 (m, 2H), 7.52-7.47 (m, 1H), 7.21-7.03 (m, 2H), 6.92-6.78 (m, 1H), 6.22-6.18 (m, 1H), 5.94-5.74 (m, 2H), 4.88-4.70 (m, 2H), 4.57-4.31 (m, 4H), 4.14-4.00 (m, 1H), 3.86-3.68 (m, 2H), 3.63-3.50 (m, 2H), 3.14-2.85 (m, 8H), 2.28-2.13 (m, 1H), 2.09-1.97 (m, 1H), 1.96-1.75 (m, 2H). MS (ESI, m/e) [M+1]$^{+}$ 549.9.

Example 8: 2-((S)-1-acryloyl-4-(6-((8-methylnaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

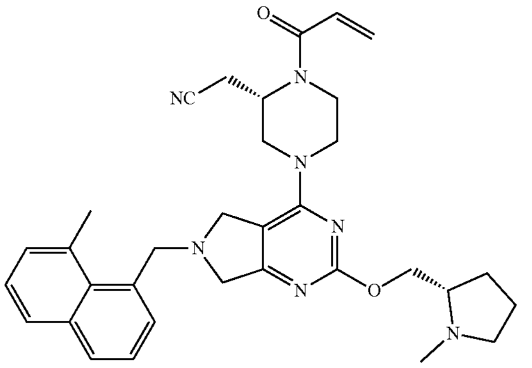 [SMILES: C=CC(=O)N1CCN(c2nc(OC[C@@H]3CCCN3C)nc3c2CN(Cc2cccc4cccc(C)c24)C3)C[C@@H]1CC#N]

Synthetic Route:

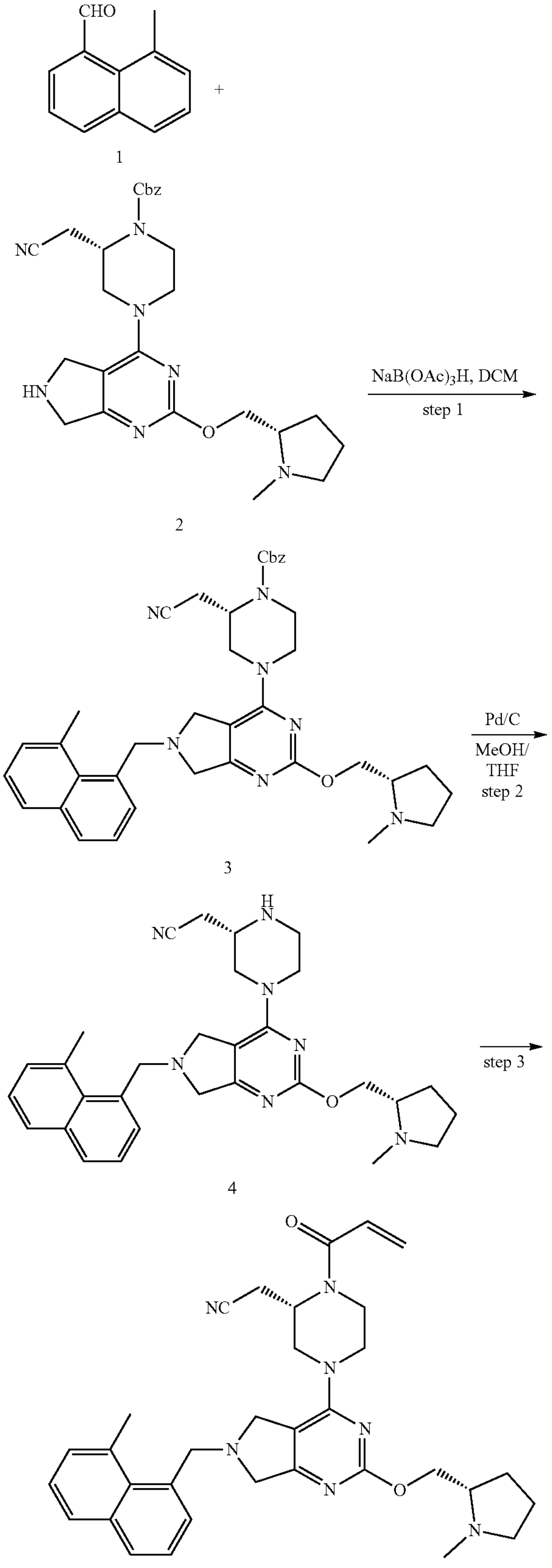

Step 1: benzyl (S)-2-(cyanomethyl)-4-(6-((8-methylnaphthalen-1-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate

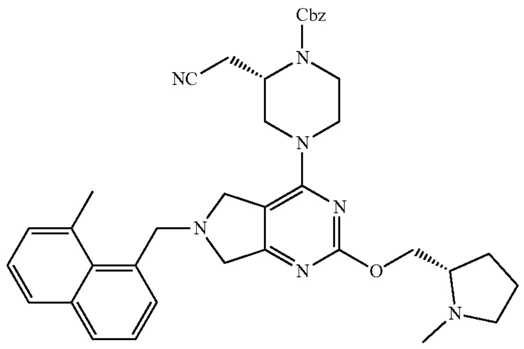 [SMILES: Cc1cccc2cccc(CN3Cc4nc(OC[C@@H]5CCCN5C)nc(N5CCN(C(=O)OCc6ccccc6)[C@@H](CC#N)C5)c4C3)c12]

To a solution of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (250 mg, 0.51 mmol) in 5 mL dichloromethane was added 8-methyl-1-naphthaldehyde (115 mg, 0.68 mmol). After the addition, the mixture was stirred at room temperature for 10 min. Then it was added sodium triacetoxyborohydride (420 mg, 2.00 mmol). Then it was stirred at room temperature for 2 h, it was diluted with dichloromethane and water. The organic layer was combined, dried over sodium sulfate and evaporated. The residue was purified by chromatography column on silica to give the title product (160 mg, 48.7%). MS (ESI, m/e) $[M+1]^+$ 645.9.

Step 2: 2-((S)-4-(6-((8-methylnaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

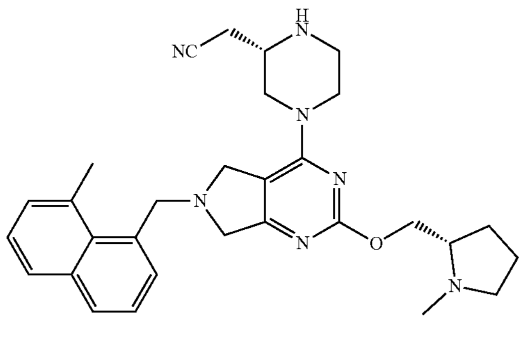 [SMILES: Cc1cccc2cccc(CN3Cc4nc(OC[C@@H]5CCCN5C)nc(N5CCN[C@@H](CC#N)C5)c4C3)c12]

To a solution of benzyl (S)-2-(cyanomethyl)-4-(6-((8-methylnaphthalen-1-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate (160 mg, 0.25 mmol) in methanol (3 mL) and tetrahydrofuran (3 mL) was added 10% Pd/C (100 mg) and it was stirred at room temperature for 16 h under hydrogen atmosphere. Then it was filtered and the filtrate was evaporated. The residue was used as crude for the next step (80 mg, 95.0%). MS (ESI, m/e) $[M+1]^+$ 511.9.

Step 3: 2-((S)-1-acryloyl-4-(6-((8-methylnaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

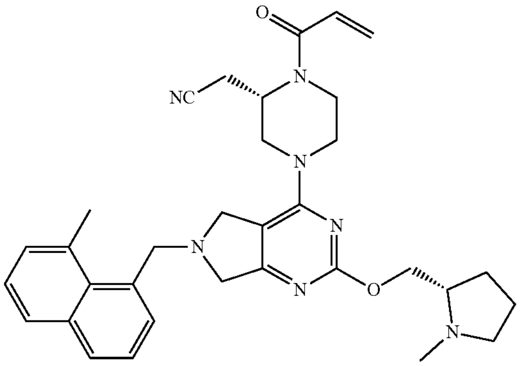 [SMILES: C=CC(=O)N1CCN(c2nc(OC[C@@H]3CCCN3C)nc3c2CN(Cc2cccc4cccc(C)c24)C3)C[C@@H]1CC#N]

To a solution of 2-((S)-4-(6-((8-methylnaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (60 mg, 0.12 mmol) in 5 mL dichloromethane was added 0.3 mL triethylamine and it was stirred at −10° C., then it was added acryloyl chloride (15 mg, 0.18 mmol) and it was stirred at −10° C. for 1 h. Then it was diluted with dichloromethane and water and the organic layer was combined, dried over sodium sulfate and evaporated. The residue was purified by Prep-TLC to give Example 8 (8 mg, 12.0%). $^1H$ NMR (400 MHz, DMSO-$d_6$) δ ppm: 7.91-7.84 (m, 1H), 7.81-7.74 (m, 1H), 7.61-7.55 (m, 1H,), 7.48-7.29 (m, 3H), 6.89-6.73 (m, 1H), 6.24-6.13 (m, 1H), 5.81-5.72 (m, 1H), 4.95-4.65 (m, 1H), 4.50-4.26 (m, 5H), 4.13-3.85 (m, 4H), 3.69-3.55 (m, 2H), 3.52-3.41 (m, 2H), 3.23-3.13 (m, 2H), 3.08-2.96 (m, 4H), 2.94-2.81 (m, 3H), 2.75 (s, 3H), 2.20-2.09 (m, 1H), 1.97-1.82 (m, 2H), 1.79-1.66 (m, 1H). MS (ESI, m/e) $[M+1]^+$ 566.7.

The following compounds were obtained by similar procedures:

Example 9: 2-((S)-1-acryloyl-4-(6-((8-chloronaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

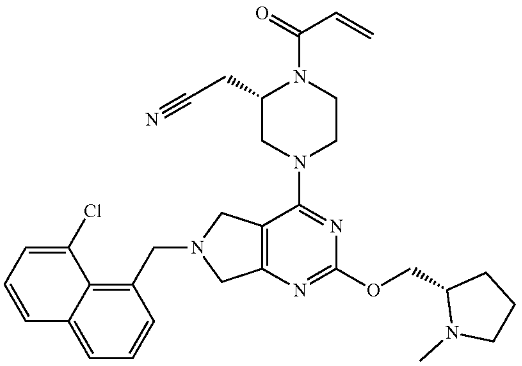 [SMILES: C=CC(=O)N1CCN(c2nc(OC[C@@H]3CCCN3C)nc3c2CN(Cc2cccc4cccc(Cl)c24)C3)C[C@@H]1CC#N]

$^1H$ NMR (400 MHz, DMSO-$d_6$) δ 7.97-7.95 (m, 1H), 7.91-7.89 (m, 1H), 7.74-7.72 (m, 1H), 7.66-7.65 (m, 1H), 7.55-7.51 (m, 1H), 7.45-7.41 (m, 1H), 6.88-6.69 (m, 1H), 6.27 (d, J=16.1 Hz, 1H), 5.82 (d, J=10.3 Hz, 1H), 4.95-4.87 (m, 2H), 4.81-4.70 (m, 3H), 4.50-4.45 (m, 1H), 4.37-4.20 (m, 1H), 4.13-4.00 (m, 1H), 3.86-3.80 (m, 2H), 3.74-3.69 (m, 2H), 3.74-3.24 (m, 2H), 3.26-3.20 (m, 2H), 3.03 (s, 3H), 2.89-2.77 (m, 3H), 2.41-2.31 (m, 1H), 2.22-1.95 (m, 3H). MS (ESI) m/e $[M+H]^+$ 586.6.

Example 10: 2-((S)-1-acryloyl-4-(6-((4-fluoronaphthalen-1-yl)methyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

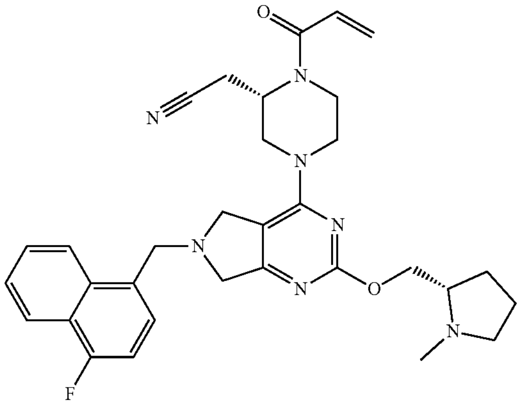 [SMILES: C=CC(=O)N1CCN(c2nc(OC[C@@H]3CCCN3C)nc3c2CN(Cc2ccc(F)c4ccccc24)C3)C[C@@H]1CC#N]

$^1H$ NMR (400 MHz, $CD_3OD$) δ 8.34 (d, J=7.9 Hz, 1H), 8.14-8.02 (m, 1H), 7.64-7.56 (m, 2H), 7.54-7.45 (m, 1H), 7.18-7.08 (m, 1H), 6.86-6.67 (m, 1H), 6.33-6.16 (m, 1H), 5.87-5.72 (m, 1H), 4.61-4.54 (m, 1H), 4.36-4.26 (m, 4H), 4.18-4.08 (m, 3H), 4.08-3.96 (m, 1H), 3.76-3.67 (m, 2H), 3.55-3.44 (m, 1H), 3.12-3.01 (m, 2H), 2.91-2.71 (m, 3H), 2.49 (s, 3H), 2.40-2.28 (m, 1H), 2.12-1.98 (m, 1H), 1.85-1.74 (m, 2H), 1.72-1.63 (m, 1H), 1.49-1.36 (m, 1H). MS (ESI, m/e) $[M+1]^+$ 570.7.

Example 11: 2-((2S)-1-acryloyl-4-(2-(((S)-1-methylpyrrolidin-2-yl)methoxy)-6-(1-(naphthalen-1-yl) ethyl)-6, 7-dihydro-5H-pyrrolo[3, 4-d]pyrimidin-4-yl)piperazin-2-yl)acetonitrile

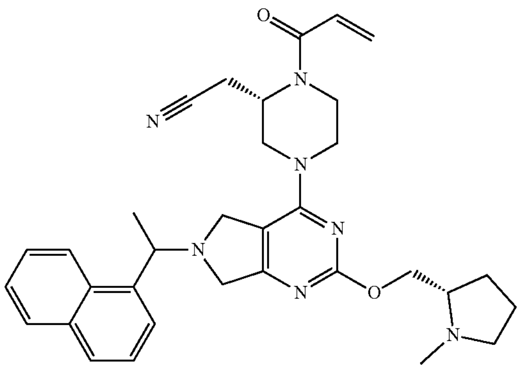

$^1H$ NMR (400 MHz, $CD_3OD$) δ 8.56-8.42 (m, 1H), 7.90 (d, J=8.4 Hz, 1H), 7.80 (d, J=8.0 Hz, 1H), 7.68 (d, J=6.9 Hz, 1H), 7.54-7.38 (m, 3H), 6.87-6.59 (m, 1H), 6.32-6.13 (m, 1H), 5.91-5.68 (m, 1), 4.68-4.55 (m, 2H), 4.51-4.38 (m, 1H), 4.31-3.93 (m, 5H), 3.91-3.70 (m, 4H), 3.69-3.56 (m, 2H), 3.51-3.40 (m, 2H), 3.28-3.11 (m, 2H), 3.01 (s, 3H), 2.92-2.69 (m, 3H), 2.39-2.32 (m, 1H), 2.23-1.95 (m, 4H). MS (ESI, m/e) $[M+1]^+$ 566.7.

Example 12: 2-((2S)-1-acryloyl-4-(6-(1, 2-dihydroacenaphthylen-1-yl)-2-((1-(tetrahydro-2H-pyran-4-yl)piperidin-4-yl)oxy)-6, 7-dihydro-5H-pyrrolo[3, 4-d]pyrimidin-4-yl)piperazin-2-yl)acetonitrile

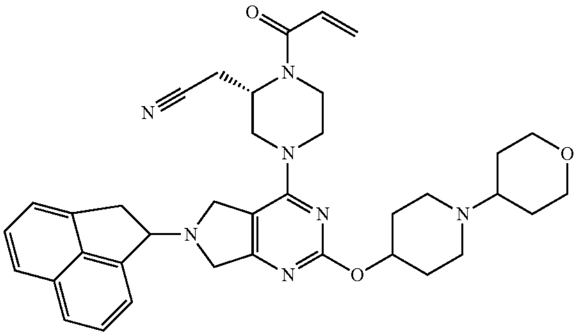 [SMILES: C=CC(=O)N1CCN(c2nc(OC3CCN(C4CCOCC4)CC3)nc3c2CN(C2Cc4cccc5cccc2c45)C3)C[C@@H]1CC#N]

Synthetic Route:

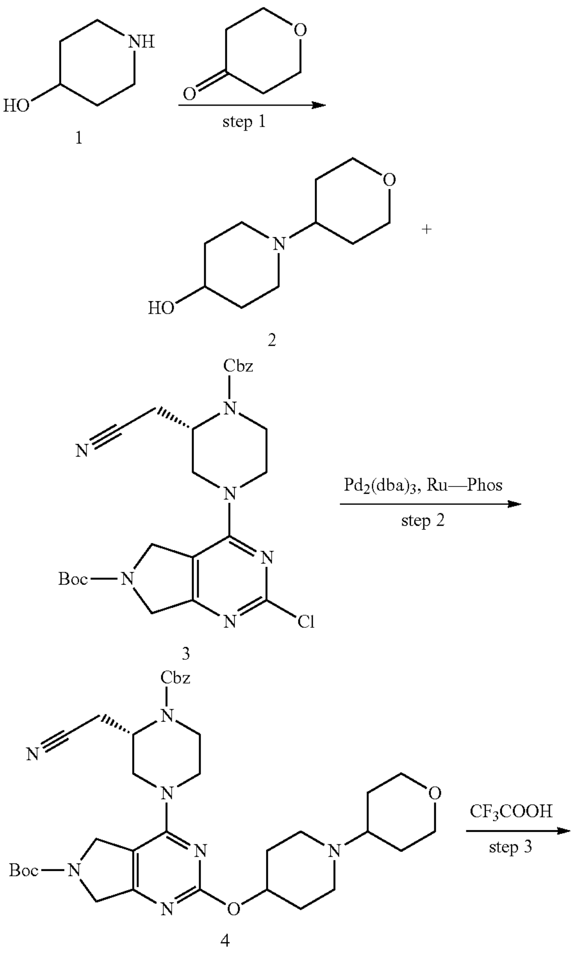

-continued

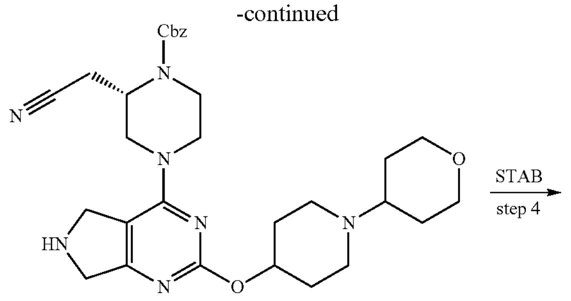

5

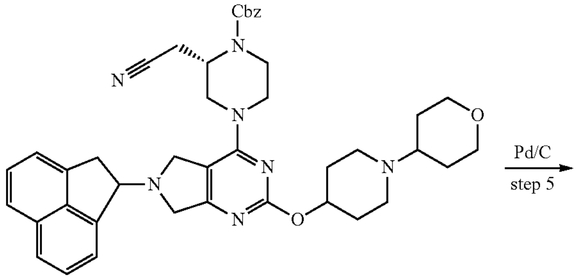

6

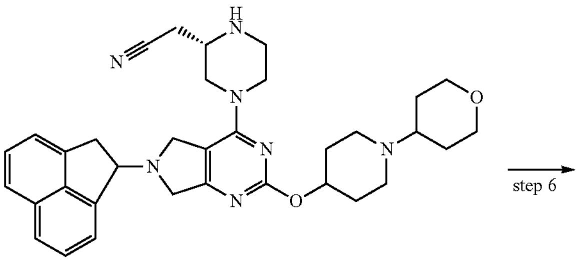

7

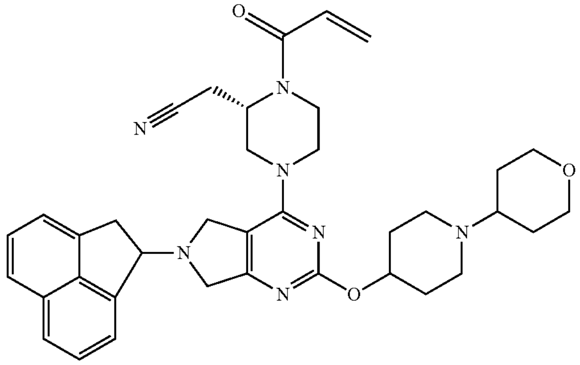

Step 1: 1-(tetrahydro-2H-pyran-4-yl)piperidin-4-ol

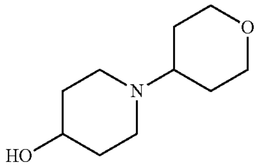 [SMILES: OC1CCN(C2CCOCC2)CC1]

To a solution piperidin-4-ol (1.50 g, 14.85 mmol), tetrahydro-4H-pyran-4-one (1.00 g, 10.00 mmol) in titanium tetraisopropanolate (5.70 g, 20.05 mmol) was stirred at room temperature for 16 h. Then it was added methanol 20 mL at 0° C., and potassium borohydride (1.08 g, 20.02 mmol) was added at 0° C. over 0.5 h. The mixture was stirred at 0° C. for 1 h. It was added 1N sodium hydrate (40 mL) and it was added ethyl acetate. After that it was filtered, the aqueous layer was extracted with ethyl acetate and the organic layer was combined, dried over sodium sulfate and evaporated. The residue was purified by chromatography column on silica to give the title product (550 mg, 29.7%). MS (ESI, m/e) $[M+1]^+$ 185.9.

Step 2: tert-butyl (S)-4-(4-((benzyloxy)carbonyl)-3-(cyanomethyl)piperazin-1-yl)-2-((1-(tetrahydro-2H-pyran-4-yl)piperidin-4-yl)oxy)-5, 7-dihydro-6H-pyrrolo[3, 4-d]pyrimidine-6-carboxylate

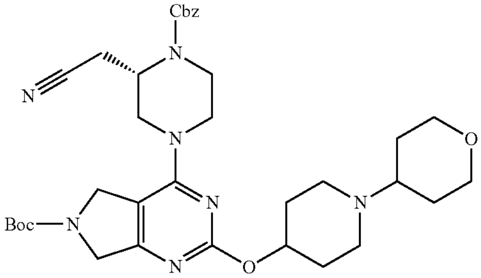 [SMILES: CC(C)(C)OC(=O)N1Cc2nc(OC3CCN(C4CCOCC4)CC3)nc(N3CCN(C(=O)OCc4ccccc4)[C@@H](CC#N)C3)c2C1]

To a solution of tert-butyl (S)-4-(4-((benzyloxy)carbonyl)-3-(cyanomethyl)piperazin-1-yl)-2-chloro-5, 7-dihydro-6H-pyrrolo[3, 4-d]pyrimidine-6-carboxylate (200 mg, 0.39 mmol), 1-(tetrahydro-2H-pyran-4-yl)piperidin-4-ol (110 mg, 0.59 mmol), tris(dibenzylideneacetone)dipalladium (38 mg, 0.04 mmol), 2-dicyclohexylphosphino-2', 6'-di-i-propoxy-1, 1'-biphenyl (38 g, 0.08 mmol) and cesium carbonate (320 mg, 1.00 mmol) in 6 mL toluene was stirred at 105° C. for 16 h under nitrogen atmosphere. Then it was cooled down to room temperature. It was filtered and the filtrate was diluted with dichloromethane and water and the organic layer was combined, dried over sodium sulfate and evaporated. The residue was purified by chromatography column on silica to give the title product (170 mg, 65.8%). MS (ESI, m/e) $[M+1]^+$ 661.9.

Step 3: benzyl (S)-2-(cyanomethyl)-4-(2-((1-(tetrahydro-2H-pyran-4-yl)piperidin-4-yl)oxy)-6, 7-dihydro-5H-pyrrolo[3, 4-d]pyrimidin-4-yl)piperazine-1-carboxylate

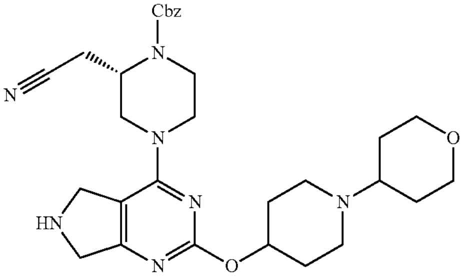 [SMILES: N#CC[C@H]1CN(c2nc(OC3CCN(C4CCOCC4)CC3)nc3c2CNC3)CCN1C(=O)OCc1ccccc1]

To a solution tert-butyl (S)-4-(4-((benzyloxy)carbonyl)-3-(cyanomethyl)piperazin-1-yl)-2-((1-(tetrahydro-2H-pyran-4-yl)piperidin-4-yl)oxy)-5, 7-dihydro-6H-pyrrolo[3, 4-d]pyrimidine-6-carboxylate (240 mg, 0.36 mmol) in 15 mL dichloromethane was added 4 mL trifluoroacetic acid. And it was stirred at room temperature for 4 h. Then it was evaporated below 35° C. The residue was diluted with dichloromethane:isopropyl alcohol=5:1 and water, the organic layer was combined, dried over sodium sulfate and evaporated to give crude product (300) mg without further purification. MS (ESI, m/e) $[M+1]^+$ 561.9.

Step 4: benzyl (2S)-2-(cyanomethyl)-4-(6-(1, 2-dihydroacenaphthylen-1-yl)-2-((1-(tetrahydro-2H-pyran-4-yl)piperidin-4-yl)oxy)-6, 7-dihydro-5H-pyrrolo[3, 4-d]pyrimidin-4-yl)piperazine-1-carboxylate

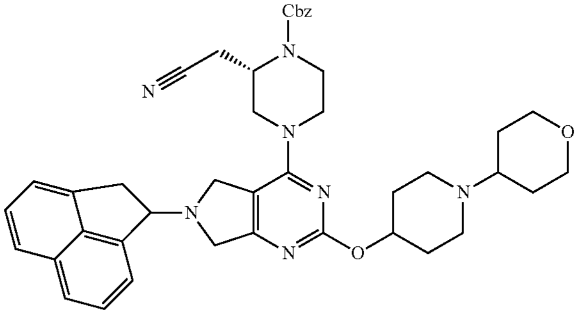 [SMILES: N#CC[C@H]1CN(c2nc(OC3CCN(C4CCOCC4)CC3)nc3c2CN(C2Cc4cccc5cccc2c45)C3)CCN1C(=O)OCc1ccccc1]

To a solution of crude benzyl (S)-2-(cyanomethyl)-4-(2-((1-(tetrahydro-2H-pyran-4-yl)piperidin-4-yl)oxy)-6, 7-dihydro-5H-pyrrolo[3, 4-d]pyrimidin-4-yl)piperazine-1-carboxylate (300 mg) in 5 mL dichloromethane was added acenaphthylene-1(2H)-one (156 mg, 1.00 mmol). After the addition, the mixture was stirred at room temperature for 10 min. Then it was added sodium triacetoxyborohydride (420 mg, 1.99 mmol). Then it was stirred at room temperature for 2 h, it was diluted with dichloromethane and water. The organic layer was combined, dried over sodium sulfate and evaporated. The residue was purified by chromatography column on silica to give the title product (240 mg, 77.4% in two steps). MS (ESI, m/e) $[M+1]^+$ 713.9.

Step 5: 2-((2S)-4-(6-(1, 2-dihydroacenaphthylen-1-yl)-2-((1-(tetrahydro-2H-pyran-4-yl)piperidin-4-yl)oxy)-6, 7-dihydro-5H-pyrrolo[3, 4-d]pyrimidin-4-yl)piperazin-2-yl)acetonitrile

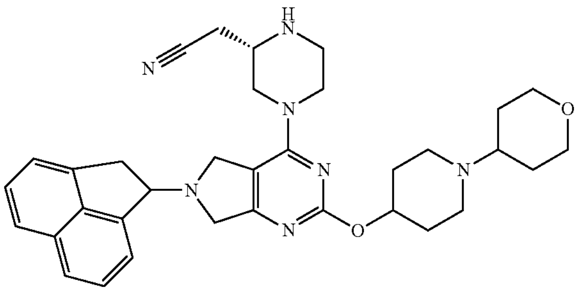 [SMILES: N#CC[C@H]1CN(c2nc(OC3CCN(C4CCOCC4)CC3)nc3c2CN(C2Cc4cccc5cccc2c45)C3)CCN1]

To a solution of benzyl (2S)-2-(cyanomethyl)-4-(6-(1, 2-dihydroacenaphthylen-1-yl)-2-((1-(tetrahydro-2H-pyran-4-yl)piperidin-4-yl)oxy)-6, 7-dihydro-5H-pyrrolo[3, 4-d]pyrimidin-4-yl)piperazine-1-carboxylate (200 mg, 0.16 mmol) in ethanol (3 mL) and tetrahydrofuran (3 mL) was added 10% Pd/C (20 mg) and it was stirred at room temperature for 48 h under hydrogen atmosphere. Then it was filtered and the filtrate was evaporated. The residue was used as crude for next step (140 mg, 86.2%). MS (ESI, m/e) $[M+1]^+$ 580.0.

Step 6: 2-((2S)-1-acryloyl-4-(6-(1, 2-dihydroacenaphthylen-1-yl)-2-((1-(tetrahydro-2H-pyran-4-yl)piperidin-4-yl)oxy)-6, 7-dihydro-5H-pyrrolo[3, 4-d]pyrimidin-4-yl)piperazin-2-yl)acetonitrile

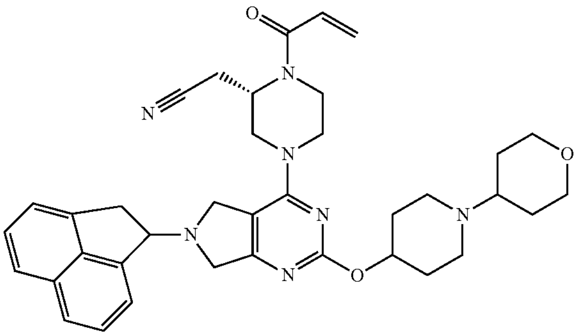 [SMILES: C=CC(=O)N1CCN(c2nc(OC3CCN(C4CCOCC4)CC3)nc3c2CN(C2Cc4cccc5cccc2c45)C3)C[C@@H]1CC#N]

To a solution of 2-((2S)-4-(6-(1, 2-dihydroacenaphthylen-1-yl)-2-((1-(tetrahydro-2H-pyran-4-yl)piperidin-4-yl)oxy)-6, 7-dihydro-5H-pyrrolo[3, 4-d]pyrimidin-4-yl)piperazin-2-yl)acetonitrile (100 mg, 0.16 mmol) in 5 mL dichloromethane was added 0.3 mL triethylamine and it was stirred at −70° C., then it was added acryloyl chloride (18 mg, 0.20 mmol) and it was stirred at −70° C. for 1 h. Then it was diluted with dichloromethane and water and the organic layer was combined, dried over sodium sulfate and evaporated. The residue was purified by Prep-TLC to give Example 12 (4 mg, 3.6%). $^1H$ NMR (400 MHz, DMSO-$d_6$) δ ppm: 7.84-7.66 (m, 2H), 7.62-7.47 (m, 3H), 7.42-7.31 (m, 1H), 6.85-6.70 (m, 1H), 6.21-6.07 (m, 1H), 5.83-5.70 (m, 1H), 5.23-5.07 (m, 1H), 5.05-4.96 (m, 1H), 4.93-4.81 (m, 1H), 4.80-4.66 (m, 1H), 4.41-4.10 (m, 4H), 4.08-3.88 (m, 3H), 3.88-3.64 (m, 3H), 3.64-3.46 (m, 3H), 3.46-3.40 (m, 2H), 3.20-2.81 (m, 8H), 2.24-2.08 (m, 1H), 2.07-1.88 (m, 3H), 1.88-1.74 (m, 1H), 1.73-1.60 (m, 2H). MS (ESI, m/e) $[M+1]^+$ 634.8.

Example 13: 2-((2S)-1-acryloyl-4-(6-(1, 2-dihydroacenaphthylen-1-yl)-2-((S)-2-(hydroxymethyl)pyrrolidin-1-yl)-6, 7-dihydro-5H-pyrrolo[3, 4-d]pyrimidin-4-yl)piperazin-2-yl)acetonitrile
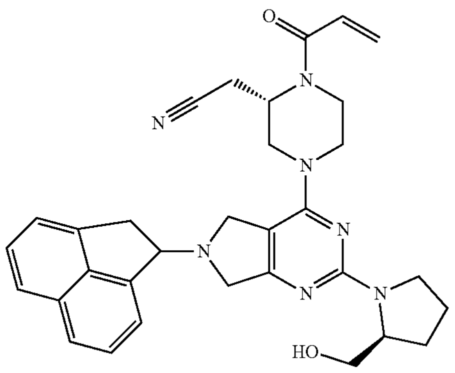 [SMILES: C=CC(=O)N1CCN(c2nc(N3CCC[C@H]3CO)nc3c2CN(C2Cc4cccc5cccc2c45)C3)C[C@@H]1CC#N]
Synthetic Route:
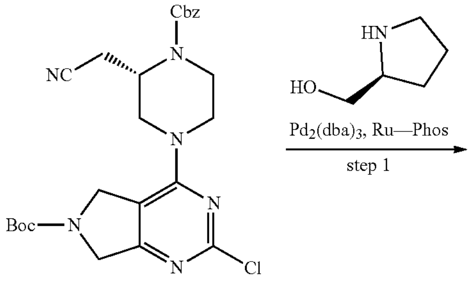
1
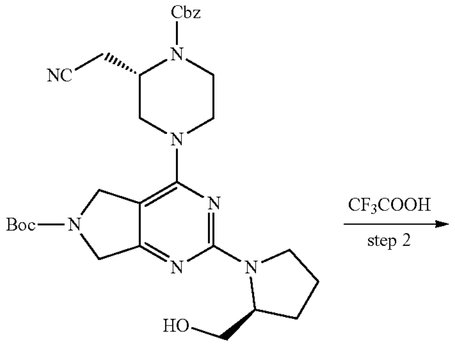
2
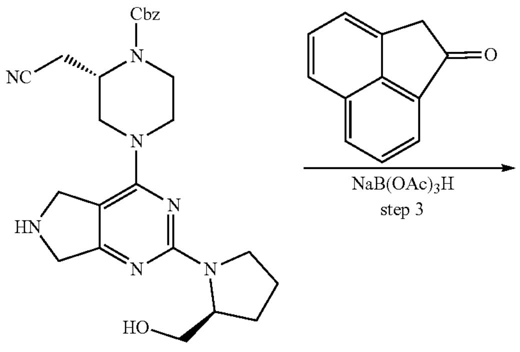
3
-continued
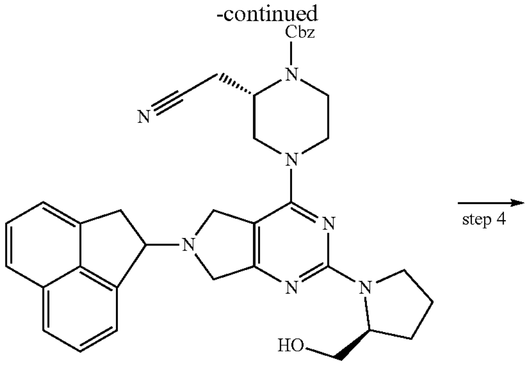
4
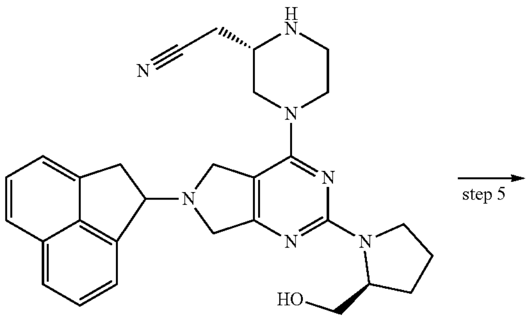
5
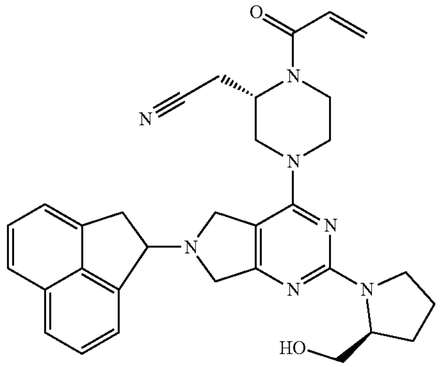
Step 1: tert-butyl(4-((S)-4-((benzyloxy)carbonyl)-3-(cyanomethyl)piperazin-1-yl)-2-((S)-2-(hydroxymethyl)pyrrolidin-1-yl)-5, 7-dihydro-6H-pyrrolo[3, 4-d]pyrimidine-6-carboxylate
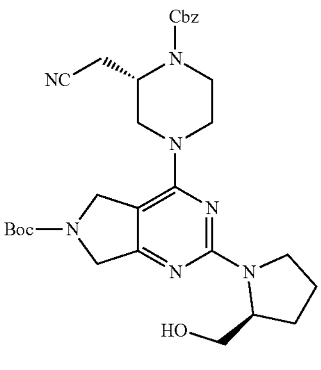 [SMILES: CC(C)(C)OC(=O)N1Cc2nc(N3CCC[C@H]3CO)nc(N3CCN(C(=O)OCc4ccccc4)[C@@H](CC#N)C3)c2C1]

To a suspension of tert-butyl (S)-4-(4-((benzyloxy)carbonyl)-3-(cyanomethyl)piperazin-1-yl)-2-chloro-5, 7-dihydro-6H-pyrrolo[3, 4-d]pyrimidine-6-carboxylate (18.40 g, 35.93 mmol), (S)-prolinol-2-ylmethanol (7.20 g, 62.60 mmol), tris(dibenzylideneacetone)dipalladium (3.30 g, 3.61 mmol), 2-dicyclohexylphosphino-2', 6'-di-i-propoxy-1, 1'-biphenyl (3.30 g, 7.07 mmol) and cesium carbonate (35.0 g 108.02 mmol) in 200 mL toluene was stirred at 100° C. for 3 h under nitrogen atmosphere. Then it was cooled down to room temperature. It was filtered and the filtrate was diluted with dichloromethane and water and the organic layer was combined, dried over sodium sulfate and evaporated. The residue was purified by chromatography column on silica to give the title product (6.00 g, 28.9%). MS (ESI, m/e) $[M+1]^+$ 577.9.

Step 2: benzyl (S)-2-(cyanomethyl)-4-(2-((S)-2-(hydroxymethyl)pyrrolidine-1-yl)-6, 7-dihydro-5H-pyrrolo[3, 4-d]pyrimidin-4-yl)piperazine-1-carboxylate

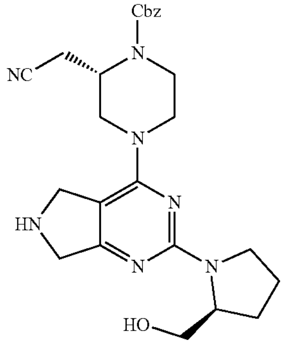 [SMILES: N#CC[C@H]1CN(c2nc(N3CCC[C@H]3CO)nc3c2CNC3)CCN1C(=O)OCc1ccccc1]

To a solution tert-butyl 4-((S)-4-((benzyloxy)carbonyl)-3-(cyanomethyl)piperazin-1-yl)-2-((S)-2-(hydroxymethyl) pyrrolidin-1-yl)-5, 7-dihydro-6H-pyrrolo[3, 4-d]pyrimidine-6-carboxylate (1.70 g, 2.95 mmol) in 8 mL dichloromethane was added 2 mL trifluoroacetic acid. And it was stirred at room temperature for 2 h. Then it was evaporated below 35° C. The residue was diluted with dichloromethane:isopropyl alcohol=5:1 and water, the organic layer was combined, dried over sodium sulfate and evaporated to give the title product (1.10 g, 78.3%) without further purification. MS (ESI, m/e) $[M+1]^+$ 477.9.

Step 3: benzyl (2S)-2-(cyanomethyl)-4-(6-(1, 2-dihydroacenaphthylen-1-yl)-2-((S)-2-(hydroxymethyl) pyrrolidin-1-yl)-6, 7-dihydro-5H-pyrrolo[3, 4-d] pyrimidin-4-yl)piperazine-1-carboxylate

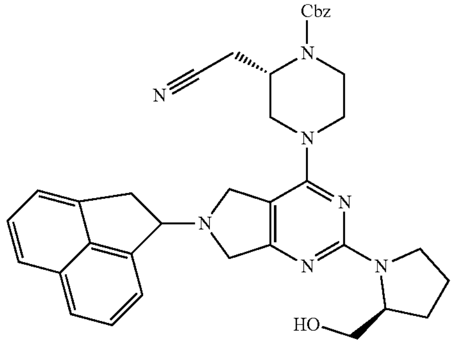 [SMILES: N#CC[C@H]1CN(c2nc(N3CCC[C@H]3CO)nc3c2CN(C2Cc4cccc5cccc2c45)C3)CCN1C(=O)OCc1ccccc1]

To a solution of benzyl (S)-2-(cyanomethyl)-4-(2-((S)-2-(hydroxymethyl)pyrrolidine-1-yl)-6, 7-dihydro-5H-pyrrolo [3, 4-d]pyrimidin-4-yl)piperazine-1-carboxylate (200 mg, 0.42 mmol) in 5 mL dichloromethane was added acenaphthylen-1(2H)-one (70 mg, 0.42 mmol). After the addition, the mixture was stirred at room temperature for 10 min. Then it was added sodium triacetoxyborohydride (260 mg, 1.23 mmol). Then it was stirred at room temperature for 2 h, it was diluted with dichloromethane and water. The organic layer was combined, dried over sodium sulfate and evaporated. The residue was purified by chromatography column on silica to the title product (140 mg, 53.0%). MS (ESI, m/e) $[M+1]^+$ 629.9.

Step 4: 2-((2S)-4-(6-(1, 2-dihydroacenaphthylen-1-yl)-2-((S)-2-(hydroxymethyl)pyrrolidin-1-yl)-6, 7-dihydro-5H-pyrrolo[3, 4-d]pyrimidin-4-yl)piperazin-2-yl)acetonitrile

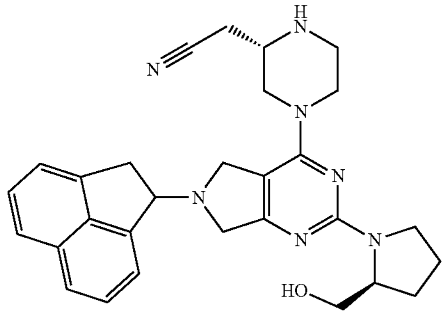 [SMILES: N#CC[C@H]1CN(c2nc(N3CCC[C@H]3CO)nc3c2CN(C2Cc4cccc5cccc2c45)C3)CCN1]

To a solution of benzyl (2S)-2-(cyanomethyl)-4-(6-(1, 2-dihydroacenaphthylen-1-yl)-2-((S)-2-(hydroxymethyl) pyrrolidin-1-yl)-6, 7-dihydro-5H-pyrrolo[3, 4-d]pyrimidin-4-yl)piperazine-1-carboxylate (140 mg, 0.22 mmol) in methanol (5 mL) and tetrahydrofuran (5 mL) was added 10% Pd/C (100 mg) and it was stirred at room temperature for 16 h under hydrogen atmosphere. Then it was filtered and the filtrate was evaporated. The residue was not purified and continued the next step to give crude title product (100 mg, 90.7%). MS (ESI, m/e) $[M+1]^+$ 495.9.

Step 5: 2-((2S)-1-acryloyl-4-(6-(1, 2-dihydroacenaphthylen-1-yl)-2-((S)-2-(hydroxymethyl)pyrrolidin-1-yl)-6, 7-dihydro-5H-pyrrolo[3, 4-d]pyrimidin-4-yl)piperazin-2-yl)acetonitrile

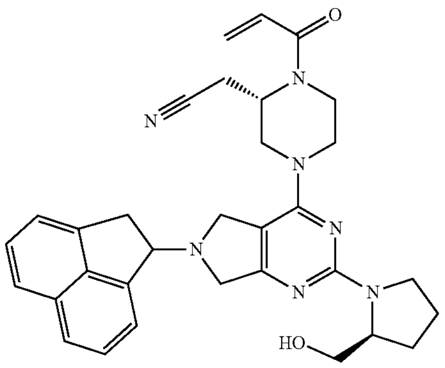 [SMILES: C=CC(=O)N1CCN(c2nc(N3CCC[C@H]3CO)nc3c2CN(C2Cc4cccc5cccc2c45)C3)C[C@@H]1CC#N]

To a solution of 2-((2S)-4-(6-(1, 2-dihydroacenaphthylen-1-yl)-2-((S)-2-(hydroxymethyl)pyrrolidin-1-yl)-6, 7-dihydro-5H-pyrrolo[3, 4-d]pyrimidin-4-yl)piperazin-2-yl)acetonitrile (100 mg, 0.20 mmol) in 5 mL dichloromethane was added 0.2 mL triethylamine and it was stirred at 0° C., then it was added acryloyl chloride (27 mg, 0.30 mmol) and it was stirred at 0° C. for 1 h. Then it was diluted with dichloromethane and water and the organic layer was combined, dried over sodium sulfate and evaporated. The residue was purified by Prep-TLC to give Example 13 (8 mg, 6.9%). $^1$H NMR (400 MHz, DMSO-$d_6$) δ ppm: 7.85-7.62 (m, 2H), 7.62-7.52 (m, 2H), 7.43-7.25 (m, 3H), 6.90-6.74 (m, 1H), 6.24-6.10 (m, 1H), 5.80-5.71 (m, 1H), 5.20-5.01 (m, 2H), 4.96-4.82 (m, 1H), 4.79-4.60 (m, 1H), 4.41-4.10 (m, 3H), 4.07-3.87 (m, 3H), 3.73-3.52 (m, 3H), 3.50-3.39 (m, 2H), 3.09-2.90 (m, 4H), 2.89-2.76 (m, 2H), 2.01-1.68 (m, 4H). MS (ESI, m/e) $[M+1]^+$ 550.6.

Example 14: 2-((2S)-1-acryloyl-4-(6-(1, 2-dihydroacenaphthylen-1-yl)-2-((R)-1-(pyridin-4-yl)ethoxy)-6, 7-dihydro-5H-pyrrolo[3, 4-d]pyrimidin-4-yl)piperazin-2-yl)acetonitrile

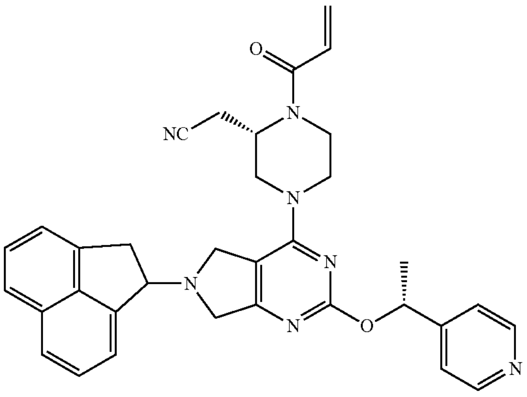 [SMILES: C=CC(=O)N1CCN(c2nc(O[C@H](C)c3ccncc3)nc3c2CN(C2Cc4cccc5cccc2c45)C3)C[C@@H]1CC#N]

Synthetic Route:

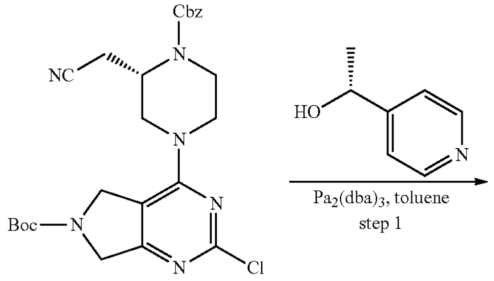

1

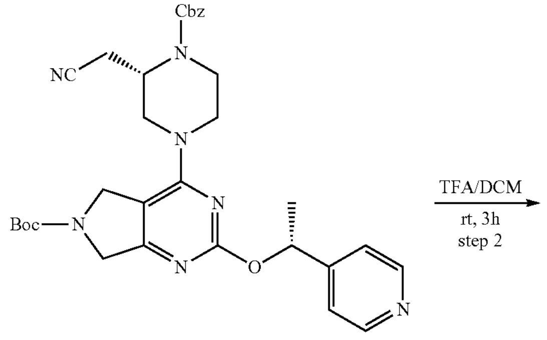

2

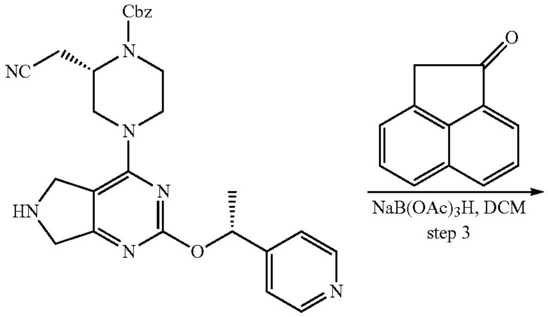

3

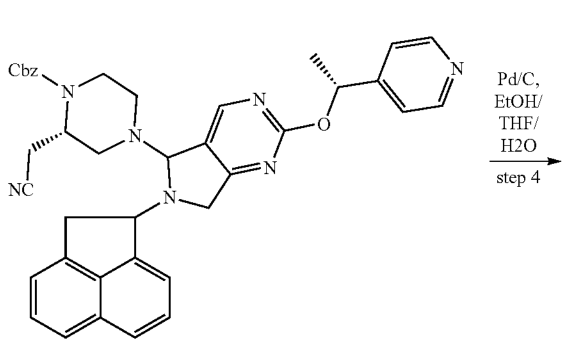

4

-continued

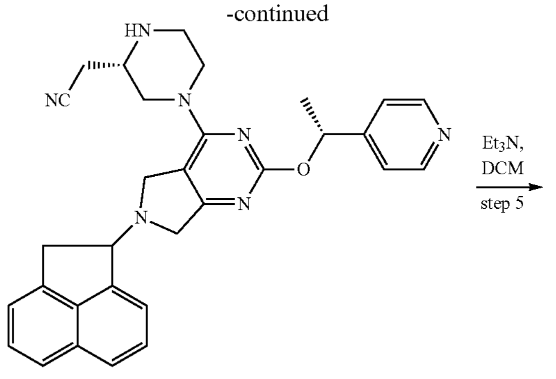

5

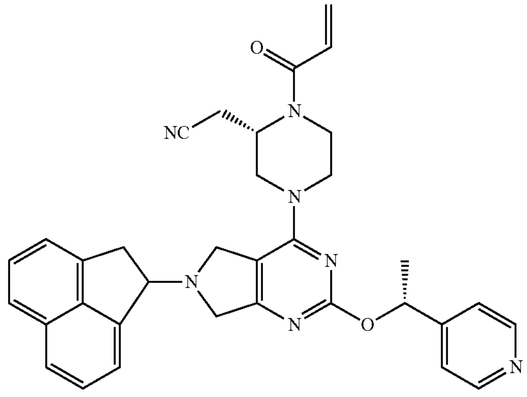

6

Step 1: tert-butyl 4-((S)-4-((benzyloxy)carbonyl)-3-(cyanomethyl)piperazin-1-yl)-2-((R)-1-(pyridin-4-yl) ethoxy)-5, 7-dihydro-6H-pyrrolo[3, 4-d]pyrimidine-6-carboxylate A solution of tert-butyl (S)-4-(4-((benzyloxy)carbonyl)-3-(cyanomethyl)piperazin-1-yl)-2-chloro-5, 7-dihydro-6H-pyrrolo[3, 4-d]pyrimidine-6-carboxylate (0.91 g, 1.7 mmol) and (R)-1-(pyridin-4-yl)ethan-1-ol (0.26 g, 2.1 mmol) in toluene (20 mL) was added $Cs_2CO_3$ (1.16 g, 3.6 mmol), $Pd_2(dba)_3$ (0.16 g, 0.017 mmol), Ru-Phos (0.16 g, 0.035 mmol), the mixture was stirred for 3 hours at 100° C. The mixture reaction was filtered, the filtrate was concentrated to dryness, then diluted with DCM and $H_2O$, extracted with DCM, washed with brine, dried over $Na_2SO_4$, concentrated and purified by the Combi flash give the title compound (0.9 g). MS(ESI): m/z 600.4 [M+1].

Step 2: benzyl (S)-2-(cyanomethyl)-4-(2-((R)-1-(pyridin-4-yl)ethoxy)-6, 7-dihydro-5H-pyrrolo[3, 4-d]pyrimidin-4-yl)piperazine-1-carboxylate A solution of tert-butyl 4-((S)-4-((benzyloxy)carbonyl)-3-(cyanomethyl)piperazin-1-yl)-2-((R)-1-(pyridin-4-yl) ethoxy)-5, 7-dihydro-6H-pyrrolo[3, 4-d]pyrimidine-6-carboxylate (1.5 g, 2.5 mmol) in TFA/DCM=1/3 (33 mL) was stirred at rt for 1.5 h, then concentrated to dryness, the residual was dissolved into $H_2O$ (20 mL), extracted with DCM, discarded the organic layer, adjusted the pH=8-9 with $Na_2CO_3$, extracted with DCM, washed with brine, dried over $Na_2SO_4$, concentrated to dryness give the title compound (1.2 g). MS(ESI): m/z 500.2 [M+1].

Step 3: benzyl (2S)-2-(cyanomethyl)-4-(6-(1, 2-dihydroacenaphthylen-1-yl)-2-((R)-1-(pyridin-4-yl) ethoxy)-6, 7-dihydro-5H-pyrrolo[3, 4-d]pyrimidin-4-yl)piperazine-1-carboxylate A solution of benzyl (S)-2-(cyanomethyl)-4-(2-((R)-1-(pyridin-4-yl)ethoxy)-6, 7-dihydro-5H-pyrrolo[3, 4-d]pyrimidin-4-yl)piperazine-1-carboxylate (0.25 g, 0.5 mmol) in DCE (10 mL) was cooed to −30° C., acenaphthylen-1(2H)-one (0.13 g, 0.75 mmol) was added, the mixture was stirred for 5 min, then STAB (0.42 g, 2.0 mmol) was added, the mixture was stirred for overnight at rt. The mixture reaction was quenched with saturated ammonium chloride solution, extracted with DCM, washed with brine, dried over $Na_2SO_4$, concentrated and purified by the Combi flash give the title compound (0.27 g). MS(ESI): m/z 651.9 [M+1]

Step 4: 2-((2S)-4-(6-(1, 2-dihydroacenaphthylen-1-yl)-2-((R)-1-(pyridin-4-yl)ethoxy)-6, 7-dihydro-5H-pyrrolo[3, 4-d]pyrimidin-4-yl)piperazin-2-yl)acetonitrile A solution of benzyl (2S)-2-(cyanomethyl)-4-(6-(1, 2-dihydroacenaphthylen-1-yl)-2-((R)-1-(pyridin-4-yl)ethoxy)-6, 7-dihydro-5H-pyrrolo[3, 4-d]pyrimidin-4-yl)piperazine-1-carboxylate (0.27 g 0.4 mmol) in EtOH/THF/$H_2O$=5 mL/5 mL/0.05 mL (10.05 mL), was added Pd/C (20%, 0.13 g), the mixture was stirred for overnight at rt. The mixture reaction was filtered, the filtrate was concentrated to dryness and purified by the Combi flash give the title compound (0.12 g). MS(ESI): m/z 518.4 [M+1].

Step 5: 2-((2S)-1-acryloyl-4-(6-(1, 2-dihydroacenaphthylen-1-yl)-2-((R)-1-(pyridin-4-yl)ethoxy)-6, 7-dihydro-5H-pyrrolo[3, 4-d]pyrimidin-4-yl piperazin-2-yl)acetonitrile

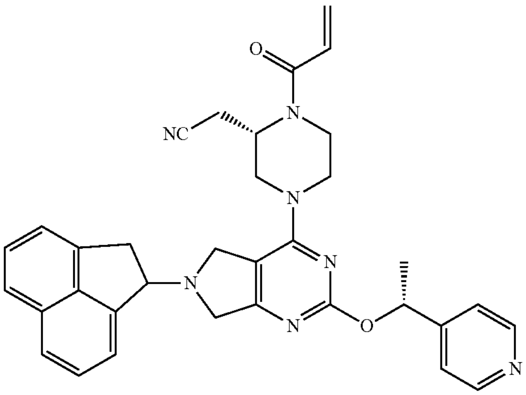 [SMILES: C=CC(=O)N1CCN(c2nc(O[C@H](C)c3ccncc3)nc3c2CN(C2Cc4cccc5cccc2c45)C3)C[C@@H]1CC#N]

A solution of 2-((2S)-4-(6-(1, 2-dihydroacenaphthylen-1-yl)-2-((R)-1-(pyridin-4-yl)ethoxy)-6, 7-dihydro-5H-pyrrolo [3, 4-d]pyrimidin-4-yl)piperazin-2-yl)acetonitrile (0.12 g, 0.23 mmol) in DCM (8 mL) was added $Et_3N$ (0.05 g, 0.46 mmol), the mixture was cooled to −70° C., then acryloyl chloride (1 d) was added, the mixture was stirred for 10 min at −70° C., quenched with saturated ammonium chloride solution, extracted with DCM, washed with brine, dried over $Na_2SO_4$, concentrated and purified by the Combi flash give Example 14 (0.04 mg). $^1H$ NMR (400 MHz, DMSO-d6) δ 8.52 (d, J=4.4 Hz, 2H), δ 7.75 (d, J=7.6 Hz, 1H), 7.68 (d, J=8.0 Hz, 1H), 7.58-7.42 (m, 3H), 7.41-7.27 (m, 3H), 6.81

(s, 1H), 6.16 (d, J=16.8 Hz, 1H), 5.95 (s, 1H), 5.76 (s, 1H), 5.10 (s, 1H), 4.86-4.66 (m, 1H), 4.23-3.36 (m, 10H), 3.23-2.66 (m, 4H), 1.52 (d, J=6.5 Hz, 3H). MS(ESI): m/z 572.6 [M+1]

Example 15: 2-((S)-1-acryloyl-4-(6-((S)-1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile and 2-((S)-1-acryloyl-4-(6-((R)-1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile

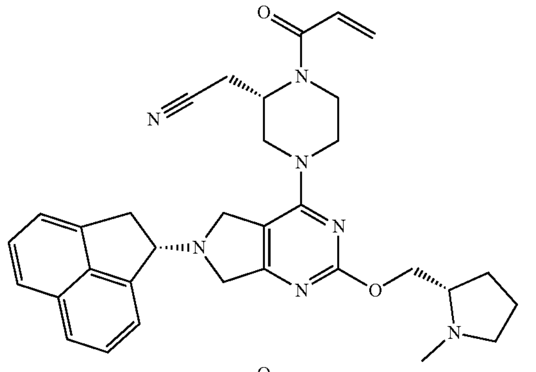

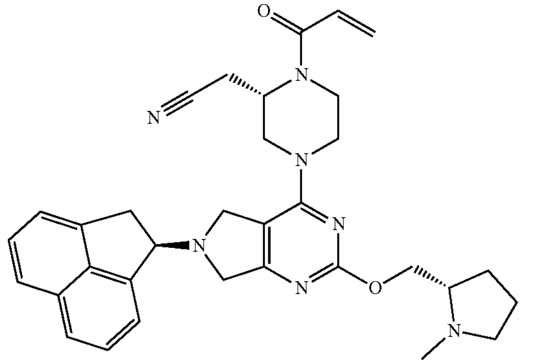

Step 1: Benzyl (2S)-2-(cyanomethyl)-4-(6-(1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazine-1-carboxylate

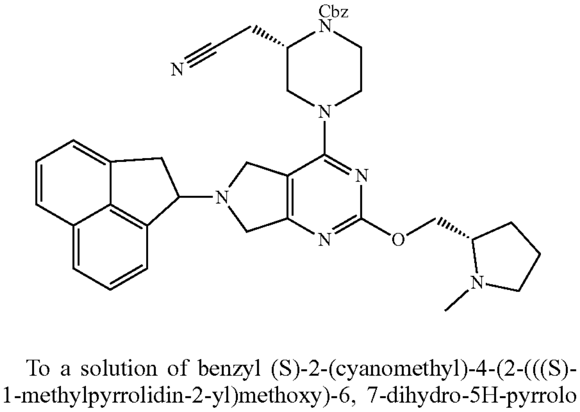

To a solution of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (800 mg, 1.63 mmol) and acenaphthylen-1(2H)-one (168 mg, 2.44 mmol) in DCM (20 mL) was added $NaB(OAc)_3H$ (517 mg, 2.44 mmol) at room temperature. The reaction solution was stirred at room temperature overnight. The solvent was concentrated to dryness. The residue was purified with chromatography on silica gel (DCM/MeOH=20:1 to 10:1) to obtain the title compounds (500 mg, 47.7% yield). MS (ESI) m/e $[M+H]^+$ 643.9.

Step 2: 2-((2S)-4-(6-(1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile

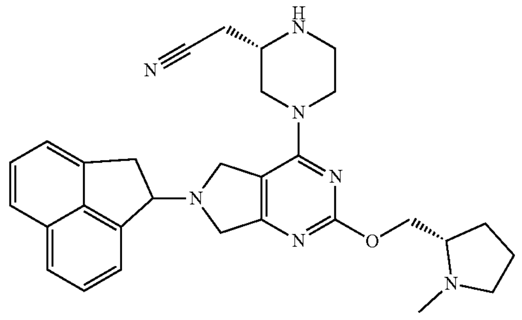 [SMILES: CN1CCC[C@H]1COc1nc2c(c(N3CCN[C@@H](CC#N)C3)n1)CN(C1Cc3cccc4cccc1c34)C2]

To s solution of benzyl (2S)-2-(cyanomethyl)-4-(6-(1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazine-1-carboxylate (500 mg, 0.78 mmol) in MeOH (10 mL) and $NH_3$/MeOH (7M, 1 mL) was added Pd/C (400 mg) at room temperature. The reaction mixture was stirred at room temperature for 2 h under $H_2$ atmosphere (4 atm). The reaction mixture was filtered over celite and evaporated in vacuo to obtain the target compounds. The crude products were used in the next step. MS (ESI) m/e $[M+H]^+$ 509.9.

Step 3: 2-((S)-1-acryloyl-4-(6-((S)-1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile and 2-((S)-1-acryloyl-4-(6-((R)-1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile

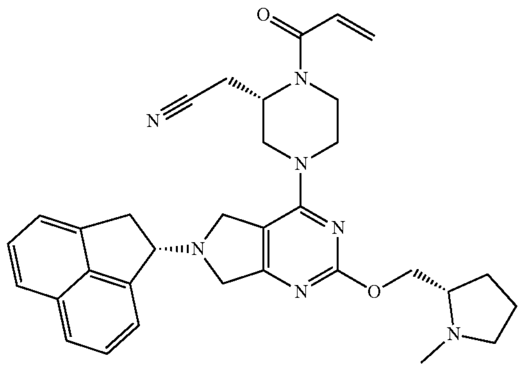

-continued

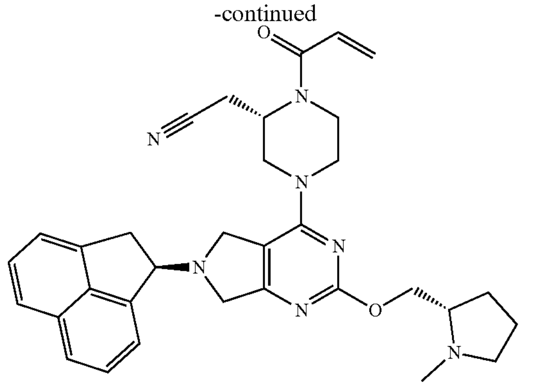

To a solution of 2-((2S)-4-(6-(1, 2-dihydroacenaphthylen-1-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile (crude used) and TEA (330 mg, 3.26 mmol) in DCM (10 mL) was added acryloyl chloride (112 mg, 2.61 mmol) at 0° C. The reaction mixture was stirred at 0° C. for 1 h. $H_2O$ (20 mL) was added, the aqueous layer was extracted with DCM (20 mL×2), the combined organic layer was washed with brine (50 mL) and dried over $Na_2SO_4$ The solvent was concentrated to dryness. The residue was purified with pre-HPLC to obtain two isomers (2TFA salt) (10 mg isomer P1, 31 mg isomer P2).

Data for isomer P1: $^1H$ NMR (400 MHz, $CDCl_3$) δ 7.77-7.74 (m, 1H), 7.67-7.65 (m, 2H), 7.32-7.31 (m, 2H), 6.54-6.50 (m, 1H), 6.37-6.33 (m, 1H), 5.80-5.78 (m, 1H), 5.22-5.20 (m, 1H). 4.86-4.69 (m, 3H), 4.51-4.46 (m, 1H), 4.36-4.34 (m, 2H), 4.03-4.01 (m, 2H), 3.93-3.86 (m, 2H), 3.71-3.67 (m, 2H), 3.52-3.30 (m, 2H), 3.29-3.13 (m, 2H), 3.03 (s, 3H), 2.87-2.78 (m, 4H), 2.38-2.33 (m, 1H), 2.19-2.18 (m, 1H), 2.08-2.02 (m, 2H). MS (ESI) m/e $[M+H]^+$ 564.6.

Data for isomer P2: $^1H$ NMR (400 MHz, $CD_3OD$) δ 7.91-7.89 (m, 1H), 7.77-7.75 (m, 2H), 7.64-7.56 (m, 2H), 7.45-7.44 (m, 1H), 6.80-6.70 (m, 1H), 6.28 (d, J=16.4 Hz, 1H), 5.83 (d, J=9.8 Hz, 1H), 5.65-5.63 (m, 1H). 4.86-4.69 (m, 3H), 4.51-4.46 (m, 1H), 4.36-4.34 (m, 2H), 4.03-4.01 (m, 2H), 3.93-3.86 (m, 2H), 3.71-3.67 (m, 2H), 3.52-3.30 (m, 2H), 3.29-3.13 (m, 2H), 3.03 (s, 3H), 2.87-2.78 (m, 4H), 2.38-2.33 (m, 1H), 2.19-2.18 (m, 1H), 2.08-2.02 (m, 2H). MS (ESI) m/e $[M+H]^+$ 564.6.

The following compounds were obtained by similar procedure:

Example 16: 2-((S)-1-acryloyl-4-(6-((S)-1, 2-dihydroacenaphthylen-1-yl)-2-(3-(dimethylamino)azetidin-1-yl)-6, 7-dihydro-5H-pyrrolo[3, 4-d]pyrimidin-4-yl)piperazin-2-yl)acetonitrile and 2-((S)-1-acryloyl-4-(6-((R)-1, 2-dihydroacenaphthylen-1-yl)-2-(3-(dimethylamino)azetidin-1-yl)-6, 7-dihydro-5H-pyrrolo[3, 4-d]pyrimidin-4-ylpiperazin-2-ylacetonitrile

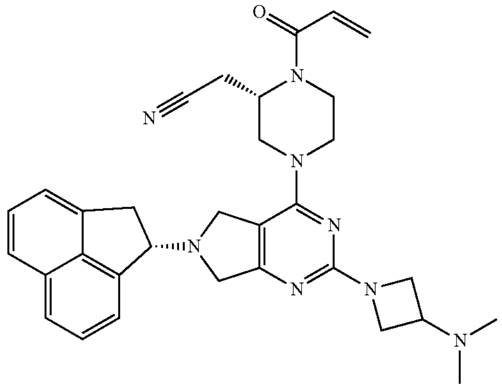

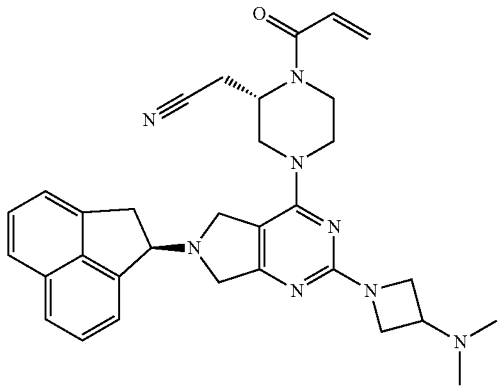

P1: $^1H$ NMR (400 MHz, $CD_3OD$) δ 7.94 (d, J=8.1 Hz, 1H), 7.79-7.77 (m, 2H), 7.66-7.59 (m, 2H), 7.48-7.47 (m, 1H), 6.94-6.66 (m, 1H), 6.28 (d, J=16.3 Hz, 1H), 5.84-5.76 (m, 2H), 4.88-4.87 (m, 2H), 4.69-4.65 (m, 1H), 4.44-4.36 (m, 5H), 4.28-4.15 (m, 3H), 4.01-3.94 (m, 3H), 3.75-3.71 (m, 1H), 3.44-3.30 (m, 2H), 2.91 (s, 6H), 2.84-2.66 (m, 3H). MS (ESI) m/e $[M+H]^+$ 549.6.

P2: $^1H$ NMR (400 MHz, $CD_3OD$) δ 7.94 (d, J=8.1 Hz, 1H), 7.79-7.77 (m, 2H), 7.66-7.59 (m, 2H), 7.48-7.47 (m, 1H), 6.94-6.66 (m, 1H), 6.28 (d, J=16.3 Hz, 1H), 5.84-5.76 (m, 2H), 4.88-4.87 (m, 2H), 4.69-4.65 (m, 1H), 4.44-4.36 (m, 5H), 4.28-4.15 (m, 3H), 4.01-3.94 (m, 3H), 3.75-3.71 (m, 1H), 3.44-3.30 (m, 2H), 2.91 (s, 6H), 2.84-2.66 (m, 3H). MS (ESI) m/e $[M+H]^+$ 549.6.

Example 17: 2-((S)-1-acryloyl-4-(6-((S)-1, 2-dihydroacenaphthylen-1-yl)-2-((1-methylpiperidin-4-yl)oxy)-6, 7-dihydro-5H-pyrrolo[3, 4-d]pyrimidin-4-yl)piperazin-2-yl)acetonitrile and 2-((S)-1-acryloyl-4-(6-((R)-1, 2-dihydroacenaphthylen-1-yl)-2-((1-methylpiperidin-4-yl)oxy)-6, 7-dihydro-5H-pyrrolo[3, 4-d]pyrimidin-4-yl)piperazin-2-yl)acetonitrile

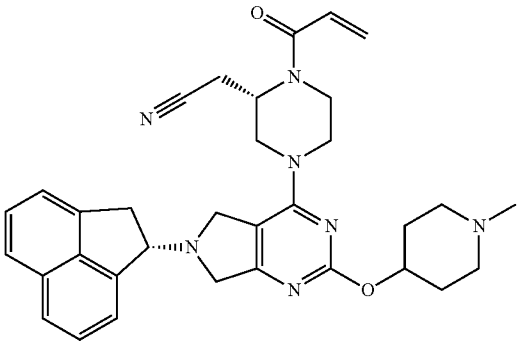

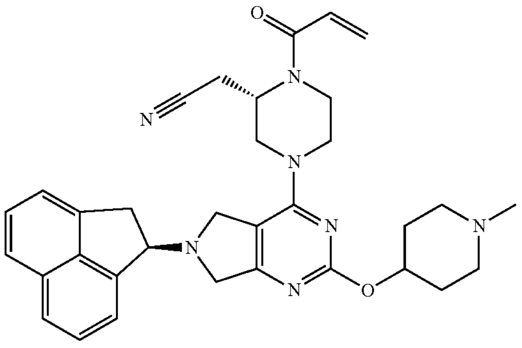

P1: 2.2 mg. $^1$H NMR (400 MHz, $CD_3OD$) δ 7.95 (d, J=8.0 Hz, 1H), 7.80-7.78 (m, 2H), 7.65-7.59 (m, 2H), 7.49-7.48 (m, 1H), 6.92-6.61 (m, 1H), 6.31-6.22 (m, 1H), 5.85-5.82 (m, 2H), 5.39-5.25 (m, 1H), 4.98 (s, 2H), 4.66-4.54 (m, 2H), 4.02-3.96 (m, 3H), 3.79-3.74 (m, 1H), 3.69-3.52 (m, 1H), 3.50-3.43 (m, 3H), 3.30-3.14 (m, 3H), 2.91 (s, 3H), 2.88-2.70 (m, 3H), 2.42-2.08 (m, 4H), 1.92-1.89 (m, 1H). MS (ESI) m/e $[M+H]^+$ 564.6.

P2: 3.8 mg. $^1$H NMR (400 MHz, $CD_3OD$) δ 7.95 (d, J=8.0 Hz, 1H), 7.80-7.78 (m, 2H), 7.65-7.59 (m, 2H), 7.49-7.48 (m, 1H), 6.92-6.61 (m, 1H), 6.31-6.22 (m, 1H), 5.85-5.82 (m, 2H), 5.39-5.25 (m, 1H), 4.98 (s, 2H), 4.66-4.54 (m, 2H), 4.02-3.96 (m, 3H), 3.79-3.74 (m, 1H), 3.69-3.52 (m, 1H), 3.50-3.43 (m, 3H), 3.30-3.14 (m, 3H), 2.91 (s, 3H), 2.88-2.70 (m, 3H), 2.42-2.08 (m, 4H), 1.92-1.89 (m, 1H). MS (ESI) m/e $[M+H]^+$ 564.6.

Example 18: (S)-2-(1-acryloyl-4-(2-((1-methylpiperidin-4-yl)oxy)-6-(naphthalen-1-ylmethyl)-6, 7-dihydro-5H-pyrrolo[3, 4-d]pyrimidin-4-yl)piperazin-2-yl)acetonitrile

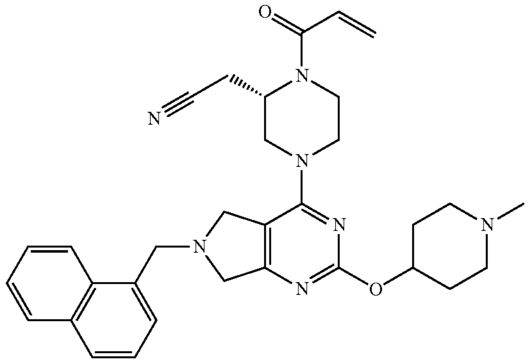 [SMILES: C=CC(=O)N1CCN(c2nc(OC3CCN(C)CC3)nc3c2CN(Cc2cccc4ccccc24)C3)C[C@@H]1CC#N]

$^1$H NMR (400 MHz, DMSO-$d_6$) δ 8.28-8.26 (m, 1H), 7.95-7.86 (m, 2H), 7.57-7.46 (m, 4H), 6.90-6.73 (m, 1H), 6.16 (d, J=16.4 Hz, 1H), 5.75 (d, J=10.0 Hz, 1H), 4.92-4.72 (m, 2H), 4.32-4.20 (m, 3H), 4.10-3.91 (m, 3H), 3.66 (s, 2H), 3.51-3.40 (m, 1H), 3.18-2.87 (m, 3H), 2.88-2.87 (m, 2H), 2.63-2.50 (m, 2H), 2.15-2.09 (m, 5H), 1.93-1.85 (m, 2H), 1.67-1.55 (m, 2H). MS (ESI) m/e $[M+H]^+$ 552.6.

Example 19: (S)-2-(1-acryloyl-4-(2-(3-(dimethylamino)azetidin-1-yl)-6-(naphthalen-1-ylmethyl)-6, 7-dihydro-5H-pyrrolo[3, 4-d]pyrimidin-4-yl)piperazin-2-yl)acetonitrile

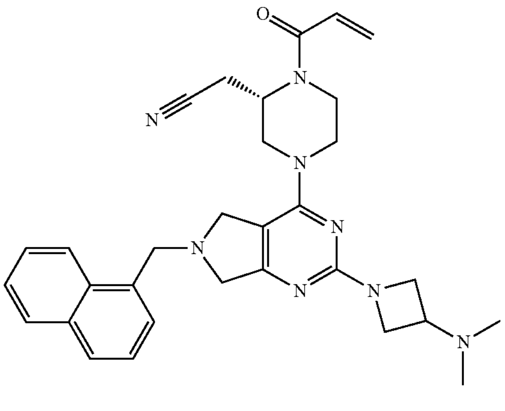 [SMILES: C=CC(=O)N1CCN(c2nc(N3CC(N(C)C)C3)nc3c2CN(Cc2cccc4ccccc24)C3)C[C@@H]1CC#N]

$^1$H NMR (400 MHz, $CD_3OD$) δ 8.24 (d, J=8.4 Hz, 1H), 8.07 (d, J=8.4 Hz, 1H), 8.02 (d, J=8.1 Hz, 1H), 7.80 (d, J=7.0 Hz, 1H), 7.72-7.68 (m, 1H), 7.65-7.59 (m, 2H), 6.87-6.70 (m, 1H), 6.28 (d, J=16.5 Hz, 1H), 5.83 (d, J=10.3 Hz, 1H), 5.09 (s, 2H), 4.90-4.83 (m, 2H), 4.67-4.63 (m, 1H), 4.45-4.37 (m, 4H), 4.31-4.18 (m, 3H), 4.06-3.88 (m, 2H), 3.53-3.36 (m, 2H), 2.91-2.73 (m, 9H). MS (ESI) m/e $[M+H]^+$ 537.6.

Example 20: 2-((S)-1-acryloyl-4-(2-(((S)-1-methylpyrrolidin-2-yl)methoxy)-6-(naphthalen-2-ylmethyl)-6, 7-dihydro-5H-pyrrolo[3, 4-d]pyrimidin-4-yl)piperazin-2-yl)acetonitrile

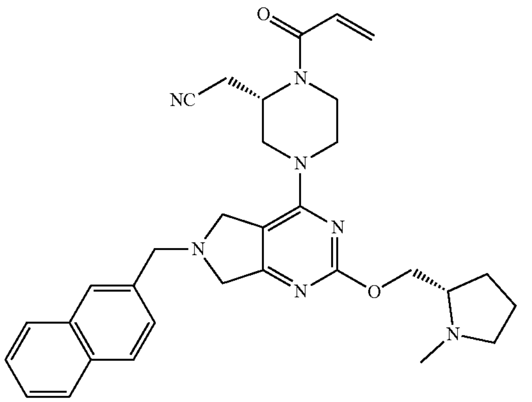 [SMILES: C=CC(=O)N1CCN(c2nc(OC[C@@H]3CCCN3C)nc3c2CN(Cc2ccc4ccccc4c2)C3)C[C@@H]1CC#N]

Synthetic Route:

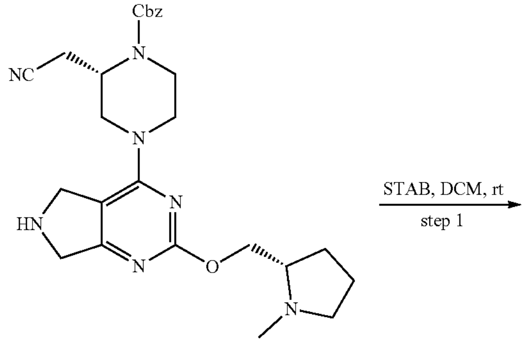

1

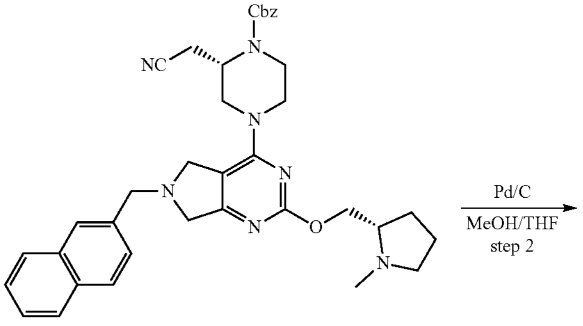

2

-continued

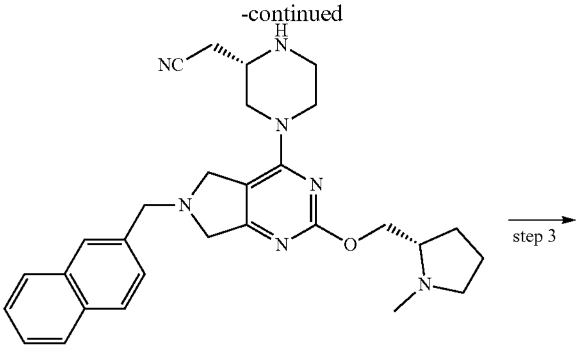

3

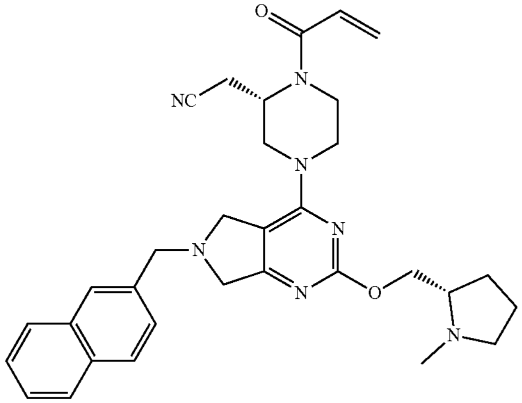

Step 1: benzyl (S)-2-(cyanomethyl)-4-(2-(((S)-1-methylpyrrolidin-2-yl)methoxy)-6-(naphthalen-2-ylmethyl)-6, 7-dihydro-5H-pyrrolo[3, 4-d]pyrimidin-4-yl)piperazine-1-carboxylate

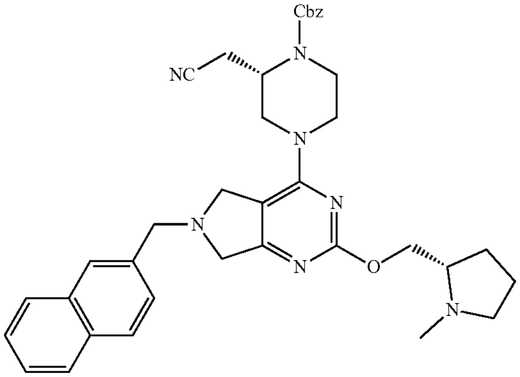 [SMILES: CN1CCC[C@H]1COc1nc2c(c(N3CCN(C(=O)OCc4ccccc4)[C@@H](CC#N)C3)n1)CN(Cc1ccc3ccccc3c1)C2]

To a solution of benzyl (S)-2-(cyanomethyl)-4-(2-(((S)-1-methylpyrrolidin-2-yl)methoxy)-6, 7-dihydro-5H-pyrrolo [3, 4-d]pyrimidin-4-yl)piperazine-1-carboxylate (50 mg, 0.10 mmol) in 5 mL dichloromethane was added 2-naphthaldehyde (31 mg, 0.20 mmol). After the addition, the mixture was stirred at room temperature for 10 min. Then it was added STAB (84 mg, 0.40 mmol). Then it was stirred at room temperature for 2 h, it was diluted with dichloromethane and water. The organic layer was combined, dried over sodium sulfate and evaporated. The residue was purified by chromatography column on silica to give the title product (60 mg, 95.0%). MS (ESI, m/e) $[M+1]^+$ 631.9.

Step 2: 2-((S)-4-(2-(((S)-1-methylpyrrolidin-2-yl)methoxy)-6-(naphthalen-2-ylmethyl)-6, 7-dihydro-5H-pyrrolo[3, 4-d]pyrimidin-4-yl)piperazin-2-yl)acetonitrile

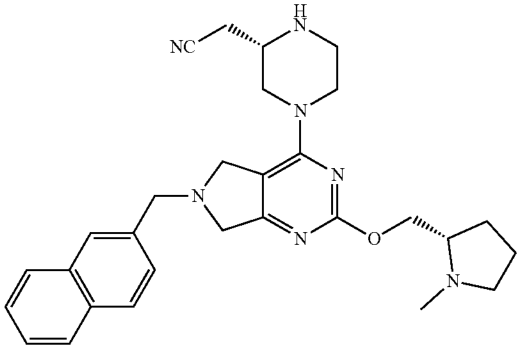 [SMILES: CN1CCC[C@H]1COc1nc2c(c(N3CCN[C@@H](CC#N)C3)n1)CN(Cc1ccc3ccccc3c1)C2]

To a solution of benzyl (S)-2-(cyanomethyl)-4-(2-(((S)-1-methylpyrrolidin-2-yl)methoxy)-6-(naphthalen-2-ylmethyl)-6, 7-dihydro-5H-pyrrolo[3, 4-d]pyrimidin-4-yl)piperazine-1-carboxylate (60 mg, 0.09 mmol) in methanol (3 mL) and tetrahydrofuran (3 mL) was added 10% Pd/C (50 mg) and it was stirred at room temperature for 16 h under hydrogen atmosphere. Then it was filtered and the filtrate was evaporated. The residue was not purified and used directly in the next step to give crude title product (50 mg, 105.0%). MS (ESI, m/e) $[M+1]^+$ 497.9.

Step 3: 2-((S)-1-acryloyl-4-(2-(((S)-1-methylpyrrolidin-2-yl)methoxy)-6-(naphthalen-2-ylmethyl)-6, 7-dihydro-5H-pyrrolo[3, 4-d]pyrimidin-4-yl)piperazin-2-yl)acetonitrile

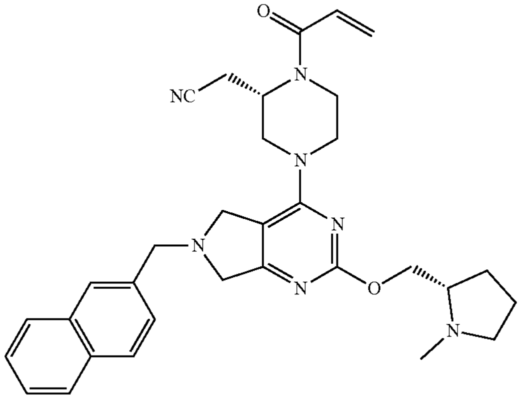 [SMILES: C=CC(=O)N1CCN(c2nc(OC[C@@H]3CCCN3C)nc3c2CN(Cc2ccc4ccccc4c2)C3)C[C@@H]1CC#N]

To a solution of 2-((S)-4-(2-(((S)-1-methylpyrrolidin-2-yl)methoxy)-6-(naphthalen-2-ylmethyl)-6, 7-dihydro-5H-pyrrolo[3, 4-d]pyrimidin-4-yl)piperazin-2-yl)acetonitrile (50 mg, 0.10 mmol) in 5 mL dichloromethane was added 0.3 mL triethylamine and it was stirred at −70° C., then it was added acryloyl chloride (18 mg, 0.20 mmol) and it was stirred at −70° C. for 2 h. Then it was diluted with dichloromethane and water and the organic layer was combined, dried over sodium sulfate and evaporated. The residue was purified by Prep-TLC to give Example 20 (8 mg, 14.4%). $^1H$ NMR (400 MHz, DMSO-$d_6$) δ ppm: 7.95-7.84 (m, 3H), 7.58-7.45 (m, 3H), 6.90-6.70 (m, 1H), 6.89-6.73 (m, 1H), 6.22-6.11 (m, 1H), 5.81-5.71 (m, 1H), 4.91-4.71 (m, 1H), 4.61-4.48 (m, 2H), 4.48-4.39 (m, 1H), 4.38-4.24 (m, 3H), 4.17-4.01 (m, 4H), 4.01-3.89 (m, 1H), 3.80-3.67 (m, 3H), 3.61-3.40 (m, 1H), 3.15-2.94 (m, 2H), 2.94-2.74 (m, 5H), 2.26-2.13 (m, 1H), 2.10-1.98 (m, 1H), 1.96-1.73 (m, 2H). MS (ESI, m/e) $[M+1]^+$ 552.6.

Example 21: 2-((S)-1-acryloyl-4-(6-((2, 3-dihydrobenzofuran-4-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

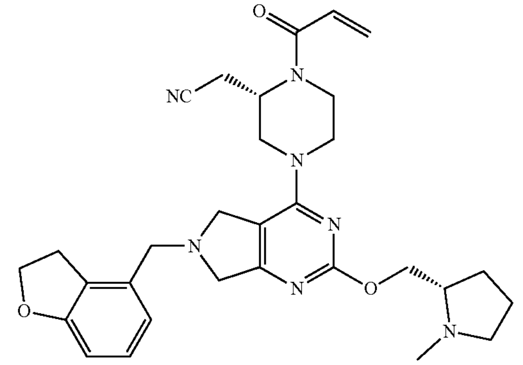 [SMILES: C=CC(=O)N1CCN(c2nc(OC[C@@H]3CCCN3C)nc3c2CN(Cc2cccc4c2CCO4)C3)C[C@@H]1CC#N]

Synthetic Route:

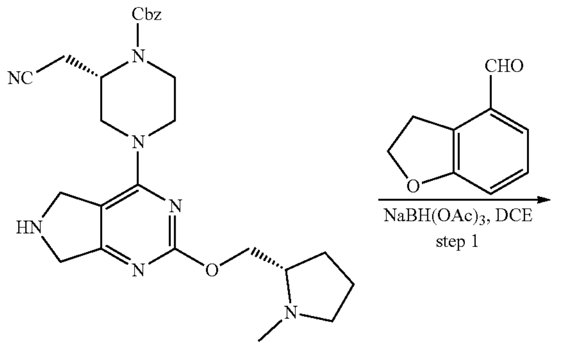

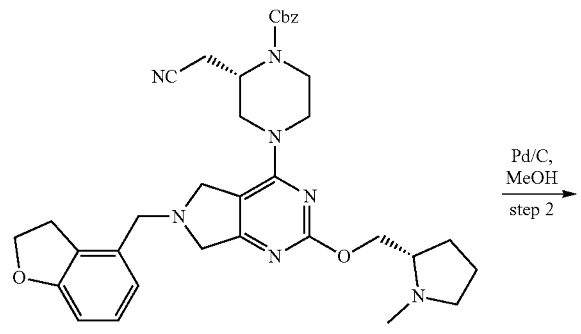

-continued

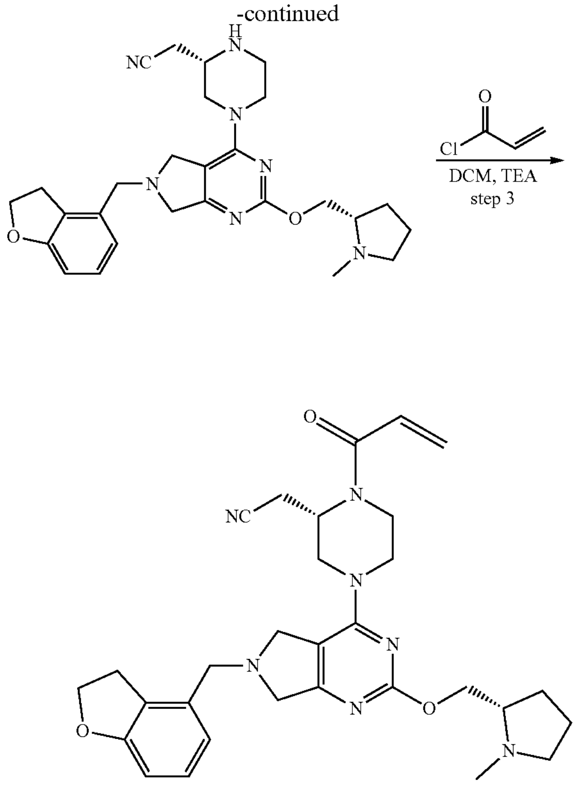

Step 1: Benzyl (S)-2-(cyanomethyl)-4-(6-((2, 3-dihydrobenzofuran-4-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate To a stirred mixture of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (200 mg, 0.406 mmol) and 2, 3-dihydrobenzofuran-4-carbaldehyde (200 mg, 1.35 mmol) in DCE (1 mL) was added sodium triacetoxyborohydride (260 mg, 1.22 mmol). The solution was stirred at room temperature for 16 h, and diluted with dichloromethane and water. The organic layer was combined, dried over sodium sulfate and evaporated. The residue was purified by chromatography column on silica to give the title product (190 mg). LCMS (ESI, m/z) $[M+1]^+$ 624.1.

Step 2: 2-((S)-4-(6-((2, 3-dihydrobenzofuran-4-yl) methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile To a solution of benzyl (S)-2-(cyanomethyl)-4-(6-((2, 3-dihydrobenzofuran-4-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate (190 mg, 0.305 mmol) in methanol (10 mL) was added 10 wt % Pd/C (200 mg) and it was stirred at room temperature for 16 h under hydrogen atmosphere. Solid was filtered and the filtrate was evaporated to afford the title product (120 mg). LCMS (ESI, m/z) $[M+1]^+$ 490.1.

Step 3: 2-((S)-1-acryloyl-4-(6-((2, 3-dihydrobenzofuran-4-yl)methyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

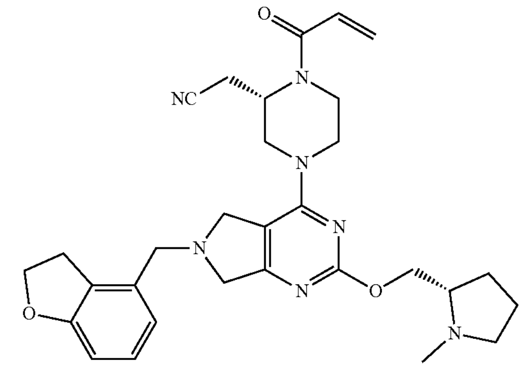 [SMILES: C=CC(=O)N1CCN(c2nc(OC[C@@H]3CCCN3C)nc3c2CN(Cc2cccc4c2CCO4)C3)C[C@@H]1CC#N]

To a solution of 2-((S)-4-(6-((2, 3-dihydrobenzofuran-4-yl)methyl)-2-(((S)-1-methylpyrrolidin-2-yl)methoxy)-6, 7-dihydro-5H-pyrrolo[3, 4-d]pyrimidin-4-yl)piperazin-2-yl) acetonitrile (120 mg, 0.24 mmol) in dichloromethane (8 mL) was added triethylamine (40 mg) and the mixture was cooled to −78° C. Acryloyl chloride (40 mg, 0.44 mmol) was added and the mixture was stirred for 1 h. The mixture was diluted with dichloromethane and water and the organic layer was combined, dried over sodium sulfate and evaporated. The residue was purified by Prep HPLC to give Example 21 (5.6 mg). $^1H$ NMR (400 MHz, DMSO-$d_6$) δ 10.05-9.85 (m, 1H), 7.18-7.07 (m, 1H), 7.05-6.91 (m, 1H), 6.85-6.68 (m, 2H), 6.19-6.05 (m, 1H), 5.77-5.66 (m, 1H), 4.91-4.10 (m, 14H), 4.02-3.78 (m, 3H), 3.12-2.60 (m, 9H), 2.27-1.65 (m, 5H). LCMS (ESI, m/z) $[M+1]^+$ 544.6.

Example 22: 2-((S)-1-acryloyl-4-(6-(2-fluoro-5-hydroxybenzyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

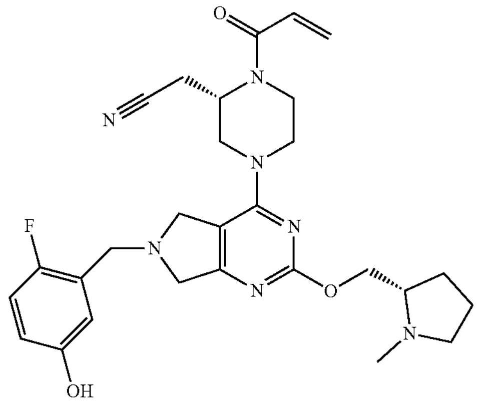 [SMILES: C=CC(=O)N1CCN(c2nc(OC[C@@H]3CCCN3C)nc3c2CN(Cc2cc(O)ccc2F)C3)C[C@@H]1CC#N]

Synthetic Route:

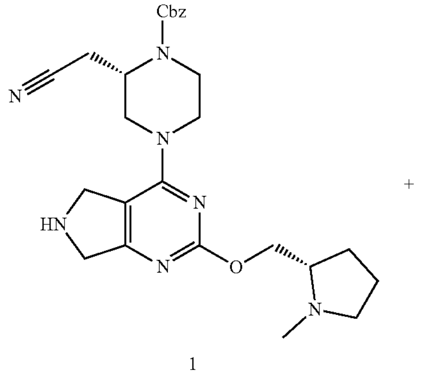

1

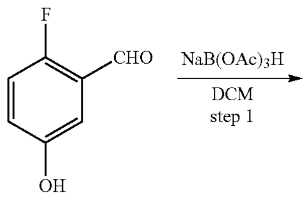

2

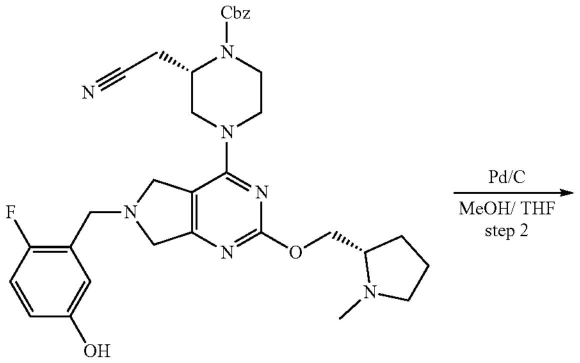

3

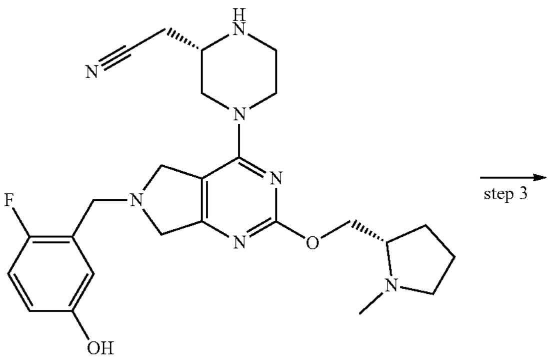

4

-continued

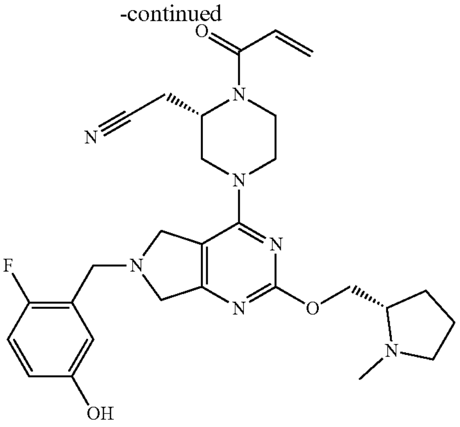

Step 1: benzyl (S)-2-(cyanomethyl)-4-(6-(2-fluoro-5-hydroxybenzyl)-2-(((S)-1-methylpyrrolidin-2-yl)methoxy)-6, 7-dihydro-5H-pyrrolo[3, 4-d]pyrimidin-4-yl)piperazine-1-carboxylate

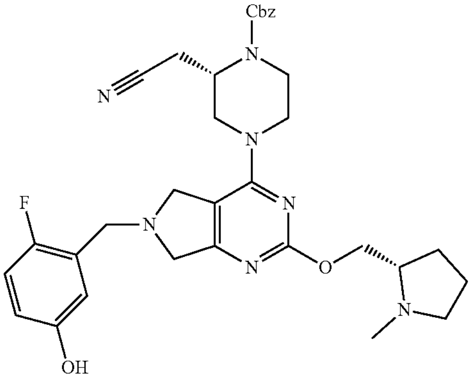 [SMILES: CN1CCC[C@H]1COc1nc2c(c(N3CCN(C(=O)OCc4ccccc4)[C@@H](CC#N)C3)n1)CN(Cc1cc(O)ccc1F)C2]

To a solution of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (200 mg, 0.41 mmol) in 20 mL dichloromethane was added 2-fluoro-5-hydroxybenzaldehyde (140 mg, 1.00 mmol). After the addition, the mixture was stirred at room temperature for 10 min. Then it was added sodium triacetoxyborohydride (420 mg, 1.99 mmol). Then it was stirred at room temperature for 2 h, and diluted with dichloromethane and water. The organic layer was combined, dried over sodium sulfate and evaporated. The residue was purified by chromatography column on silica to give the title product (100 mg, 39.6%). MS (ESI, m/e) [M+1]+ 615.9.

Step 2: 2-((S)-4-(6-(2-fluoro-5-hydroxybenzyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

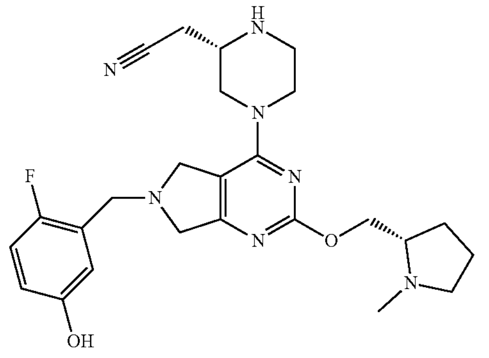 [SMILES: CN1CCC[C@H]1COc1nc2c(c(N3CCN[C@@H](CC#N)C3)n1)CN(Cc1cc(O)ccc1F)C2]

To a solution of benzyl (S)-2-(cyanomethyl)-4-(6-(2-fluoro-5-hydroxybenzyl)-2-(((S)-1-methylpyrrolidin-2-yl)methoxy)-6, 7-dihydro-5H-pyrrolo[3, 4-d]pyrimidin-4-yl)piperazine-1-carboxylate (60 mg, 0.09 mmol) in methanol (3 mL) and tetrahydrofuran (3 mL) was added 10% Pd/C 100 mg and it was stirred at room temperature for 16 h under hydrogen atmosphere. Then it was filtered and the filtrate was evaporated. The residue was not purified and continued the next step to give crude title product (60 mg, 76.7%). MS (ESI, m/e) $[M+1]^4$ 481.9.

Step 3: 2-((S)-1-acryloyl-4-(6-(2-fluoro-5-hydroxybenzyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

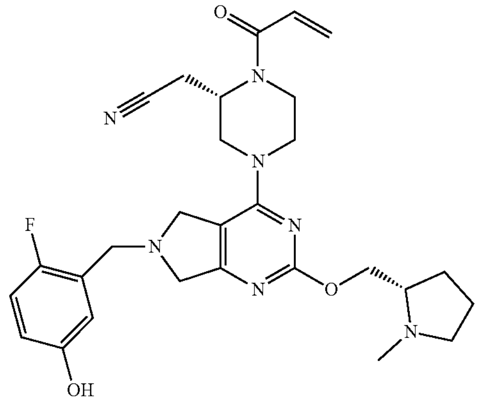 [SMILES: C=CC(=O)N1CCN(c2nc(OC[C@@H]3CCCN3C)nc3c2CN(Cc2cc(O)ccc2F)C3)C[C@@H]1CC#N]

To a solution of 2-((S)-4-(6-(2-fluoro-5-hydroxybenzyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (60 mg, 0.12 mmol) in 5 mL dichloromethane was added 0.2 mL triethylamine and it was stirred at −70° C., then it was added acryloyl chloride (14 mg, 0.15 mmol) and it was stirred at −70° C. for 1 h. Then it was diluted with dichloromethane and water and the organic layer was combined, dried over sodium sulfate and evaporated. The residue was purified by Prep-TLC to give Example 22 (4 mg, 6.1%). $^1$H NMR (400 MHz, DMSO-d) 8 ppm: 9.35 (s, 1H), 7.02-6.94 (m, 1H), 6.92-6.75 (m, 2H), 6.70-6.63 (m, 1H), 6.23-6.13 (m, 1H), 5.81-5.71 (m, 1H), 4.95-4.74 (m, 1H), 4.56-4.26 (m, 4H), 4.16-3.96 (m, 4H), 3.94-3.79 (m, 2H), 3.75-3.61 (m, 2H), 3.59-3.41 (m, 2H), 3.30-3.17 (m, 1H), 3.13-2.93 (m, 2H), 2.91-2.71 (m, 5H), 2.24-2.10 (m, 1H), 2.04-1.81 (m, 2H), 1.82-1.68 (m, 1H). MS (ESI, ne) $[M+1]^+$ 536.5.

Example 23: 2-((S)-1-acryloyl-4-(6-(2-fluoro-6-hydroxybenzyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

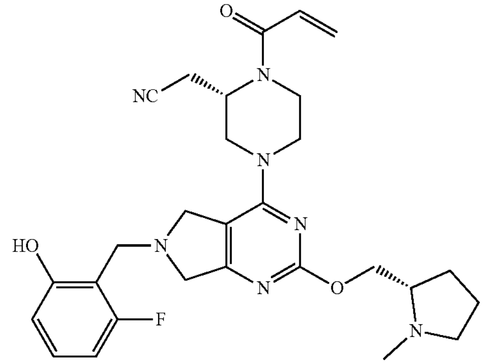 [SMILES: C=CC(=O)N1CCN(c2nc(OC[C@@H]3CCCN3C)nc3c2CN(Cc2c(O)cccc2F)C3)C[C@@H]1CC#N]

Synthetic Route:

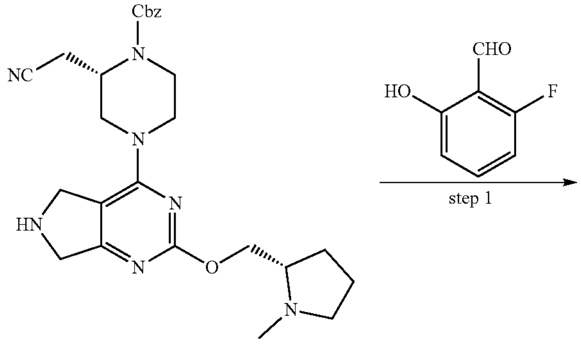

1

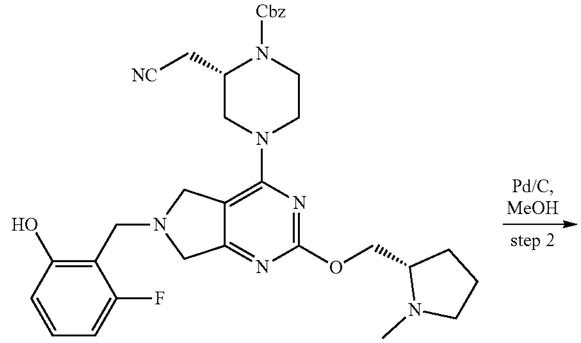

2

-continued

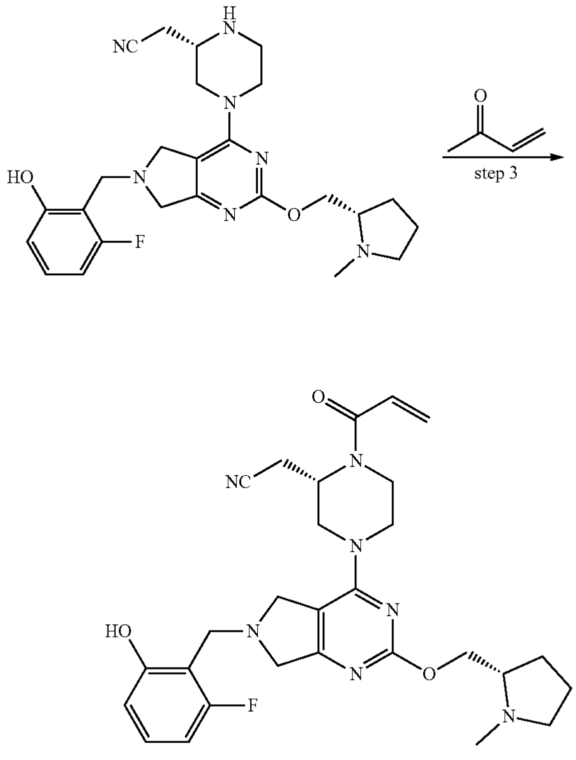

Step 1: benzyl (S)-2-(cyanomethyl)-4-(6-(2-fluoro-6-hydroxybenzyl)-2-(((S)-1-methylpyrrolidin-2-yl)methoxy)-6, 7-dihydro-5H-pyrrolo[3, 4-d]pyrimidin-4-yl)piperazine-1-carboxylate

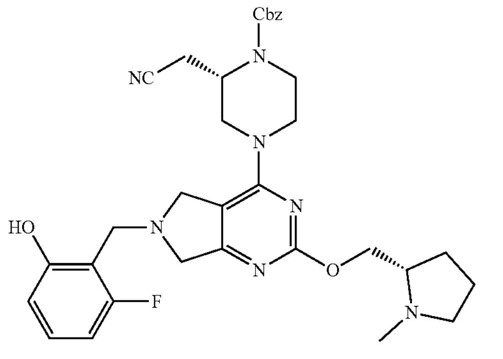 [SMILES: CN1CCC[C@H]1COc1nc2c(c(N3CCN(C(=O)OCc4ccccc4)[C@@H](CC#N)C3)n1)CN(Cc1c(O)cccc1F)C2]

To a solution of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (260 mg, 0.53 mmol) in 50 mL acetonitrile was added 2-fluoro-6-hydroxybenzaldehyde (140 mg, 1 mmol). After the addition, the mixture was stirred at room temperature for 10 min. Then it was added sodium triacetoxyborohydride (300 mg, 1.42 mmol). Then it was stirred at room temperature for 20 hours, and then it was concentrated. The residue was purified by chromatography column on silica (eluting with DCM/MeOH=10/1) to give the title product (300 mg, 92%). MS (ESI, m/e) [M+1]+ 616.1.

Step 2: 2-((S)-4-(6-(2-fluoro-6-hydroxybenzyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

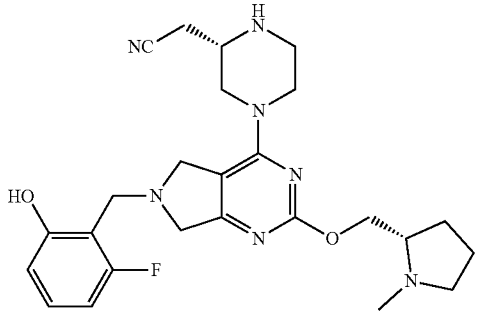 [SMILES: CN1CCC[C@H]1COc1nc2c(c(N3CCN[C@@H](CC#N)C3)n1)CN(Cc1c(O)cccc1F)C2]

To a solution of benzyl (S)-2-(cyanomethyl)-4-(6-(2-fluoro-6-hydroxybenzyl)-2-(((S)-1-methylpyrrolidin-2-yl)methoxy)-6, 7-dihydro-5H-pyrrolo[3, 4-d]pyrimidin-4-yl)piperazine-1-carboxylate (300 mg, 0.49 mmol) in methanol (20 mL) was added 10% Pd/C (200 mg) and it was stirred at room temperature for 24 h under hydrogen atmosphere. Then it was filtered and the filtrate was evaporated. The residue was used as crude title product for the next step (225 mg, 95.0%). MS (ESI, m/e) $[M+H]^+$ 482.1.

Step 3: 2-((S)-1-acryloyl-4-(6-(2-fluoro-6-hydroxybenzyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

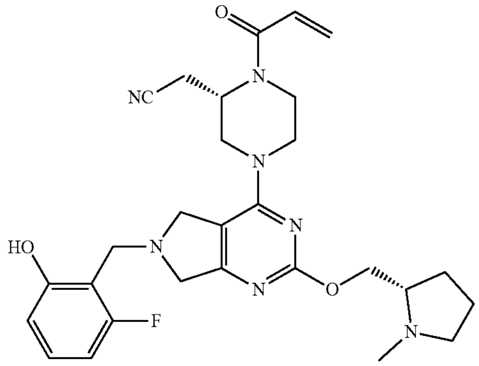 [SMILES: C=CC(=O)N1CCN(c2nc(OC[C@@H]3CCCN3C)nc3c2CN(Cc2c(O)cccc2F)C3)C[C@@H]1CC#N]

To a solution of 2-((S)-4-(6-(2-fluoro-6-hydroxybenzyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (220 mg, 0.46 mmol) in DCM (20 mL) was added TEA (140 mg, 1.4 mmol) and acryloyl chloride (140 mg, 1.5 mmol) at lower −20° C. (dry ice/EtOH) in dropwise, stirred for 0.5 hour at this temperature. The resulting solution was washed with $NaHCO_3/H_2O$ (sat., 20 mL) and concentrated to give a residue which was further purified by Prep-HPLC to give Example 23 (10 mg, 4.1%). $^1H$ NMR (400 MHz, DMSO-$d_6$) δ 8.52 (s, 1H), 7.17-7.11 (m, 1H), 6.89-6.73 (s, 1H), 6.65-6.57 (m, 2H), 6.30-6.26 (m, 1H), 5.83-5.81 (m, 1H), 4.96 (s, 1H), 4.77-4.68 (m, 2H), 4.45-4.41 (m, 1H), 4.25-4.19 (m, 2H), 4.09-4.05 (m, 4H), 3.83 (s, 2H), 3.59-3.48 (m, 3H), 3.39-3.37 (m, 2H), 3.04-3.01 (m, 1H), 2.94-2.87 (m, 4H), 2.80-2.75 (m, 1H), 2.34-2.25 (m, 1H), 2.13-1.89 (m, 3H). MS (ESI, m/e) [M+H]+ 536.6.

Example 24: 2-((S)-1-acryloyl-4-(6-((8-hydroxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

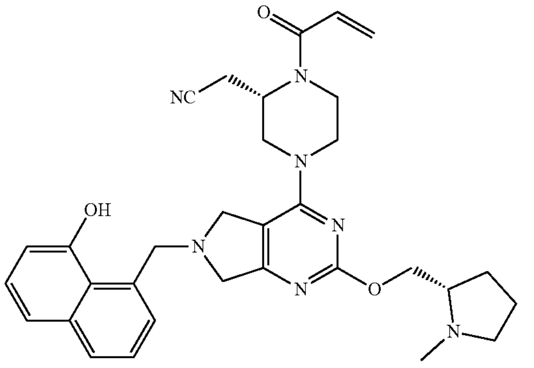

Synthetic Route:

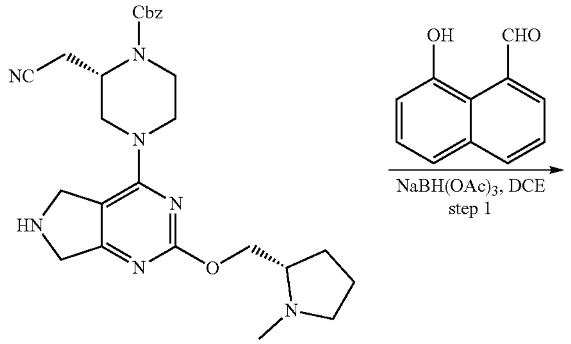

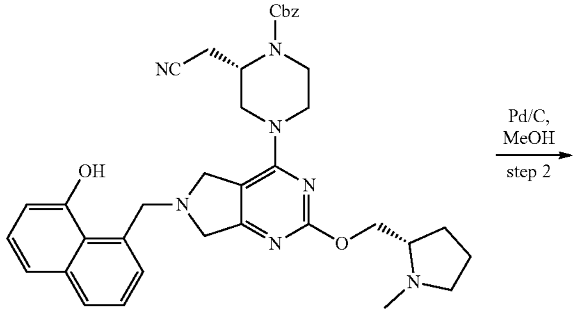

-continued

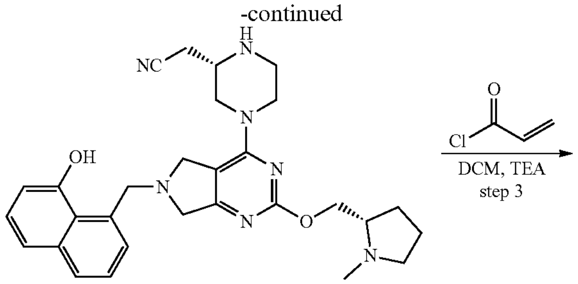

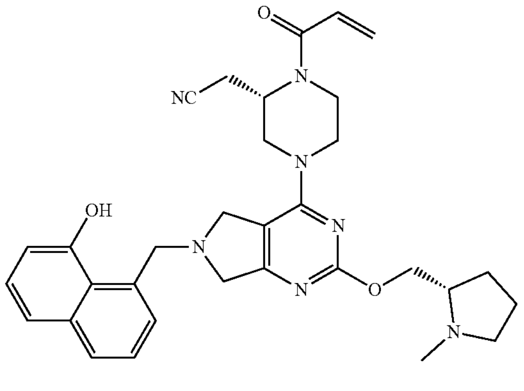 [SMILES: C=CC(=O)N1CCN(c2nc(OC[C@@H]3CCCN3C)nc3c2CN(Cc2cccc4cccc(O)c24)C3)C[C@@H]1CC#N]

Step 1: Benzyl (S)-2-(cyanomethyl)-4-(6-((8-hydroxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate To a stirred mixture of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (200 mg, 0.406 mmol) and 8-hydroxy-1-naphthaldehyde (200 mg, 1.16 mmol) in DCE (1 mL) was added sodium triacetoxyborohydride (260 mg, 1.22 mmol). The solution was stirred at room temperature for 16 h, and diluted with dichloromethane and water. The organic layer was combined, dried over sodium sulfate and evaporated. The residue was purified by chromatography column on silica to give the title product (200 mg). LCMS (ESI, m/z) $[M+1]^+$ 648.1.

Step 2: 2-((S)-4-(6-((8-hydroxynaphthalen-1-yl) methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile To a solution of benzyl (S)-2-(cyanomethyl)-4-(6-((8-hydroxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate (200 mg, 0.308 mmol) in methanol (10 mL) was added 10 wt % Pd/C (200 mg) and it was stirred at room temperature for 16 h under hydrogen atmosphere. Solid was filtered and the filtrate was evaporated to afford the title product (120 mg). LCMS (ESI, m/z) $[M+1]^+$ 514.1.

Step 3: 2-((S)-1-acryloyl-4-(6-((8-hydroxynaphthalen-1-yl)methyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

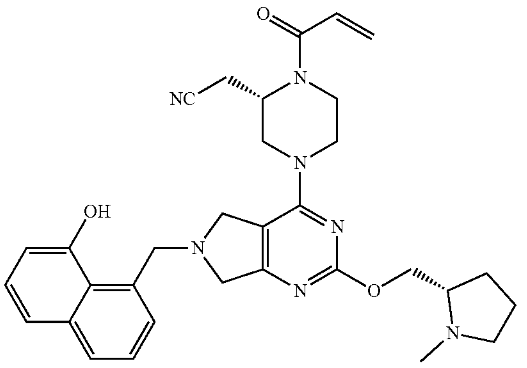 [SMILES: C=CC(=O)N1CCN(c2nc(OC[C@@H]3CCCN3C)nc3c2CN(Cc2cccc4cccc(O)c24)C3)C[C@@H]1CC#N]

To a solution of 2-((S)-4-(6-((8-hydroxynaphthalen-1-yl) methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (60 mg, 0.12 mmol) in dichloromethane (4 mL) was added triethylamine (20 mg) and the mixture was cooled to −78° C. Acryloyl chloride (20 mg, 0.22 mmol) was added and the mixture was stirred for 1 h. The mixture was diluted with dichloromethane and water and the organic layer was combined, dried over sodium sulfate and evaporated. The residue was purified by Prep HPLC to give Example 24 (2.1 mg). $^1$H NMR (400 MHz, DMSO-$d_6$) δ 13.77-13.50 (m, 1H), 8.29 (s, 1H), 7.83 (d, J=8.1 Hz, 1H), 7.45-7.30 (m, 4H), 6.87-6.70 (m, 2H), 6.20-6.10 (m, 1H), 5.80-5.70 (m, 1H), 4.91-4.65 (m, 1H), 4.40-4.20 (m, 7H), 4.18-3.80 (m, 5H), 3.20-2.83 (m, 6H), 2.35-2.29 (m, 3H), 2.20-2.10 (m, 1H), 1.96-1.84 (m, 1H), 1.72-1.48 (m, 3H). LCMS (ESI, m/z) $[M+1]^+$ 568.7.

The following compounds were obtained by similar procedures:

Example 25: 2-((S)-1-acryloyl-4-(6-((3-hydroxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

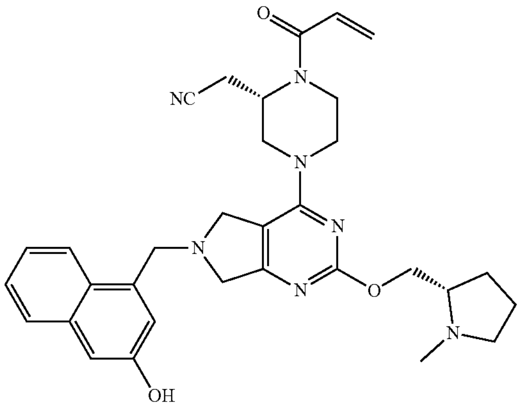 [SMILES: C=CC(=O)N1CCN(c2nc(OC[C@@H]3CCCN3C)nc3c2CN(Cc2cc(O)cc4ccccc24)C3)C[C@@H]1CC#N]

$^1$H NMR (400 MHz, $CD_3OD$) δ 8.14 (d, J=8.3 Hz, 1H), 7.65 (d, J=8.1 Hz, 1H), 7.39-7.36 (m, 1H), 7.30-7.26 (m, 1H), 7.17 (s, 1H), 7.07 (s, 1H), 6.78-6.72 (m, 1H), 6.26 (d, J=16.6 Hz, 1H), 5.81 (d, J=9.3 Hz, 1H), 5.06-4.90 (m, 1H), 4.64-4.60 (m, 1H), 4.35-4.29 (m, 4H), 4.17-4.03 (m, 4H), 3.78 (s, 2H), 3.51-3.48 (m, 1H), 3.31-3.03 (m, 2H), 2.90-2.84 (dd, J=16.2, 7.4 Hz, 4H), 2.54 (s, 3H), 2.50-2.33 (m, 1H), 2.12-2.07 (m, 1H), 1.90-1.75 (m, 2H), 1.73-1.70 (m, 1H). MS (ESI) m/e $[M+H]^4$ 568.7.

Example 26: 2-((S)-1-acryloyl-4-(2-(((S)-1-methylpyrrolidin-2-yl)methoxy)-6-(naphthalen-2-yl)-6, 7-dihydro-5H-pyrrolo[3, 4-d]pyrimidin-4-yl)piperazin-2-1 acetonitrile

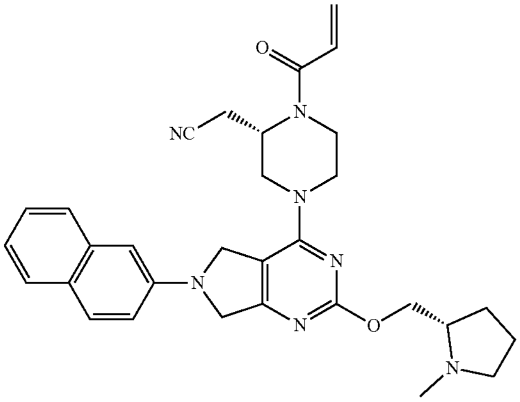

Synthetic Route:

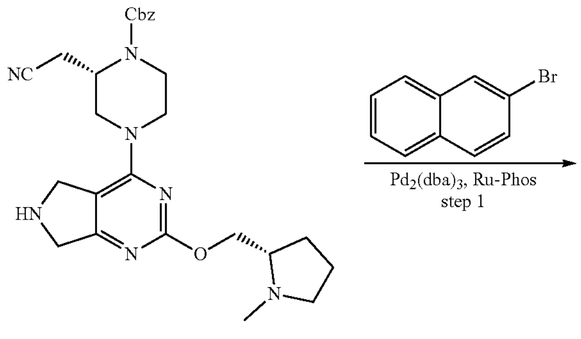

1

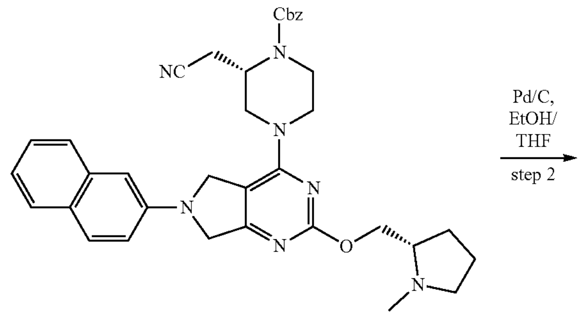

2

-continued

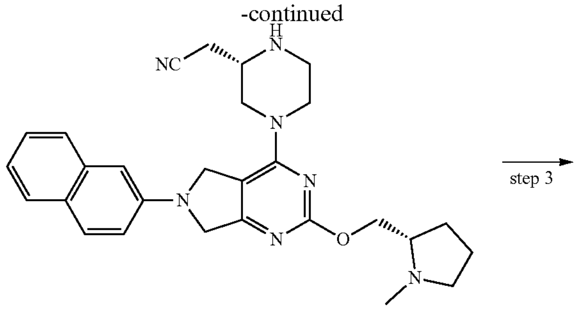

3

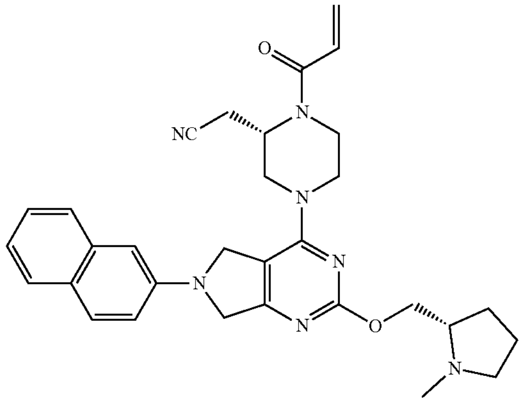 [SMILES: C=CC(=O)N1CCN(c2nc(OC[C@@H]3CCCN3C)nc3c2CN(c2ccc4ccccc4c2)C3)C[C@@H]1CC#N]

Step 1: benzyl (S)-2-(cyanomethyl)-4-(2-(((S)-1-methylpyrrolidin-2-yl)methoxy)-6-(naphthalen-2-yl)-6, 7-dihydro-5H-pyrrolo[3, 4-d]pyrimidin-4-yl)piperazine-1-carboxylate

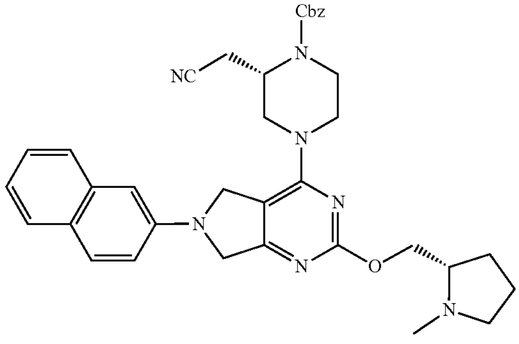 [SMILES: CN1CCC[C@H]1COc1nc2c(c(N3CCN(C(=O)OCc4ccccc4)[C@@H](CC#N)C3)n1)CN(c1ccc3ccccc3c1)C2]

To a solution of benzyl (S)-2-(cyanomethyl)-4-(2-(((S)-1-methylpyrrolidin-2-yl)methoxy)-6, 7-dihydro-5H-pyrrolo [3, 4-d]pyrimidin-4-yl)piperazine-1-carboxylate (240 mg, 0.49 mmol) in 5 mL toluene was added 2-bromonaphthalene (125 mg, 0.60 mmol), tris(dibenzylideneacetone)dipalladium (47 mg, 0.05 mmol), 2-dicyclohexylphosphino-2', 6'-di-i-propoxy-1, 1'-biphenyl (47 mg, 0.10 mmol) and cesium carbonate (330 mg 1.00 mmol) in 5 mL toluene was stirred at 105° C. for 8 h under nitrogen atmosphere, and it was cooled to room temperature. it was diluted with dichloromethane and water. The organic layer was combined, dried over sodium sulfate and evaporated. The residue was purified by chromatography column on silica to give the title product (160 mg, 52.9%). MS (ESI, m/e) $[M+1]^+$ 617.9.

Step 2: 2-((S)-4-(2-(((S)-1-methylpyrrolidin-2-yl)methoxy)-6-(naphthalen-2-yl)-6, 7-dihydro-5H-pyrrolo[3,4-d]pyrimidin-4-yl)piperazin-2-yl)acetonitrile

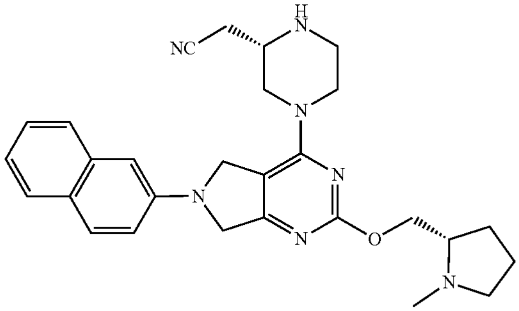 [SMILES: CN1CCC[C@H]1COc1nc2c(c(N3CCN[C@@H](CC#N)C3)n1)CN(c1ccc3ccccc3c1)C2]

To a solution of benzyl (S)-2-(cyanomethyl)-4-(2-(((S)-1-methylpyrrolidin-2-yl)methoxy)-6-(naphthalen-2-yl)-6, 7-dihydro-5H-pyrrolo[3, 4-d]pyrimidin-4-yl)piperazine-1-carboxylate (106 mg, 0.16 mmol) in ethanol (3 mL) and tetrahydrofuran (3 mL) was added 10% Pd/C (100 mg), ammonia in methanol (0.5 mL, 7 M) and it was stirred at room temperature for 40 h under hydrogen atmosphere. Then it was filtered and the filtrate was evaporated. The residue was not purified and used directly in the next step to give crude product (100 mg, 79.8%). MS (ESI, m/e) $[M+1]^+$ 483.9.

Step 3: 2-((S)-1-acryloyl-4-(2-(((S)-1-methylpyrrolidin-2-yl)methoxy)-6-(naphthalen-2-yl)-6, 7-dihydro-5H-pyrrolo[3, 4-d]pyrimidin-4-yl)piperazin-2-yl) acetonitrile

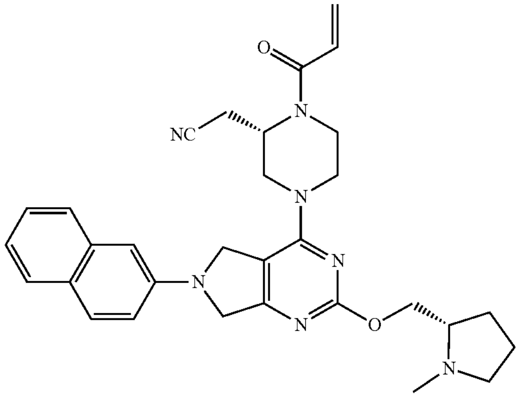 [SMILES: C=CC(=O)N1CCN(c2nc(OC[C@@H]3CCCN3C)nc3c2CN(c2ccc4ccccc4c2)C3)C[C@@H]1CC#N]

To a solution of 2-((S)-4-(2-(((S)-1-methylpyrrolidin-2-yl)methoxy)-6-(naphthalen-2-yl)-6, 7-dihydro-5H-pyrrolo [3, 4-d]pyrimidin-4-yl)piperazin-2-yl)acetonitrile (100 mg, 0.21 mmol) in 8 mL dichloromethane was added 0.3 mL triethylamine and it was stirred at −10° C., then it was added acryloyl chloride (18 mg, 0.20 mmol) and it was stirred at −10° C. for 1 h. Then it was diluted with dichloromethane and water and the organic layer was combined, dried over sodium sulfate and evaporated. The residue was purified by chromatography column on silica gel to give Example 26 (3 mg, 2.7%). $^1H$ NMR (400 MHz, DMSO-$d_6$) δ ppm: 7.86-7.80 (m, 1H), 7.78-7.73 (m, 1H), 7.71-7.67 (m, 1H), 7.42-

7.35 (m, 1H), 7.27-7.15 (m, 2H), 7.02-6.97 (m, 1H), 6.93-6.78 (m, 1H), 6.24-6.13 (m, 1H), 5.84-5.77 (m, 1H), 5.00-4.76 (m, 3H), 4.67-4.60 (m, 1H), 4.57-4.42 (m, 4H), 3.85-3.74 (m, 1H), 3.63-3.52 (m, 1H), 3.21-3.07 (m, 3H), 3.06-2.85 (m, 7H), 2.30-2.19 (m, 1H), 2.10-2.00 (m, 2H), 2.00-1.90 (m, 1H), 1.90-1.80 (m, 1H). MS (ESI, m/e) [M+1]$^+$ 537.9.

Example 27: 2-((S)-1-acryloyl-4-(6-(2, 3-dihydro-1H-inden-4-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile

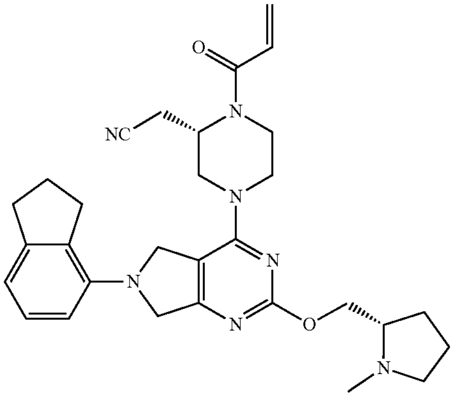 [SMILES: C=CC(=O)N1CCN(c2nc(OC[C@@H]3CCCN3C)nc3c2CN(c2cccc4c2CCC4)C3)C[C@@H]1CC#N]

Synthetic Route:

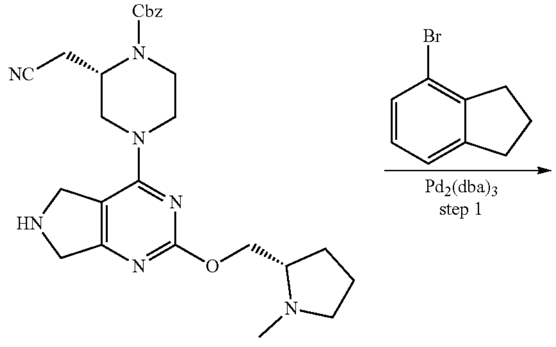

1

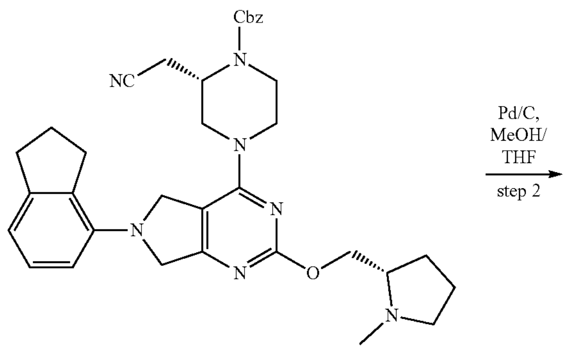

2

-continued

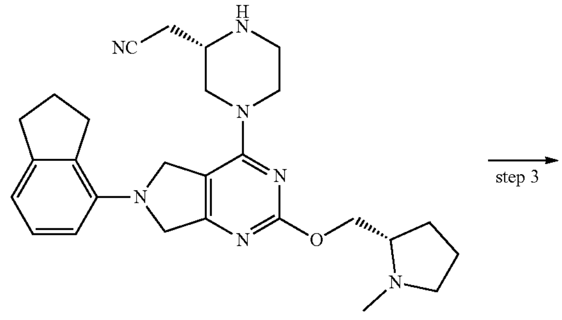

3

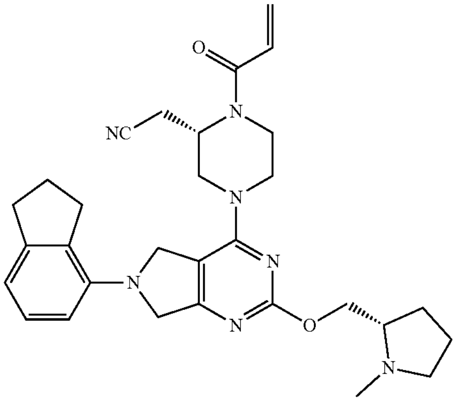

Step 1: benzyl (S)-2-(cyanomethyl)-4-(6-(2, 3-dihydro-1H-inden-4-yl)-2-(((S)-1-methylpyrrolidin-2-yl)methoxy)-6, 7-dihydro-5H-pyrrolo[3, 4-d]pyrimidin-4-yl)piperazine-1-carboxylate

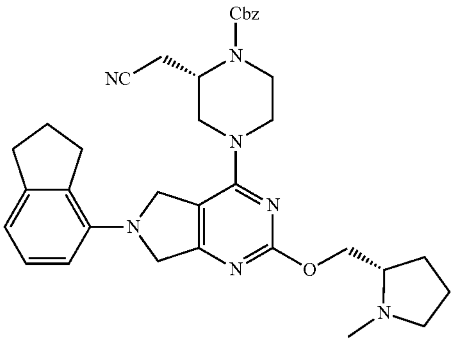 [SMILES: CN1CCC[C@H]1COc1nc2c(c(N3CCN(C(=O)OCc4ccccc4)[C@@H](CC#N)C3)n1)CN(c1cccc3c1CCC3)C2]

To a solution of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (200 mg, 0.41 mmol) in 5 mL toluene was added 4-bromo-2, 3-dihydro-1H-indene (110 mg, 0.56 mmol), tris(dibenzylideneacetone)dipalladium (38 mg, 0.04 mmol), 2-dicyclohexylphosphino-2', 6'-di-i-propoxy-1, 1'-biphenyl (40 mg, 0.09 mmol) and cesium carbonate (320 mg 0.99 mmol) in 6 mL toluene was stirred at 100° C. for 16 h under nitrogen atmosphere, and it was cooled to room temperature. It was diluted with dichloromethane and water. The organic layer was combined, dried over sodium sulfate and evaporated.

The residue was purified by chromatography column on silica to give the title product (160 mg, 64.7%). MS (ESI, m/e) $[M+1]^4$ 607.9.

Step 2: 2-((S)-4-(6-(2, 3-dihydro-1H-inden-4-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile

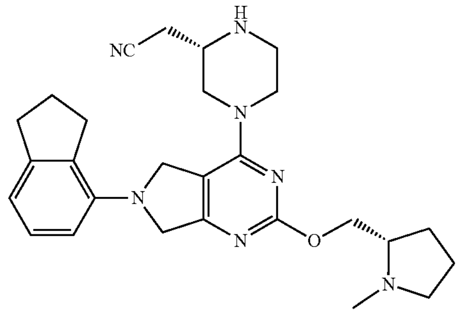 [SMILES: CN1CCC[C@H]1COc1nc2c(c(N3CCN[C@@H](CC#N)C3)n1)CN(c1cccc3c1CCC3)C2]

To a solution of benzyl (S)-2-(cyanomethyl)-4-(6-(2, 3-dihydro-1H-inden-4-yl)-2-(((S)-1-methylpyrrolidin-2-yl)methoxy)-6, 7-dihydro-5H-pyrrolo[3, 4-d]pyrimidin-4-yl)piperazine-1-carboxylate (160 mg, 0.26 mmol) in methanol (3 mL) and tetrahydrofuran (3 mL) was added 10% Pd/C (100 mg), ammonia in methanol (0.2 mL, 7 M) and it was stirred at room temperature for 16 h under hydrogen atmosphere. Then it was filtered and the filtrate was evaporated. The residue was not purified and used directly in the next step to give crude product (65 mg, 52.1%). MS (ESI, m/e) $[M+1]^+$ 473.9.

Step 3: 2-((S)-1-acryloyl-4-(6-(2, 3-dihydro-1H-inden-4-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile

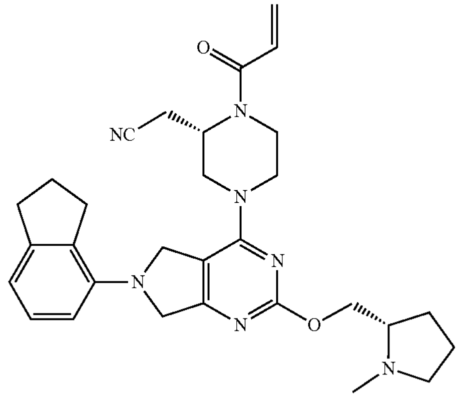 [SMILES: C=CC(=O)N1CCN(c2nc(OC[C@@H]3CCCN3C)nc3c2CN(c2cccc4c2CCC4)C3)C[C@@H]1CC#N]

To a solution of crude 2-((S)-4-(6-(2, 3-dihydro-1H-inden-4-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile (60 mg, 0.13 mmol) in 5 mL dichloromethane was added 0.3 mL triethylamine and it was stirred at −10° C., then it was added acryloyl chloride (17 mg, 0.18 mmol) and it was stirred at −10° C. for 1 h. Then it was diluted with dichloromethane and water and the organic layer was combined, dried over sodium sulfate and evaporated. The residue was purified by chromatography column on silica gel to give Example 27 (11 mg, 15.2%). $^1$H NMR (400 MHz, DMSO-$d_6$) δ ppm: 7.38-7.27 (m, 1H), 7.06-6.96 (m, 1H), 6.90-6.76 (m, 1H), 6.72-6.64 (m, 1H), 6.62-6.54 (m, 1H), 6.24-6.12 (m, 1H), 5.83-5.71 (m, 1H), 4.95-4.69 (m, 3H), 4.60-4.45 (m, 2H), 4.44-4.32 (m, 2H), 4.25-3.97 (m, 2H), 3.90-3.42 (m, 3H), 3.22-3.02 (m, 3H), 3.02-2.84 (m, 6H), 2.83-2.71 (m, 3H), 2.26-2.07 (m, 1H), 2.07-1.89 (m, 3H), 1.89-1.66 (m, 2H). MS (ESI, m/e) $[M+1]^+$ 528.6.

The following compounds were obtained by similar procedure:

Example 28: 2-((S)-1-acryloyl-4-(6-(8-methylnaphthalen-1-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile

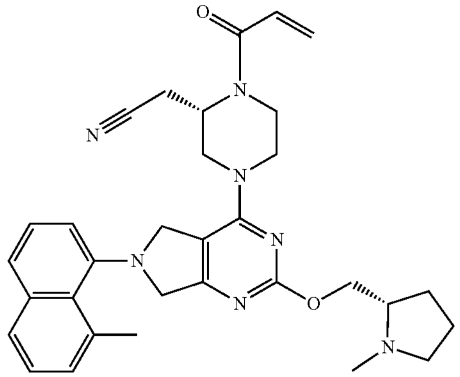 [SMILES: C=CC(=O)N1CCN(c2nc(OC[C@@H]3CCCN3C)nc3c2CN(c2cccc4cccc(C)c24)C3)C[C@@H]1CC#N]

1H NMR (400 MHz, DMSO-$d_6$) δ 7.78-7.76 (m, 2H), 7.68-7.67 (m, 1H), 7.52-7.48 (m, 1H), 7.40-7.36 (m, 1H), 7.30-7.29 (m, 1H), 6.83-6.74 (m, 1H), 6.17 (d, J=16.6 Hz, 1H), 5.76 (d, J=9.8 Hz, 1H), 4.66-4.45 (m, 5H), 4.37-4.25 (m, 3H), 4.11-0.397 (m, 2H), 3.75-3.33 (m, 4H), 3.06-2.87 (m, 10H), 2.31-2.14 (m, 1H), 2.02-1.83 (m, 3H). MS (ESI) m/e $[M+H]^+$ 551.9.

General Synthetic Route of Amide Coupling:

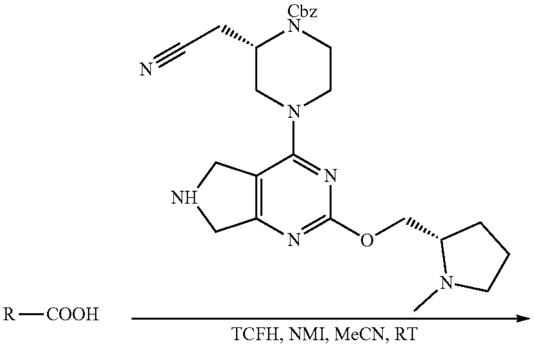

-continued
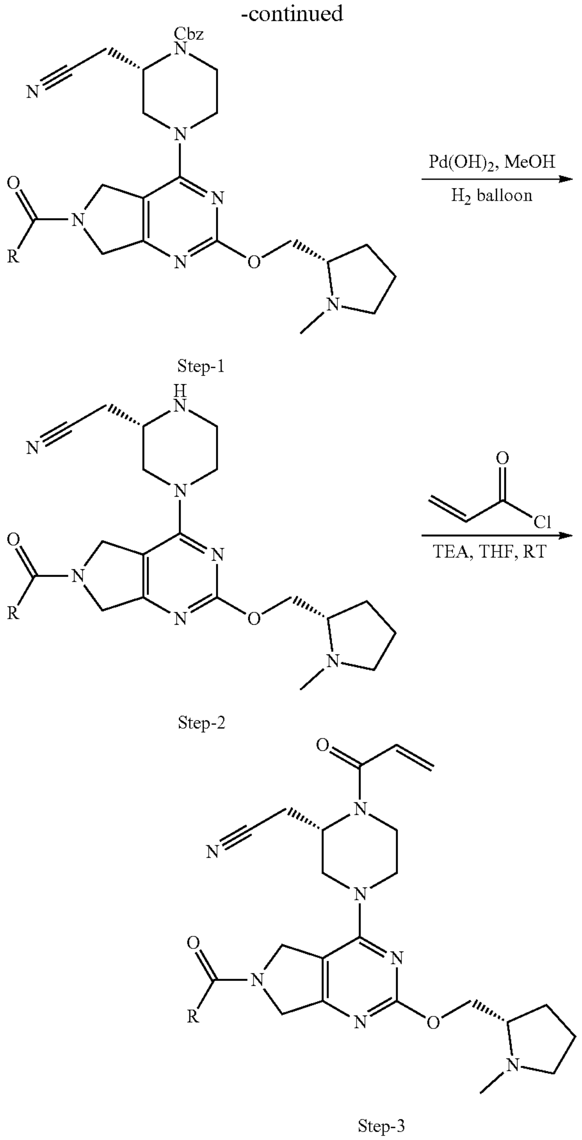
Example 29: 2-((S)-1-acryloyl-4-(6-(3-hydroxy-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile
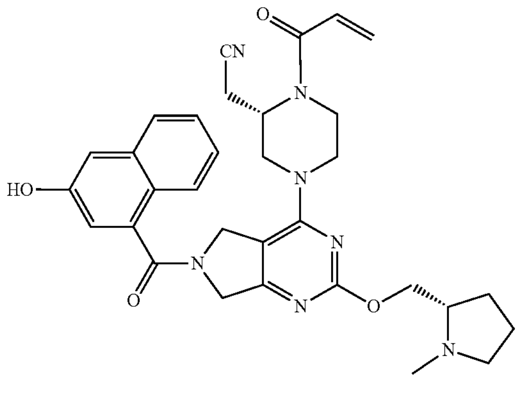 [SMILES: C=CC(=O)N1CCN(c2nc(OC[C@@H]3CCCN3C)nc3c2CN(C(=O)c2cc(O)cc4ccccc24)C3)C[C@@H]1CC#N]
Synthetic Route:
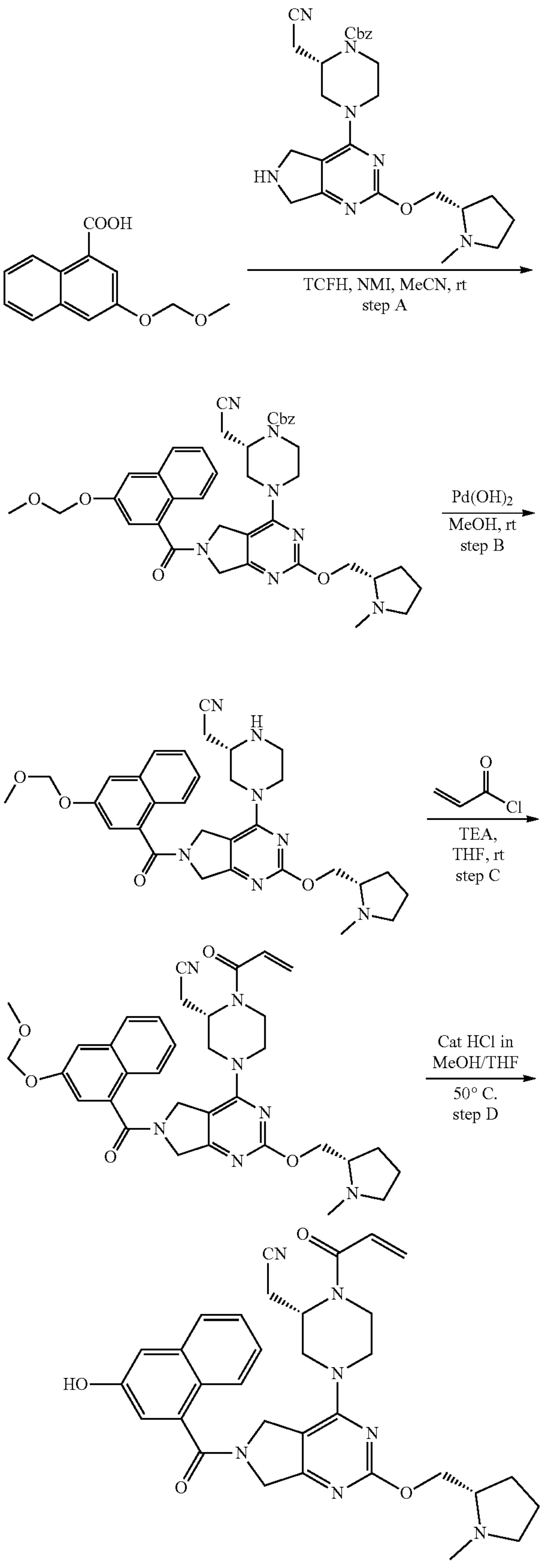

-continued

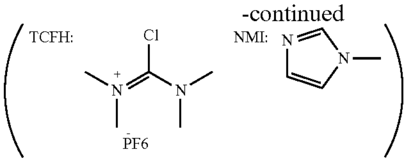

Step A: benzyl (S)-2-(cyanomethyl)-4-(6-(3-(methoxymethoxy)-1-naphthoyl)-2-(((S)-1-methylpyrrolidin-2-yl)methoxy)-6, 7-dihydro-5H-pyrrolo[3, 4-d]pyrimidin-4-yl)piperazine-1-carboxylate To the mixture of TCFH (155.68 mg, 0.556 mmol, 1.05 eq), NMI (152 mg, 1.85 mmol, 3.5 eq) in MeCN (5 mL) at RT were added 3-(methoxymethoxy)-1-naphthoic acid (135.13 mg, 0.58 mmol) and benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (260 mg, 0.53 mmol) at RT. The resulting mixture was stirred at RT for 16 h. After completed, the reaction was diluted with water (30 mL), extracted with DCM (50 mL×3). The combined organic layers were washed with brine, dried over Na2SO4, filtered and evaporated in vacuo to give the residue. The residue was purified by silica gel column chromatography, eluted with 0-10% MeOH in DCM to give the product (200 mg, 53.6%). MS (ESI) m/z $[M+H]^+$ 705.9.

Step B: 2-((S)-4-(6-(3-(methoxymethoxy)-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile To a stirred mixture of product from Step A (200 mg, 0.283 mmol) in MeOH was added $Pd(OH)_2$ (50 mg) at room temperature. The resulting mixture was stirred for 2 h at RT under hydrogen balloon. After completed, the reaction mixture was filtered and the filtrate was evaporated in vacuo give the residue. The residue was purified by silica gel column chromatography, eluted with 0-20% MeOH in DCM to give the product (100 mg, 61.7%). MS (ESI) m/z $[M+H]^+$ 571.9.

Step C: 2-((S)-1-acryloyl-4-(6-(3-(methoxymethoxy)-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile To a stirred mixture of product from Step B (100 mg, 0.175 mmol, 1 eq) in THF were added triethylamine (35.3 mg, 0.35 mmol, 2 eq) and acryloyl chloride (31.6 mg, 0.35 mmol, 2 eq) at 0° C. The resulting mixture was stirred for 1 h at RT. After completed, the solvent was evaporated in vacuo give the residue. The residue was purified by silica gel column chromatography, eluted with 0-10% MeOH in DCM to give the title product (60 mg, 54.8%). MS (ESI) m/z $[M+H]^+$ 625.9.

Step D: 2-((S)-1-acryloyl-4-(6-(3-hydroxy-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

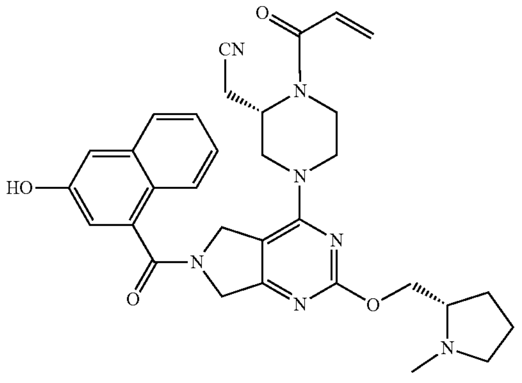 [SMILES: C=CC(=O)N1CCN(c2nc(OC[C@@H]3CCCN3C)nc3c2CN(C(=O)c2cc(O)cc4ccccc24)C3)C[C@@H]1CC#N]

To a stirred mixture of product from Step C (40 mg, 0.064 mmol) in MeOH/THF (2 ml/2 ml) was added HCl (3 drops) at room temperature. The resulting mixture was stirred for 2 h at 50° C. After completed, the reaction mixture was evaporated in vacuo give the residue. The residue was purified by silica gel column chromatography, eluted with 0-20% MeOH in DCM to give Example 29 (7.18 mg, 19.4%). $^1H$ NMR (400 MHz, DMSO-d6) δ 10.06-9.72 (m, 1H), 7.80-7.66 (m, 2H), 7.47-7.14 (m, 4H), 6.87-6.75 (m, 1H), 6.24-6.09 (m, 1H), 5.82-5.69 (m, 1H), 5.17-4.94 (m, 2H), 4.79-4.36 (m, 5H), 4.25-4.85 (m, 5H), 3.17-2.69 (m, 9H), 2.18-1.75 (m, 4H). MS (ESI) m/z $[M+H]^+$ 582.6.

Example 30: 2-((S)-1-acryloyl-4-(6-(8-chloro-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

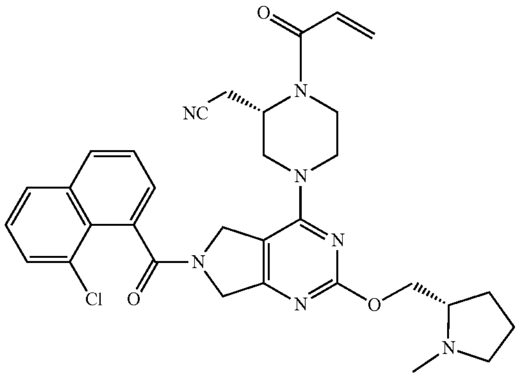

Step 1: benzyl (S)-4-(6-(8-chloro-1-naphthoyl)-2-(((S)-1-methylpyrrolidin-2-yl)methoxy)-6, 7-dihydro-5H-pyrrolo[3, 4-d]pyrimidin-4-yl)-2-(cyanomethyl)piperazine-1-carboxylate

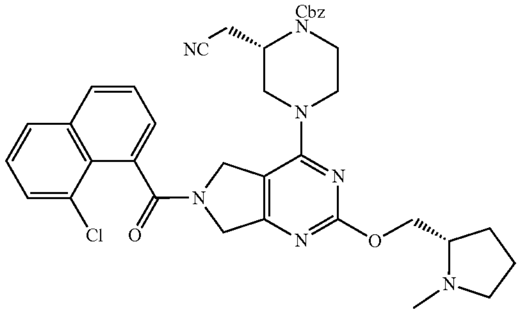

To the mixture of TCFH (179.6 mg, 0.64 mmol), NMI (175.3 mg, 2.13 mmol) in MeCN (5 mL) at RT were added 8-chloro-1-naphthoic acid (138.4 mg, 0.67 mmol) and benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (300 mg, 0.61 mmol) at RT. The resulting mixture was stirred at RT for 16 h. After completed, the reaction was diluted with water (50 mL), extracted with DCM (50 mL) for three times. The combined organic layers were washed with brine, dried over $Na_2SO_4$, filtered and evaporated in vacuo to give the residue. The residue was purified by silica gel column chromatography, eluted with 0-10% MeOH in DCM to give the title product (200 mg, 72.2%). MS (ESI) m/z $[M+H]^+$ 679.9.

Step 2: 2-((S)-4-(6-(8-chloro-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

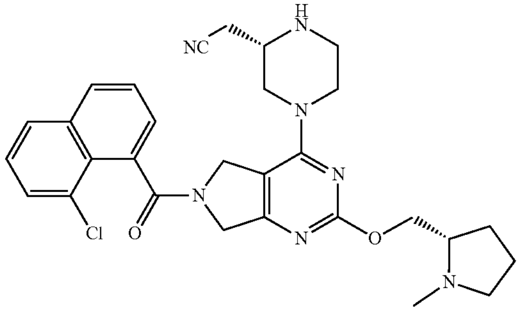

To a stirred mixture of benzyl (S)-4-(6-(8-chloro-1-naphthoyl)-2-(((S)-1-methylpyrrolidin-2-yl)methoxy)-6, 7-dihydro-5H-pyrrolo[3, 4-d]pyrimidin-4-yl)-2-(cyanomethyl) piperazine-1-carboxylate (180 mg, 0.265 mmol) in MeOH was added $Pd(OH)_2$ (100 mg) at room temperature. The resulting mixture was stirred for 2 h at RT under hydrogen balloon. After completed, the reaction mixture was filtered and the filtrate was evaporated in vacuo give the residue. The residue was purified by silica gel column chromatography, eluted with 0-20% MeOH in DCM to give the title product (100 mg, 69.2%). MS (ESI) m/z $[M+H]^+$ 545.9.

Step 3: 2-((S)-1-acryloyl-4-(6-(8-chloro-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

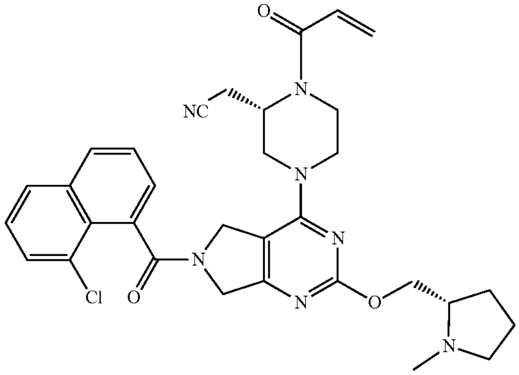

To a stirred mixture of 2-((S)-4-(6-(8-chloro-1-naphthoyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (140 mg, 0.256 mmol) in THF were added triethylamine (51.8 mg, 0.513 mmol) and acryloyl chloride (46.5 mg, 0.513 mmol) at RT. The resulting mixture was stirred for 1 h at RT. After completed, the solvent was evaporated in vacuo give the residue. The residue was purified by silica gel column chromatography, eluted with 0-10% MeOH in DCM to give Example 30 (6.98 mg, 4.56%). $^1H$ NMR (400 MHz, DMSO-$d_6$) δ 8.23-8.21 (m, 1H), 8.15-8.13 (m, 1H), 7.82-7.66 (m, 4H), 6.95-6.75 (m, 1H), 6.29-6.15 (m, 1H), 5.88-5.75 (m, 1H), 5.11-4.99 (m, 2H), 4.71-4.57 (m, 5H), 4.23-4.10 (m, 3H), 3.84-3.57 (m, 2H), 3.03-2.82 (m, 9H), 2.24-1.80 (m, 4H). MS (ESI) m/z $[M+H]^+$ 600.6.

The following compounds were obtained by similar procedures:

Example 31: 2-((S)-1-acryloyl-4-(6-(5-methyl-1H-indazole-4-carbonyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

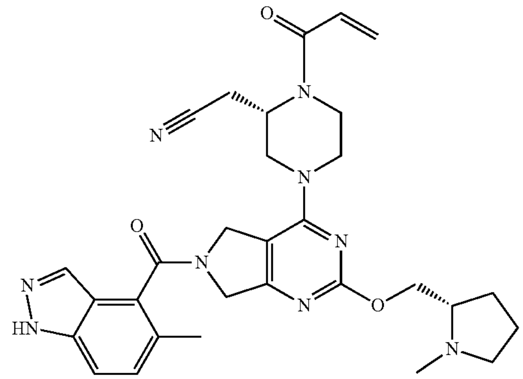 [SMILES: C=CC(=O)N1CCN(c2nc(OC[C@@H]3CCCN3C)nc3c2CN(C(=O)c2c(C)ccc4[nH]ncc24)C3)C[C@@H]1CC#N]

$^1H$ NMR (400 MHz, DMSO-$d_6$) δ 13.24-13.22 (m, 1H), 7.89-7.84 (m, 1H), 7.52-7.50 (m, 1H), 7.30-7.25 (m, 1H), 6.86-6.82 (m, 1H), 6.20-6.11 (m, 1H), 5.76-5.76 (m, 1H), 5.12-4.95 (m, 2H), 4.65-4.45 (m, 5H), 4.07-3.98 (m, 3H), 3.82-3.65 (m, 3H), 3.10-3.00 (m, 6H), 2.96-2.80 (m, 3H), 2.47 (s, 3H), 2.47-2.31 (m, 4H). LC-MS $(M+H)^+$ 570.6.

Example 32: 2-((S)-4-(6-(1-naphthoyl)-2-(((S)-1-methylpyrrolidin-2-yl)methoxy)-6, 7-dihydro-5H-pyrrolo[3, 4-d]pyrimidin-4-yl)-1-acryloylpiperazin-2-yl)acetonitrile

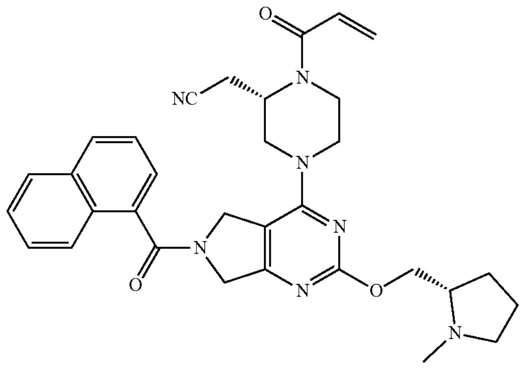 [SMILES: C=CC(=O)N1CCN(c2nc(OC[C@@H]3CCCN3C)nc3c2CN(C(=O)c2cccc4ccccc24)C3)C[C@@H]1CC#N]

Example 32 was prepared in the same manner from 1-naphthoic acid. $^1$H NMR (400 MHz, DMSO-$d_6$) δ 8.06-8.02 (m, 2H), 7.86-7.82 (m, 1H), 7.62-7.58 (m, 4H), 6.86-6.73 (m, 1H), 6.23-6.03 (m, 1H), 5.81-5.69 (m, 1H), 5.16-4.65 (m, 4H), 4.44-4.40 (m, 1H), 4.18-3.98 (m, 5H), 3.85-3.65 (m, 2H), 3.06-2.67 (m, 6H), 2.30-2.27 (m, 3H), 1.67-1.47 (m, 4H). MS (ESI) m/z $[M+H]^+$ 566.6.

Example 33: 2-((S)-1-acryloyl-4-(6-(8-methyl-1-naphthoyl)-2-(((S)-1-methylpyrrolidin-2-yl)methoxy)-6, 7-dihydro-5H-pyrrolo[3,4-d]pyrimidin-4-yl)piperazin-2-yl)acetonitrile

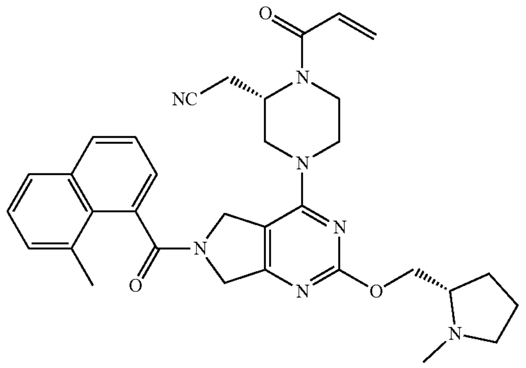 [SMILES: C=CC(=O)N1CCN(c2nc(OC[C@@H]3CCCN3C)nc3c2CN(C(=O)c2cccc4cccc(C)c24)C3)C[C@@H]1CC#N]

Example 33 was prepared in the same manner from 8-methyl-1-naphthoic acid. $^1$H NMR (400 MHz, DMSO-$d_6$) δ 8.11-8.09 (m, 1H), 7.96-7.94 (m, 1H), 7.54-7.48 (m, 4H), 6.92-6.72 (m, 1H), 6.19-6.15 (m, 1H), 5.88-5.75 (m, 1H), 5.14-4.87 (m, 3H), 4.75-4.56 (m, 4H), 4.35-4.08 (m, 3H), 3.77-3.61 (m, 2H), 3.01-2.85 (m, 9H), 2.62 (s, 3H), 2.24-1.79 (m, 4H). MS (ESI) m/z $[M+H]^+$ 580.7.

Example 34: 2-((S)-1-acryloyl-4-(6-(2-methyl-1-naphthoyl)-2-(((S)-1-methylpyrrolidin-2-yl) methoxy)-6, 7-dihydro-5H-pyrrolo[3, 4-d]pyrimidin-4_yl)piperazin-2-yl)acetonitrile

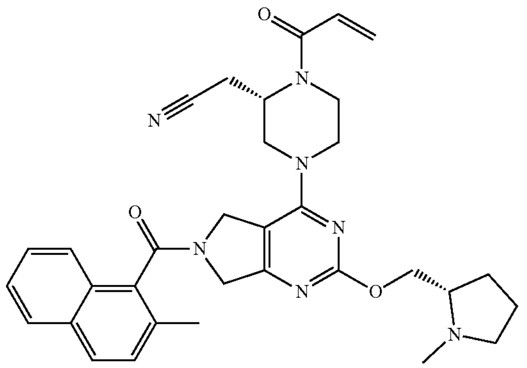 [SMILES: C=CC(=O)N1CCN(c2nc(OC[C@@H]3CCCN3C)nc3c2CN(C(=O)c2c(C)ccc4ccccc24)C3)C[C@@H]1CC#N]

$^1$H NMR (400 MHz, DMSO-$d_6$) δ 8.02-8.00 (m, 2H), 7.72-7.53 (m, 4H), 6.94-6.72 (m, 1H), 6.30-6.18 (m, 1H), 5.89-5.86 (m, 1H), 5.38-5.22 (m, 2H), 4.63-4.54 (m, 4H), 4.20-4.16 (m, 2H), 3.77-3.57 (m, 4H), 3.11-2.73 (m, 9H), 2.56 (s, 3H), 2.07-1.78 (m, 4H). MS (ESI) m/z $[M+H]^+$ 580.6.

Example 35: 2-((S)-1-acryloyl-4-(6-(8-cyclopropyl-1-naphthoyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

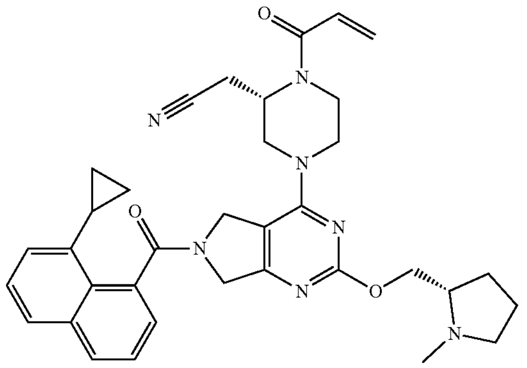 [SMILES: C=CC(=O)N1CCN(c2nc(OC[C@@H]3CCCN3C)nc3c2CN(C(=O)c2cccc4cccc(C5CC5)c24)C3)C[C@@H]1CC#N]

$^1$H NMR (400 MHz, DMSO-d6) δ 8.13-8.11 (m, 1H), 7.96-7.92 (m, 1H), 7.66-7.55 (m, 4H), 6.91-6.75 (m, 1H), 6.29-6.16 (m, 1H), 5.88-5.76 (m, 1H), 5.13-4.98 (m, 2H), 4.59-4.19 (m, 8H), 3.85-3.65 (m, 3H), 3.12-2.87 (m, 9H), 2.26-2.23 (m, 1H), 2.14-1.81 (m, 3H), 1.00-0.96 (m, 1H), 0.74-0.59 (m, 3H). MS (ESI) m/z $[M+H]^+$ 606.7.

Example 36: 2-((S)-1-acryloyl-4-(6-(2-fluoro-6-hydroxybenzoyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

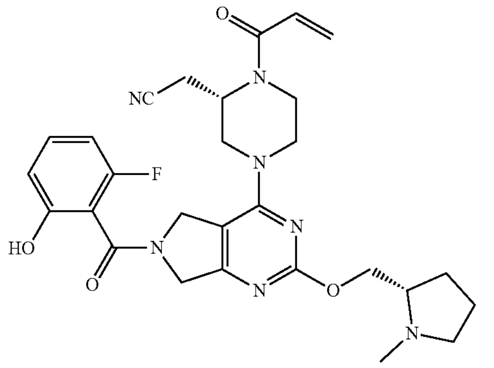 [SMILES: C=CC(=O)N1CCN(c2nc(OC[C@@H]3CCCN3C)nc3c2CN(C(=O)c2c(O)cccc2F)C3)C[C@@H]1CC#N]

$^1$H NMR (400 MHz, DMSO-d6) δ 9.70-9.65 (m, 1H), 744-7.42 (m, 1H), 732-7.27 (m, 2H), 6.80-6.78 (m, 1H), 6.22-6.13 (m, 1H), 5.81-5.74 (m, 1H), 5.02-4.73 (m, 3H), 4.63-4.20 (m, 6H), 3.85-3.65 (m, 3H), 3.11-2.67 (m, 9H), 2.23-1.80 (m, 4H). MS (ESI) m/z $[M+H]^+$ 550.6.

Example 37: 2-((S)-1-acryloyl-4-(6-(2-chloro-3-methylbenzoyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

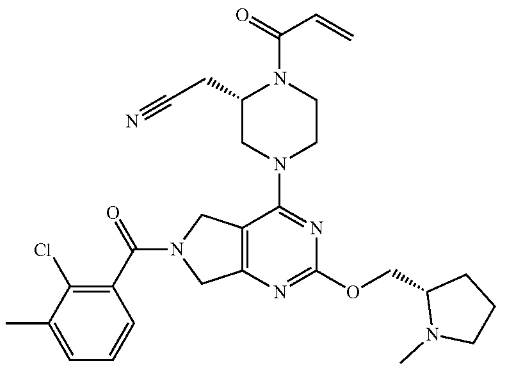 [SMILES: C=CC(=O)N1CCN(c2nc(OC[C@@H]3CCCN3C)nc3c2CN(C(=O)c2cccc(C)c2Cl)C3)C[C@@H]1CC#N]

$^1$H NMR (400 MHz, $CD_3OD$) δ 7.46-7.45 (m, 1H), 7.38-7.34 (m, 1H), 7.30-7.27 (J m, 1H), 6.91-6.78 (m, 1H), 6.32-6.22 (m, 1H), 5.86-5.79 (m, 1H), 5.10 (s, 2H), 5.06-4.88 (m, 2H), 4.85-4.64 (m, 3H), 4.54-4.47 (m, 2H), 4.35 (s, 1H), 4.22-4.12 (m, 1H), 3.99-3.81 (m, 2H), 3.52-3.41 (m, 2H), 3.26-3.20 (m, 2H), 3.04-3.00 (m, 3H), 2.83-2.72 (m, 1H), 2.45-2.35 (m, 4H), 2.17-2.03 (m, 3H). MS (ESI) m/e $[M+H]^+$ 564.5.

General Synthetic Route of Urea Formation:

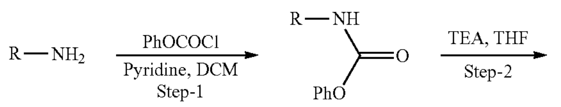

-continued

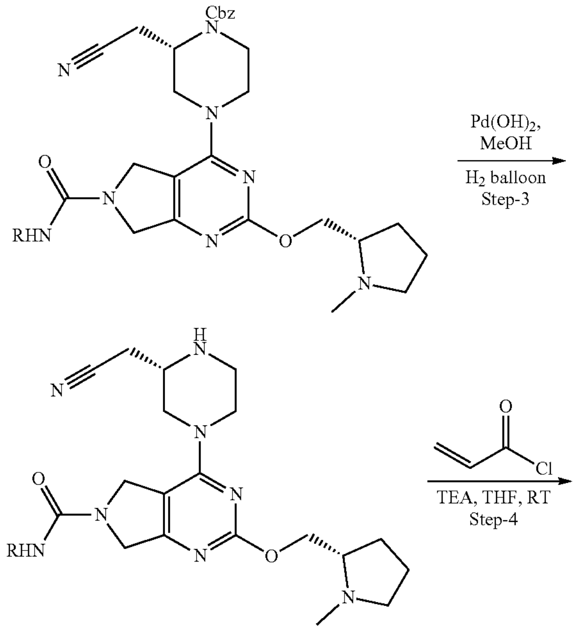

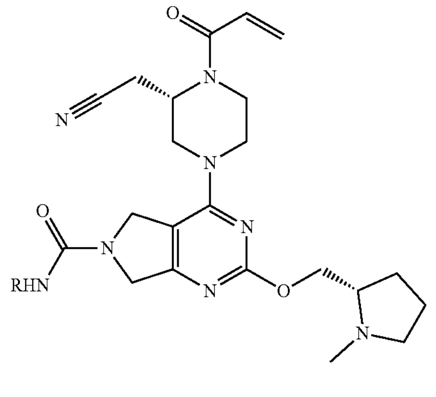

Example 38: 4-((S)-4-acryloyl-3-(cyanomethyl)piperazin-1-yl)-2-(((S)-1-methylpyrrolidin-2-yl) methoxy)-N-(naphthalen-1-yl)-5, 7-dihydro-6H-pyrrolo[3, 4-d]pyrimidine-6-carboxamide

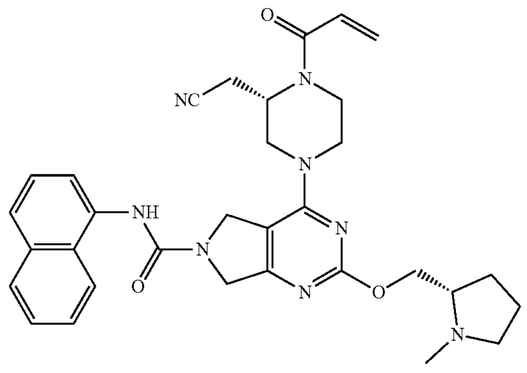 [SMILES: C=CC(=O)N1CCN(c2nc(OC[C@@H]3CCCN3C)nc3c2CN(C(=O)Nc2cccc4ccccc24)C3)C[C@@H]1CC#N]

Step 1: phenyl naphthalen-1-ylcarbamate

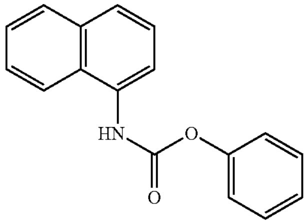 [SMILES: O=C(Nc1cccc2ccccc12)Oc1ccccc1]

To the mixture of naphthalen-1-amine (2.0 g, 13.96 mmol), pyridine (1.68 ml, 20.95 mmol) in DCM (50 mL) at RT was added phenyl carbonochloridate (2.61 g, 16.76 mmol) by dropwise and then stirred at RT for 1 h. After completed, the reaction was diluted with water (200 mL), extracted with DCM (150 mL×3). The combined organic layers were washed with brine, dried over $Na_2SO_4$, filtered and evaporated in vacuo to give the residue. The residue was purified by silica gel column chromatography, eluted with 0-10% MeOH in DCM to give phenyl naphthalen-1-ylcarbamate (2.9 g, 79.0%). MS (ESI) m/z $[M+H]^+$ 263.9.

Step 2: benzyl (S)-2-(cyanomethyl)-4-(2-(((S)-1-methylpyrrolidin-2-yl)methoxy)-6-(naphthalen-1-ylcarbamoyl)-6, 7-dihydro-5H-pyrrolo[3, 4-d]pyrimidin-4-yl)piperazine-1-carboxylate

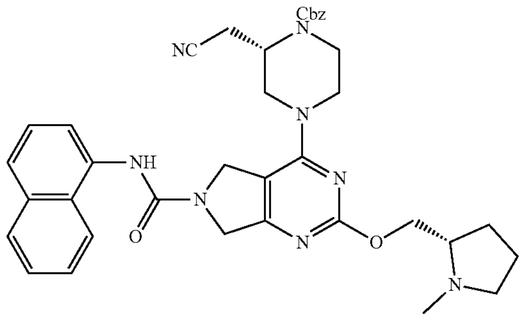 [SMILES: CN1CCC[C@H]1COc1nc2c(c(N3CCN(C(=O)OCc4ccccc4)[C@@H](CC#N)C3)n1)CN(C(=O)Nc1cccc3ccccc13)C2]

To a stirred mixture of phenyl naphthalen-1-ylcarbamate (88.4 mg, 0.33 mmol) and benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (150 mg, 0.30 mmol) in THF was added triethylamine (0.42 ml, 3.05 mmol) at room temperature. The resulting mixture was stirred for 2 h at 65° C. After completed, the solvent was evaporated in vacuo give the residue. The residue was purified by silica gel column chromatography, eluted with 0-10% MeOH in DCM to give the title product (150 mg, 74.4%). MS (ESI) m/z $[M+H]^+$ 660.9.

Step 3: 4-((S)-3-(cyanomethyl)piperazin-1-yl)-2-(((S)-1-methylpyrrolidin-2-yl)methoxy)-N-(naphthalen-1-yl)-5, 7-dihydro-6H-pyrrolo[3, 4-d]pyrimidine-6-carboxamide

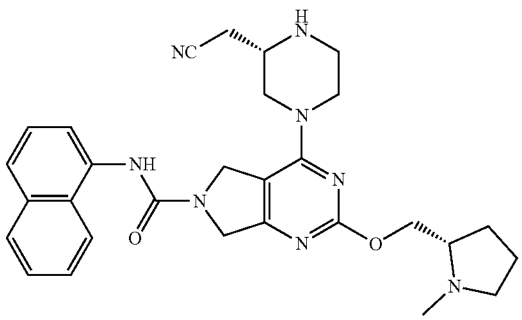 [SMILES: CN1CCC[C@H]1COc1nc2c(c(N3CCN[C@@H](CC#N)C3)n1)CN(C(=O)Nc1cccc3ccccc13)C2]

To a stirred mixture of benzyl (S)-2-(cyanomethyl)-4-(2-(((S)-1-methylpyrrolidin-2-yl)methoxy)-6-(naphthalen-1-ylcarbamoyl)-6, 7-dihydro-5H-pyrrolo[3, 4-d]pyrimidin-4-yl)piperazine-1-carboxylate (100 mg, 0.15 mmol) in MeOH (5 ml) was added $Pd(OH)_2$ (50 mg) at room temperature. The resulting mixture was stirred for 2 h at RT under hydrogen balloon. After completed, the reaction mixture was filtered and the filtrate was evaporated in vacuo give the residue. The residue was purified by silica gel column chromatography, eluted with 0-20% MeOH in DCM to give the title product (70 mg, 87.9%). MS (ESI) m/z $[M+H]^+$ 526.9.

Step 4: 4-((S)-4-acryloyl-3-(cyanomethyl)piperazin-1-yl)-2-(((S)-1-methylpyrrolidin-2-yl)methoxy)-N-(naphthalen-1-yl)-5, 7-dihydro-6H-pyrrolo[3, 4-d] pyrimidine-6-carboxamide

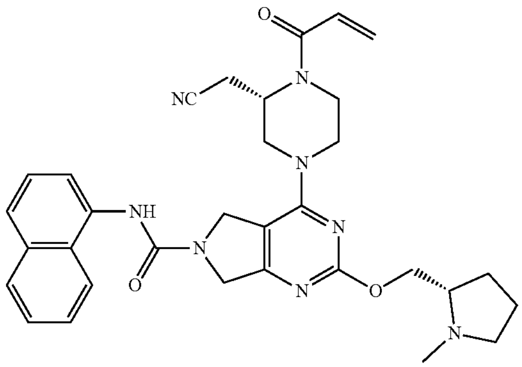 [SMILES: C=CC(=O)N1CCN(c2nc(OC[C@@H]3CCCN3C)nc3c2CN(C(=O)Nc2cccc4ccccc24)C3)C[C@@H]1CC#N]

To a stirred mixture of 4-((S)-3-(cyanomethyl)piperazin-1-yl)-2-(((S)-1-methylpyrrolidin-2-yl)methoxy)-N-(naphthalen-1-yl)-5, 7-dihydro-6H-pyrrolo[3, 4-d]pyrimidine-6-carboxamide (35 mg, 0.06 mmol) in THF were added triethylamine (69.7 mg, 0.6 mmol) and acryloyl chloride (6.25 mg, 0.06 mmol) at RT. The resulting mixture was stirred for 1 h at RT. After completed, the solvent was evaporated in vacuo give the residue. The residue was purified by silica gel column chromatography, eluted with 0-10% MeOH in DCM to give Example 38 (1.66 mg, 4.3%). H NMR (400 MHz, DMSO-$d_6$) δ 8.64 (s, 1H), 8.14-8.11 (m, 1H), 8.02-8.00 (m, 1H), 7.86-7.84 (m, 1H), 7.60-7.57 (m, 4H), 6.92-6.89 (m, 1H), 6.28-6.23 (m, 1H), 5.86-5.84 (m, 1H), 5.04-5.00 (m, 2H), 4.59-4.45 (m, 5H), 4.21-3.57 (m, 5H), 3.17-2.99 (m, 9H), 2.35-1.89 (m, 4H). MS (ESI) m/z $[M+H]^+$ 581.5.

The following compounds were obtained by similar procedures:

Example 39: 4-((S)-4-acryloyl-3-(cyanomethyl)piperazin-1-yl)-N-(8-methylnaphthalen-1-yl)-2-(((S)-1-methylpyrrolidin-2-yl)methoxy)-5, 7-dihydro-6H-pyrrolo[3, 4-d]pyrimidine-6-carboxamide

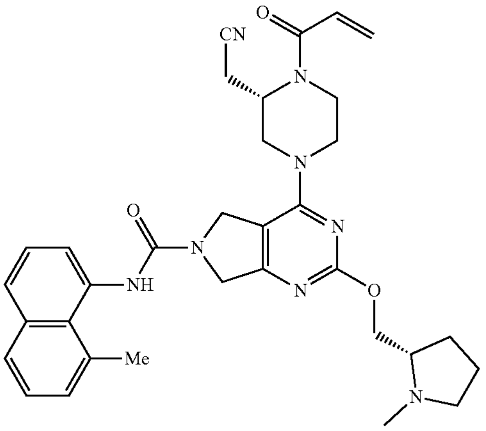 [SMILES: C=CC(=O)N1CCN(c2nc(OC[C@@H]3CCCN3C)nc3c2CN(C(=O)Nc2cccc4cccc(C)c24)C3)C[C@@H]1CC#N]

1H NMR (400 MHz, DMSO-$d_6$) δ 8.53 (s, 1H), 7.84-7.82 (m, 2H), 7.47-7.28 (m, 4H), 6.87-6.85 (m, 1H), 6.20-6.16 (m, 1H), 5.85-5.75 (m, 1H), 4.89-4.85 (m, 3H), 4.53-4.13 (m, 7H), 3.72-3.55 (m, 2H), 3.25-2.92 (m, 6H), 2.80 (s, 3H), 2.38 (s, 3H), 1.95-1.60 (m, 4H). MS (ESI) m/z $[M+H]^+$ 595.6.

Example 40: 2-((S)-4-(6-(9H-fluoren-9-yl)-2-(((S)-1-methylpyrrolidin-2-yl)methoxy)-6, 7-dihydro-5H-pyrrolo[3, 4-d]pyrimidin-4-yl)-1-acryloylpiperazin-2-yl)acetonitrile

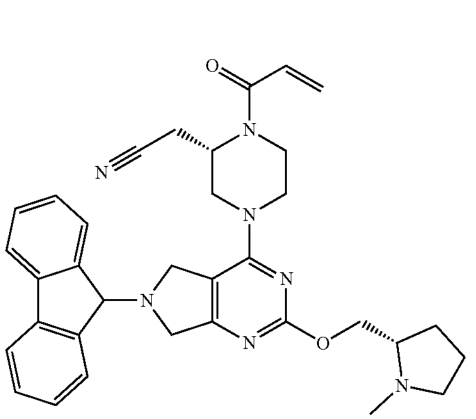

Synthetic Route:

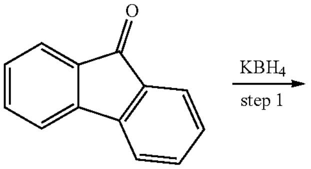

1

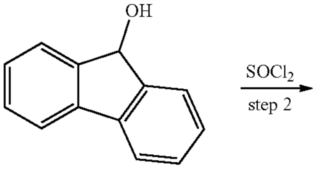

2

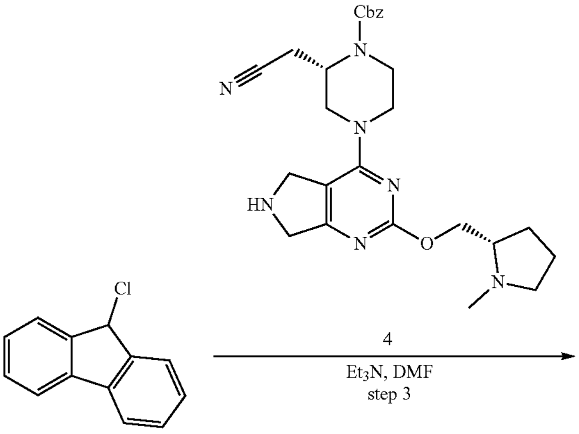

3

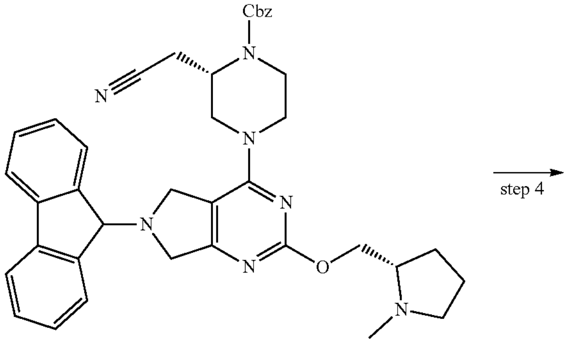

5

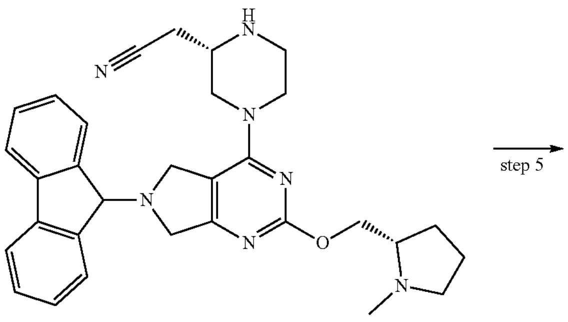

6

-continued

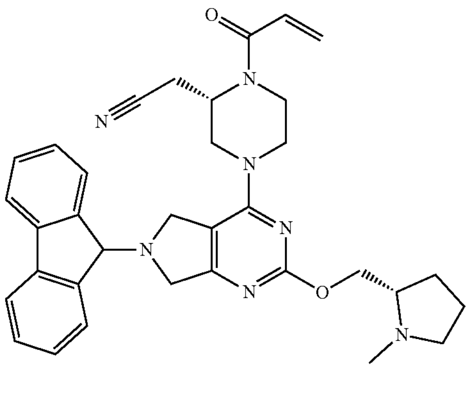 [SMILES: C=CC(=O)N1CCN(c2nc(OC[C@@H]3CCCN3C)nc3c2CN(C2c4ccccc4-c4ccccc42)C3)C[C@@H]1CC#N]

Step 1: 9H-fluoren-9-ol

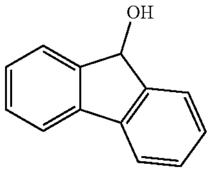 [SMILES: OC1c2ccccc2-c2ccccc21]

To a solution of 9H-fluoren-9-ol (468 mg, 2.60 mmol) in 10 mL methanol was added potassium borohydride (310 mg, 5.75 mmol). After the addition, the mixture was stirred at room temperature for 4 h. Then it was diluted with dichloromethane and water. The organic layer was combined, dried over sodium sulfate and evaporated. The crude 9H-fluoren-9-ol (400 mg, 2.20 mmol) was not purified and used directly in the next step. MS (ESI, m/e) $[M+1]^+$ 184.9.

Step 2: 9-chloro-9H-fluorene

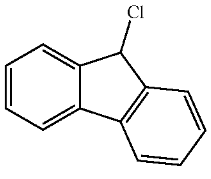 [SMILES: ClC1c2ccccc2-c2ccccc21]

To a solution of 9H-fluoren-9-ol (400 mg, 2.20 mmol) in dichloromethane (20 mL) was added thionyl chloride (0.5 mL), then 1 drop N, N-dimethylformamide was added and it was stirred at room temperature for 3 h. Then it was evaporated and the residue was purified by chromatography column on silica to give 9-chloro-9H-fluorene (400 mg, 90.9%).

Step 3: benzyl (S)-4-(6-(9H-fluoren-9-yl)-2-(((S)-1-methylpyrrolidin-2-yl)methoxy)-6, 7-dihydro-5H-pyrrolo[3, 4-d]pyrimidin-4-yl)-2-(cyanomethyl)piperazine-1-carboxylate

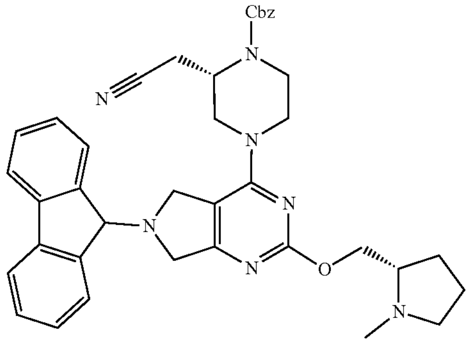 [SMILES: CN1CCC[C@H]1COc1nc2c(c(N3CCN(C(=O)OCc4ccccc4)[C@@H](CC#N)C3)n1)CN(C1c3ccccc3-c3ccccc31)C2]

To a solution of benzyl (S)-2-(cyanomethyl)-4-(2-(((S)-1-methylpyrrolidin-2-yl)methoxy)-6, 7-dihydro-5H-pyrrolo [3, 4-d]pyrimidin-4-yl)piperazine-1-carboxylate (500 mg, 1.02 mmol) in 10 mL N, N-dimethylformamide was added 9-chloro-9H-fluorene (177 mg, 0.88 mmol) and 0.3 mL triethylamine. Then it was stirred at 60° C. for 16 h, it was diluted with dichloromethane and water. The organic layer was combined, dried over sodium sulfate and evaporated. The residue was purified by chromatography column on silica to give the title product (260 mg, 45.1%). MS (ESI, m/e) $[M+1]^+$ 655.9.

Step 4: 2-((S)-4-(6-(9H-fluoren-9-yl)-2-(((S)-1-methylpyrrolidin-2-yl)methoxy)-6, 7-dihydro-5H-pyrrolo[3, 4-d]pyrimidin-4-yl)piperazin-2-ylacetonitrile

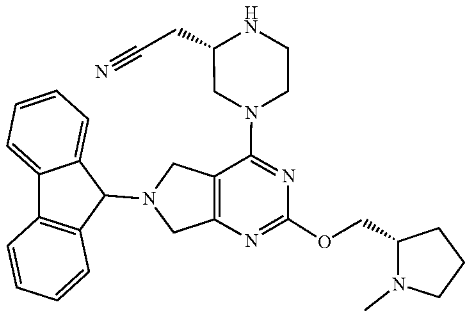 [SMILES: CN1CCC[C@H]1COc1nc2c(c(N3CCN[C@@H](CC#N)C3)n1)CN(C1c3ccccc3-c3ccccc31)C2]

To a solution of benzyl (S)-4-(6-(9H-fluoren-9-yl)-2-(((S)-1-methylpyrrolidin-2-yl)methoxy)-6, 7-dihydro-5H-pyrrolo[3, 4-d]pyrimidin-4-yl)-2-(cyanomethyl)piperazine-1-carboxylate (260 mg, 0.40 mmol) in methanol (6 mL) and tetrahydrofuran (6 mL) was added 10% Pd/C (150 mg) and it was stirred at room temperature for 16 h under hydrogen atmosphere. Then it was filtered and the filtrate was evaporated. The residue was use as crude title product for next step (150 mg, 72.5%). MS (ESI, m/e) $[M+1]^+$ 521.9.

Step 5: 2-((S)-4-(6-(9H-fluoren-9-yl)-2-(((S)-1-methylpyrrolidin-2-yl)methoxy)-6, 7-dihydro-5H-pyrrolo[3, 4-d]pyrimidin-4-yl)-1-acryloylpiperazin-2-yl)acetonitrile

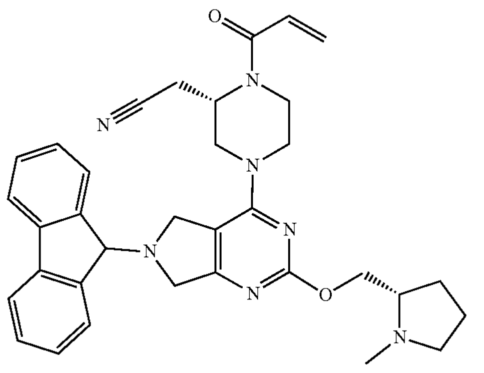 [SMILES: C=CC(=O)N1CCN(c2nc(OC[C@@H]3CCCN3C)nc3c2CN(C2c4ccccc4-c4ccccc42)C3)C[C@@H]1CC#N]

To a solution of 2-((S)-4-(6-(9H-fluoren-9-yl)-2-(((S)-1-methylpyrrolidin-2-yl)methoxy)-6, 7-dihydro-5H-pyrrolo[3, 4-d]pyrimidin-4-yl)piperazin-2-yl)acetonitrile (61 mg, 0.12 mmol) in 5 mL dichloromethane was added 0.3 mL triethylamine and it was stirred at −70° C., then it was added acryloyl chloride (11 mg, 0.12 mmol) and it was stirred at −70° C. for 0.5 h. Then it was diluted with dichloromethane and water and the organic layer was combined, dried over sodium sulfate and evaporated. The residue was purified by Prep-TLC to give Example 40 (18 mg, 26.1%). $^1$H NMR (400 MHz, DMSO-$d_6$) δ ppm: 7.88-7.79 (m, 2H), 7.69-7.58 (m, 2H), 7.43-7.34 (m, 2H), 7.33-7.24 (m, 2H), 6.90-6.65 (m, 1H), 6.23-6.05 (m, 1H), 5.79-5.68 (m, 1H), 5.33-5.22 (m, 1H), 4.91-4.61 (m, 1H), 4.42-4.16 (m, 5H), 4.13-3.80 (m, 2H), 3.73-3.56 (m, 2H), 3.49-3.35 (m, 2H), 3.24-3.08 (m, 2H), 3.08-2.92 (m, 2H), 2.88-2.74 (m, 2H), 2.70-2.53 (m, 3H), 2.10-1.94 (m, 1H), 1.89-1.71 (m, 2H), 1.69-1.58 (m, 1H). MS (ESI, m/e) [M+1]$^+$ 576.6.

Example 41: 2-((S)-1-acryloyl-4-(6-((5-methyl-1H-indazol-4-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

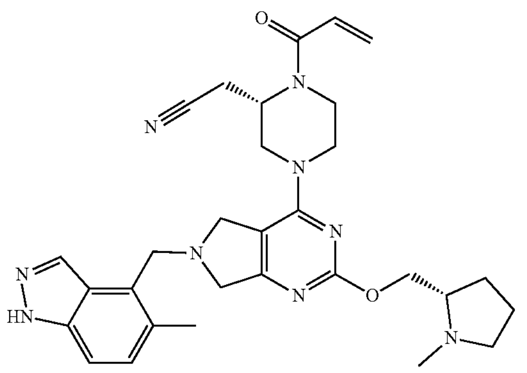 [SMILES: C=CC(=O)N1CCN(c2nc(OC[C@@H]3CCCN3C)nc3c2CN(Cc2c(C)ccc4[nH]ncc24)C3)C[C@@H]1CC#N]

Synthetic Route:

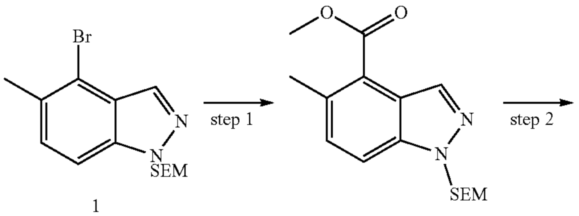

1

2

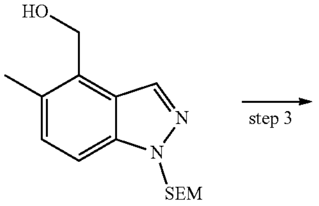

3

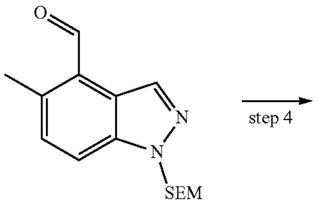

4

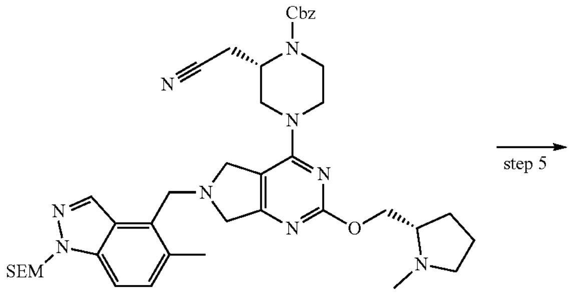

5

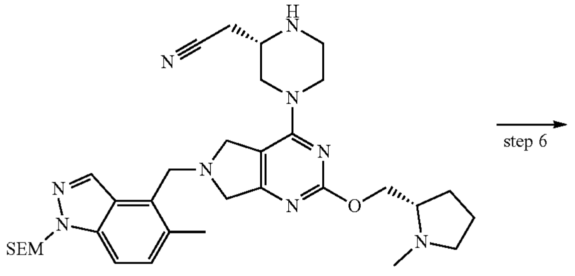

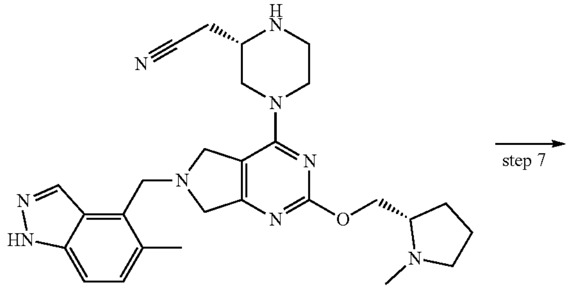

-continued

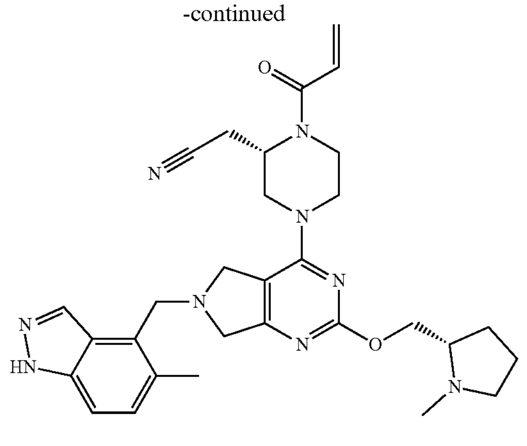

Step 1: methyl 5-methyl-1-((2-(trimethylsilyl) ethoxy)methyl)-1H-indazole-4-carboxylate A mixture of 4-bromo-5-methyl-1-((2-(trimethylsilyl) ethoxy)methyl)-1H-indazole (1.2 g, 3.5 mmol), triethylamine (1.06 g, 10.5 mmol), MeOH (50 mL), DMF (10 mL), and Pd(dppf)Cl2 (0.25 g, 0.35 mmol) was purged with nitrogen. The mixture was stirred under carbon monoxide (2 atm) at 80° C. for 16 h. Upon completion, the mixture was cooled to room temperature, and dilute with EtOAc (60 mL). The mixture was washed with water and saturated sodium chloride. The organic layer was dried over sodium sulfate, filtered, and the filtrate was concentrated under reduced pressure. The residue was purified by silica gel column chromatography, eluted with 0-50% EtOAc/hexane to afford the title compound (0.5 g, 45.4% yield). MS (ESI, m/e) $[M+1]^+$ 321.

Step 2: (5-methyl-1-((2-(trimethylsilyl)ethoxy) methyl)-1H-indazol-4-yl)methanol To a solution of methyl 5-methyl-1-((2-(trimethylsilyl) ethoxy)methyl)-1H-indazole-4-carboxylate (0.5 g, 1.56 mmol) in THF (30 mL) was added $LiAlH_4$ (0.178 g, 4.69 mmol) at 0° C. After being stirred for 2 h at room temperature, the reaction was quenched by adding $Na_2SO_4.10H_2O$. After being stirred for another 1 h at room temperature, the crude material was filtered through Celite pad, and the resulting filtrate was concentrated in vacuo to give crude title product (0.3 g). This material was used in the next reaction without further purification. MS (ESI, m/e) $[M+1]^+$ 293.

Step 3: 5-methyl-1-((2-(trimethylsilyl)ethoxy) methyl)-1H-indazole-4-carbaldehyde Dess-Martin reagent (0.43 g, 2.02 mmol) was added to a mixture of (5-methyl-1-((2-(trimethylsilyl)ethoxy)methyl)-1H-indazol-4-yl)methanol (0.3 g, 1.02 mmol) and dichloromethane (20 ml). The reaction was kept at room temperature. After the mixture was stirred for 2 h, it was washed with water (3×30 ml), dried with anhydrous $MgSO_4$, filtered, and vacuum evaporated to afford the title product (0.2 g, 68.9% yield). MS (ESI, m/e) $[M+1]^+$ 291.

Step 4: benzyl (S)-2-(cyanomethyl)-4-(6-((5-methyl-1-((2-(trimethylsilyl)ethoxy)methyl)-1H-indazol-4-yl)methyl)-2-(((S)-1-methylpyrrolidin-2-yl)methoxy)-6, 7-dihydro-5H-pyrrolo[3, 4-d] pyrimidin-4-yl)piperazine-1-carboxylate To a solution of benzyl (S)-2-(cyanomethyl)-4-(2-(((S)-1-methylpyrrolidin-2-yl)methoxy)-6, 7-dihydro-5H-pyrrolo[3, 4-d]pyrimidin-4-yl)piperazine-1-carboxylate (120 mg, 0.24 mmol) in 5 mL acetonitrile was added 5-methyl-1-((2-(trimethylsilyl)ethoxy)methyl)-1H-indazole-4-carbaldehyde (80 mg, 0.27 mmol). After the addition, the mixture was stirred at room temperature for 10 min. Then it was added sodium triacetoxyborohydride (63 mg, 0.30 mmol). Then it was stirred at room temperature for 16 h, it was diluted with dichloromethane and water. The organic layer was combined, dried over sodium sulfate and evaporated. The residue was purified by chromatography column on silica to give the title product (150 mg, 71.1%). MS (ESI, m/e) $[M+1]^+$ 766.

Step 5: 2-((S)-4-(6-((5-methyl-1-((2-(trimethylsilyl) ethoxy)methyl)-1H-indazol-4-yl)methyl)-2-(((S)-1-methylpyrrolidin-2-yl)methoxy)-6, 7-dihydro-5H-pyrrolo[3, 4-d]pyrimidin-4-yl)piperazin-2-yl) acetonitrile To a solution of benzyl (S)-2-(cyanomethyl)-4-(6-((5-methyl-1-((2-(trimethylsilyl)ethoxy)methyl)-1H-indazol-4-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate (150 mg, 0.19 mmol) in methanol (3 mL) was added 10% Pd/C 20 mg and it was stirred at room temperature for 16 h under hydrogen atmosphere. Then it was filtered and the filtrate was evaporated. The residue was not purified and used in the next step directly (80 mg). MS (ESI, m/e) $[M+1]^+$ 632.

Step 6: 2-((S)-4-(6-((5-methyl-1H-indazol-4-yl) methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile 2-((S)-4-(6-((5-methyl-1-((2-(trimethylsilyl)ethoxy) methyl)-1H-indazol-4-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (80 mg, 0.13 mmol) was dissolved in dichloromethane (10 mL) and trifluoro acetic acid (3 ml) was added. The reaction mixture was stirred at room temperature for 16 h then concentrated to afford the title product (40 mg crude). MS (ESI, m/e) $[M+1]^+$ 502.

Step 7: 2-((S)-1-acryloyl-4-(6-((5-methyl-1H-indazol-4-yl)methyl)-2-(((S)-1-methylpyrrolidin-2-yl) methoxy)-6, 7-dihydro-5H-pyrrolo[3, 4-d]pyrimidin-4-yl)piperazin-2-yl)acetonitrile

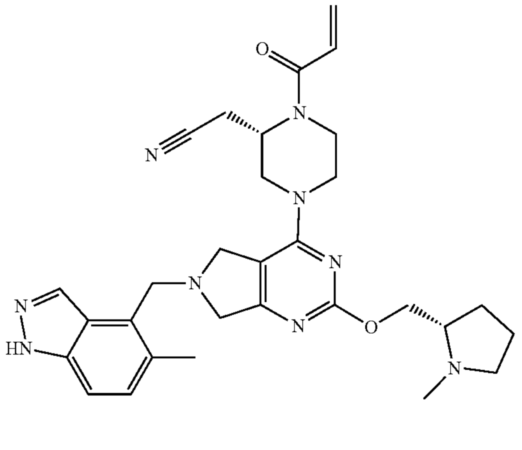 [SMILES: C=CC(=O)N1CCN(c2nc(OC[C@@H]3CCCN3C)nc3c2CN(Cc2c(C)ccc4[nH]ncc24)C3)C[C@@H]1CC#N]

To a solution of 2-((S)-4-(6-((5-methyl-1H-indazol-4-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (40 mg, 0.08 mmol) in 5 mL dichloromethane was added 0.3 mL triethylamine and it was stirred at −30° C., then it was added acryloyl chloride (18 mg, 0.20 mmol) and it was stirred at −30° C. for 1 h. Then it was diluted with dichloromethane and water and the organic layer was combined, dried over sodium sulfate and evaporated. The residue was purified by Prep-TLC to give Example 41 (1.36 mg, 2.3%). $^1$H NMR (400 MHz, $CD_3OD$) δ 8.46-8.38 (m, 1H), 8.24 (s, 1H), 7.39 (d, J=8.5 Hz, 1H), 7.26 (d, J=8.5 Hz, 1H), 6.87-6.61 (m, 11H), 6.27 (d, J=16.9 Hz, 11H), 5.87-5.71 (m, 11H), 4.81-4.51 (m, 4H), 4.47-4.39 (m, 1H), 4.26 (s, 2H), 4.18 (s, 2H), 4.08-3.98 (m, 1H), 3.81-3.70 (m, 3H), 3.64-3.59 (m, 1H), 3.52-3.44 (m, 1H), 3.18-3.09 (m, 1H), 3.01-2.64 (m, 7H), 2.51 (s, 3H), 2.40-2.32 (m, 1H), 2.18-1.93 (m, 3H). MS (ESI, m/e) $[M+1]^+$ 556.7.

Example 42: 2-((S)-1-acryloyl-4-(6-((2-hydroxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile

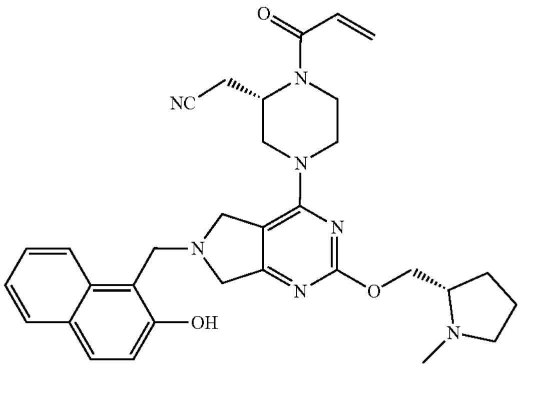 [SMILES: C=CC(=O)N1CCN(c2nc(OC[C@@H]3CCCN3C)nc3c2CN(Cc2c(O)ccc4ccccc24)C3)C[C@@H]1CC#N]

Synthetic Route:

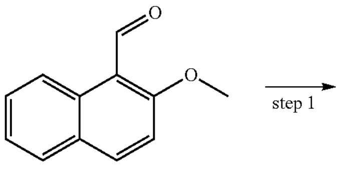

1

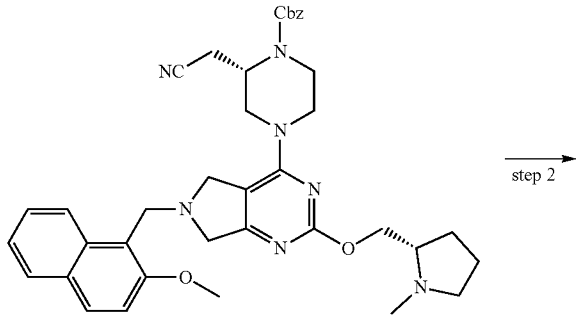

2

-continued

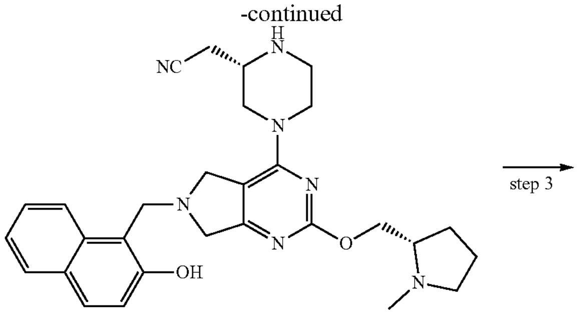

3

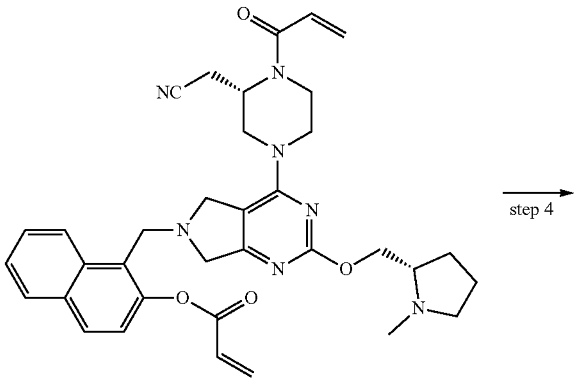

4

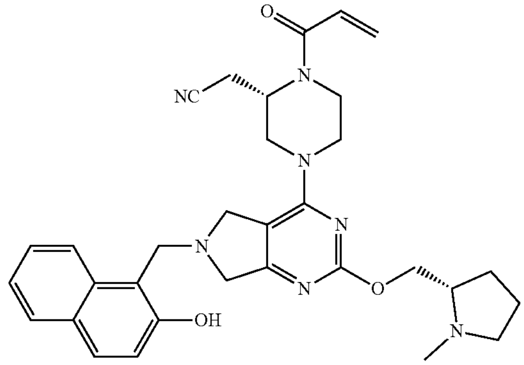

5

Step 1: benzyl (S)-2-(cyanomethyl)-4-(6-((2-methoxynaphthalen-1-yl)methyl)-2-(((S)-1-methylpyrrolidin-2-yl)methoxy)-6, 7-dihydro-5H-pyrrolo [3, 4-d]pyrimidin-4-yl)piperazine-1-carboxylate To a solution of benzyl (S)-2-(cyanomethyl)-4-(2-(((S)-1-methylpyrrolidin-2-yl)methoxy)-6, 7-dihydro-5H-pyrrolo [3, 4-d]pyrimidin-4-yl)piperazine-1-carboxylate (490 mg, 0.96 mmol) in 15 mL acetonitrile was added 2-methoxy-1-naphthaldehyde (180 mg, 0.96 mmol). After the addition, the mixture was stirred at room temperature for 10 min. Then it was added sodium triacetoxyborohydride (250 mg, 1.2 mmol). Then it was stirred at room temperature for 16 h, it was diluted with dichloromethane and water. The organic layer was combined, dried over sodium sulfate and evaporated. The residue was purified by chromatography column on silica to give the title product (400 mg, 60%). MS (ESI, m/e) $[M+1]^+$ 662.

Step 2: 2-((S)-4-(6-((2-hydroxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile 100 mg benzyl (S)-2-(cyanomethyl)-4-(6-((2-methoxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate (0.15 mmol) were dissolved in 15 mL dichloromethane and cooled to 0° C. 3 mL boron tribromide was added and the mixture was stirred over night at room temperature. The solid was filtrated off and washed with MTBE. The organic layer was purified using column chromatography (MeOH:DCM=1:20) to afford the desired compound (40 mg, 52%). MS (ESI, m/e) [M+1]+514.

Step 3: 1-((4-((S)-4-acryloyl-3-(cyanomethyl)piperazin-1-yl)-2-(((S)-1-methylpyrrolidin-2-yl)methoxy)-5, 7-dihydro-6H-pyrrolo[3, 4-d]pyrimidin-6-yl)methyl)naphthalen-2-yl acrylate To a solution of 2-((S)-4-(6-((2-hydroxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazin-2-yl)acetonitrile (40 mg, 0.07 mmol) in 5 mL dichloromethane was added 0.3 mL triethylamine and it was stirred at −30° C. Then acryloyl chloride (18 mg, 0.20 mmol) was added and it was stirred at −30° C. for 1 h. Then it was diluted with dichloromethane and water and the organic layer was combined, dried over sodium sulfate and evaporated. The residue was purified by Prep-TLC to afford the title product (40 mg). MS (ESI, m/e) $[M+1]^+$ 622.

Step 4: 2-((S)-1-acryloyl-4-(6-((2-hydroxynaphthalen-1-yl)methyl)-2-(((S)-1-methylpyrrolidin-2-yl)methoxy)-6, 7-dihydro-5H-pyrrolo[3,4-d]pyrimidin-4-yl)piperazin-2-yl)acetonitrile

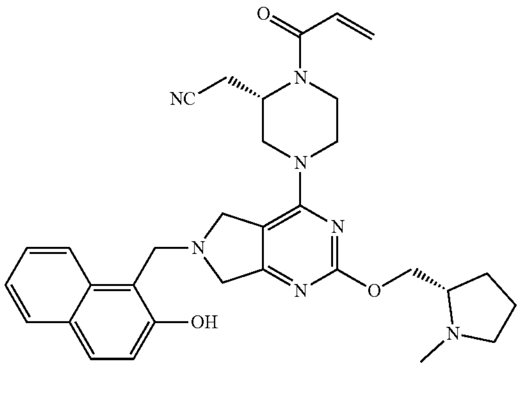 [SMILES: C=CC(=O)N1CCN(c2nc(OC[C@@H]3CCCN3C)nc3c2CN(Cc2c(O)ccc4ccccc24)C3)C[C@@H]1CC#N]

1-((4-((S)-4-acryloyl-3-(cyanomethyl)piperazin-1-yl)-2-(((S)-1-methylpyrrolidin-2-yl)methoxy)-5, 7-dihydro-6H-pyrrolo[3, 4-d]pyrimidin-6-yl)methyl)naphthalen-2-yl acrylate (40 mg, 0.06 mmol) was added to lithium hydroxide (1N in water) 3 mL and the solution was stirred for 1 h at room temperature. The solution was adjust to pH=7 with hydrochloric acid (1N). The crude product was purified by Prep-HPLC to afford Example 42 (1.8 mg, 5% yield). $^1$H NMR (400 MHz, $CD_3OD$) δ 8.46 (s, 1H), 8.04 (d, J=8.6 Hz, 1H), 7.74 (dd, J=18.1, 8.5 Hz, 2H), 7.46 (t, J=7.5 Hz, 1H), 7.30 (d, J=7.2 Hz, 1H), 7.10 (d, J=9.1 Hz, 1H), 6.86-6.68 (m, 1H), 6.27 (d, J=16.6 Hz, 1H), 5.88-5.73 (m, 11H), 4.99-4.92 (m, 1H), 4.78-4.71 (m, 2H), 4.63-4.55 (m, 1H), 4.53-4.41 (m, 3H), 4.29 (s, 2H), 4.09-3.99 (m, 1H), 3.90 (s, 2H), 3.76-3.69 (m, 1H), 3.63-3.57 (m, 1H), 3.17-3.01 (m, 2H), 2.97-2.85 (m, 5H), 2.84-2.67 (m, 2H), 2.37-2.24 (m, 1H), 2.17-2.09 (m, 1H), 2.05-1.94 (m, 2H). MS (ESI, m/e) [M+1]+ 568.7.

Example 43: 2-((S)-1-acryloyl-4-(6-acryloyl-2-(((S)-1-methylpyrrolidin-2-yl)methoxy)-6, 7-dihydro-5H-pyrrolo[3, 4-d]pyrimidin-4-yl)piperazin-2-yl)acetonitrile

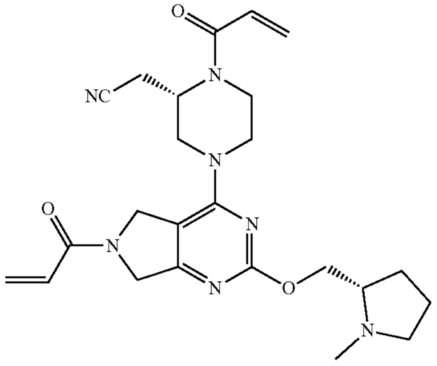 [SMILES: C=CC(=O)N1Cc2nc(OC[C@@H]3CCCN3C)nc(N3CCN(C(=O)C=C)[C@@H](CC#N)C3)c2C1]

Synthetic Route:

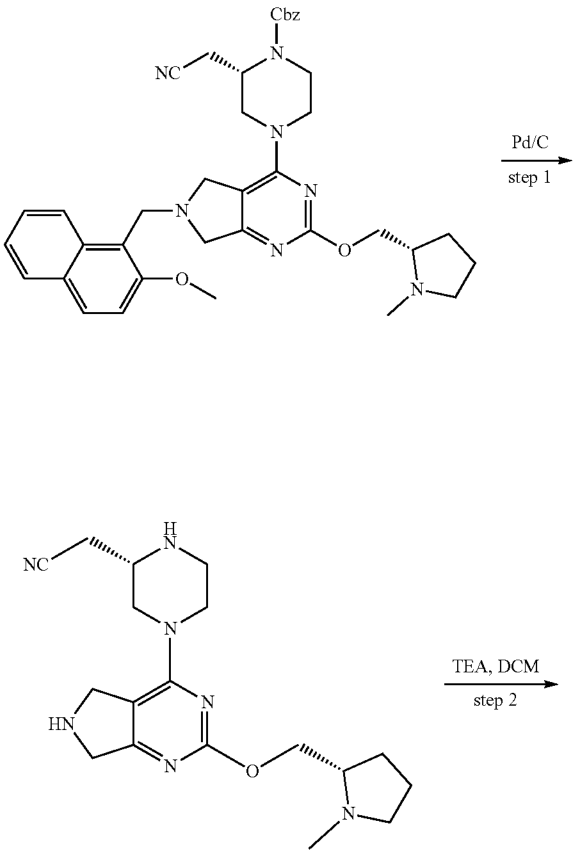

-continued

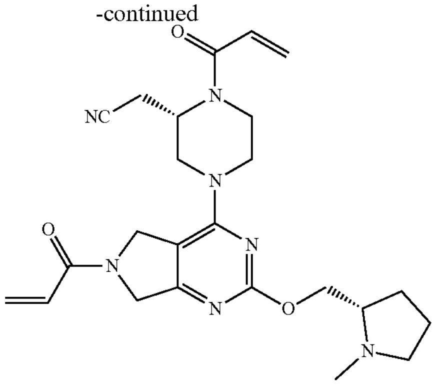

Step 1: 2-((S)-4-(2-(((S)-1-methylpyrrolidin-2-yl)methoxy)-6, 7-dihydro-5H-pyrrolo[3, 4-d]pyrimidin-4-yl)piperazin-2-yl)acetonitrile To a solution of benzyl (S)-2-(cyanomethyl)-4-(6-((2-methoxynaphthalen-1-yl)methyl)-2-(((S)-1-methylpyrrolidin-2-yl)methoxy)-6, 7-dihydro-5H-pyrrolo[3, 4-d]pyrimidin-4-yl)piperazine-1-carboxylate (100 mg, 0.15 mmol) in methanol (10 mL) was added 10% Pd/C 20 mg and it was stirred at room temperature for 16 h under hydrogen atmosphere. Then it was filtered and the filtrate was evaporated. The residue was used crude for the next step. MS (ESI, m/e) $[M+1]^+$ 358.

Step 2: 2-((S)-1-acryloyl-4-(6-acryloyl-2-(((S)-1-methylpyrrolidin-2-yl)methoxy)-6, 7-dihydro-5H-pyrrolo[3, 4-d]pyrimidin-4-yl)piperazin-2-yl)acetonitrile

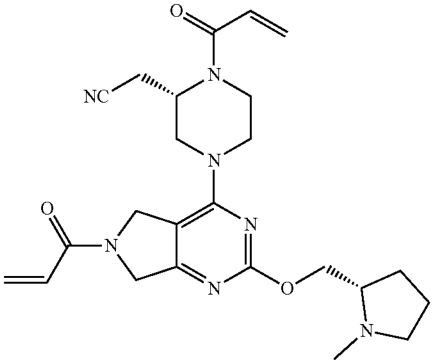 [SMILES: C=CC(=O)N1Cc2nc(OC[C@@H]3CCCN3C)nc(N3CCN(C(=O)C=C)[C@@H](CC#N)C3)c2C1]

To a solution of 2-((S)-4-(2-(((S)-1-methylpyrrolidin-2-yl)methoxy)-6, 7-dihydro-5H-pyrrolo[3, 4-d]pyrimidin-4-yl)piperazin-2-yl)acetonitrile (40 mg 0.11 mmol) in 5 mL dichloromethane was added 0.3 mL triethylamine and it was stirred at −30° C., then it was added acryloyl chloride (18 mg, 0.20 mmol) and it was stirred at −30° C. for 1 h. Then it was diluted with dichloromethane and water and the organic layer was combined, dried over sodium sulfate and evaporated. The residue was purified by Prep-TLC to give Example 43 (4.71 mg, 9% yield). $^1H$ NMR (400 MHz, $CD_3OD$) δ 6.85-6.73 (m, 1H), 6.72-6.62 (m, 1H), 6.44-6.35 (m, 1H), 6.35-6.25 (m, 1H), 5.90-5.77 (m, 2H), 5.16 (s, 1H), 5.03-4.93 (m, 2H), 4.79 (s, 3H), 4.62-4.57 (m, 1H), 4.56-4.46 (m, 1H), 4.27-4.04 (m, 2H), 3.91-3.82 (m, 1H), 3.76-3.65 (m, 1H), 3.52-3.39 (m, 2H), 3.27-3.17 (m, 1H), 3.12-3.03 (m, 3H), 3.02-2.85 (m, 2H), 2.83-2.75 (m, 1H), 2.48-2.32 (m, 1H), 2.27-1.98 (m, 3H). MS (ESI, m/e) $[M+1]^+$ 466.6.

Example F: Biological Assays

Biochemical Functional Assay:
Bioanalysis

The KRAS (aa 1-169) G12C, C51S, C80L, C118S with a His-tag was expressed, purified and loaded with GDP in house. All protein and substrate solutions were prepared in assay buffer containing 25 mM HEPES pH7.5, 10 mM $MgCl_2$, and 0.01% Triton X-100. Purified GDP-loaded KRAS (aa 1-169) G12C, C51S, C80L, C118S protein was pre-incubated with a serially diluted compound at 24° C. for 3 hrs. Purified SOS1 (aa 564-1049) protein, GTPγS (Sigma) and GST-cRaf RBD (aa 1-149) were then added to each well and incubated at 24° C. for additional 3 hrs. This addition initiates the nucleotide exchange reaction and transition of inactive GDP loaded KRAS G12C to active GTPγS KRAS G12C which binds to GST-cRaf RBD. Following the incubation, Mab Anti-6HIS-Tb cryptate (Cisbio) and Mab Anti GST-XL665 (Cisbio) were added and further incubated at 24° C. for 3 hrs. The binding interaction between active GTPγS KRAS G12C and GST-cRaf RBD brings the Tb and XL665 into close proximity enabling an increased FRET signal (Ex337 nm, Em665 nm/620 nm). The inhibition percentage of nucleotide exchange reaction in presence of increasing concentrations of compounds was calculated based on the ratio of fluorescence at 665 nm to that at 620 nm detected on a BMG PHERAstar FSX instrument. The $IC_{50}$ value of each compound was calculated from fitting the data to the four-parameter logistic model by Dotmatics.

Data Analysis

| Example No. | $IC_{50}$ (nM) | Example No. | $IC_{50}$ (nM) |
|---|---|---|---|
| 1 | 3280 | 29 | 2.42 |
| 2 | 46000 | 30 | 15 |
| 3 | 23700 | 31 | 301 |
| 5 | 56.1 | 32 | 39.5 |
| 6 | 27.7 | 33 | 22.4 |
| 7 | 174 | 34 | 505 |
| 8 | 495 | 35 | 256 |
| 9 | 265 | 36 | 238 |
| 10 | 415 | 37 | 27.9 |
| 11 | 170 | 38 | 1570 |
| 12 | 379 | 40 | 1510 |
| 15 | 492 (P1); 5.27 (P2) | 41 | 77.2 |
| 16 | 5650 (P1); 256 (P2) | 42 | 9980 |
| 17 | 2200 (P1); 949 (P2) | 44 | 9010 |
| 18 | 1560 | 45 | 12.6 |
| 19 | 976 | 46 | 172 |
| 20 | 2880 | 47 | 102 |
| 21 | 92.5 | 50 | 6.16 |
| 22 | 9.63 | 51 | 16.1 |
| 23 | 28.1 | 52 | 8.51 |
| 24 | 101 | 53 | 14.9 |
| 25 | 3.27 | 54 | 639 |
| 26 | 1080 | 55 | <5.1 |
| 27 | 3720 | 56 | 941 |
| 28 | 178 | | |

It is to be understood that, if any prior art publication is referred to herein; such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A compound of Formula (I):

(I)

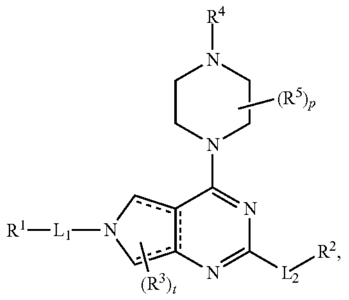

or a pharmaceutically acceptable salt thereof, or a stereoisomer thereof, wherein:

is a single bond or a double bond;

$L_1$ and $L_2$ are each selected from a single bond, —CO—NH—, —NH—CO—, —O—, —$NR^a$—, —$NR^a(CH_2)_m$—, —S—, —$(CH_2)_m$—, —O—$(CH_2)_m$—, —O—$CH(R^a)$—, —$CH(R^a)$—, —$CH(R^a)$—$(CH_2)_m$—, —$(CH_2)_m$—O—, —CO—, —$SO_2$—, cycloalkylene, oxetandiyl, tetrahydrofurandiyl, tetrahydropyrandiyl, azetidindiyl, pyrrilidindiyl, piperidindiyl, or piperizindiyl;

$R^1$ is selected from —$C_{2-4}$alkenyl, 5- to 6-membered carbocyclic aromatic ring, 7- to 12-membered bi-carbocyclic ring, 10- to 15-membered tri-carbocyclic ring, or 7- to 12-membered bicyclic heteroaryl comprising at least one heteroatom selected from N, O and S with the remaining ring atoms being carbon; wherein each of said —$C_{2-4}$alkenyl, 5- to 6-membered carbocyclic aromatic ring, 7- to 12-membered bi-carbocyclic ring, 10- to 15-membered tri-carbocyclic ring, or 7- to 12-membered bicyclic heteroaryl is optionally substituted with at least one $R^6$, wherein each $R^6$ is independently selected from halogen, hydroxy, oxo, —$NR^bR^c$, —$C_{1-8}$ alkyl, —$C_{1-8}$alkoxy, -halo$C_{1-8}$ alkyl, cycloalkyl, heterocyclyl, aryl, or heteroaryl, wherein $R^b$ and $R^c$ are independently hydrogen, deuterium, or —$C_{1-8}$alkyl;

$R^2$ is selected from —$NR^bR^c$, cycloalkyl, heterocyclyl, aryl, or heteroaryl, wherein each of said cycloalkyl, heterocyclyl, aryl, or heteroaryl is optionally substituted with at least one $R^6$ each $R^6$ is independently selected from —$C_{1-8}$alkyl, halogen, hydroxy, oxo, —$C_{1-8}$alkoxy, —$NR^bR^c$, cycloalkyl, heterocyclyl, aryl, or heteroaryl, wherein said —$C_{1-8}$alkyl, —$C_{1-8}$alkoxy, cycloalkyl, heterocyclyl, aryl, or heteroaryl is optionally substituted with at least one hydroxy, amino, CN, cycloalkyl, heterocyclyl, aryl or heteroaryl;

$R^3$ is selected from hydrogen, oxo, —$C_{1-8}$alkyl, —$C_{2-8}$ alkenyl, —$C_{2-8}$alkynyl, cycloalkyl, heterocyclyl, aryl, or heteroaryl, wherein each of said —$C_{1-8}$alkyl, —$C_{2-8}$ alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^5$ is selected from —$C_{1-8}$alkyl, —$C_{2-8}$alkenyl, —$C_{2-8}$ alkynyl, oxo, —$NR^bR^c$, —CO—$NR^dR^c$, cycloalkyl, heterocyclyl, aryl, heteroaryl, —$(CH_2)_m$—CN, or hydrogen;

$R^4$ is selected from

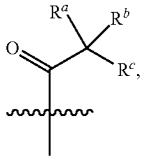

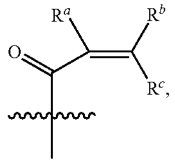

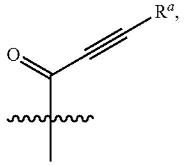

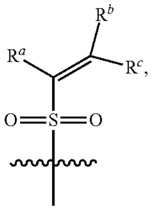

or

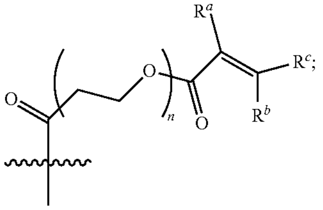

wherein each of $R^a$, $R^b$ and $R^c$ is independently hydrogen, deuterium (D), cyano (CN), halogen, hydroxy, —$C_{1-8}$ alkoxy, —$C_{1-8}$alkyl, —$C_{2-8}$alkenyl, —$C_{2-8}$alkynyl, cycloalkyl, heterocyclyl, aryl, heteroaryl, —$NR^dR^e$, or —CO—$NR^dR^e$, wherein each of said —$C_{1-8}$alkyl, —$C_{2-8}$alkenyl, —$C_{2-8}$alkynyl, cycloalkyl, heterocyclyl, aryl, or heteroaryl is optionally substituted with $R^f$; or (i) $R^a$ and $R^b$ or (ii) $R^a$ and $R^c$, together with the atom(s) to which they are attached, form a 4- to 6 membered ring, wherein said ring is optionally substituted with at least one $R^g$;

each $R^f$ is independently selected from halogen, hydroxy, oxo, —$C_{1-8}$alkoxy, —$NR^dR^e$, —CO—$NR^dR^e$, —$NR^d$—CO—$R^e$, cycloalkyl, heterocyclyl, aryl, or heteroaryl, wherein each said —$C_{1-8}$alkoxy, cycloalkyl, heterocyclyl, aryl, or heteroaryl is optionally substituted with halogen, hydroxy or —$C_{1-4}$alkyl;

$R^d$, $R^e$, and $R^g$ are each independently hydrogen, deuterium (D), halogen, oxo, or —$C_{1-8}$alkyl, wherein each said —$C_{1-8}$alkyl is optionally substituted with at least one halogen, oxo, $CF_3$ or —$COCH_3$;

p, q, and t are independently selected from 0, 1, 2, 3 or 4; and each m and n are independently 0, 1, 2, 3, 4, 5 or 6.

2. The compound according to claim 1, wherein:

a) $R^1$ is selected from phenyl, naphthalene, indane, fluorene, indazole, dihydroacenaphthylene, quinoline, isoquinoline, or indole, wherein said phenyl, naphthalene, indane, fluorene, indazole, dihydroacenaphthylene, quinoline, isoquinoline, or indole is optionally substituted with at least one $R^6$, wherein each $R^6$ is independently selected from —$C_{1-8}$alkyl, —$C_{1-8}$alkoxy, -halo$C_{1-8}$ alkyl, oxo, halogen, hydroxy, —$NH_2$, and $C_{3-6}$ cycloalkyl; or b) $R^1$ is selected from

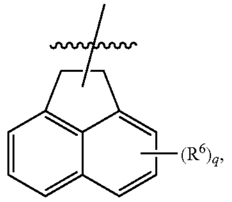
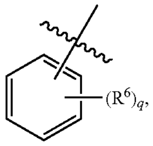
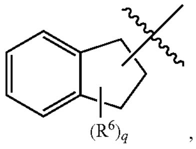
,
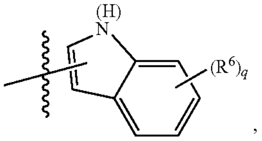
,
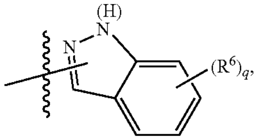
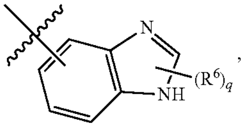
,
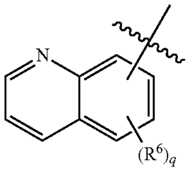
,
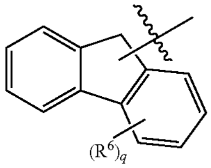
,
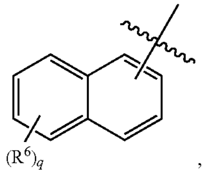
,
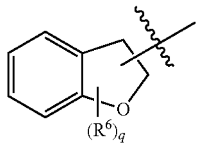
,
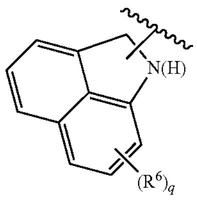
,
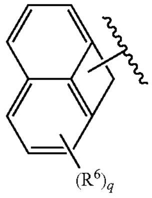
, -continued

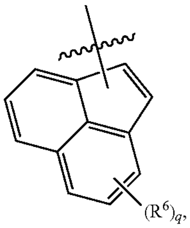
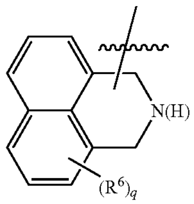
, or
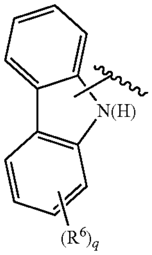
, wherein each $R^6$ is independently selected from F, Br, $C_1$, OH, —$OCH_3$, oxo, CN, —$NH_2$, —$CF_3$, —$CF_2H$, $CH_2CH_3$, or $CH_3$; wherein q is 0, 1 or 2.

3. The compound according to claim 1, wherein:

a) $R^1$ is selected from

—CH=$CH_2$,
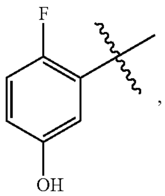
,
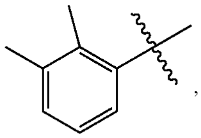
,
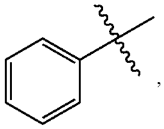
,
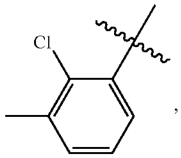
,
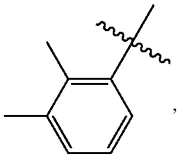
,
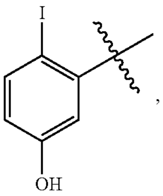
,
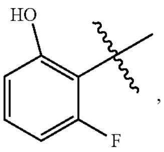
,
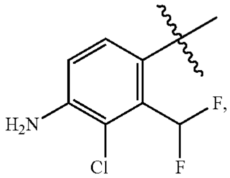
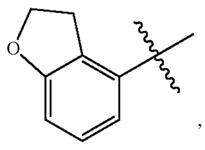
,
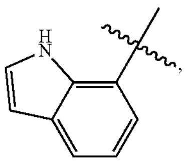
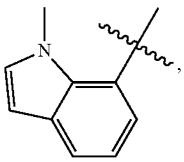

-continued
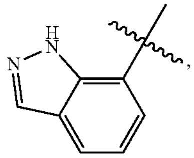 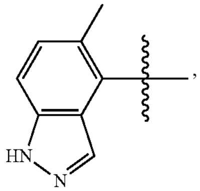
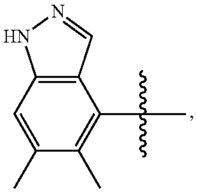 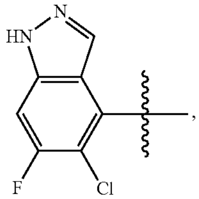
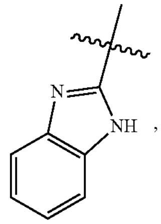 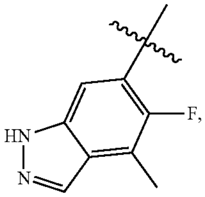
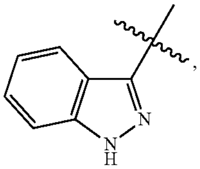 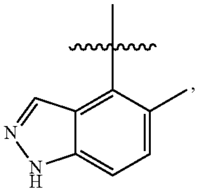
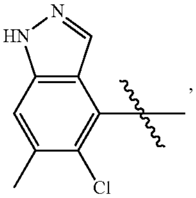 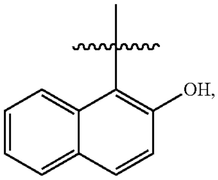
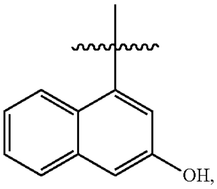 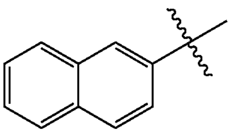 ,
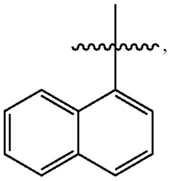 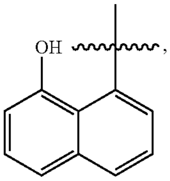 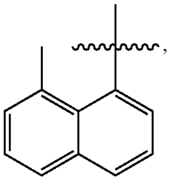
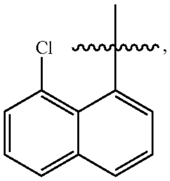 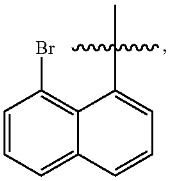 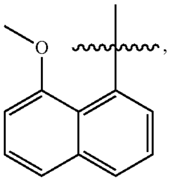
-continued
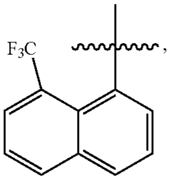 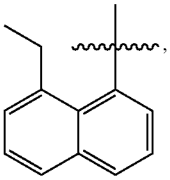 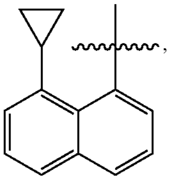
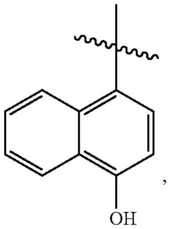 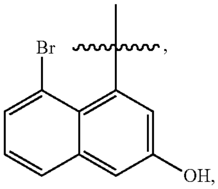
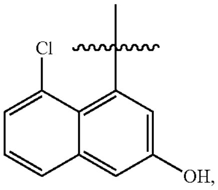 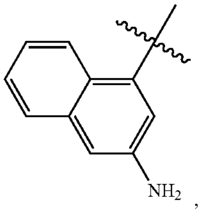
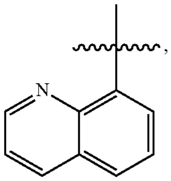 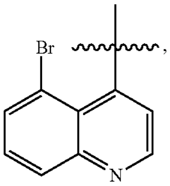
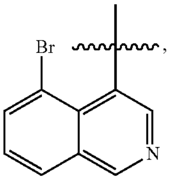 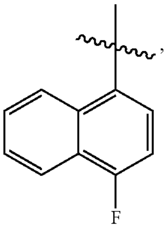
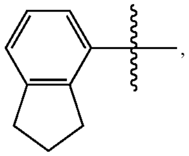 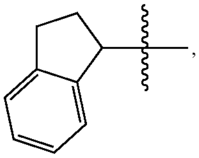
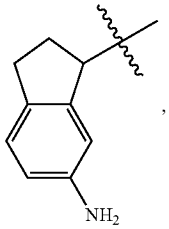 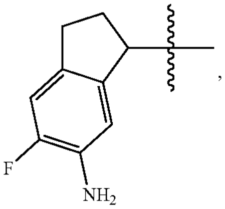
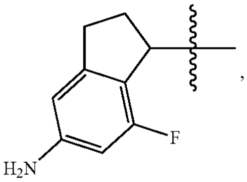 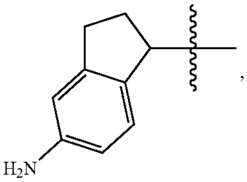

-continued
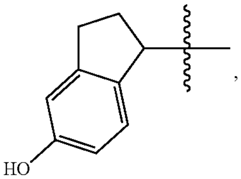,
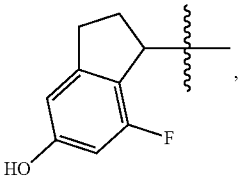,
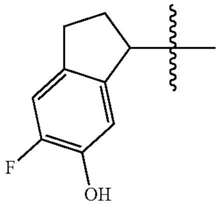,
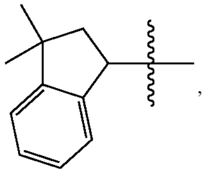,
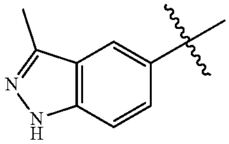,
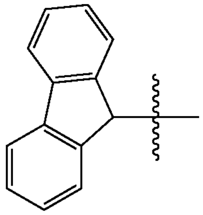,
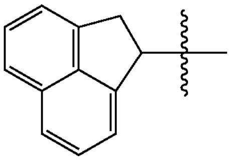,
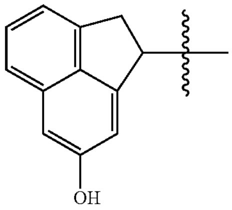,
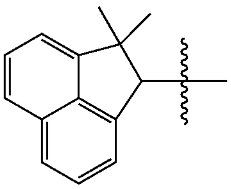,
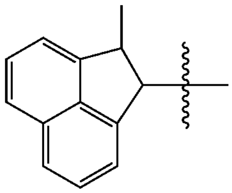,
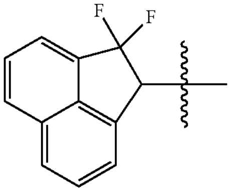,
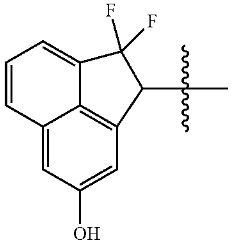,
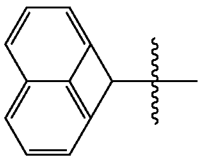,
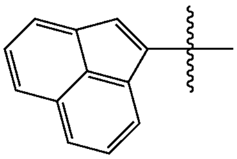,
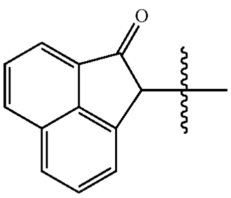,
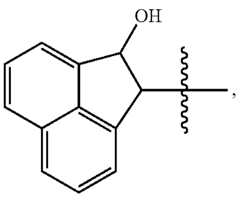,
-continued
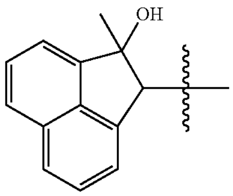,
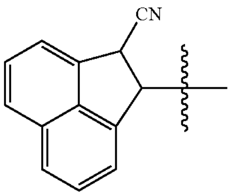,
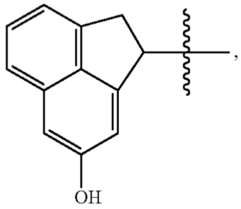,
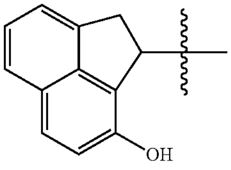,
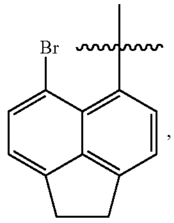,
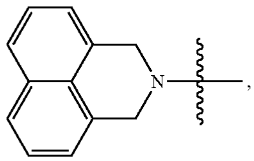,
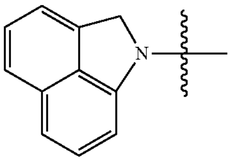,
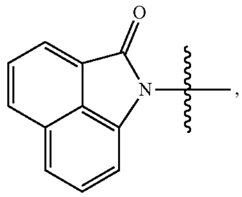, or
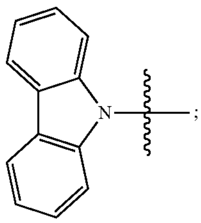;
or
b) $R^1$ is selected from
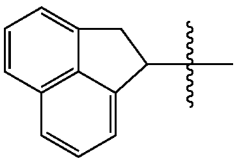,
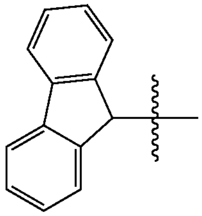,
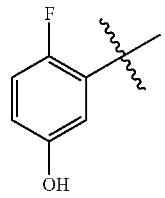,
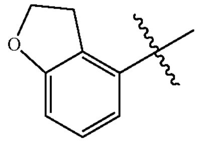, -continued

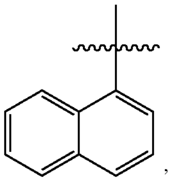, 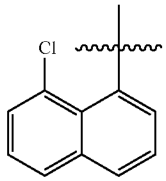, 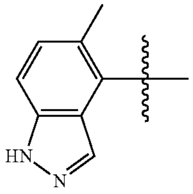,

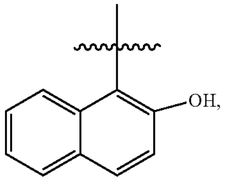 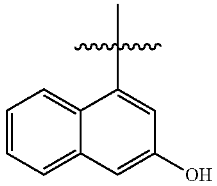,

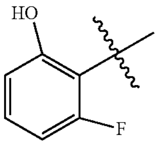, 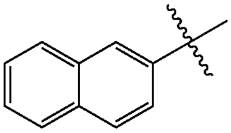,

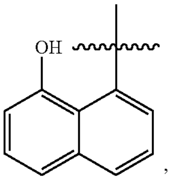, 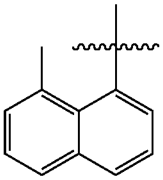, 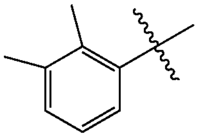,

—CH═CH$_2$, 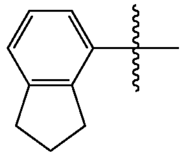, or

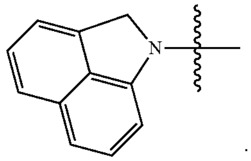.

4. The compound according to claim 1, wherein $L_1$ is selected from a single bond, —CO—NH—, —$CH_2$—, —CO—, or —$CH(CH_3)$—.

5. The compound according to claim 1, wherein:

a) $L_2$ is selected from a single bond, —O—, —O—$(CH_2)_m$—, —O—$CH(R^a)$—, —O—$CH(R^a)$—$(CH_2)_m$—, cyclopropylene, azetidindiyl, or —$NR^a(CH_2)_m$—, wherein m is 1 or 2; and $R^a$ is selected from hydrogen, methyl, or deuterium; or b) $L_2$ is selected from a single bond, —O—$CH_2$—, —O—$CH_2CH_2$—, —O—$CH_2CH_2CH_2$—, —O—, —O—$CH(CH_3)$—, —NH—$CH_2$—, —NH—$CH_2CH_2$—, —O—$CH(CH_3)CH_2$—,

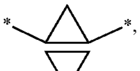

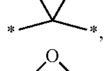

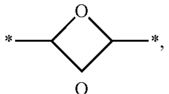

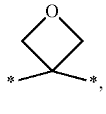

-continued

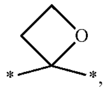

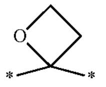 or

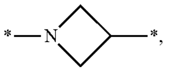

wherein the asterisks refers to linking positions.

6. The compound according to claim 1, wherein $R^2$ is selected from

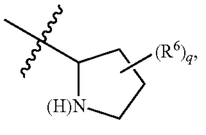

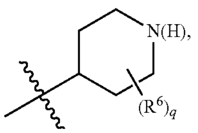

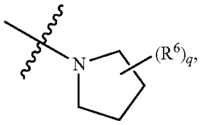

—$NR^bR^c$,

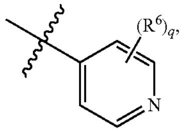

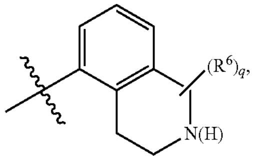 or

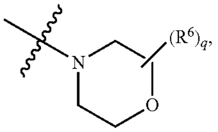

wherein each $R^6$ is independently selected from halogen, hydroxy, —$C_{1-8}$alkyl, —$C_{1-8}$alkoxy or heterocyclyl, wherein —$C_{1-8}$alkyl is optionally substituted with hydroxy or halogen; each q is 0, 1, 2 or 3; and $R^b$ and $R^c$ are each independently hydrogen, deuterium, halogen, or —$C_{1-8}$alkyl.

7. The compound according to claim 6, wherein $R^6$ is selected from $CH_3$, OH, $CH_2OH$, F, —$CHF_2$, —$OCH_3$, Cl, Br, or

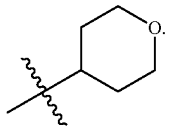 [SMILES: *C1CCOCC1]
8. The compound according to claim 1, wherein:
a) $R^2$ is selected from
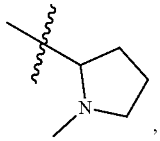, 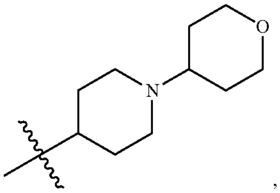,
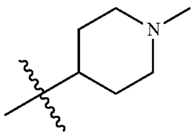, 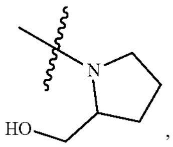, 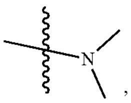,
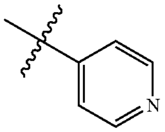, 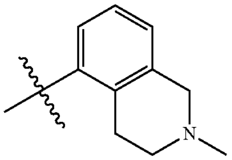,
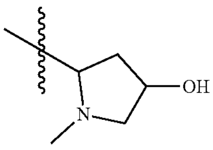, 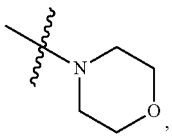,
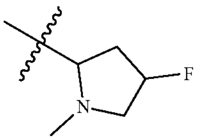, 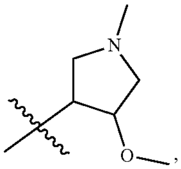, 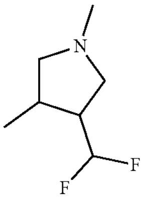,
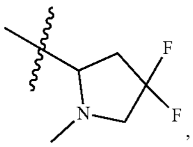, or 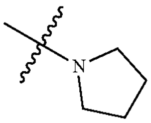;
or
b) wherein $R^2$ is selected from
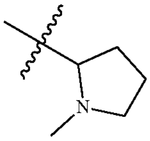, 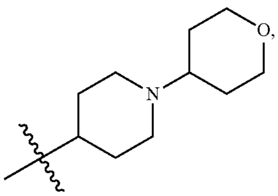
-continued
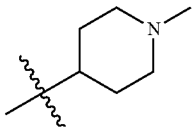, 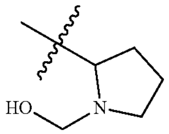,
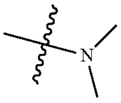, or 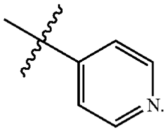
9. The compound according to claim 1, wherein $R^3$ is selected from hydrogen, oxo, or $—C_{1-8}$alkyl.
10. The compound according to claim 1, wherein
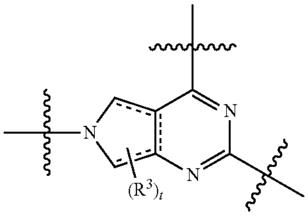
is selected from
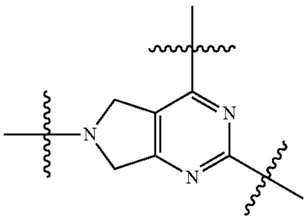,
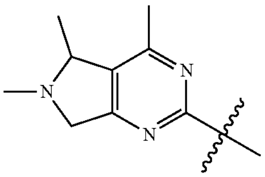,
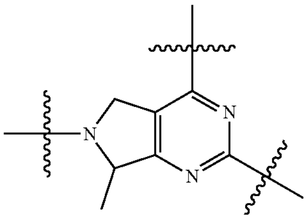,
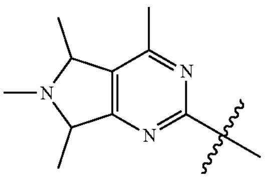, -continued

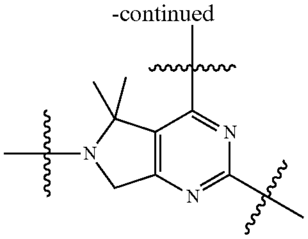

,

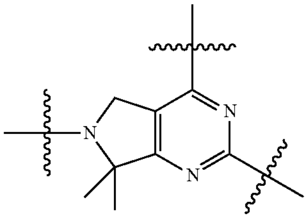

,

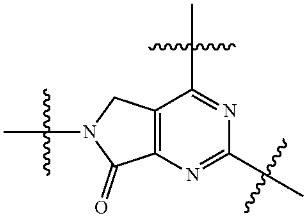

,

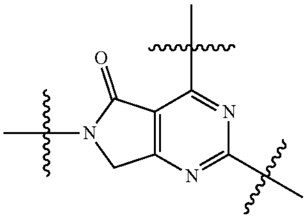

, or

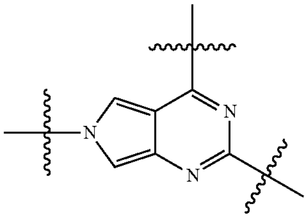

.

11. The compound according to claim 1, wherein:

$R^4$ is

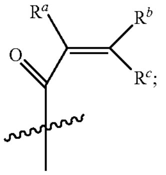

$R^a$ is selected from hydrogen, deuterium, halogen, —$C_{1-8}$ alkyl or —$C_{1-8}$alkoxy, wherein said —$C_{1-8}$alkyl or —$C_{1-8}$alkoxy is optionally substituted with at least one halogen, hydroxy, —$C_{1-8}$alkoxy, or —$NR^dCOR^e$;

$R^b$ is selected from hydrogen or —$C_{1-8}$alkyl;

$R^c$ is selected from hydrogen, halogen, —$C_{1-8}$alkyl, —CN, —$NR^dR^e$, —CO—$NR^dR^e$, or heteroaryl, wherein said —$C_{1-8}$alkyl is optionally substituted with at least one $R^f$;

each $R^f$ is independently selected from halogen, hydroxy, —$NR^dR^e$, —$C_{1-8}$alkoxy, or —$C_{4-7}$ heterocyclyl, wherein each said —$C_{1-8}$alkoxy or —$C_{4-7}$ heterocyclyl is optionally substituted with halogen, hydroxy or —$C_{1-4}$alkyl;

$R^d$ and $R^e$ are each independently hydrogen, deuterium, halogen, or —$C_{1-8}$alkyl, wherein said —$C_{1-8}$alkyl is optionally substituted with at least one halogen or —$COCH_3$; or $R^a$ and $R^b$ together with the atoms to which they are attached, form a 4- to 6-membered ring selected from

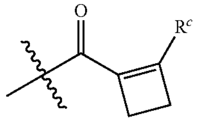

or

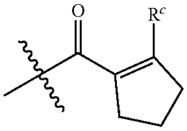

;

and $R^e$ is selected from hydrogen, hydroxy, —$C_{1-8}$alkoxy, or —$C_{1-8}$alkyl, wherein said ring is optionally substituted with oxo.

12. The compound according to claim 1, wherein:

a) $R^4$ is selected from

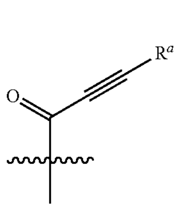

or

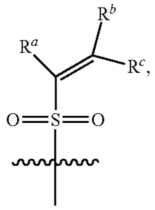

wherein $R^a$ is selected from hydrogen, hydroxy, or —$C_{1-8}$ alkyl; and each $R^b$ and $R^c$ are independently selected from hydrogen or —$C_{1-8}$alkyl; or b) $R^4$ is selected from

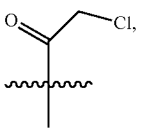

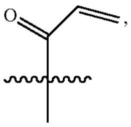

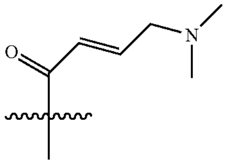

,

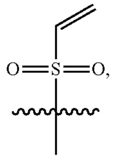

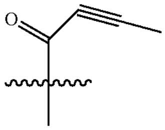

,

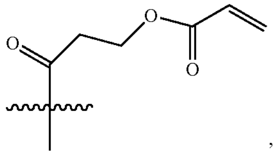

,

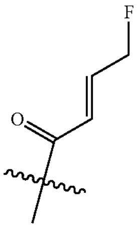

,

-continued
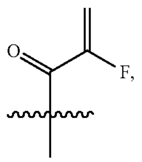,
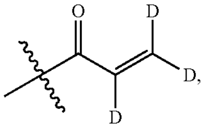,
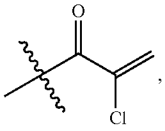,
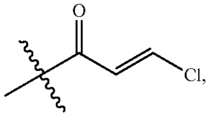,
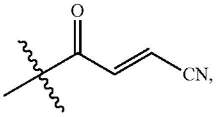,
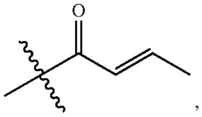,
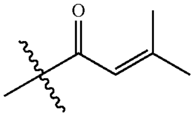,
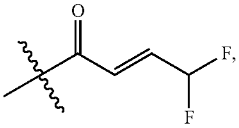,
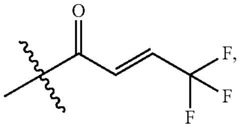,
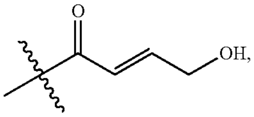,
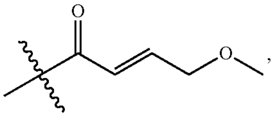,
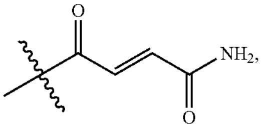,
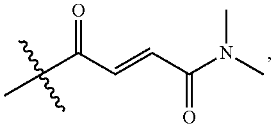,
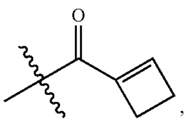,
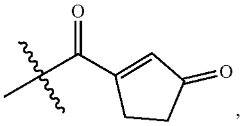,
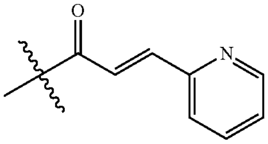,
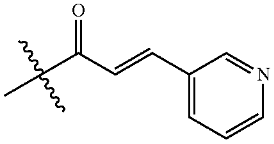,
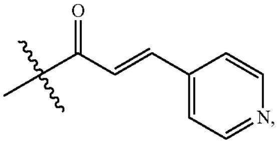,
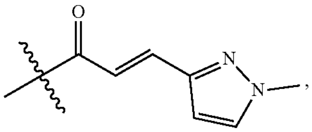,
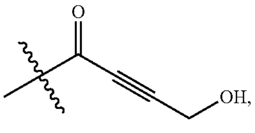,
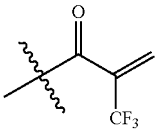,
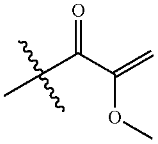,
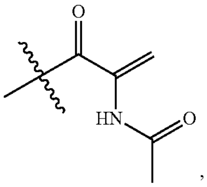,
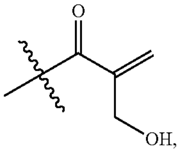,
-continued
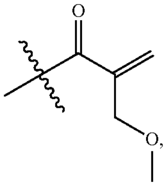,
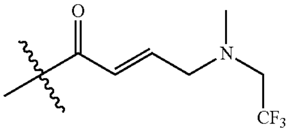,
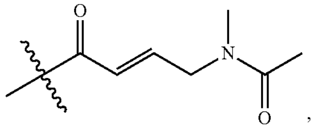,
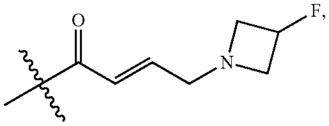,
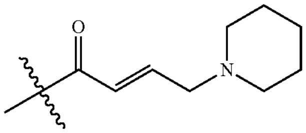,
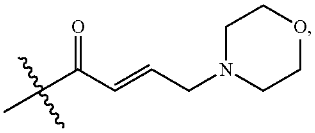,
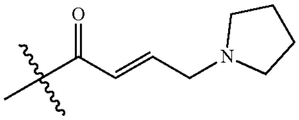,
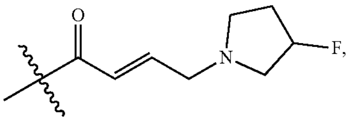,
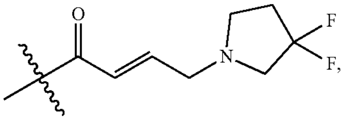, or
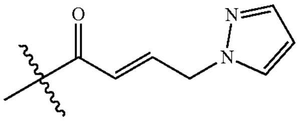.
13. The compound according to claim 1, wherein $R^4$ is selected from
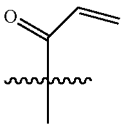,
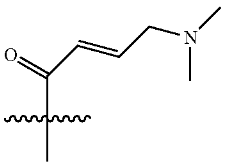,
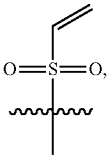,
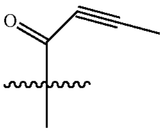,
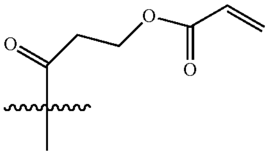.

14. The compound according to claim 1, wherein $R^5$ is selected from $-(CH_2)_m-CN$ or hydrogen; m is 0 or 1; and p=1.
15. The compound according to claim 1 selected from
1
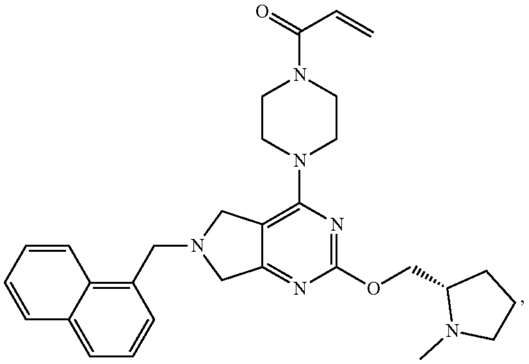
,
2
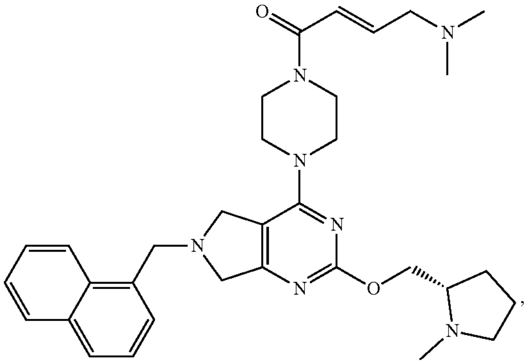
,
3
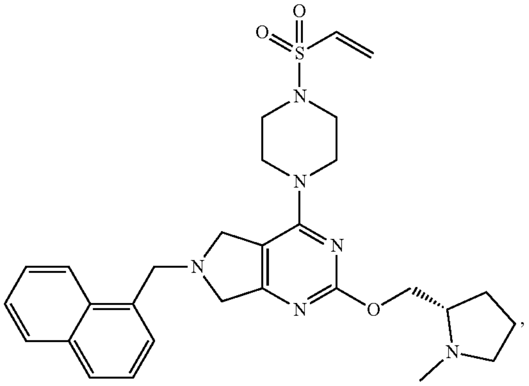
,
4
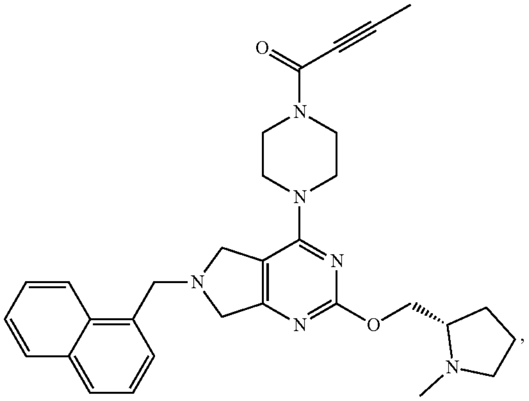
,
-continued
5
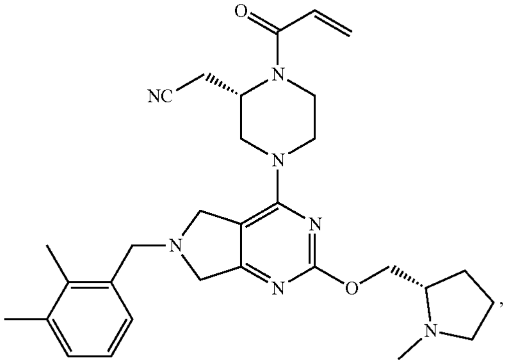
,
6
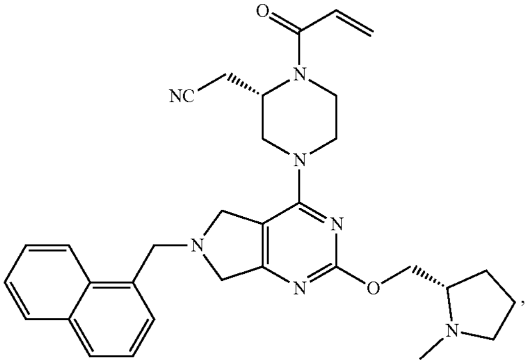
,
7
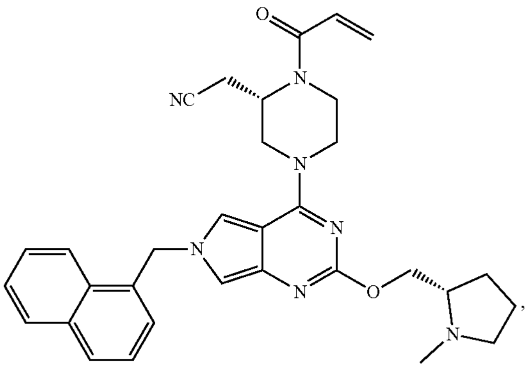
,
8
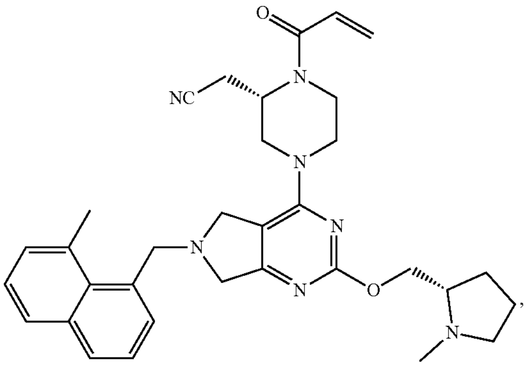
, 9
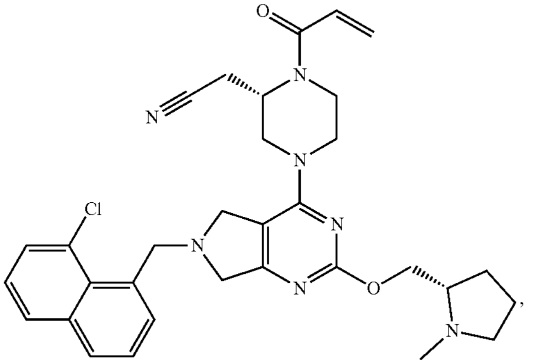
10
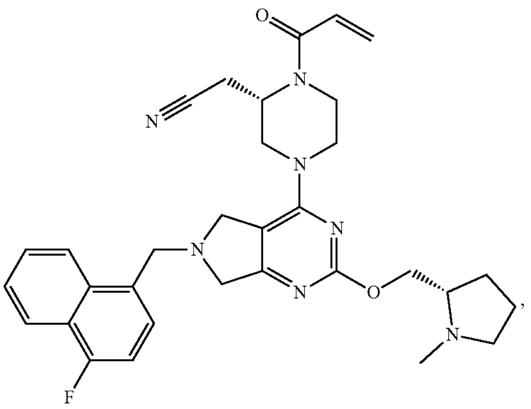
11
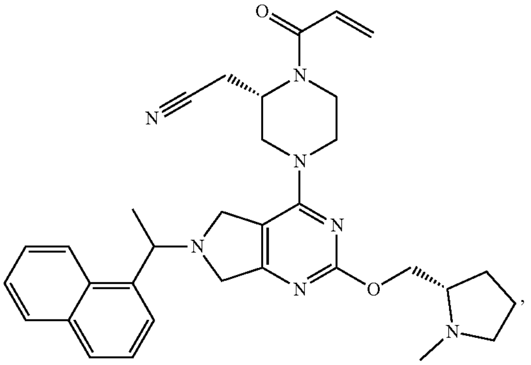
12
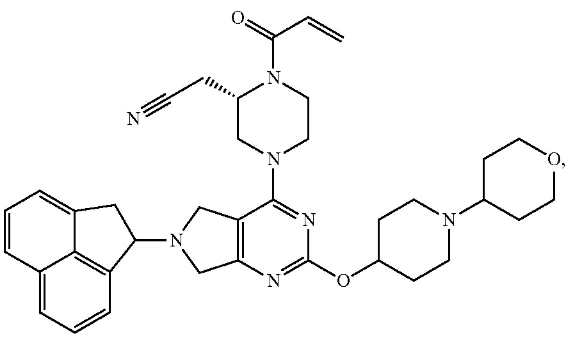
13
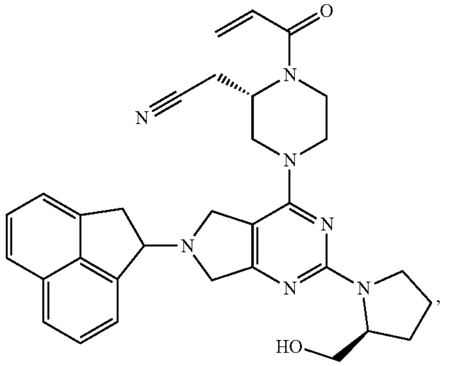
14
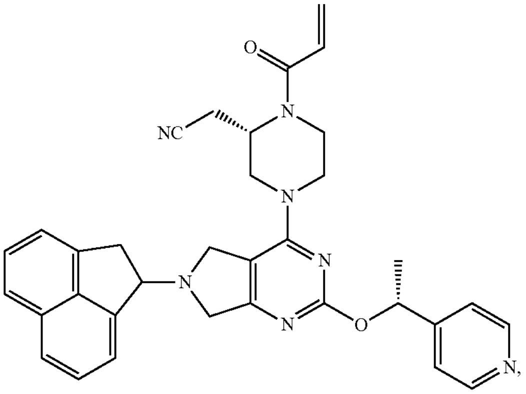
15
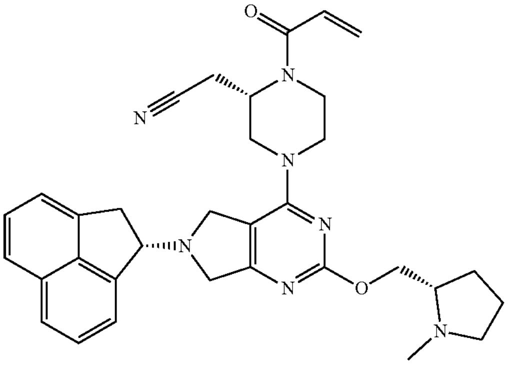
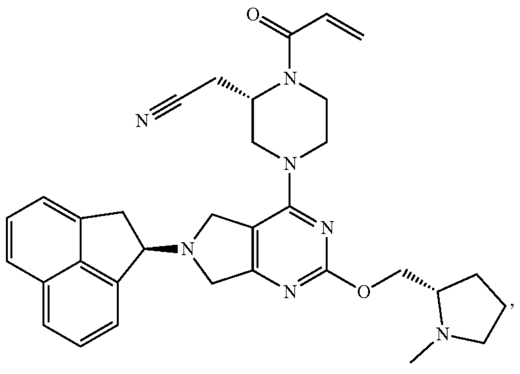

-continued
16
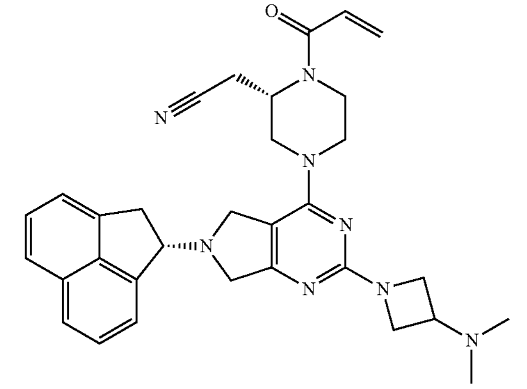
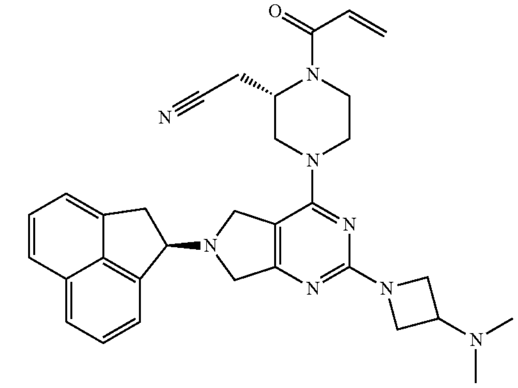
,
17
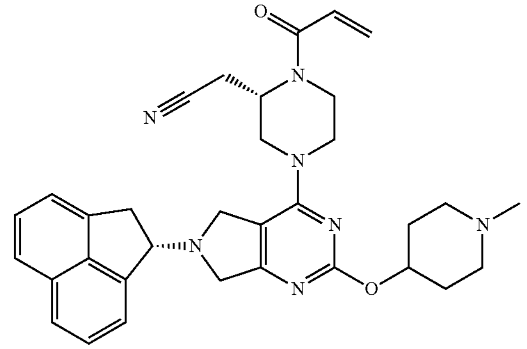
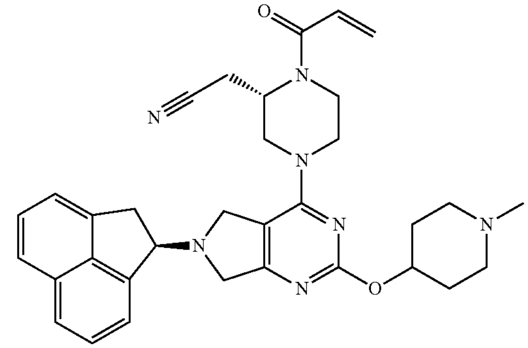
,
-continued
18
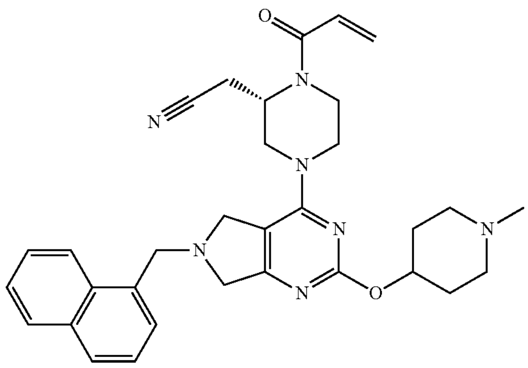
,
19
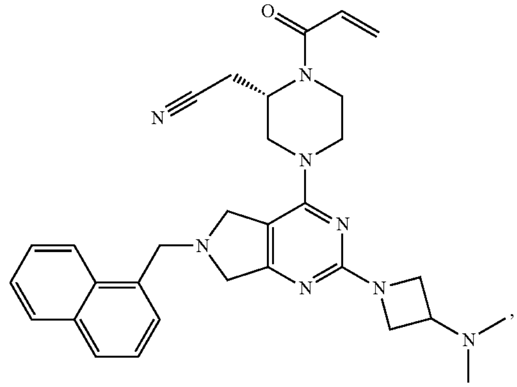
,
20
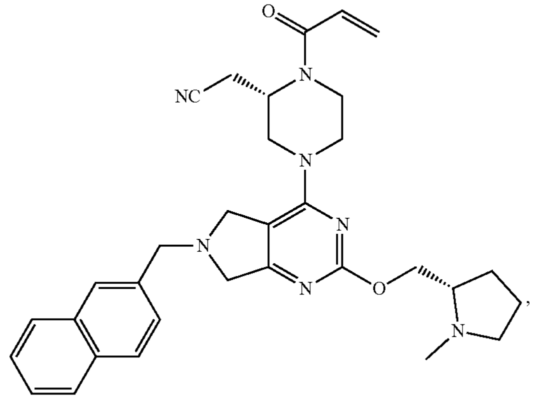
,
21
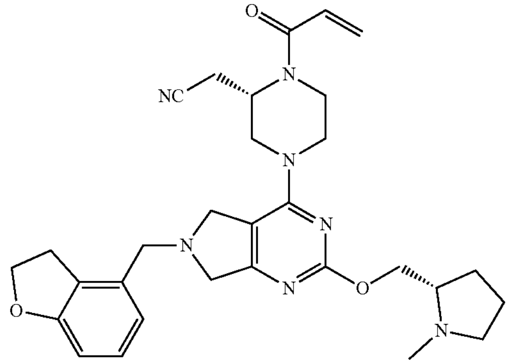
, 22
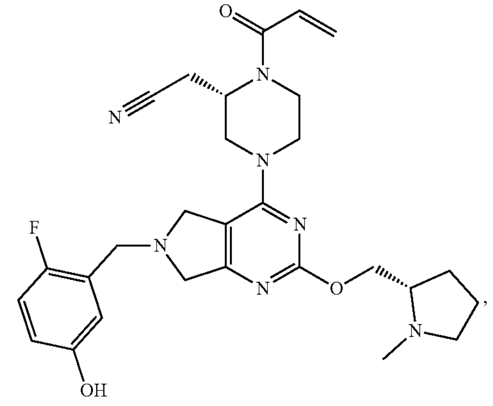
23
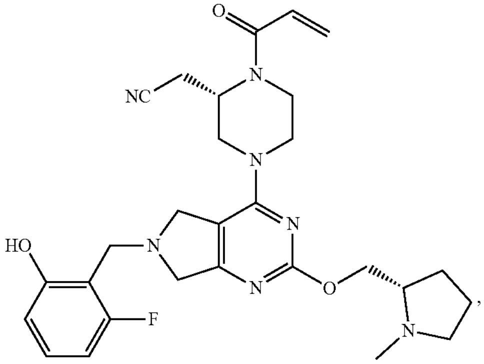
24
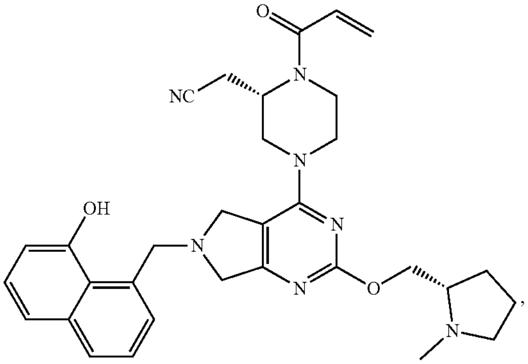
25
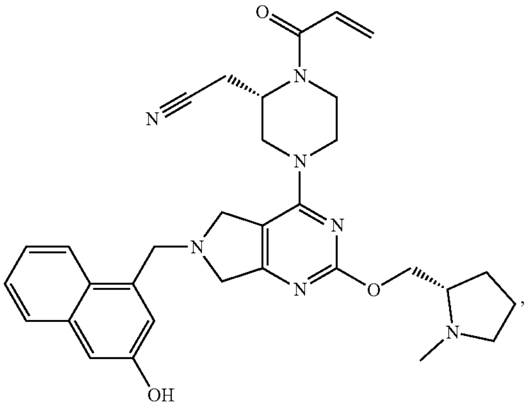
26
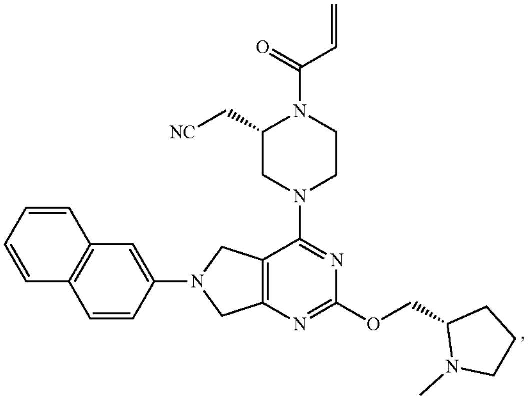
27
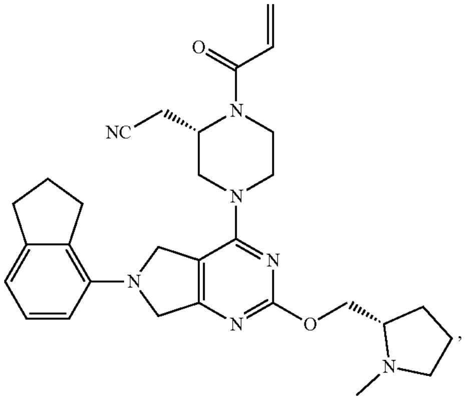
28
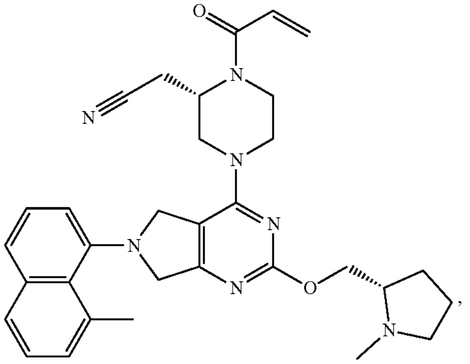
29
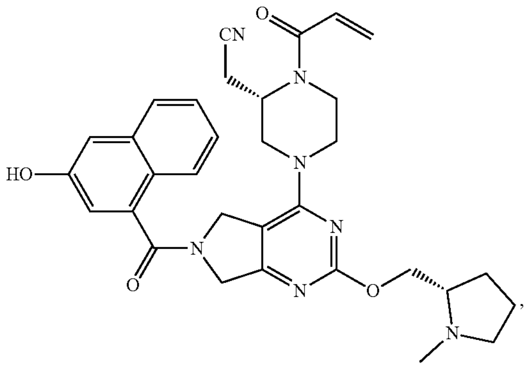

-continued
30
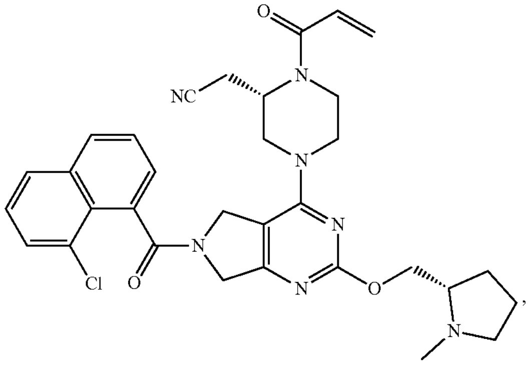,
31
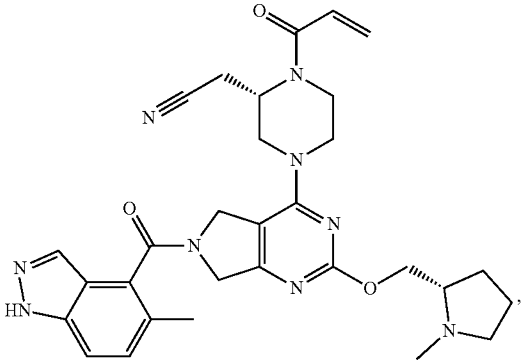,
32
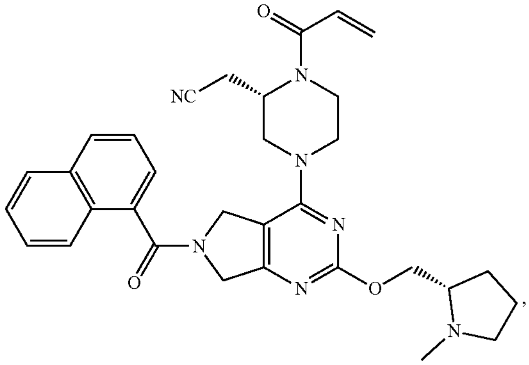,
33
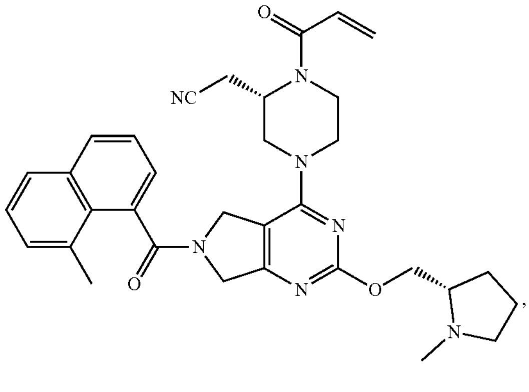,
-continued
34
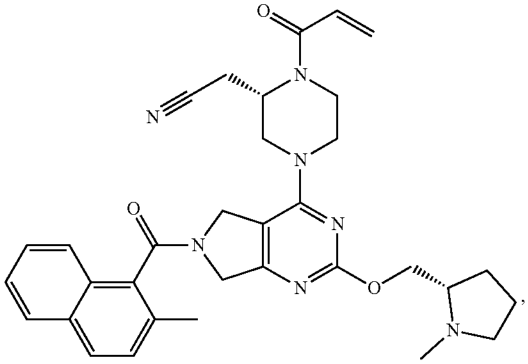,
35
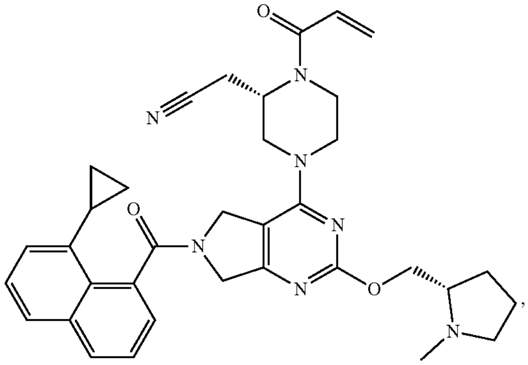,
36
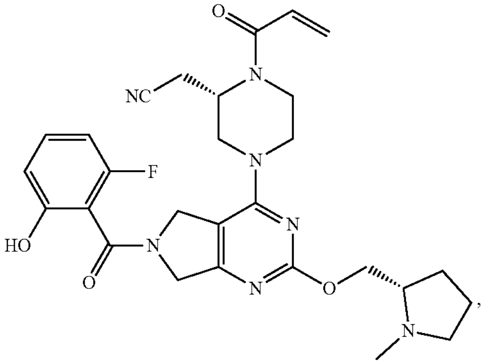,
37
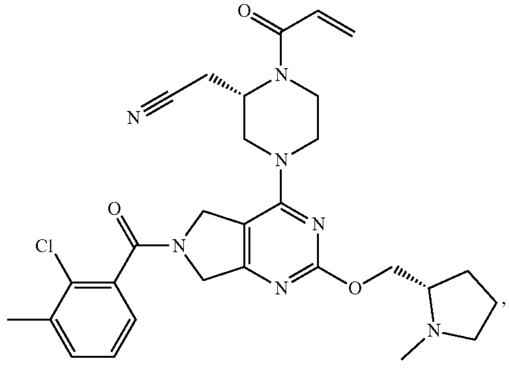, -continued
38
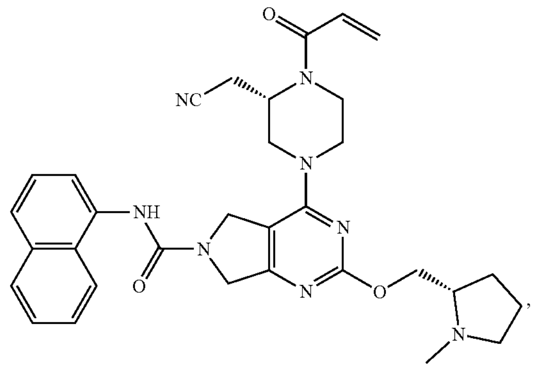
39
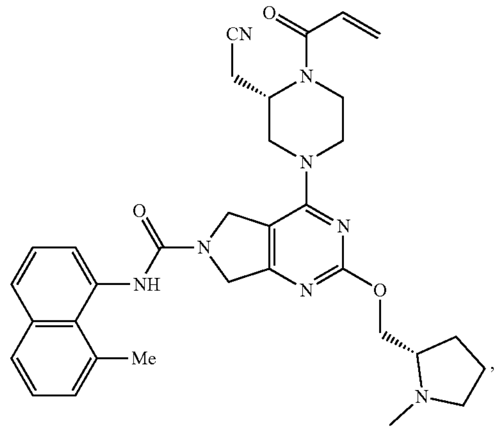
40
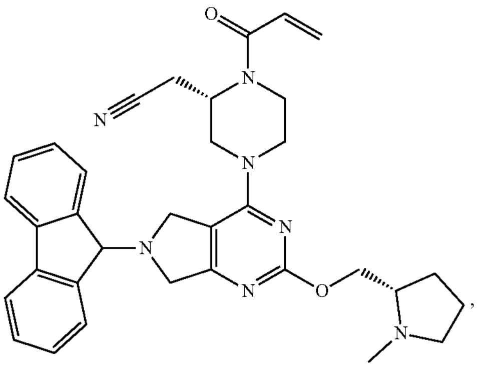
41
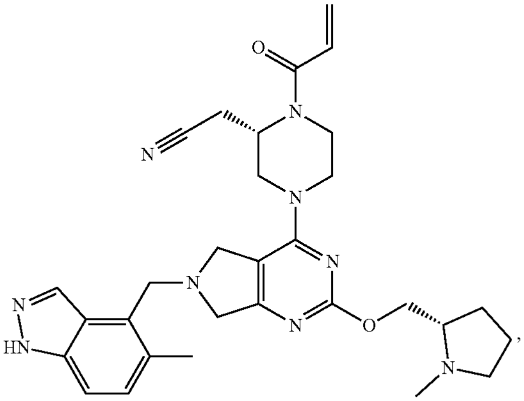
-continued
42
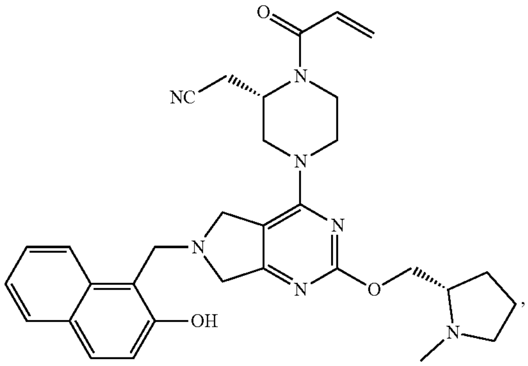
43
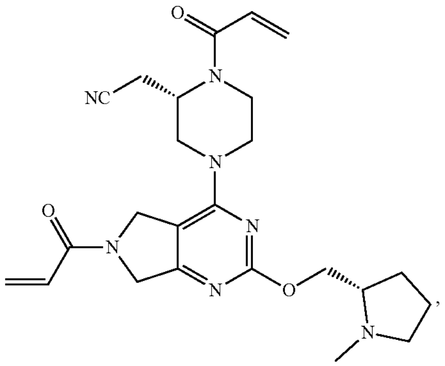
44
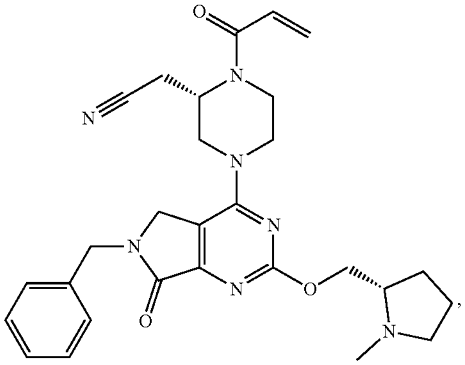
45
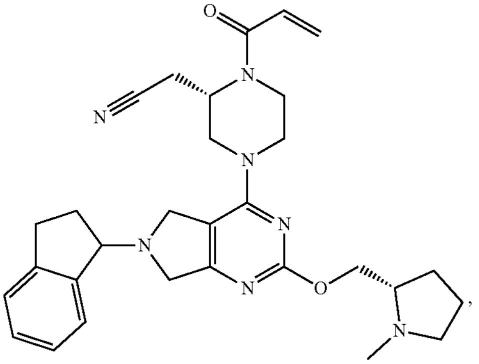

-continued
46
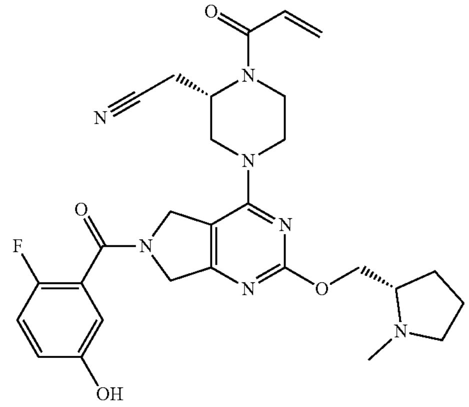
,
47
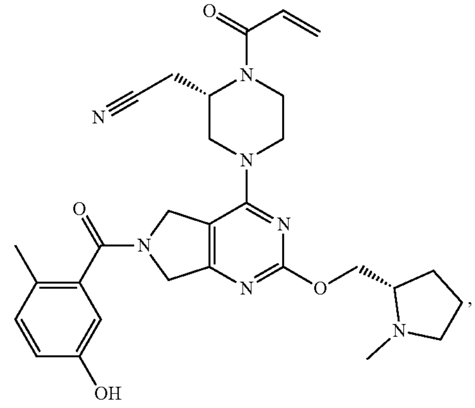
,
48
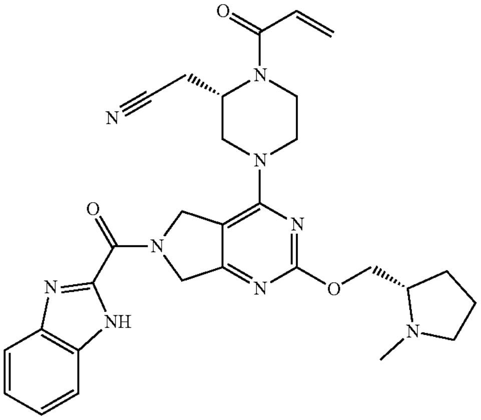
,
49
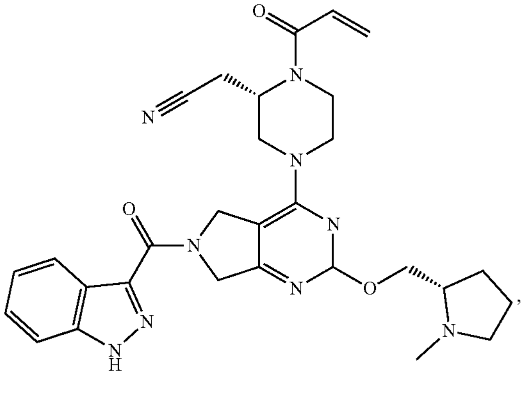
,
-continued
50
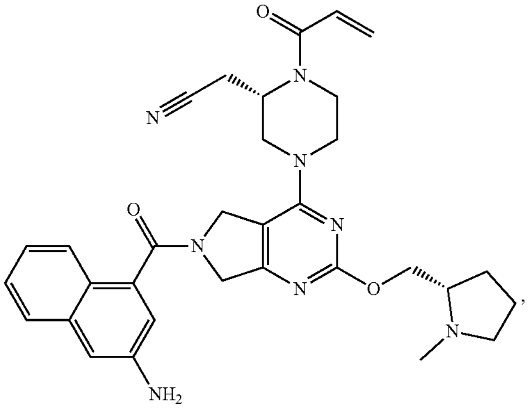
,
51
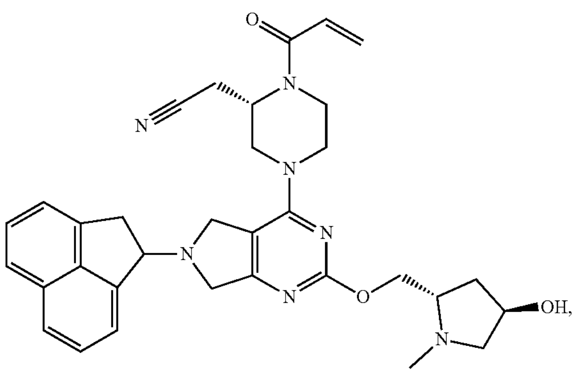
,
52
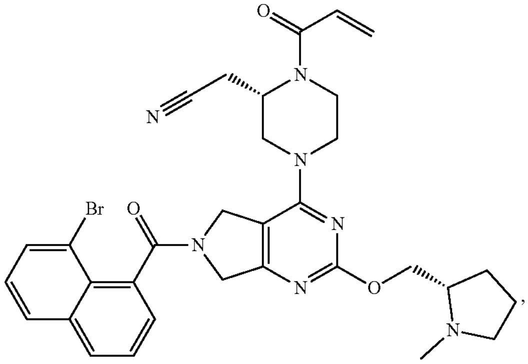
,
53
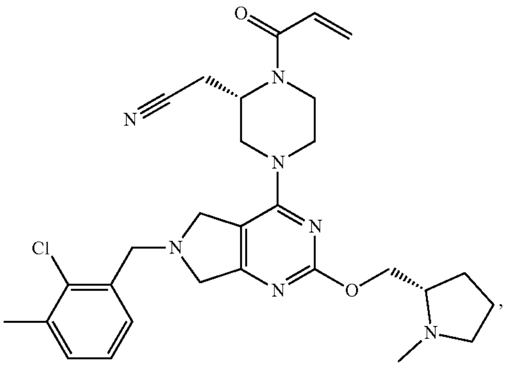
, -continued
54
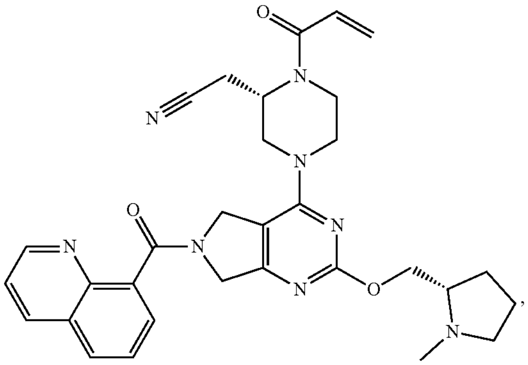
55
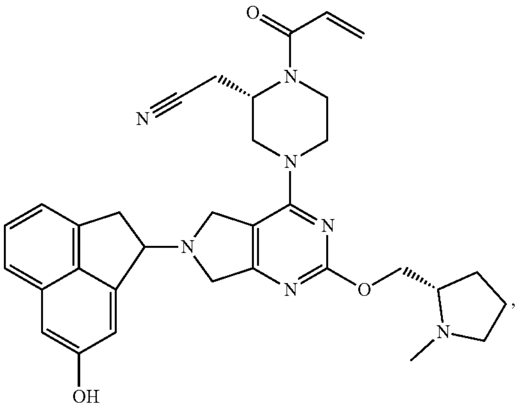
56
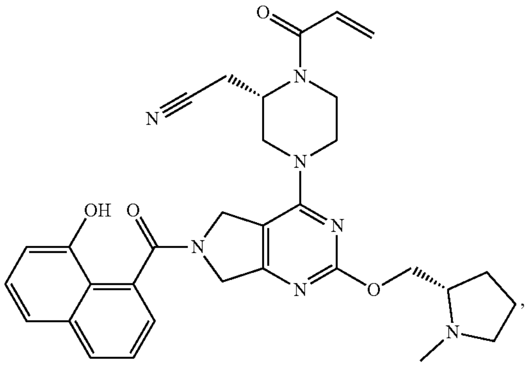
57
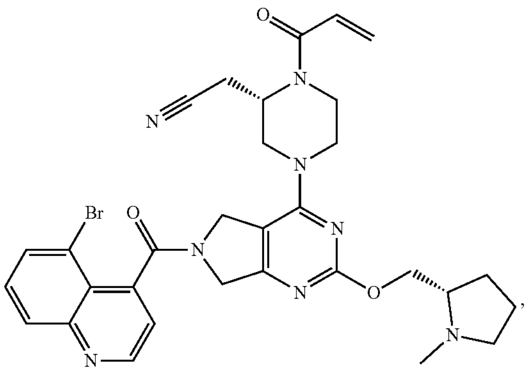
-continued
58
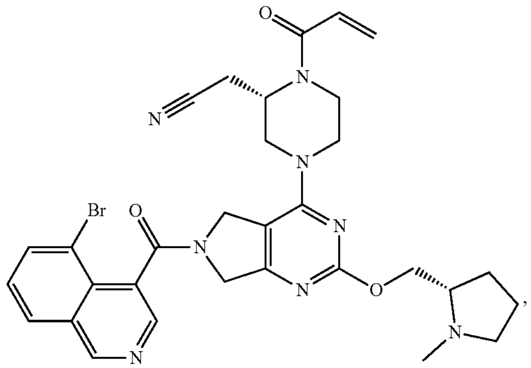
59
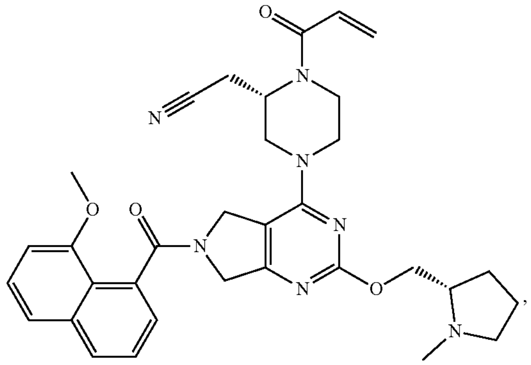
60
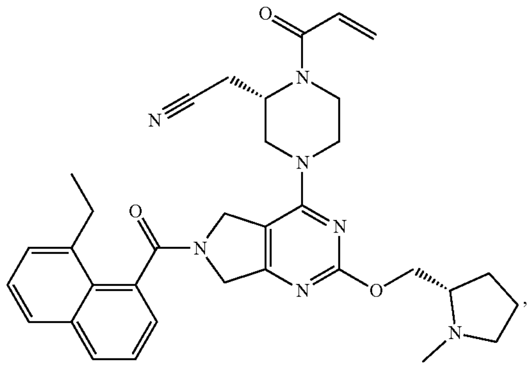
61
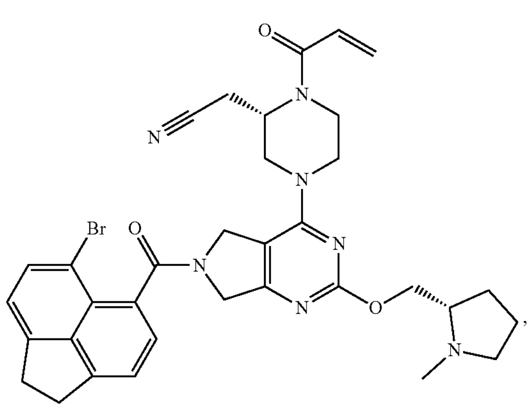

-continued
62
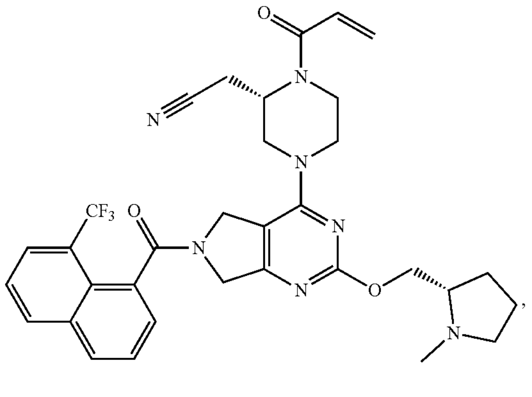
63
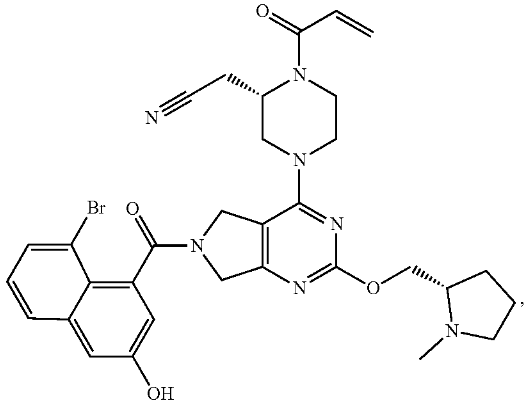
64
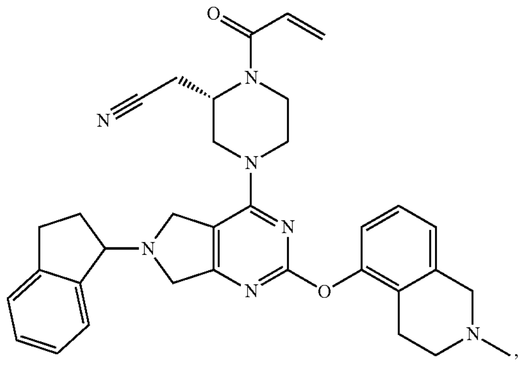
65
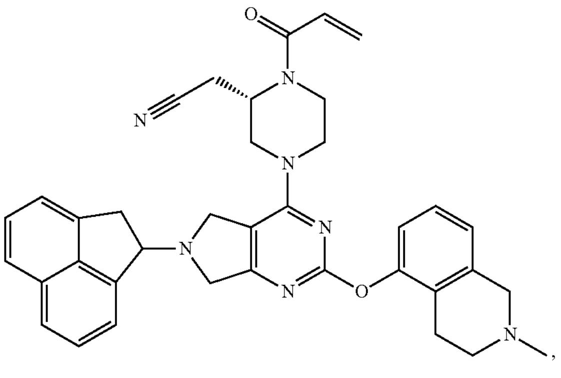
-continued
66
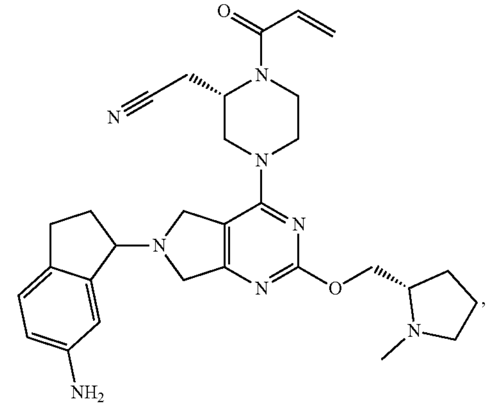
67
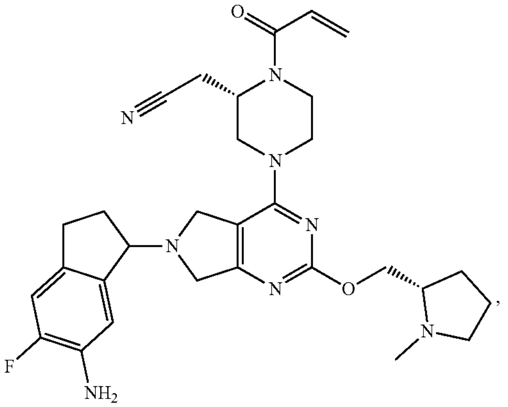
68
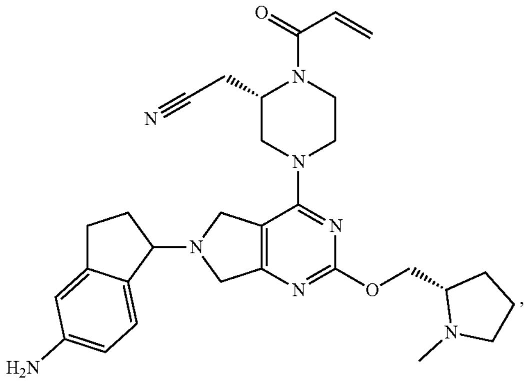
69
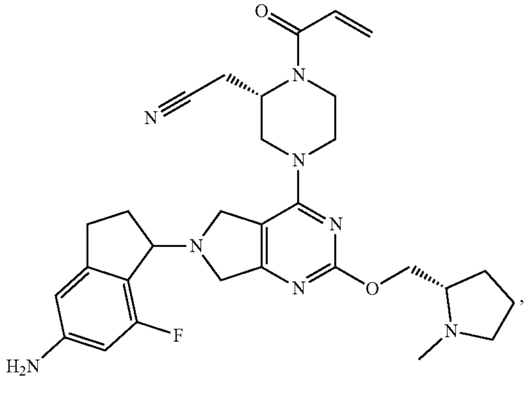

-continued
70
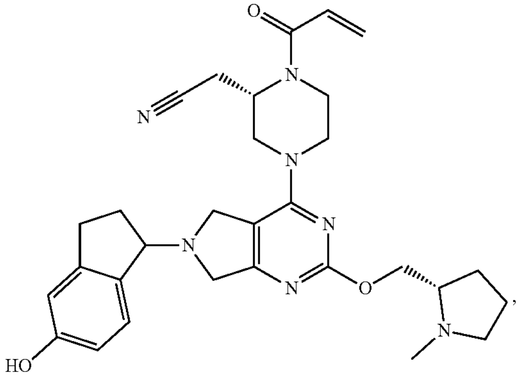
71
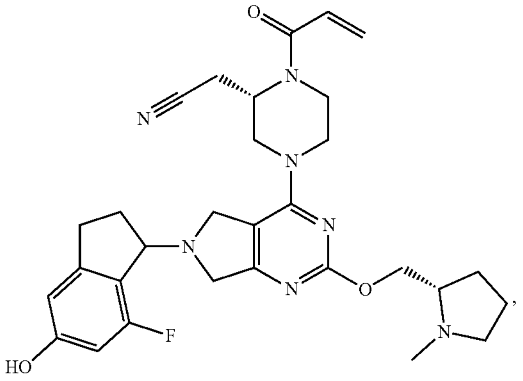
72
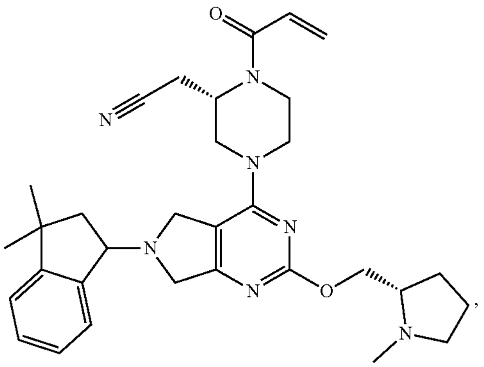
73
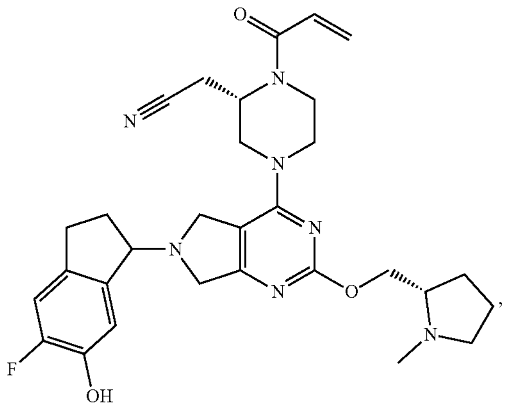
-continued
74
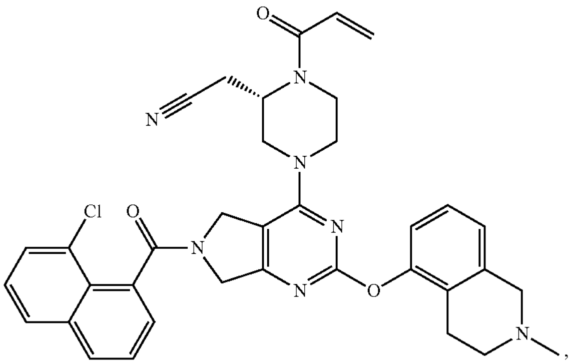
75
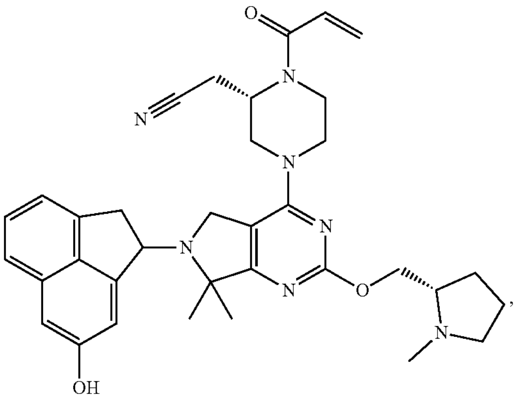
76
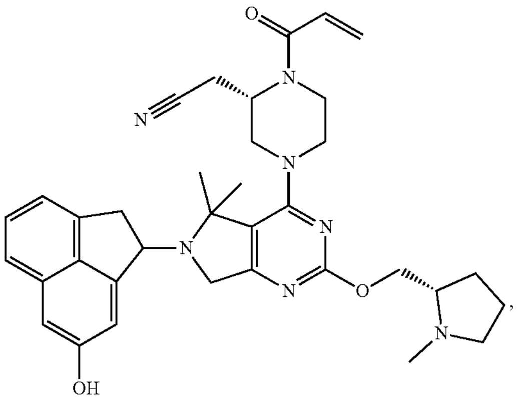
77
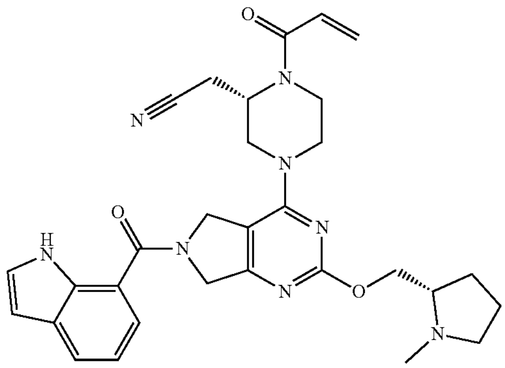

-continued
78
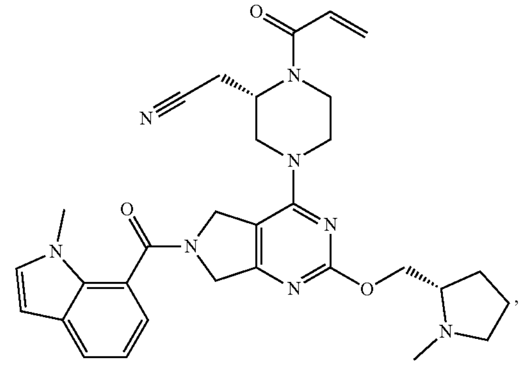
79
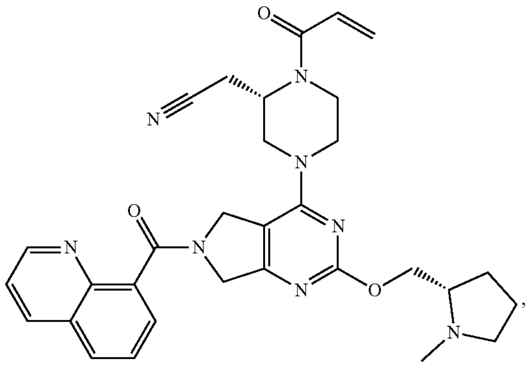
80
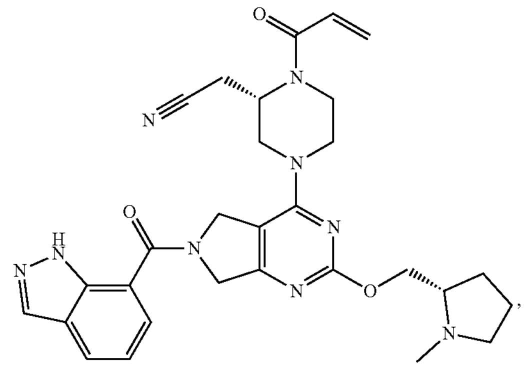
81
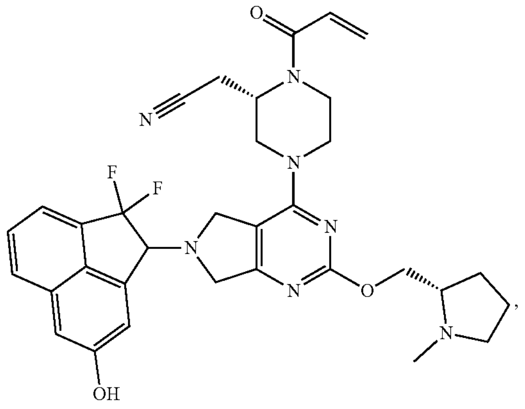
-continued
82
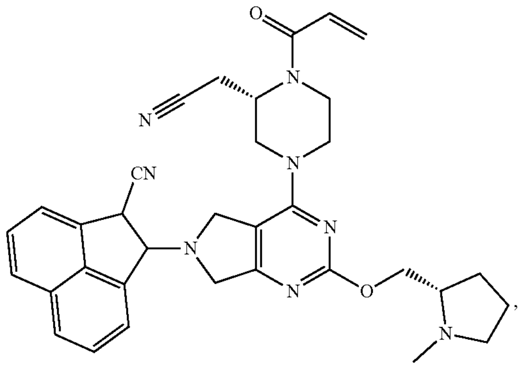
83
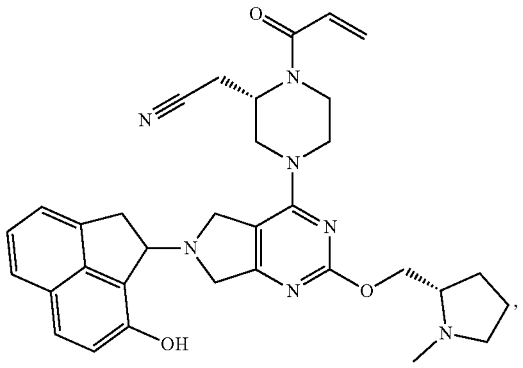
84
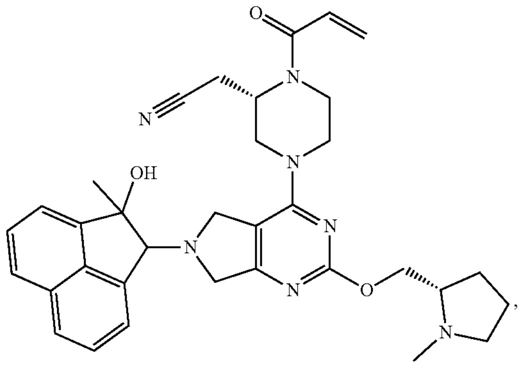
83
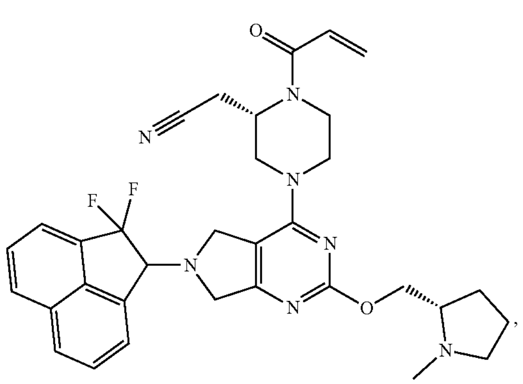

-continued
84
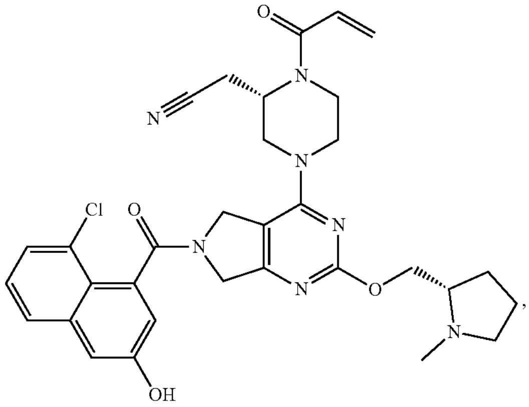
85
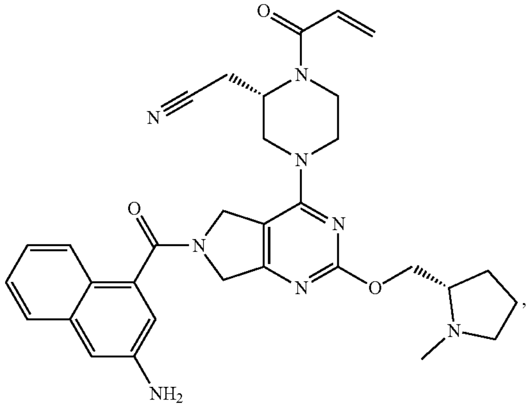
88
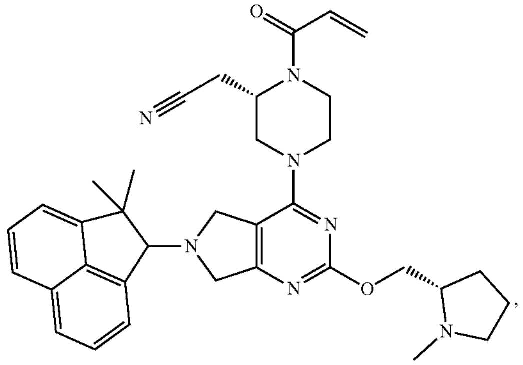
89
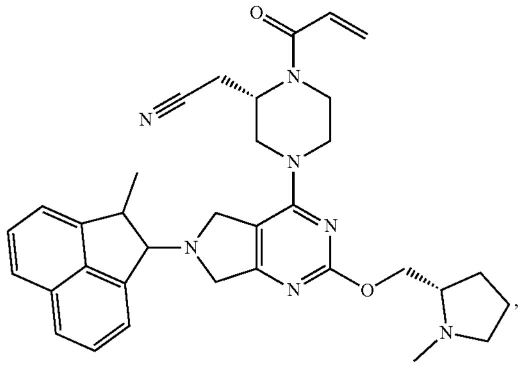
-continued
90
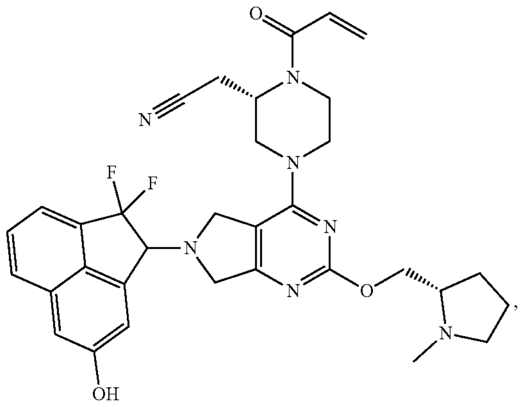
91
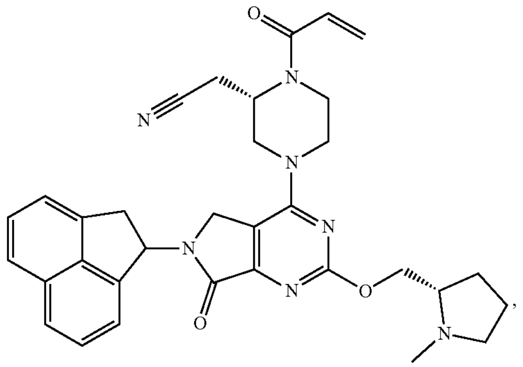
92
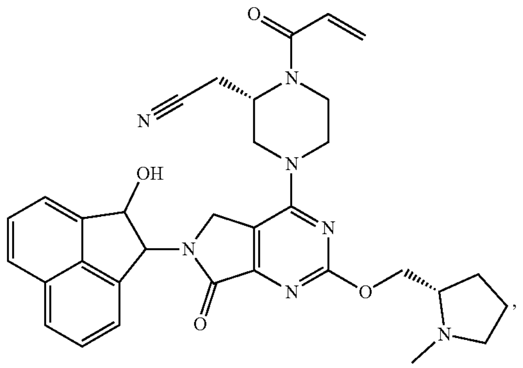

-continued
93
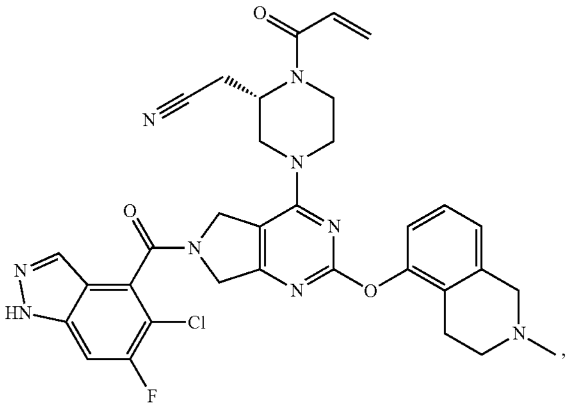
94
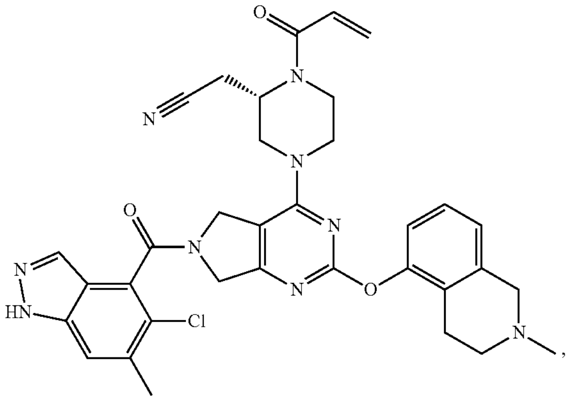
95
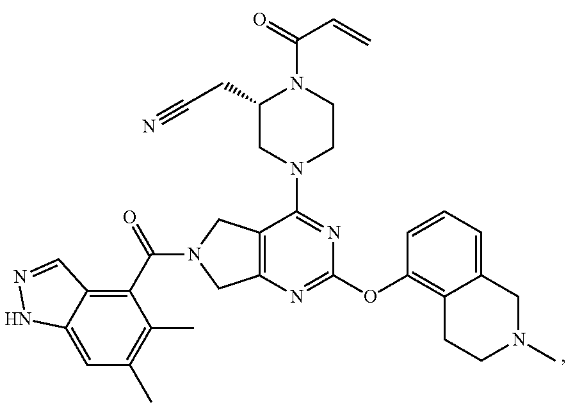
-continued
96
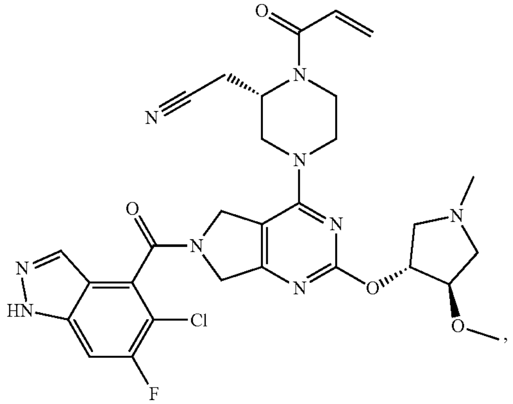
97
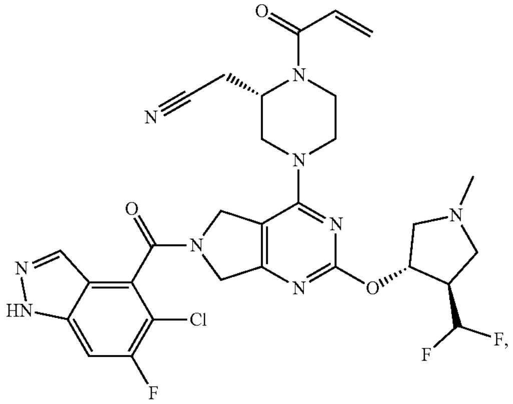
98
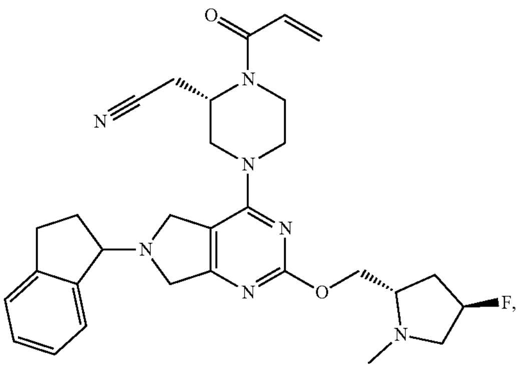
or
99
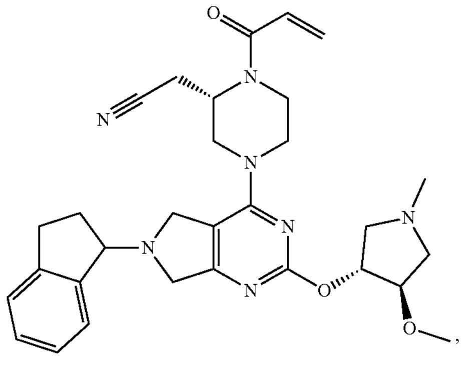
or a pharmaceutically acceptable salt thereof, or a stereoisomer thereof.

16. A compound of Formula (II):

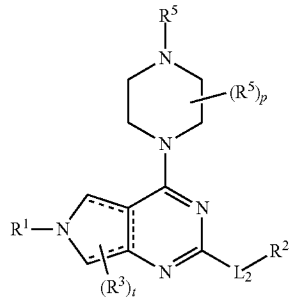

or a pharmaceutically acceptable salt thereof, or a stereoisomer thereof, wherein:

is a single bond or a double bond;

$L_2$ is selected from single bond, —CO—NH—, —NH—CO—, —O—, —$NR^a$—, —$NR^a(CH_2)_m$—, —S—, —$(CH_2)_m$—, —O—$(CH_2)_m$—, —O—$CH(R^a)$—, —$CH(R^a)$—, —$CH(R^a)$ $(CH_2)_m$—, —$(CH_2)_m$—O—, —CO—, —$SO_2$—, cycloalkylene, oxetandiyl, tetrahydrofurandiyl, tetrahydropyrandiyl, azetidindiyl, pyrrilidindiyl, piperidindiyl, or piperizindiyl;

$R^1$ is selected from hydrogen, Boc or Cbz;

$R^2$ is selected from —$NR^bR^c$, cycloalkyl, heterocyclyl, aryl, or heteroaryl, wherein each of said cycloalkyl, heterocyclyl, aryl, or heteroaryl is optionally substituted with at least one $R^6$;

each $R^6$ is independently selected from —$C_{1-8}$alkyl, halogen, hydroxy, oxo, —$C_{1-8}$alkoxy, —$NR^bR^c$, cycloalkyl, heterocyclyl, aryl, or heteroaryl, wherein said —$C_{1-8}$alkyl, —$C_{1-8}$alkoxy, cycloalkyl, heterocyclyl, aryl, or heteroaryl is optionally substituted with at least one hydroxy, amino, CN or cycloalkyl, heterocyclyl, aryl or heteroaryl;

$R^3$ is selected from hydrogen, oxo, —$C_{1-8}$alkyl, —$C_{2-8}$ alkenyl, —$C_{2-8}$alkynyl, cycloalkyl, heterocyclyl, aryl, or heteroaryl, wherein each of said —$C_{1-8}$alkyl, —$C_{2-8}$ alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^5$ is selected from —$C_{1-8}$alkyl, —$C_{2-8}$alkenyl, —$C_{2-8}$ alkynyl, oxo, —$NR^bR^c$, —CO—$NR^dR^e$, cycloalkyl, heterocyclyl, aryl, heteroaryl, —$(CH_2)_m$—CN, or hydrogen;

$R^4$ is selected from hydrogen, Fmoc, Ac, Bn, PMB, Tr, Ts, Boc, or Cbz;

each $R^a$, $R^b$ and $R^c$ are independently hydrogen, deuterium (D), cyano (CN), halogen, hydroxy, —$C_{1-8}$ alkoxy, —$C_{1-8}$alkyl, —$C_{2-8}$alkenyl, —$C_{2-8}$alkynyl, cycloalkyl, heterocyclyl, aryl, heteroaryl, —$NR^dR^e$, or —CO—$NR^dR^e$, each of said —$C_{1-8}$alkyl, —$C_2$-8alkenyl, —$C_{2-8}$alkynyl, cycloalkyl, heterocyclyl, aryl, or heteroaryl is optionally substituted with $R^f$; or (i) $R^a$ and $R^b$, or (ii) $R^a$ and $R^c$ together with the atom(s) to which they are attached, form a 4- to 6 membered ring, wherein said ring is optionally substituted with at least one $R^g$;

each $R^f$ is selected from halogen, hydroxy, oxo, —$C_{1-8}$alkoxy, —$NR^dR^e$, —CO—$NR^dR^e$, —$NR^d$—CO—$R^e$, cycloalkyl, heterocyclyl, aryl, or heteroaryl, wherein each said —$C_{1-8}$alkoxy, cycloalkyl, heterocyclyl, aryl, or heteroaryl is optionally substituted with halogen, hydroxy or —$C_{1-4}$alkyl;

$R^d$, $R^e$, and $R^g$ are each independently hydrogen, deuterium, halogen, oxo, or —$C_{1-8}$alkyl; wherein each said —$C_{1-8}$alkyl is optionally substituted with at least one halogen, oxo, $CF_3$ or —$COCH_3$;

p, q, and t are independently selected from 0, 1, 2, 3 or 4; and each m is independently 0, 1, 2, 3, 4, 5 or 6.

17. The compound according to claim 16, wherein:

a) $L_2$ is selected from —O—, —O—$(CH_2)_m$—, —O—$CH(R^a)$—, cyclopropylene, azetidindiyl, or —$NR^a$ $(CH_2)_m$; m is 1 or 2; and $R^a$ is selected from hydrogen, methyl, or deuterium; or b) $L_2$ is selected from single bond, —O—$CH_2$—, —O—$CH_2CH_2$—, —O—$CH_2CH_2CH_2$—, —O—, —O—$CH(CH_3)$—, —NH—$CH_2$—, —NH—$CH_2CH_2$—, or —O—$CH(CH_3)CH_2$—,

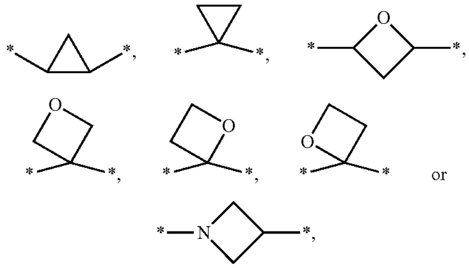

wherein the asterisks refers to linking positions.

18. The compound according to claim 16, wherein:

a) $R^2$ is selected from

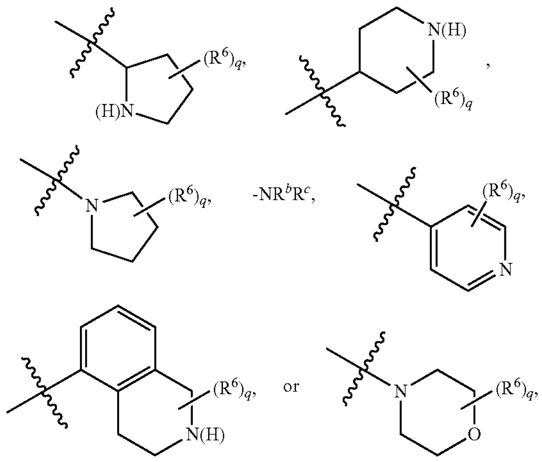

wherein each $R^6$ is independently selected from halogen, hydroxy, —$C_{1-8}$alkyl, —$C_{1-8}$alkoxy or heterocyclyl, wherein —$C_{1-8}$alkyl is optionally substituted with hydroxy; each q is 0, 1, 2 or 3; and $R^b$ and $R^c$ are each independently hydrogen, deuterium, halogen, or —$C_{1-8}$alkyl; or b) $R^2$ is selected from
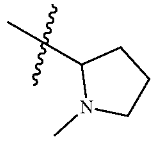
,
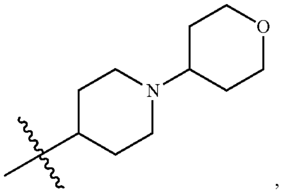
,
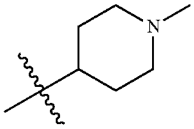
,
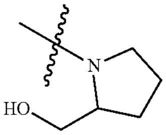
,
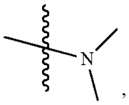
,
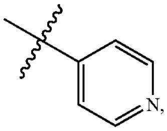
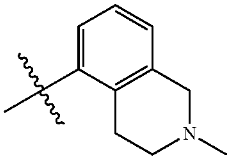
,
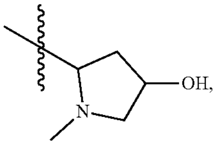
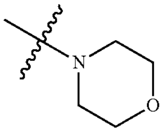
,
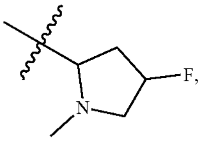
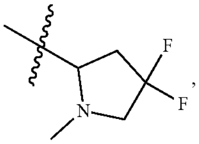
, or
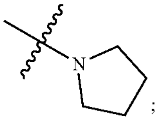
;
c) $R^2$ is selected from
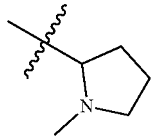
,
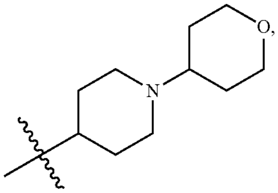
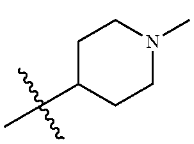
,
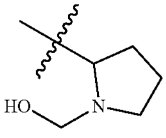
,
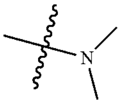
, or
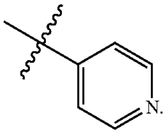
19. The compound according to claim 18, wherein $R^6$ is selected from $CH_3$, OH, $CH_2OH$, F, Cl, $—CHF_2$, $—OCH_3$, Br, or
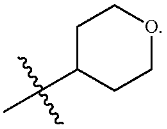
20. The compound according to claim 16, wherein $R^3$ is selected from hydrogen, oxo, or $—C_{1-8}$alkyl.
21. The compound according to claim 16, wherein
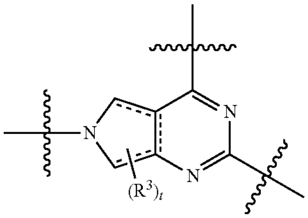
is selected from
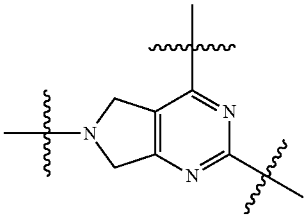
,
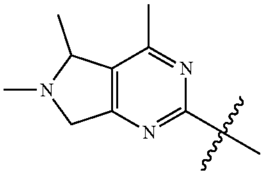
,
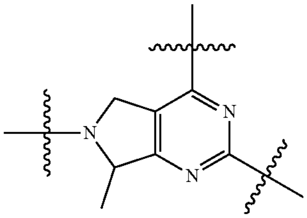
,
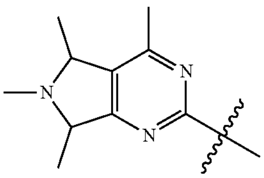
,
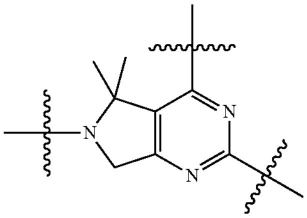
, -continued

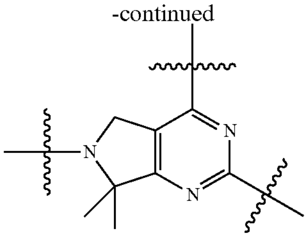

,

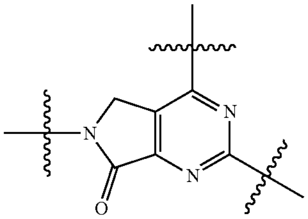

,

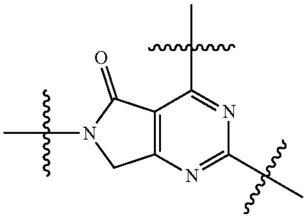

, or

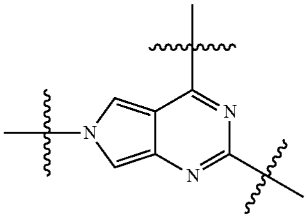

.

22. The compound according to claim 16, wherein $R^4$ is selected from hydrogen, Boc, or Cbz.

23. The compound according to claim 16, selected from

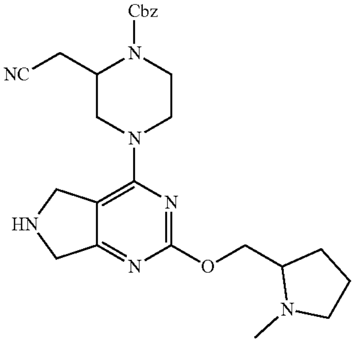

,

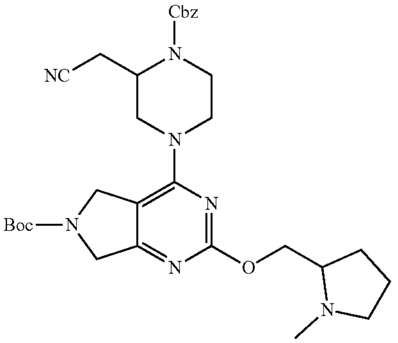

,

-continued

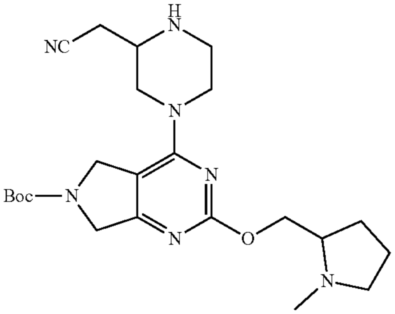

,

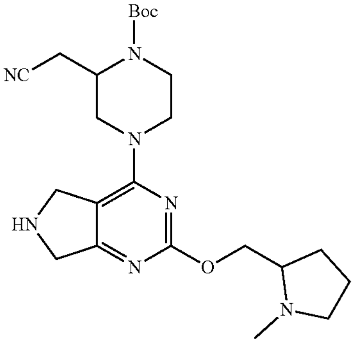

,

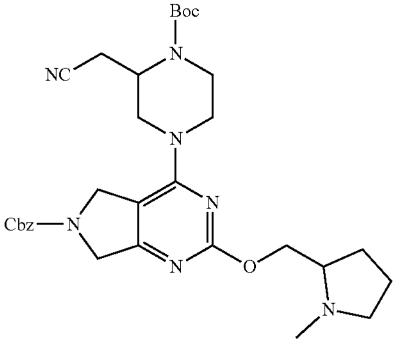

, or

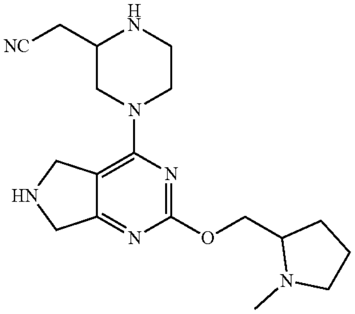

, or a pharmaceutically acceptable salt thereof.

24. A pharmaceutical composition comprising the compound of claim 1, or a stereoisomer thereof, or a pharmaceutically acceptable salt thereof and a pharmaceutically acceptable excipient.

25. A method of treating cancer, comprising administering a subject in need thereof the compound of claim 1, or a stereoisomer thereof, or a pharmaceutically acceptable salt thereof.

* * * * *